United States Patent
Marshall et al.

(10) Patent No.: US 12,410,262 B2
(45) Date of Patent: *Sep. 9, 2025

(54) PEPTIDE CONJUGATES OF CYTOTOXINS AS THERAPEUTICS

(71) Applicant: Cybrexa 2, Inc., New Haven, CT (US)

(72) Inventors: Daniel Richard Marshall, New Haven, CT (US); Johanna Marie Csengery, New Fairfield, CT (US); Robert John Maguire, New Haven, CT (US); Robert A. Volkmann, Mystic, CT (US)

(73) Assignee: Cybrexa 2, Inc., New Haven, CT (US)

( * ) Notice: Subject to any disclaimer, the term of this patent is extended or adjusted under 35 U.S.C. 154(b) by 363 days.

This patent is subject to a terminal disclaimer.

(21) Appl. No.: 18/174,981

(22) Filed: Feb. 27, 2023

(65) Prior Publication Data

US 2024/0010755 A1 Jan. 11, 2024

Related U.S. Application Data

(63) Continuation of application No. 16/925,094, filed on Jul. 9, 2020, now Pat. No. 11,634,508.

(60) Provisional application No. 63/040,859, filed on Jun. 18, 2020, provisional application No. 62/872,643, filed on Jul. 10, 2019.

(51) Int. Cl.
*A61P 35/00* (2006.01)
*A61K 31/4745* (2006.01)
*A61K 38/00* (2006.01)
*C07D 491/147* (2006.01)
*C07D 491/16* (2006.01)
*C07D 491/22* (2006.01)
*C07K 14/00* (2006.01)
*C07K 19/00* (2006.01)

(52) U.S. Cl.
CPC .......... *C07K 19/00* (2013.01); *A61K 31/4745* (2013.01); *A61P 35/00* (2018.01); *C07D 491/147* (2013.01); *C07D 491/16* (2013.01); *C07D 491/22* (2013.01); *C07K 14/00* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,658,920 A | 8/1997 | Terasawa et al. |
| 5,770,605 A | 6/1998 | Terasawa et al. |
| 5,834,476 A | 11/1998 | Terasawa et al. |
| 6,100,283 A | 8/2000 | Griffin et al. |
| 6,172,230 B1 | 1/2001 | Kamihara et al. |
| 6,291,671 B1 | 9/2001 | Inoue et al. |
| 6,310,082 B1 | 10/2001 | Griffin et al. |
| 6,337,400 B1 | 1/2002 | Kamihara et al. |
| 6,436,912 B1 | 8/2002 | Inoue et al. |
| 6,495,541 B1 | 12/2002 | Webber et al. |
| 6,504,029 B1 | 1/2003 | Kamihara et al. |
| 6,548,494 B1 | 4/2003 | Webber et al. |
| 6,552,197 B2 | 4/2003 | Kamihara et al. |
| 6,696,437 B1 | 2/2004 | Lubisch et al. |
| 6,811,996 B1 | 11/2004 | Inoue et al. |
| 6,815,435 B2 | 11/2004 | Takahashi et al. |
| 6,835,807 B1 | 12/2004 | Susaki et al. |
| 6,838,450 B2 | 1/2005 | Inoue et al. |
| 6,844,318 B2 | 1/2005 | Copeland et al. |
| 7,041,818 B2 | 5/2006 | Susaki et al. |
| 7,151,102 B2 | 12/2006 | Martin et al. |
| 7,196,085 B2 | 3/2007 | Martin et al. |
| 7,276,497 B2 | 10/2007 | Chari et al. |
| 7,301,019 B2 | 11/2007 | Widdison et al. |
| 7,374,762 B2 | 5/2008 | Amphlett et al. |
| 7,411,063 B2 | 8/2008 | Widdison et al. |
| 7,449,464 B2 | 11/2008 | Martin et al. |
| 7,473,796 B2 | 1/2009 | Chari et al. |
| 7,494,649 B2 | 2/2009 | Amphlett et al. |
| 7,501,120 B2 | 3/2009 | Amphlett et al. |
| 7,514,080 B2 | 4/2009 | Amphlett et al. |
| 7,531,530 B2 | 5/2009 | Helleday et al. |
| 7,692,006 B2 | 4/2010 | Menear |
| 7,771,727 B2 | 8/2010 | Fuselier et al. |
| 7,781,596 B1 | 8/2010 | Lubisch et al. |
| 7,811,572 B2 | 10/2010 | Dai et al. |
| 7,851,432 B2 | 12/2010 | Chari et al. |
| 7,989,598 B2 | 8/2011 | Steeves et al. |
| 8,012,485 B2 | 9/2011 | Amphlett et al. |
| 8,067,613 B2 | 11/2011 | Gandhi |
| 8,071,623 B2 | 12/2011 | Jones et al. |
| 8,076,451 B2 | 12/2011 | Reshetnyak et al. |

(Continued)

FOREIGN PATENT DOCUMENTS

| | | |
|---|---|---|
| AU | 2007247969 | 11/2007 |
| CN | 1195985 | 10/1998 |

(Continued)

OTHER PUBLICATIONS

Liu et al., "Perspectives on Biologically Active Camptothecin Derivatives," Medicinal Research Reviews, Mar. 2015, 35(4):753-789, 38 pages.

Office Action in Chinese Appln. No. 202080057842.4, dated Jul. 10, 2024, 32 pages (with machine translation).

Akaiwa et al., "Antibody-Drug Conjugate Payloads: Study of Auristatin Derivatives." Chem. Pharm. Bull., Mar. 2020, 68(3):201-211.

Gores et al., "Swelling, reductive stress, and cell death during chemical hypoxia in hepatocytes, " Am. J. Physiol., Aug. 1989, 257(2):C347-C354.

Harms et al., "The pKa Values of Acidic and Basic Residues Buried at the Same Internal Location in a Protein Are Governed by Different Factors," J. Mol. Biol., May 2009, 389(1):34-47, 30 pages.

(Continued)

*Primary Examiner* — Noble E Jarrell
(74) *Attorney, Agent, or Firm* — Fish & Richardson P.C.

(57) ABSTRACT

The present invention relates to peptide conjugates of cytotoxins such as topoisomerase I inhibitors which are useful for the treatment of diseases such as cancer.

19 Claims, 15 Drawing Sheets

Specification includes a Sequence Listing.

(56) References Cited

U.S. PATENT DOCUMENTS

| | | |
|---|---|---|
| 8,088,387 B2 | 1/2012 | Steeves et al. |
| 8,137,669 B2 | 3/2012 | Goldmakher et al. |
| 8,163,888 B2 | 4/2012 | Steeves et al. |
| 8,198,417 B2 | 6/2012 | Steeves et al. |
| 8,383,122 B2 | 2/2013 | Dai et al. |
| 8,388,960 B2 | 3/2013 | Goldmakher et al. |
| 8,435,528 B2 | 5/2013 | Chari et al. |
| 8,563,509 B2 | 10/2013 | Chari et al. |
| 8,603,483 B2 | 12/2013 | Chen et al. |
| 8,624,003 B2 | 1/2014 | Kellogg et al. |
| 8,685,920 B2 | 4/2014 | Chari et al. |
| 8,697,736 B2 | 4/2014 | Penning et al. |
| 8,703,909 B2 | 4/2014 | Reshetnyak et al. |
| 8,754,190 B2 | 6/2014 | Ashley et al. |
| 8,795,673 B2 | 8/2014 | Li et al. |
| 8,841,425 B2 | 9/2014 | Chari et al. |
| 8,859,756 B2 | 10/2014 | Ross et al. |
| 8,933,205 B2 | 1/2015 | Dai et al. |
| 9,090,629 B2 | 7/2015 | Chari et al. |
| 9,150,649 B2 | 10/2015 | Singh et al. |
| 9,289,508 B2 | 3/2016 | Reshetnyak et al. |
| 9,376,500 B2 | 6/2016 | Kellogg et al. |
| 9,428,543 B2 | 8/2016 | Li et al. |
| 9,676,823 B2 | 6/2017 | Reshetnyak et al. |
| 9,771,432 B2 | 9/2017 | Kellogg et al. |
| 9,789,204 B2 | 10/2017 | Dai et al. |
| 9,808,537 B2 | 11/2017 | Masuda et al. |
| 9,814,781 B2 | 11/2017 | Reshetnyak et al. |
| 9,872,924 B2 | 1/2018 | Naito et al. |
| 9,914,748 B2 | 3/2018 | Li et al. |
| 9,919,059 B2 | 3/2018 | Wong et al. |
| 9,999,680 B2 | 6/2018 | Widdison |
| 10,064,855 B2 | 9/2018 | Langecker et al. |
| 10,195,288 B2 | 2/2019 | Masuda et al. |
| 10,383,878 B2 | 8/2019 | Hettmann et al. |
| 10,413,615 B2 | 9/2019 | Hutchins |
| 10,435,432 B2 | 10/2019 | Li et al. |
| 10,695,396 B2 | 6/2020 | Fukuda et al. |
| 10,729,782 B2 | 8/2020 | Naito et al. |
| 10,844,135 B2 | 11/2020 | Chari et al. |
| 10,933,069 B2 | 3/2021 | Marchall et al. |
| 11,555,019 B2 | 1/2023 | Marshall et al. |
| 11,634,508 B2 | 4/2023 | Marshall et al. |
| 2003/0105109 A1 | 6/2003 | Lavielle et al. |
| 2004/0235840 A1 | 11/2004 | Chari et al. |
| 2005/0256030 A1 | 11/2005 | Feng |
| 2008/0233107 A1 | 9/2008 | Reshetnyak et al. |
| 2012/0039990 A1 | 2/2012 | Reshetnyak et al. |
| 2012/0045524 A1 | 2/2012 | Wernet et al. |
| 2012/0266262 A1 | 10/2012 | Ashkenazi et al. |
| 2015/0051153 A1 | 2/2015 | Reshetnyak et al. |
| 2016/0303254 A1 | 10/2016 | Kolakowski et al. |
| 2017/0035906 A1 | 2/2017 | Naito et al. |
| 2017/0112891 A1 | 4/2017 | Dragovich et al. |
| 2017/0145044 A1 | 5/2017 | Hudson et al. |
| 2017/0207277 A1 | 7/2017 | Park |
| 2017/0226220 A1 | 8/2017 | Chari et al. |
| 2017/0267727 A1 | 9/2017 | Thevenin et al. |
| 2017/0267765 A1 | 9/2017 | Tsao |
| 2017/0274093 A1 | 9/2017 | Goldenberg et al. |
| 2018/0043013 A1 | 2/2018 | Chari et al. |
| 2018/0071403 A1 | 3/2018 | Naito et al. |
| 2018/0221500 A1 | 8/2018 | Reshetnyak et al. |
| 2019/0008981 A1 | 1/2019 | Masuda et al. |
| 2019/0010229 A1 | 1/2019 | Amphlett et al. |
| 2019/0030177 A1 | 1/2019 | Dai et al. |
| 2019/0151328 A1 | 5/2019 | Hettmann et al. |
| 2019/0175684 A1 | 6/2019 | Fukuda et al. |
| 2019/0209580 A1 | 7/2019 | Marshall et al. |
| 2020/0237926 A1 | 7/2020 | Reshetnyak et al. |
| 2020/0306243 A1 | 10/2020 | Howard et al. |
| 2021/0009536 A1 | 1/2021 | Marshall et al. |
| 2021/0009719 A1 | 1/2021 | Marshall et al. |
| 2021/0299137 A1 | 9/2021 | Marshall et al. |
| 2023/0416331 A1 | 12/2023 | Maguire et al. |
| 2024/0067616 A1 | 2/2024 | Marshall et al. |
| 2024/0093250 A1 | 3/2024 | Maguire et al. |
| 2024/0226308 A1 | 7/2024 | Paralkar et al. |

FOREIGN PATENT DOCUMENTS

| | | | |
|---|---|---|---|
| CN | 1342161 | 3/2002 | |
| CN | 1418112 | 5/2003 | |
| CN | 101370497 | 2/2009 | |
| CN | 102014956 | 4/2011 | |
| CN | 101098854 | 12/2012 | |
| CN | 106163559 | 11/2016 | |
| CN | 109232719 | 1/2019 | |
| CN | 110312549 | 10/2019 | |
| EP | 1838715 | 10/2010 | |
| EP | 2399609 | 12/2011 | |
| EP | 1945647 | 1/2012 | |
| EP | 1928503 | 10/2012 | |
| EP | 1853322 | 6/2014 | |
| EP | 3130608 | 2/2017 | |
| EP | 2691155 | 11/2018 | |
| EP | 2437790 | 2/2019 | |
| JP | H11-510154 | 9/1999 | |
| JP | 2002-534523 | 10/2002 | |
| JP | 2004-520450 | 7/2004 | |
| JP | 2018-535212 | 11/2018 | |
| KR | 20160105146 | 9/2016 | |
| NC | 2016/0001001 | 8/2016 | |
| TW | I249527 | 2/2006 | |
| TW | I460175 | 11/2014 | |
| WO | WO 9902530 | 1/1999 | |
| WO | WO 2000042040 | 7/2000 | |
| WO | WO 2001041534 | 6/2001 | |
| WO | WO 2002/098883 | 12/2002 | |
| WO | WO 2003080047 | 10/2003 | |
| WO | WO 2004087713 | 10/2004 | |
| WO | WO 2004103272 | 12/2004 | |
| WO | WO 2004110498 | 12/2004 | |
| WO | WO 2005012305 | 2/2005 | |
| WO | WO 2005012524 | 2/2005 | |
| WO | WO 2005037992 | 4/2005 | |
| WO | WO 2005053662 | 6/2005 | |
| WO | WO-2005112919 A2 * | 12/2005 | ........... A61K 31/403 |
| WO | WO 2006012527 | 2/2006 | |
| WO | WO 2006033003 | 3/2006 | |
| WO | WO 2006033006 | 3/2006 | |
| WO | WO 2006033007 | 3/2006 | |
| WO | WO 2006062779 | 6/2006 | |
| WO | WO 2006078809 | 7/2006 | |
| WO | WO 2006078816 | 7/2006 | |
| WO | WO 2006113623 | 10/2006 | |
| WO | WO 2007024536 | 3/2007 | |
| WO | WO 2007056550 | 5/2007 | |
| WO | WO 2008114114 | 9/2008 | |
| WO | WO 2009002993 | 12/2008 | |
| WO | WO 2009026177 | 2/2009 | |
| WO | WO 2009134952 | 11/2009 | |
| WO | WO 2009134976 | 11/2009 | |
| WO | WO 2010141566 | 12/2010 | |
| WO | WO 2011066418 | 6/2011 | |
| WO | WO 2011098971 | 8/2011 | |
| WO | WO 2011106639 | 9/2011 | |
| WO | WO 2012047354 | 4/2012 | |
| WO | WO 2012061590 | 5/2012 | |
| WO | WO 2012135517 | 10/2012 | |
| WO | WO 2013055987 | 4/2013 | |
| WO | WO 2014057687 | 4/2014 | |
| WO | WO 2014061277 | 4/2014 | |
| WO | WO 2014066002 | 5/2014 | |
| WO | WO 2014107024 | 7/2014 | |
| WO | WO 2014134483 | 9/2014 | |
| WO | WO 2015095755 | 6/2015 | |
| WO | WO 2015108986 | 7/2015 | |
| WO | WO 2015117002 | 8/2015 | |
| WO | WO 2015146132 | 10/2015 | |
| WO | WO 2015155976 | 10/2015 | |
| WO | WO 2015155998 | 10/2015 | |
| WO | WO 2016004043 | 1/2016 | |
| WO | WO 2016028689 | 2/2016 | |

(56) References Cited

FOREIGN PATENT DOCUMENTS

| | | |
|---|---|---|
| WO | WO 2016057398 | 4/2016 |
| WO | WO 2016081584 | 5/2016 |
| WO | WO 2016083433 | 6/2016 |
| WO | WO 2017064675 | 4/2017 |
| WO | WO 2017180834 | 10/2017 |
| WO | WO 2017199042 | 11/2017 |
| WO | WO 2017210608 | 12/2017 |
| WO | WO 2018023098 | 2/2018 |
| WO | WO 2018057912 | 3/2018 |
| WO | WO 2018095422 | 5/2018 |
| WO | WO 2018227132 | 12/2018 |
| WO | WO 2019044946 | 3/2019 |
| WO | WO 2019136298 | 7/2019 |
| WO | WO 2019140271 | 7/2019 |
| WO | WO 2019219891 | 11/2019 |
| WO | WO 2019236954 | 12/2019 |
| WO | WO 2020160009 | 8/2020 |
| WO | WO 2021007402 | 1/2021 |
| WO | WO 2021007435 | 1/2021 |
| WO | WO 2022150596 | 7/2022 |

OTHER PUBLICATIONS

Helft et al., "A Phase I Study of Cantuzumab Mertansine Administered as a Single Intravenous Infusion Once Weekly in Patients with Advanced Solid Tumors," Clin. Cancer Res., Jul. 2004, 10(13):4363-4368.
International Preliminary Report on Patentability in International Appln. No. PCT/US2022/071967, mailed on Nov. 9, 2023, 10 pages.
International Preliminary Report on Patentability in International Appln. No. PCT/US2022/079973, mailed May 30, 2024, 8 pages.
International Search Report and Written Opinion in International Appln. No. PCT/US2022/071967, mailed on Jul. 21, 2022, 19 pages.
KADCYLA (ado-trastuzumab emtansine) Prescribing Information, Revised May 2019, 31 pages.
Legarza et al., "Novel Camptothecin Derivatives," in vivo, Jan. 1, 2005, 19(1):283-92.
Office Action in Chinese Appln. No. 202080057629.3, dated May 30, 2024, 16 pages (with English translation).
Search Report in Malaysia Appln. No. PI2020003488, dated Nov. 23, 2023, 7 pages (with English translation).
Search Report in Taiwan Appln. No. 109123269, dated Mar. 6, 2024, 9 pages (with English translation).
Search Report in Taiwan Appln. No. 109123266, dated Mar. 5, 2024, 8 pages (with English translation).
Seeli et al., "Guar gum oleate-graft-poly(methacrylic acid) hydrogel as a colon-specific controlled drug delivery carrier," Carbohydrate Polymers, Feb. 2017, 158:51-57.
Sehn et al., "Polatuzumab Vedotin in Relapsed or Refractory Diffuse Large B-Cell Lymphoma," J. Clin. Oncol., Jan. 2020, 38(2):155-165, 22 pages.
Singhal et al., "Oxygen battle in the gut: Hypoxia and hypoxia-inducible factors in metabolic and inflammatory responses in the intestine," J. Biol. Chem., Jul. 2020, 295(30):10493-10505.
Venditto et al., "Cancer Therapies Utilizing the Camptothecins: A review of the in vivo literature," Molecular pharmaceutics, Apr. 5, 2010, 7(2):307-49.
Zeng et al., "Hypoxia-activated prodrugs and redox-responsive nanocarriers," Int. J. Nanomed., Oct. 2018, 13:6551-6574.
Adams et al., "The cleavage of meso-epoxides with homochiral thiols: synthesis of (+)- and (−)-trans-1-mercaptocyclohexan-2-ol," Tetrahedron: Asymmetry, Oct. 1999, 10(21):4129-4142.
Maheswara et al., "A new strategy for chemoselective O-acylation of ß-mercapto alcohols via alkylsilyl and stannyl protection," Tetrahedron Letters, Jan. 2009, 50(4):480-483.
Office Action and Search Report in Eurasian Appln. No. 202391970, dated Aug. 28, 2024, 18 pages (with English translation).

[No. Author Listed], "Research progress of PARP inhibitors combined with chemotherapy drugs in the treatment of malignant tumors," Tumor, Dec. 2013, 372-377, 1 page (English abstract).
Adiyala et al., "Development of pyrrolo [2,1-c][1,4] benzodiazepine ß-glucoside prodrugs for selective therapy of cancer," Bioorganic Chemistry, Feb. 2018, 76:288-293.
Aiello et al., "Abstract #6249: CBX-12: A low pH targeting alphalex™-exatecan conjugate for the treatment of solid tumors," Abstract, Cancer Research, Aug. 2020, 80(16): 4 pages, URL <https://cancerres.aacrjournals.org/content/80/16_Supplement/6249>.
Aiello et al., "Abstract #6249: CBX-12: A low pH targeting alphalex™-exatecan conjugate for the treatment of solid tumors," Poster, presented at the AACR Annual Meeting 2020, Philadelphia, PA, Apr. 27-28, 2020 and Jun. 22-24, 2020, 1 page.
Aiello et al., "Abstract #63: Development of tumor-targeted PARP inhibitors for the treatment of solid cancers," Poster, presented at the Dublin, Ireland meeting "Molecular Targets and Cancer Therapeutics," Dublin, Ireland, Nov. 13, 2018, 1 page.
Anderson et al., "Protease-Sensitive Nanomaterials for Cancer Therapeutics and Imaging," Ind. Eng. Chem Res., Apr. 2017, 56(20):5761-5777.
Atzrodt et al., "The Renaissance of H/D Exchange," Angewandte Chemie International Edition, Oct. 2007, 46(41):7744-7765.
Bargh et al., "Cleavable linkers in antibody-drug conjugates," Chem. Soc. Rev., Aug. 2019, 48(16):4361-4374, 15 pages.
Berge et al., "Pharmaceutical Salts," Journal of Pharmaceutical Sciences, Jan. 1977, 66(1):1-19.
Burns et al., "Inhibition of Cancer Cell Proliferation and Breast Tumor Targeting of pHLIP-Monomethyl Auristatin E Conjugates," Mol. Pharmaceutics, Mar. 2015, 9 pages.
Burns et al., "Therapeutic Efficacy of a Family of pHLIP-MMAF Conjugates in Cancer Cells & Mouse Models," Mol. Pharmaceutics, Jan. 2017, 31 pages.
Caculitan et al., "Cathepsin B Is Dispensable for Cellular Processing of Cathepsin B-Cleavable Antibody-Drug Conjugates," Cancer Res., Dec. 2017, 77(24):7027-7037.
Catcott et al., "Microscale screening of antibody libraries as maytansinoid antibody-drug conjugates," mAbs, Jan. 2016, 8(3):513-523.
Catsburg et al., "Adherence to cancer prevention guidelines and risk of breast cancer," International Journal of Cancer, 2014, 135:2444-2452.
Chang et al., "Stapled α-helical peptide drug development: A potent dual inhibitor of MDM2 and MDMX for p53-dependent cancer therapy," Proceedings of the National Academy of Sciences, Sep. 2013, 110(36):E3445-E3454.
Cheng et al., "MicroRNA silencing for cancer therapy targeted to the tumor microenvironment," Nature, Feb. 2015, 518:107-110.
Choi et al., "Protease-Activated Drug Development," Theranostics, Feb. 2012, 2(2):156-178.
CO Office Action in Colombia Appln. No. NC2020/0009665, dated Sep. 26, 2022, 21 pages (with English translation).
Corso et al., "Innovative Linker Strategies for Tumor-Targeted Drug Conjugates," Chem. Eur. J., Nov. 2019, 25(65):14740-14757, 17 pages.
Dahan et al., "Dipeptidyl Peptidase IV as a Potential Target for Selective Prodrug Activation and Chemotherapeutic Action in Cancers," Mol. Pharmaceutics, Nov. 2014, 11(12):4385-4394.
De Marco, "Recombinant polypeptide production in E. coli: towards a rational approach to improve the yields of functional proteins," Microbial Cell Factories, Nov. 2013, 12(1): 101, 8 pages.
Diez-Torrubia et al., "Application of the Dipeptidyl Peptidase IV (DPPIV/CD26) Based Prodrug Approach to Different Amine-Containing Drugs," J. Med. Chem. 2010, 53(2):559-572.
Diez-Torrubia et al., "Dipeptidyl Peptidase IV (DPPIV/CD26)-Based Prodrugs of Hydroxy-Containing Drugs," ChemMedChem, Apr. 2012, 7(4):618-628.
Dougherty et al., "Enhancing the Cell Permeability of Stapled Peptides with a Cyclic Cell-Penetrating Peptide," Journal of Medicinal Chemistry, Oct. 2019, 62(22):10098-10107.
Dougherty et al., "Understanding Cell Penetration of Cyclic Peptides," Chemical Reviews, May 2019, 119(17):47 pages.

(56) References Cited

OTHER PUBLICATIONS

Ducret, "Lipase-catalyzed enantioselective esterification of ibuprofen in organic solvents under controlled water activity," Enzyme and Microbial Technology, Mar. 1998, 22(4):212-216.
Fan et al, "Going Beyond Common Drug Metabolizing Enzymes: Case Studies of Biotransformation Involving Aldehyde Oxidase, g-Glutamyl Transpeptidase, Cathepsin B, Flavin-Containing Monooxygenase, and ADP-Ribosyltransferase," Drug Metabolism and Disposition, Aug. 2016, 44(8):1253-1261.
Fang, "Development of Synthetic Lethality Anticancer Therapeutics," J. Med. Chem., Jun. 2014, 57:7859-7873.
Garcia-Aparicio et al., "Design and Discovery of a Novel Dipeptidyl-peptidase IV (CD26)-Based Prodrug Approach," J. Med. Chem., Aug. 2006, 49(17):5339-5351.
Gayle et al., "Abstract #6242: Development of alphalex™-toxin low pH targeting conjugates for the treatment of solid tumors," Abstract, Cancer Research, Aug. 2020, 80(16): 3 pages, URL <https://cancerres.aacrjournals.org/content/80/16_Supplement/6242.short>.
Gayle et al., "Abstract #6242: Development of alphalex™-toxin low pH targeting conjugates for the treatment of solid tumors," Poster, presented at the AACR Annual Meeting 2020, Philadelphia, PA, Apr. 27-28, 2020 and Jun. 22-24, 2020, 1 page.
Grinda et al., "A self-immolative dendritic glucuronide prodrug of doxorubicin," Med. Chem. Commun., 2012, 3:68-70.
Guerlavais et al., "Advancements in Stapled Peptide Drug Discovery & Development," Annual Reports in Medicinal Chemistry, Jan. 2014, 49:331-345.
Harris, "Hypoxia—a key regulatory factor in tumour growth," Nat Rev Cancer, Jan. 2002, 2(1):38-47.
Hegan et al., "Inhibition of poly(ADP-ribose) polymerase downregulates BRCA1 and RAD51 in a pathway mediated by E2F4 and p130," PNAS, Feb. 2010, 107(5):2201-2206.
Herceg et al., "Design, synthesis and in vitro evaluation of ß-glucuronidase-sensitive prodrug of 5-aminolevulinic acid for photodiagnosis of breast cancer cells," Bioorganic Chemistry, Aug. 2018, 78:372-380.
International Preliminary Report on Patentability in International Appln. No. PCT/US2019/012413, mailed Jul. 16, 2020, 8 pages.
International Preliminary Report on Patentability in International Appln. No. PCT/US2020/041348, mailed Jan. 20, 2022, 8 pages.
International Preliminary Report on Patentability in International Appln. No. PCT/US2020/041411, mailed Jan. 20, 2022, 8 pages.
International Search Report and Written Opinion in International Appln. No. PCT/US2019/012413, dated Mar. 26, 2019, 19 pages.
International Search Report and Written Opinion in International Appln. No. PCT/US2020/041348, dated Oct. 15, 2020, 16 pages.
International Search Report and Written Opinion in International Appln. No. PCT/US2020/041411, mailed Nov. 10, 2020, 17 pages.
International Search Report and Written Opinion in International Appln. No. PCT/US2022/011629, mailed May 9, 2022, 22 pages.
International Search Report and Written Opinion in International Appln. No. PCT/US2022/079973, mailed Mar. 6, 2023, 15 pages.
Joubert et al., "Antibody-Drug Conjugates: The Last Decade," Pharmaceuticals, 2020, 13, 245, 31 pages.
JP Office Action in Japanese Appln. No. 2020-557122, dated Nov. 22, 2022, 9 pages (with English translation).
Kalafatovic et al., "MMP-9 triggered self-assembly of doxorubicin nanofiber depots halts tumor growth," Biomaterials, Aug. 2016, 98:192-202.
Karabadzhak et al., "pHLIP-FIRE, a Cell Insertion-Triggered Fluorescent Probe for Imaging Tumors Demonstrates Targeted Cargo Delivery In Vivo," ACS Chem. Biol., Sep. 2014, 9(11):2545-2553.
Kerekes et al., "Aurora Kinase Inhibitors Based on the Imidazo[1,2-a]pyrazine Core: Fluorine and Deuterium Incorporation Improve Oral Absorption and Exposure," Journal of Medicinal Chemistry, Jan. 2011, 54(1):201-210.
Kim et al., "Matrix metalloproteinase-inspired suicidal treatments of diabetic ulcers with siRNA-decorated nanofibrous meshes," Gene Therapy, Apr. 2013, 20:378-385.

Kleiner-Grote et al., "Secretion of recombinant proteins from E. coli," Engineering in Life Sciences, Aug. 2018, 18(8):532-550.
Kolakowski et al., "The Methylene Alkoxy Carbamate Self-Immolative Unit: Utilization for the Targeted Delivery of Alcohol-Containing Payloads with Antibody-Drug Conjugates," Angew. Chem. Int. Ed., Jul. 2016, 55(28):7948-7951.
Kostova et al., "The Chemistry Behind ADCs," Pharmaceuticals, May 2021, 14(5), 442, 46 pages.
Kumar et al., "Lipase catalysis in organic solvents: advantages and applications," Biol. Proced. Online, Jan. 2016, 18(2):11 pages.
Kumazawa et al., "Potent and broad antitumor effects of DX-8951f, a water-soluble camptothecin derivative, against various human tumors xenografted in nude mice," Cancer Chemotherapy and Pharmacology, Jul. 1998, 42(3):210-220.
Kurth et al., "A thioxanone-based chiral template: asymmetric induction in the [2,3]-sigmatropic rearrangement of sulfur ylides. Enantioselective preparation of C.beta.-chiral pent-4-enoic acids," J. Org. Chem., Apr. 1990, 55(8):2286-2288.
Lewis Phillips et al., "Targeting HER2-Positive Breast Cancer with Trastuzumab-DM1, an Antibody-Cytotoxic Drug Conjugate," Cancer Research, Nov. 2008, 68(22):9280-9290.
Li et al., "Synthesis and Evaluation of Camptothecin Antibody-Drug Conjugates," ACS Medicinal Chemistry Letters, Sep. 2019, 10(10):1386-1392.
Li et al., "Topoisomerase I in Human Disease Pathogenesis and Treatments," Genomics, Proteomics & Bioinformatics, Jun. 2016, 14(3):166-171.
Lopus, "Antibody-DM1 conjugates as cancer therapeutics," Cancer Letters, Aug. 2011, 307(2):113-118.
Lu et al., "Linkers Having a Crucial Role in Antibody-Drug Conjugates," Int. J. Mol. Sci., Apr. 2016, 17(4):1-22.
Mckertish et al., "Advances and Limitations of Antibody Drug Conjugates for Cancer," Biomedicines, Jul. 2021, 9(8):872, 25 pages.
Merrifield, "Solid Phase Peptide Synthesis. I. The Synthesis of a Tetrapeptide," Journal of the American Chemical Society, Jul. 1963, 85(14):2149-2154.
Miletic et al., "Immobilization of Candida antarctica lipase B on polystyrene nanoparticles," Macromolecular Rapid Communications, Jan. 2010, 31(1):71-74.
Mistry et al., "Clinical Advances of Hypoxia-Activated Prodrugs in Combination With Radiation Therapy," International Journal of Radiation: Oncology Biology Physics, Aug. 2017, 98(5):1183-1196.
Monaco et al., "Catalytic Asymmetric Synthesis of Thiols," Journal of the American Chemical Society, Nov. 2014, 136(49):4 pages.
Moshinikova et al., "Antiproliferative Effect of pHILIP-Amanitin," Biochemistry, Jan. 2013, 52(7):1171-1178.
Nakada et al., "Novel antibody drug conjugates containing exatecan derivative-based cytotoxic payloads," Bioorganic & Medicinal Chemistry Letters, Mar. 2016, 26(6):4 pages.
Nguyen et al., "A Novel Soluble Peptide with pH-Responsive Membrane Insertion," Biochemistry, Oct. 2015, 54(43):6567-6575.
Office Action in Singapore Appln. No. 11202200132S, dated Aug. 15, 2023, 8 pages.
Office Action in Singapore Appln. No. 11202200134V, dated Aug. 14, 2023, 10 pages.
Ogitani et al., "Wide application of a novel topoisomerase I inhibitor-based drug conjugation technology," Bioorganic & Medicinal Chemistry Letters, Oct. 2016, 26(20):5069-5072.
Pacher et al., "Role of Poly(ADP-ribose) polymerase 1 (PARP-1) in Cardiovascular Diseases: The Therapeutic Potential of PARP Inhibitors," Cardiovasc Drug Rev., Oct. 2007; 25(3): 235-260.
PARP Inhibitors for Cancer Therapy, Cancer Drug Discovery and Development, vol. 83, Curtin and Sharma (ed)., 2015, Part V, 475-579.
Pétursson, "Protecting Groups in Carbohydrate Chemistry," Journal of Chemical Education, Nov. 1997, 74(11):1297-1303.
Reagan-Shaw et al., "Dose translation from animal to human studies revisited, " The FASEB Journal, Mar. 2008, 22(3):659-661.
Simplicio et al., "Prodrugs for Amines," Molecules, Mar. 2008, 13(3):519-547.

(56) References Cited

OTHER PUBLICATIONS

Son et al., "Therapeutic Effect of pHLIPmediated CEACAM6 Gene Silencing in Lung Adenocarcinoma," Scientific Reports, Sep. 2019, 9(1):11607, 11 pages.
Sugimori et al., "Synthesis and Antitumor Activity of Ring A- and F-Modified Hexacyclic Camptothecin Analogues," J. Med. Chem., Jun. 1998, 41(13):2308-2318.
Tahara et al., "The Use of Olaparib (AZD2281) Potentiates SN-38 Cytotoxicity in Colon Cancer Cells by Indirect Inhibition of Rad51-Mediated Repair of DNA Double-Strand Breaks," Molecular Cancer Therapeutics, May 2014, 13(5):1170-1180.
Tangutur, "Microtubule Targeting Agents as Cancer Chemotherapeutics: An Overview of Molecular Hybrids as Stabilizing and Destabilizing Agents," Curr Top Med Chem, Sep. 2017, 17(22):2523-2537.
Tannock et al., "Acid pH in tumors and its potential for therapeutic exploitation," Cancer Res., Aug. 1989, 49(16):4373-4384, 13 pages.
Tesauro et al., "Peptide-Based Drug-Delivery Systems in Biotechnological Applications: Recent Advances and Perspectives," Molecules, Jan. 2019, 24(2):27 pages.
Vasquez-Montes et al., "Divalent Cations and Lipid Composition Modulate Membrane Insertion and Cancer-Targeting Action of pHLIP," Journal of Molecular Biology, Dec. 2019, 431(24):5004-5018.
Vrettos et al., "On the design principles of peptide-drug conjugates for targeted drug delivery to the malignant tumor site," Beilstein J. Org. Chem., Apr. 2018, 14:930-954.
Wang et al., "Development and Characterization of a Novel Peptide—Drug Conjugate with DM1 for Treatment of FGFR2-Positive Tumors," Biomedicines, Jul. 2021, 9(8):849, 14 pages.
Weerakkody et al., "Family of pH (low) insertion peptides for tumor targeting," Proceedings of the National Academy of Sciences, Apr. 2013, 110(15):5834-5839.
White et al., "Discovery of an SSTR2-Targeting Maytansinoid Conjugate (PEN-221) with Potent Activity in Vitro and in Vivo," J. Med. Chem., Mar. 2019, 62(5):2708-2719.
Wickstrom et al., "Melflufen—a peptidase-potentiated alkylating agent in clinical trials," Oncotarget, Sep. 2017, 8(39):66641-66655.
Widdison et al.. "Semisynthetic Maytansine Analogues for the Targeted Treatment of Cancer," Journal of Medicinal Chemistry, Jun. 2006, 49(14):4392-4408.
Wyatt et al., "Peptides of pHLIP family for targeted intracellular and extracellular delivery of cargo molecules to tumors," Proceedings of the National Academy of Sciences, Mar. 2018, 115(12):E2811-E2818.
Xu et al., "Design, synthesis and biological evaluation of deuterated nintedanib for improving pharmacokinetic properties," Journal of Labelled Compounds and Radiopharmaceuticals, Jun. 2015, 58(7):308-312.
Yang et al., "Enzyme-mediated hydrolytic activation of prodrugs," Acta Pharamaceutica Sinica B, Oct. 2011, 1(3):143-159.
Yao et al., "MMP-Responsive 'Smart' Drug Delivery and Tumor Targeting," Trends in Pharmacological Sciences, Aug. 2018, 39(8):766-781.
Zdarta et al., "A General Overview of Support Materials for Enzyme Immobilization: Characteristics, Properties, Practical Utility," Catalysts, Feb. 2018, 8(92):1-27.
Zhang et al., "Design of acid-activated cell penetrating peptide for delivery of active molecules into cancer cells," Bioconjugate Chemistry, American Chemical Society, Jul. 2011, 22(7):1410-1415.
Zhang et al., "Linker Immolation Determines Cell Killing Activity of Disulfide—Linked Pyrrolobenzodiazepine Antibody-Drug Conjugates," ACS Medicinal Chemistry Letters, Aug. 2016, 7(11):6 pages.
Zhao et al., "Recombinant production of medium-to large-sized peptides in *Escherichia coli* using a cleavable self-aggregating tag," Microbial Cell Factories, Dec. 2016, 15(1):136, 9 pages.
Zhong et al., "Cathepsin B-cleavable doxorubicin prodrugs for targeted cancer therapy (Review), " International Journal of Oncology, Feb. 2013, 42(2):373-383.

\* cited by examiner

PEPTIDE CONJUGATES OF CYTOTOXINS AS THERAPEUTICS

CROSS-REFERENCE TO RELATED APPLICATIONS

This application is a continuation of U.S. patent application Ser. No. 16/925,094, filed Jul. 9, 2020, which claims the benefit of U.S. Provisional Application No. 63/040,859 filed Jun. 18, 2020 and U.S. Provisional Application No. 62/872,643 filed Jul. 10, 2019, the entire contents of each of which are incorporated herein by reference.

FIELD OF THE INVENTION

The present invention relates to peptide conjugates of cytotoxins such as topoisomerase I inhibitors which are useful for the treatment of diseases such as cancer.

SEQUENCE LISTING

This application contains a Sequence Listing that has been submitted electronically as an XML file named 43236-0009002_SL_ST26.xml. The XML file, created on Jun. 30, 2023, is 309,877 bytes in size. The material in the XML file is hereby incorporated by reference in its entirety.

BACKGROUND OF THE INVENTION

Cancer is a group of diseases characterized by aberrant control of cell growth. The annual incidence of cancer is estimated to be in excess of 1.6 million in the United States alone. While surgery, radiation, chemotherapy, and hormones are used to treat cancer, it remains the second leading cause of death in the U.S. It is estimated that about 600,000 Americans will die from cancer each year.

Treatment of cancer in humans by systemic administration of pharmaceutical agents often functions by slowing or terminating the uncontrolled replication that is a characteristic of cancer cells. One class of such agents is topoisomerase I inhibitors. Topoisomerase 1 enzymes function to relax supercoiled DNA and alleviate DNA helical constraints and play a role in transcriptional regulation. See Li, M., Genomics Proteomics Bioinformatics 14 (2016), 166-171. Topoisomerase I is essential for the development in the mammalian system due to its dynamic functions in DNA replication and transcription. However, due to its direct role in transcriptional regulation, topoisomerase I dysfunction may lead to abnormal cellular functions. See Li, M., Genomics Proteomics Bioinformatics 14 (2016), 166-171. Thus, several human diseases such as cancer, neurodegenerative diseases, and autoimmune diseases, are linked to topoisomerase I regulation and activity.

Inhibitors of topoisomerase I have been developed and continue to be developed as anti-cancer agents. In particular, topoisomerase I inhibitors are widely used for the treatment of colorectal, gastric, and other cancers. See Ogitani, Bioorg. Med. Chem. Lett. 26 (2016), 5069-5072. Although topoisomerase I inhibitors are useful in the treatment of cancer, the compounds also exhibit side effects, including neutropenia and severe diarrhea. Preferential delivery of topoisomerase inhibitors to these diseased tissues could avoid these serious side effects. Thus, there is a need for more selective delivery of topoisomerase I inhibitors to diseased tissue.

SUMMARY

The present disclosure provides, inter alia, a compound of Formula (I):

$$R^8\text{-}Q\text{-}R^7 \qquad (I)$$

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure also provides methods of treating a disease or condition (e.g., cancer) by administering to a human or other mammal in need of such treatment a therapeutically effective amount of a compound of the disclosure. In some embodiments, the disease or condition is characterized by acidic or hypoxic diseased tissues.

The present disclosure also provides use of a compounds described herein in the manufacture of a medicament for use in therapy. The present disclosure also provides the compounds described herein for use in therapy.

The present disclosure also provides methods for synthesizing the compounds of the disclosure and intermediates useful in these methods.

BRIEF DESCRIPTION OF THE DRAWINGS

As shown in FIG. 10, Compound 29 is released much faster than Compound 11 under similar gluathione exposure.

DETAILED DESCRIPTION

Figure 1:
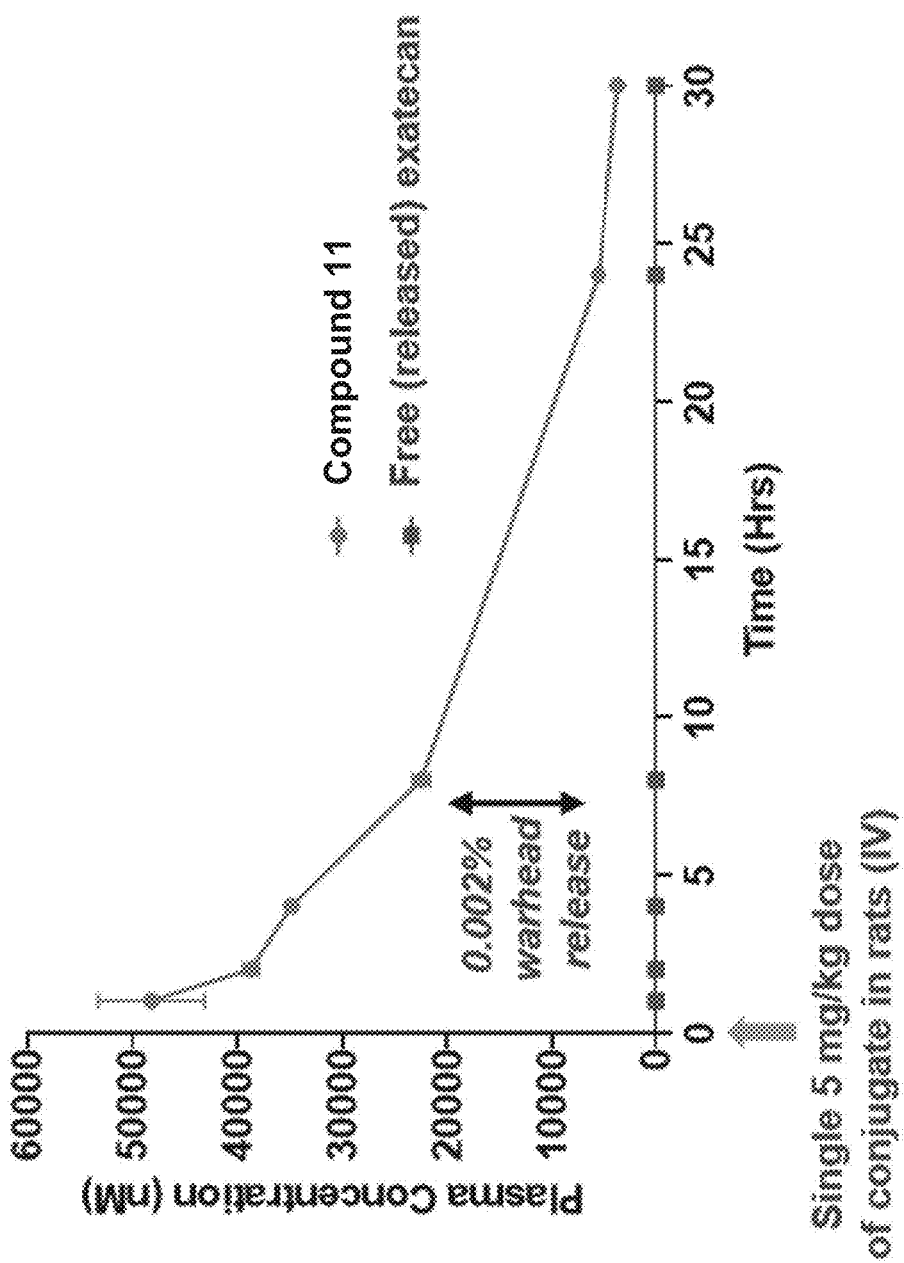
FIG. 1 shows a plot of the plasma concentration of Compound 11 and released exatecan after a single IV dose of 5 mg/kg of Compound 11 in a rat (data are expressed as means±SEM).

Provided herein is a compound of Formula (I):

$$R^8\text{-}Q\text{-}R^7 \quad (I)$$

or a pharmaceutically acceptable salt thereof, wherein:
  $R^7$ is a peptide;
  $R^8$ is a small molecule topoisomerase I targeting moiety, which binds to topoisomerase I; and
  Q is a linker, which is covalently linked to moiety $R^7$ and $R^8$.

Also provided herein is a compound of Formula (I):

$$R^8\text{-}Q\text{-}R^7 \quad (I)$$

or a pharmaceutically acceptable salt thereof, wherein:
  $R^7$ is a peptide capable of selectively delivering $R^8Q$- across a cell membrane having an acidic or hypoxic mantle having a pH less than about 6.0;
  $R^8$ is a small molecule topoisomerase I targeting moiety, which binds to topoisomerase I; and
  Q is a linker, which is covalently linked to moiety $R^7$ and $R^8$.

Provided herein is a compound of Formula (I):

$$R^8\text{-}Q\text{-}R^7 \quad (I)$$

or a pharmaceutically acceptable salt thereof, wherein:
  $R^7$ is a peptide;
  $R^8$ is selected from the group consisting of:

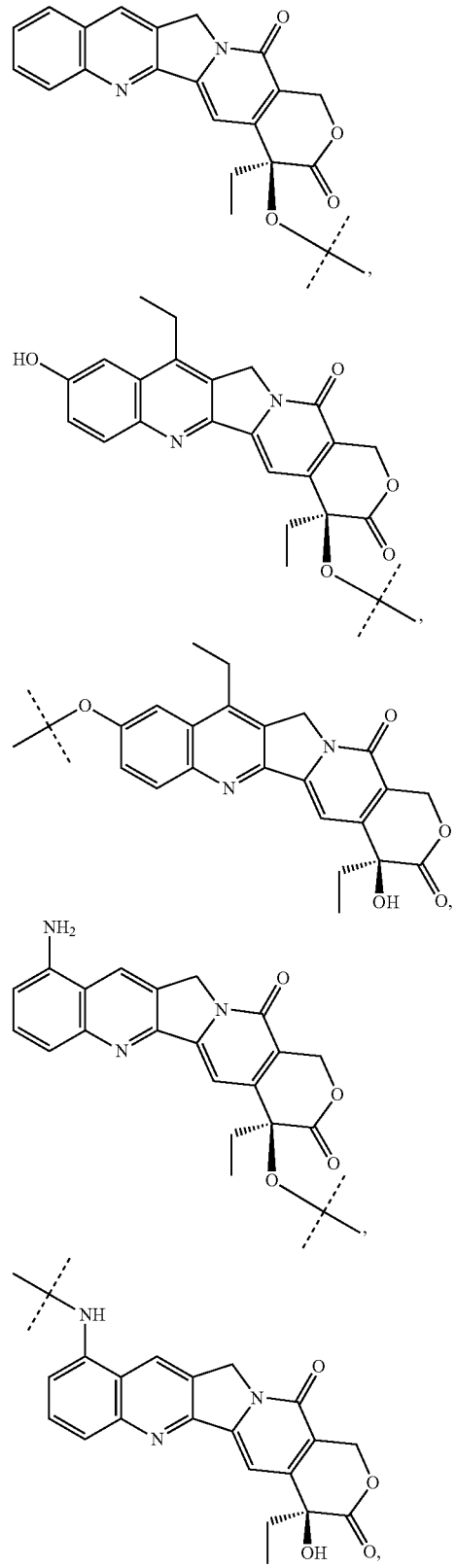

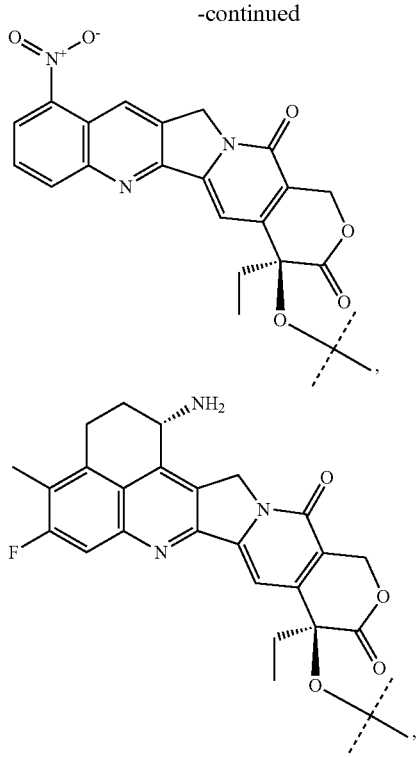
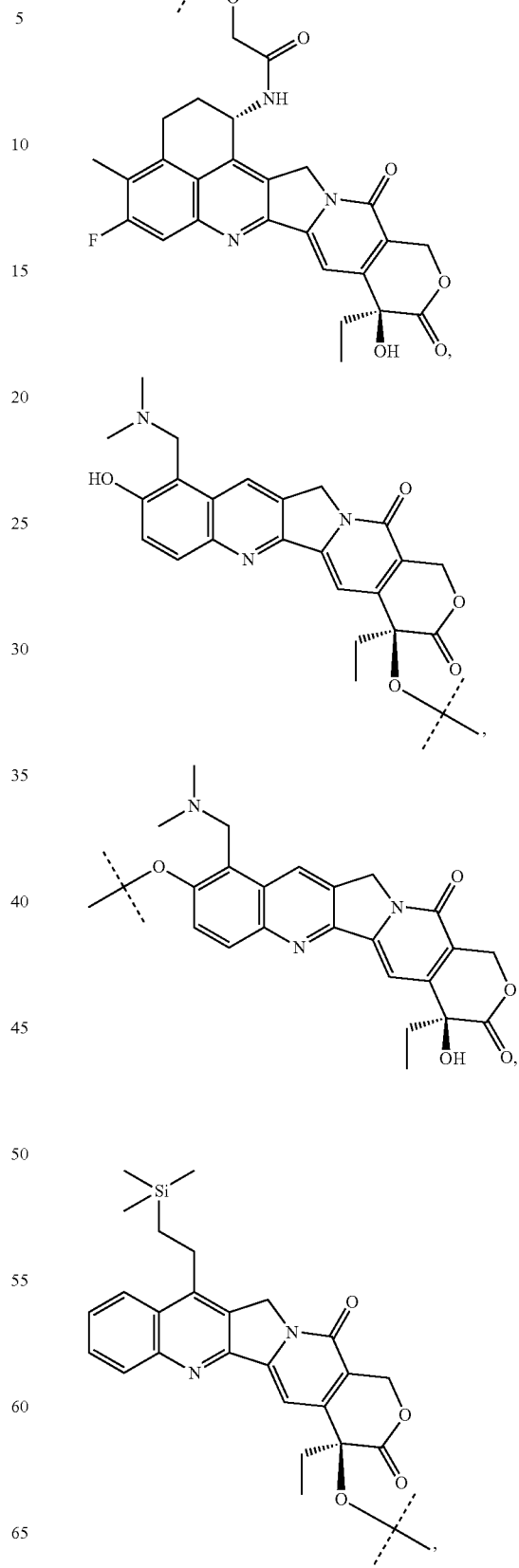

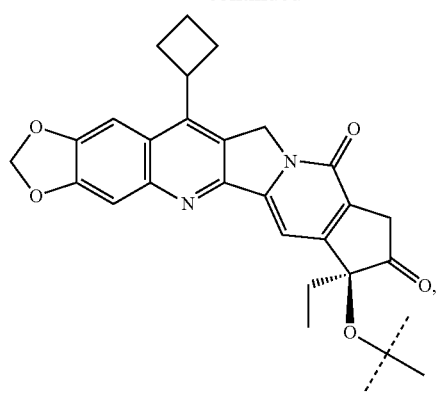
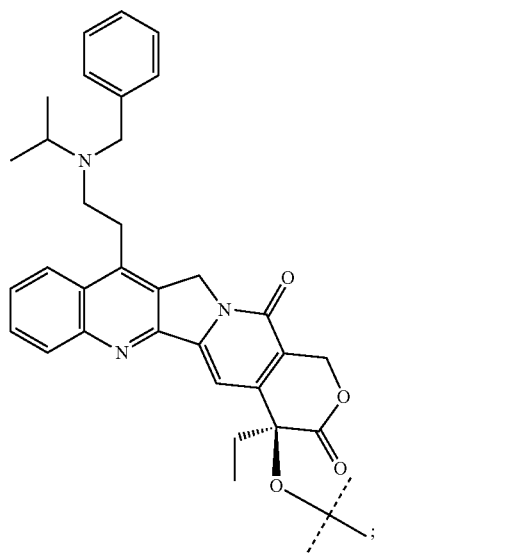
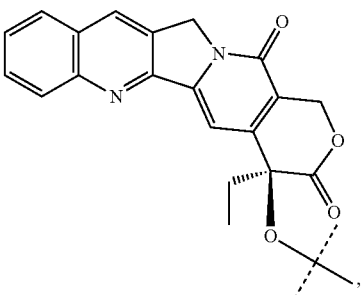
Q is a linker, which is covalently linked to moiety $R^7$ and $R^8$.
Provided herein is a compound of Formula (I):
$$R^8\text{-}Q\text{-}R^7 \qquad (I)$$
or a pharmaceutically acceptable salt thereof, wherein:
$R^7$ is a peptide;
$R^8$ is selected from the group consisting of:
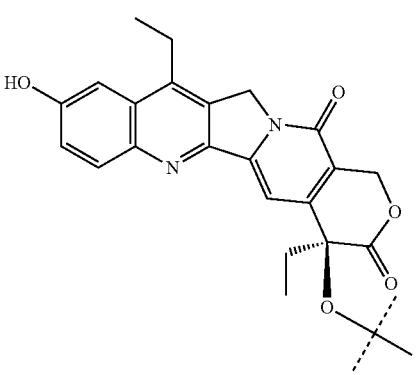
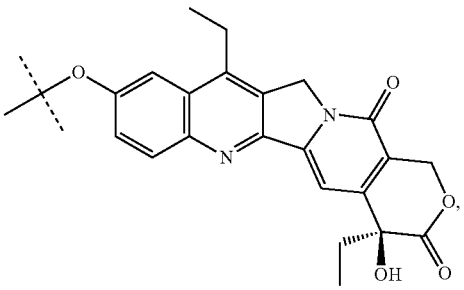

9
-continued
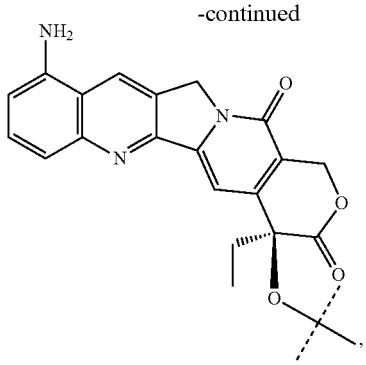
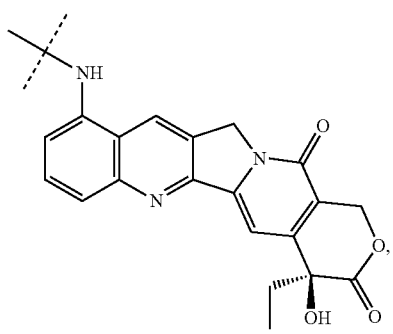
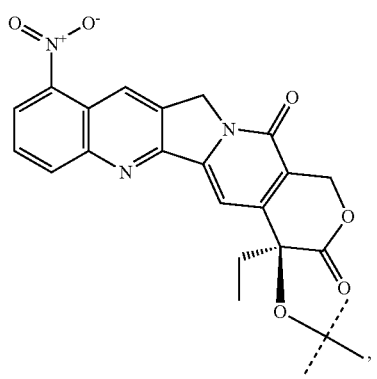
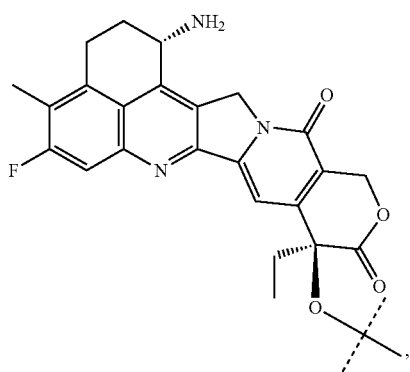
10
-continued
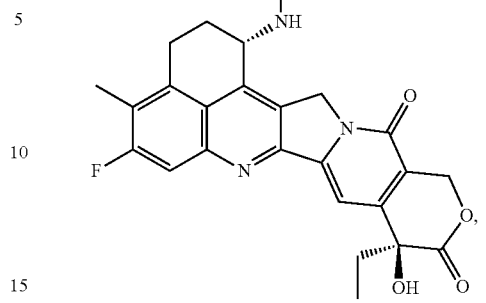
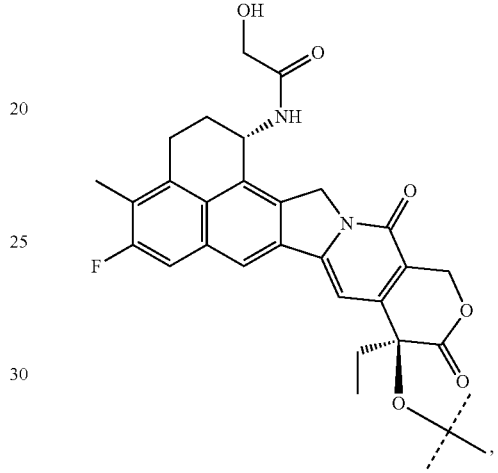
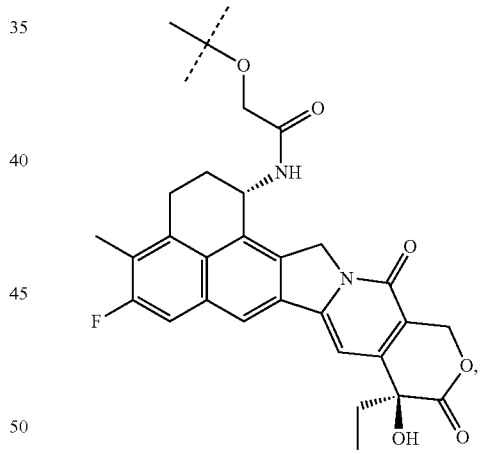
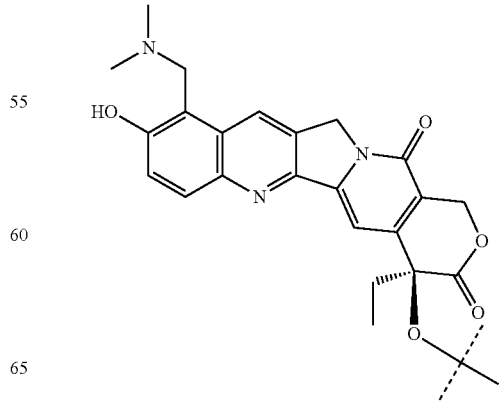

-continued
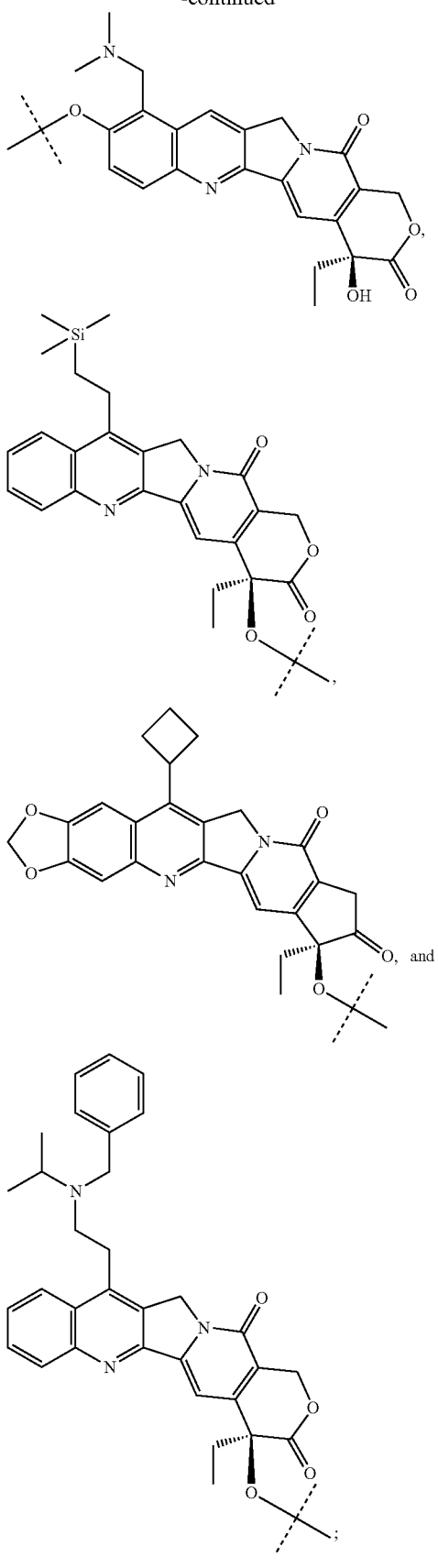
and
Q is a linker, which is covalently linked to moiety $R^7$ and $R^8$.
Provided herein is a compound of Formula (I):
$$R^8\text{-}Q\text{-}R^7 \qquad (I)$$
or a pharmaceutically acceptable salt thereof, wherein:
$R^7$ is a peptide;
$R^8$ is selected from the group consisting of:
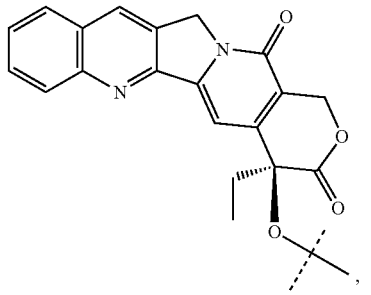
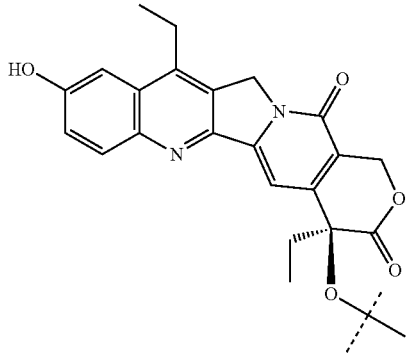
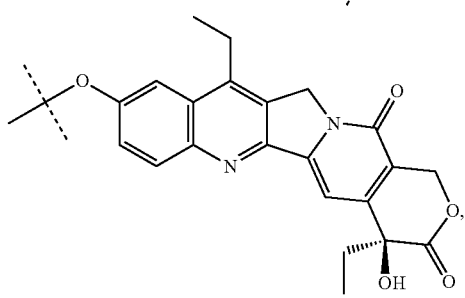
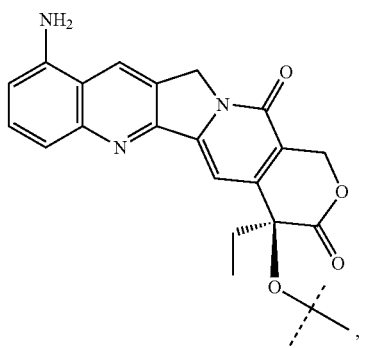

-continued
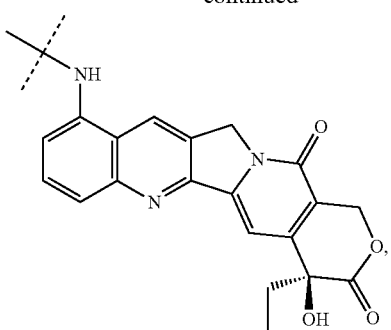
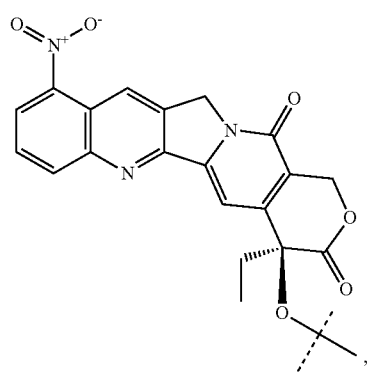
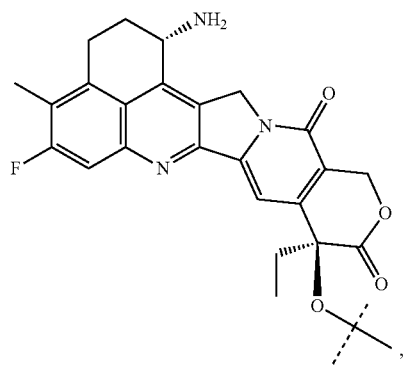
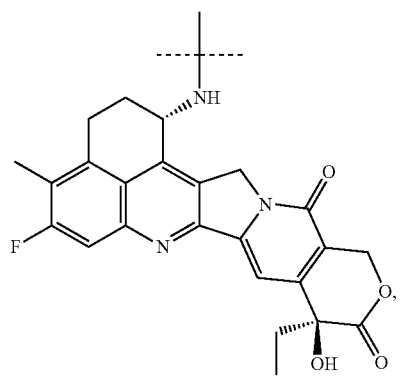
-continued
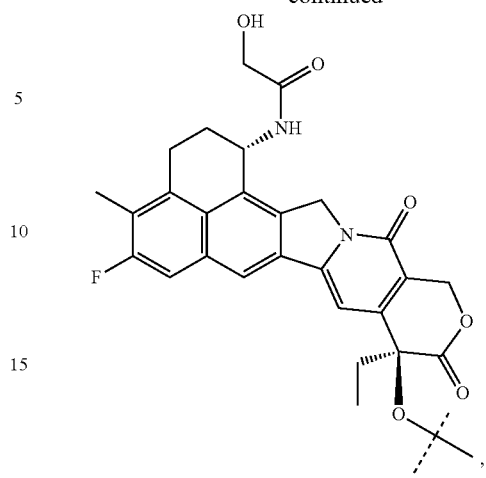
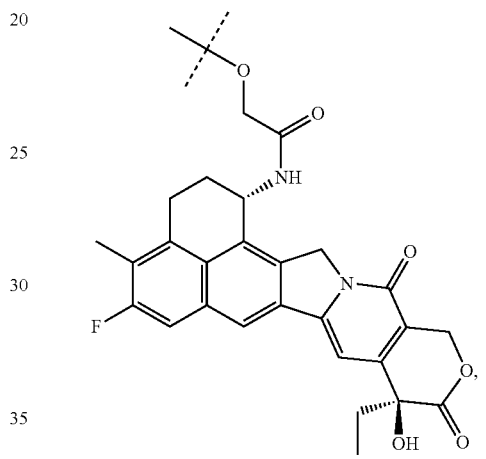
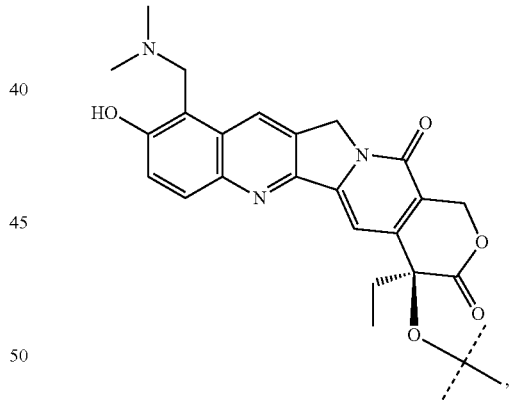
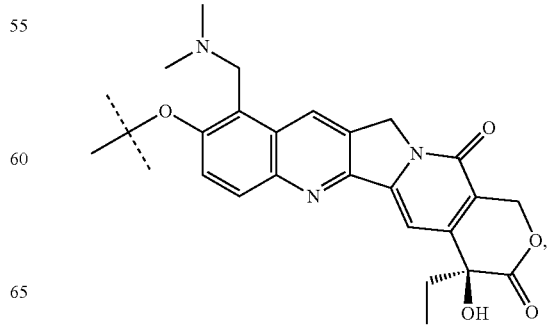

-continued
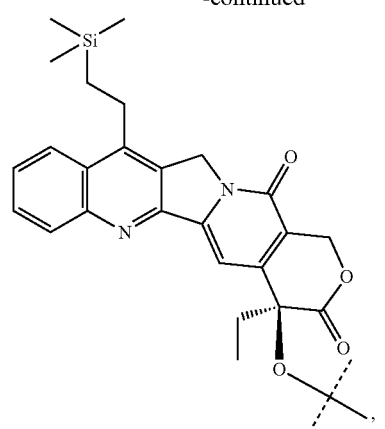
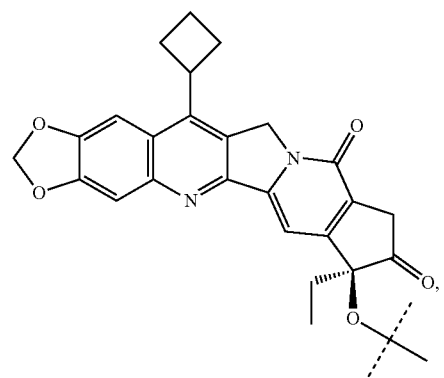
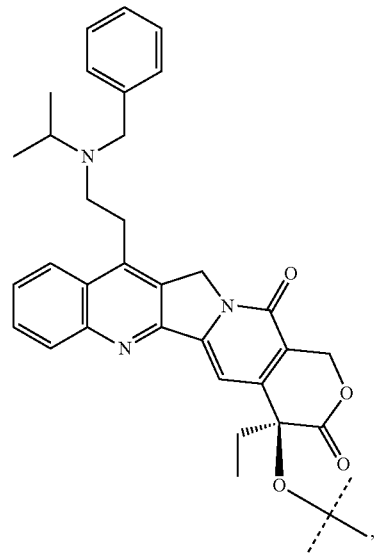
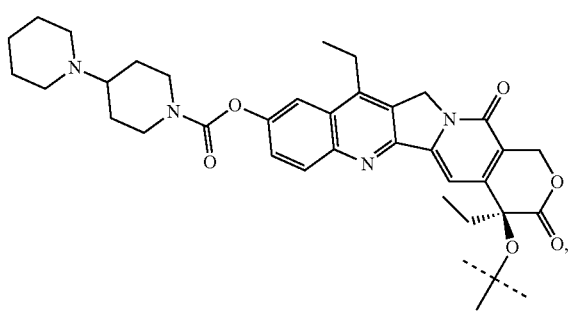
-continued
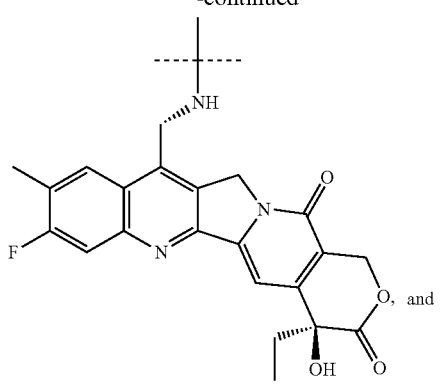
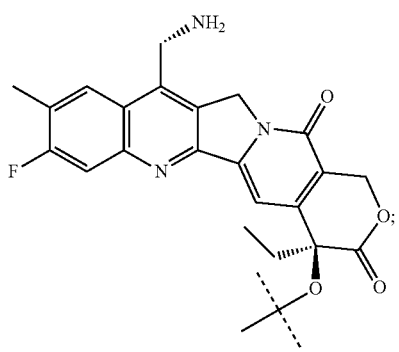
Q is selected from the group consisting of
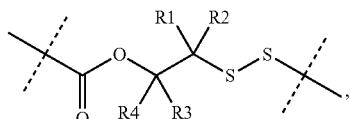
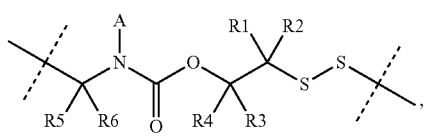
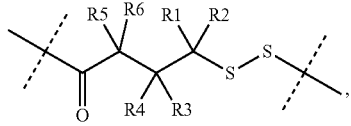
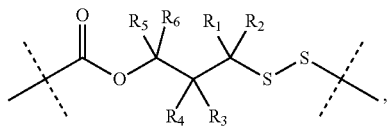
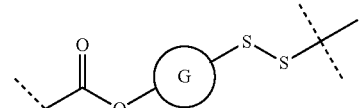
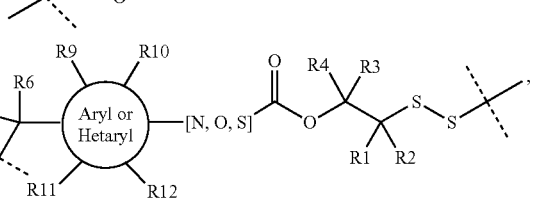

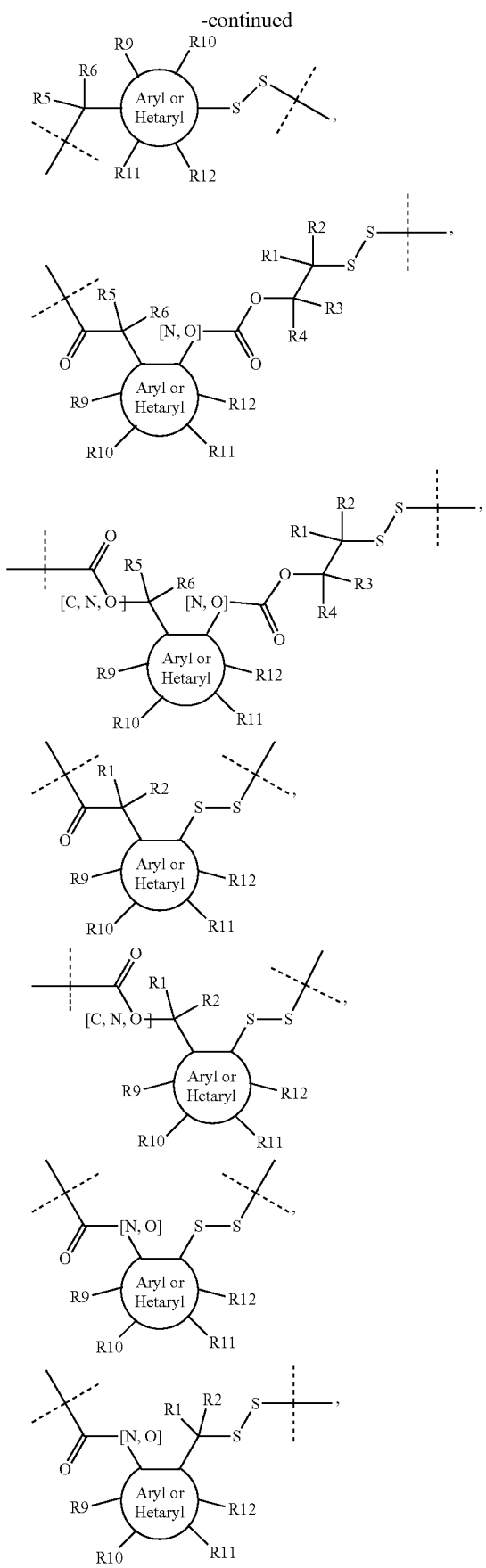
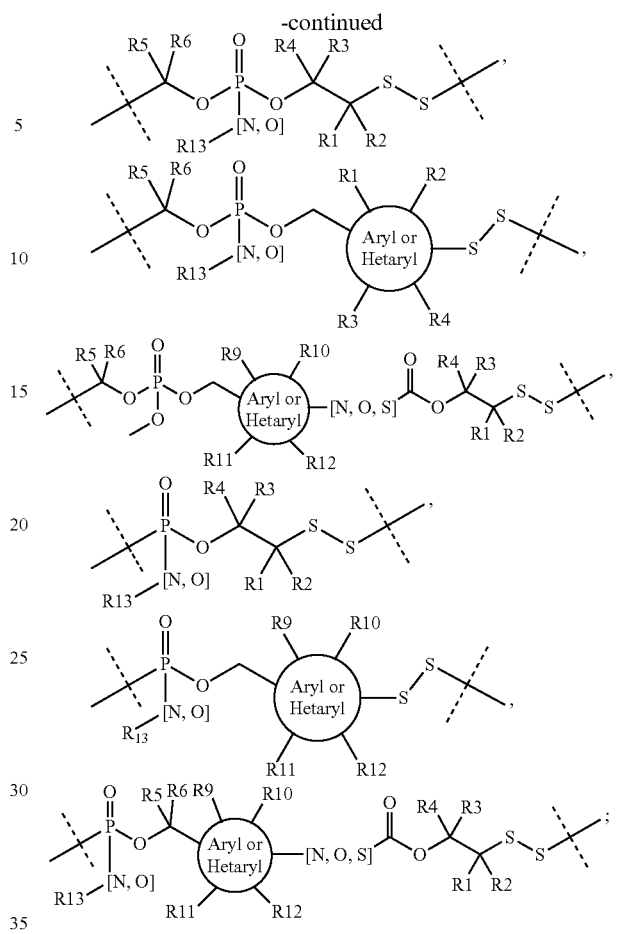

$R^1$, $R^2$, $R^3$, $R^4$, $R^5$, $R^6$, $R^9$, $R^{10}$, $R^{11}$, and $R^{12}$ are each independently selected from H, $C_{1-4}$ alkyl, $C_{1-4}$ alkenyl, $C_{6-10}$ aryl, $C_{3-10}$ cycloalkyl, 5-10 membered heteroaryl, 4-10 membered heterocycloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, $C_{3-10}$ cycloalkyl, 5-10 membered heteroaryl, and 4-10 membered heterocycloalkyl, are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^2$ together with the carbon atom to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^3$ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or R² and R³ together with the carbon atoms to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or R³ and R⁴ together with the carbon atom to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or R⁵ and R⁶ together with the carbon atom to which they are attached form a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

$R^{13}$ is H or $C_{1-6}$ alkyl;

A is H or $C_{1-4}$ alkyl;

$R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH_3$;

(Aryl or Hetaryl)

is $C_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S;

Ring G is a $C_{3-14}$ cycloalkyl group or 4-14 membered heterocycloalkyl group, each optionally substituted with 1, 2, or 3 substituents independently selected from $C_{1-4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$; and $NR^{c1}C(O)NR^{c1}R^{d1}$;

[N, O, S] is NH, O, or S;

[N, O] is NH or O;

[C, N, O] is $CR^XR^Y$, NH, or O; and each $R^X$ and $R^Y$ are independently selected from H and $C_{1-4}$ alkyl.

Provided herein is a compound of Formula (I):

$R^8$-Q-$R^7$     (I)

or a pharmaceutically acceptable salt thereof, wherein:

$R^7$ is a peptide;

$R^8$ is selected from the group consisting of:

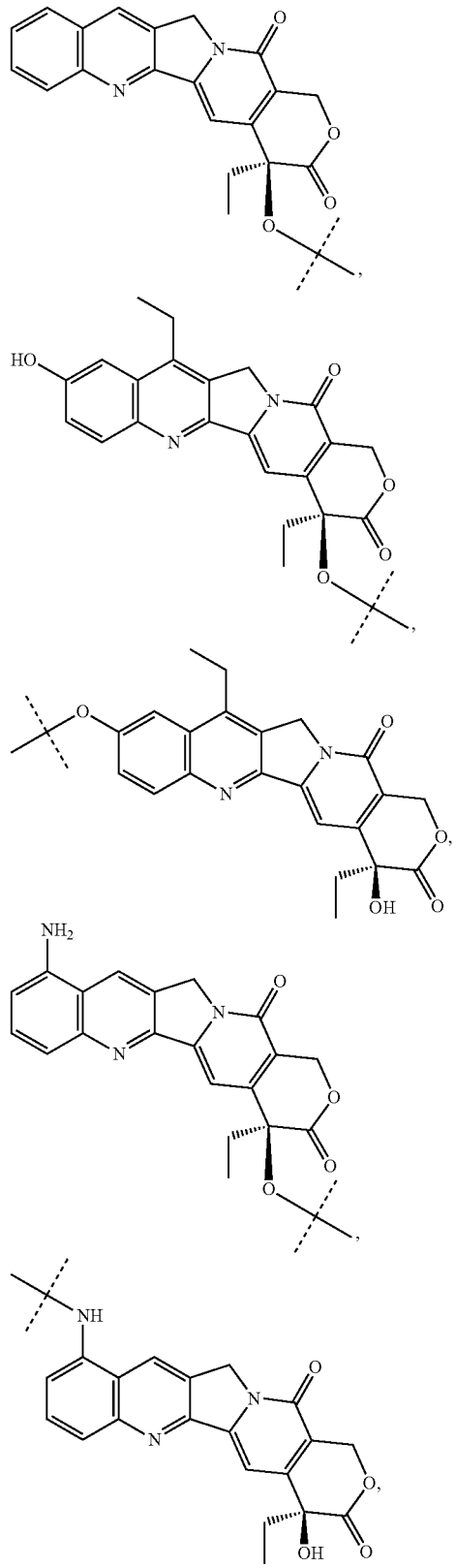

21
-continued
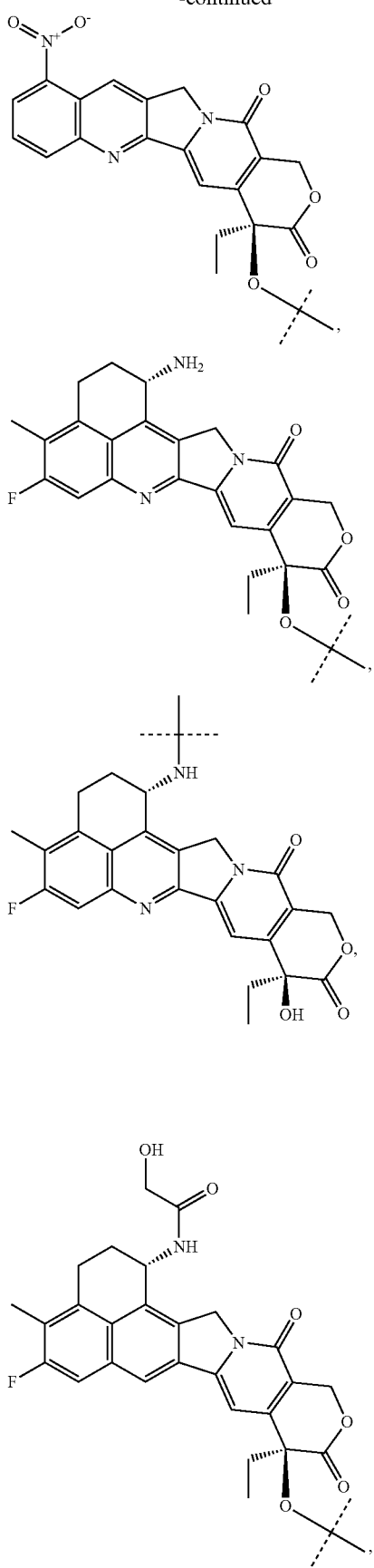
22
-continued
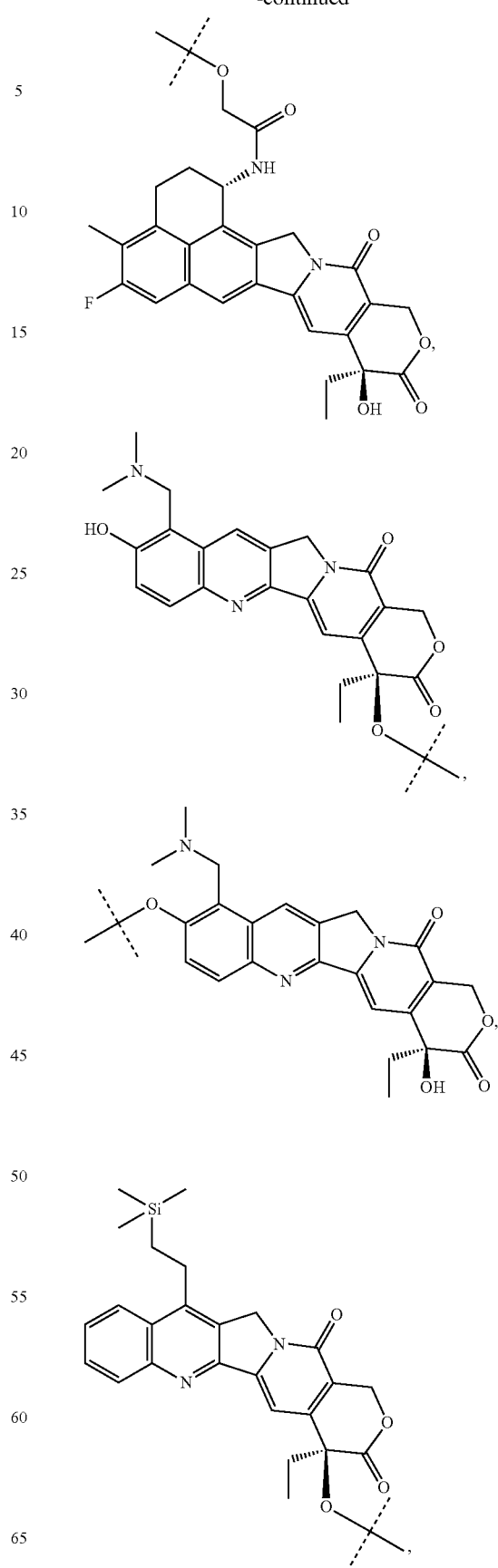

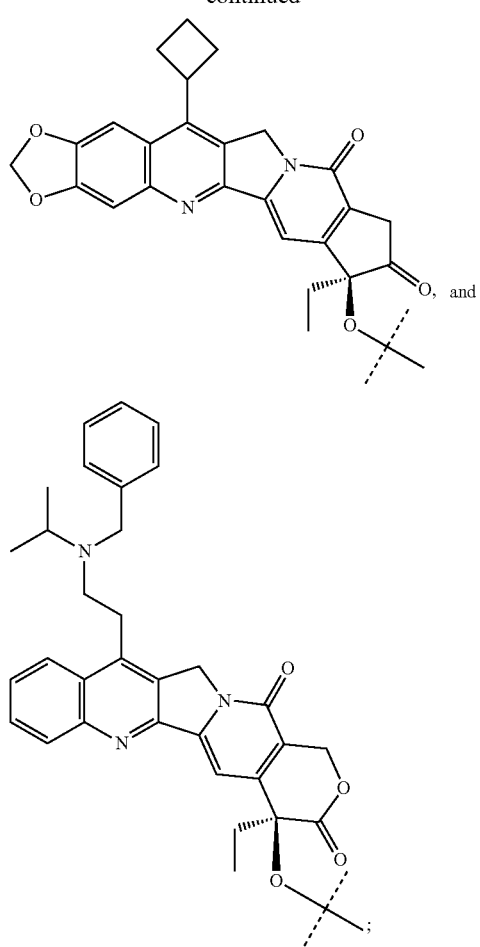
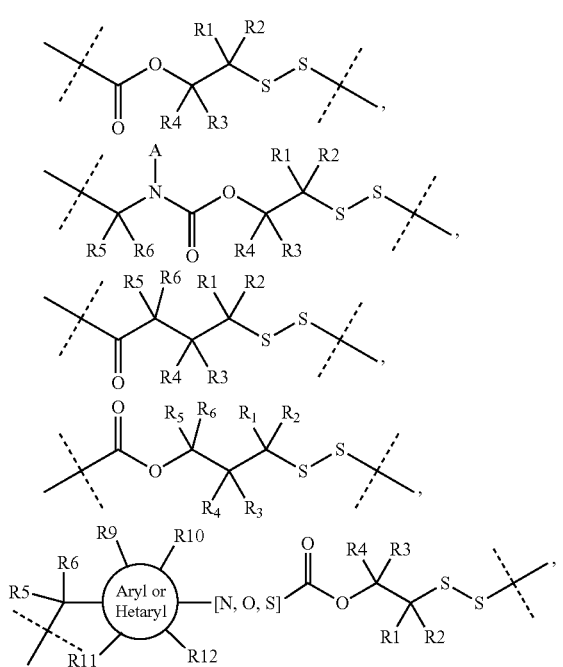
Q is selected from the group consisting of
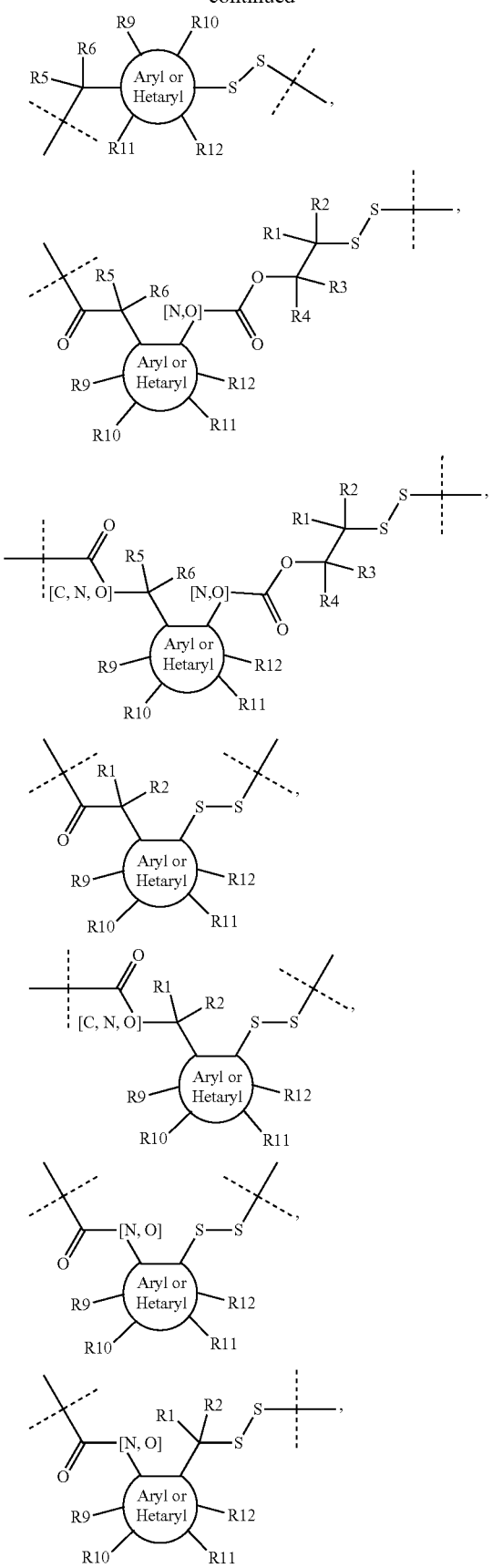

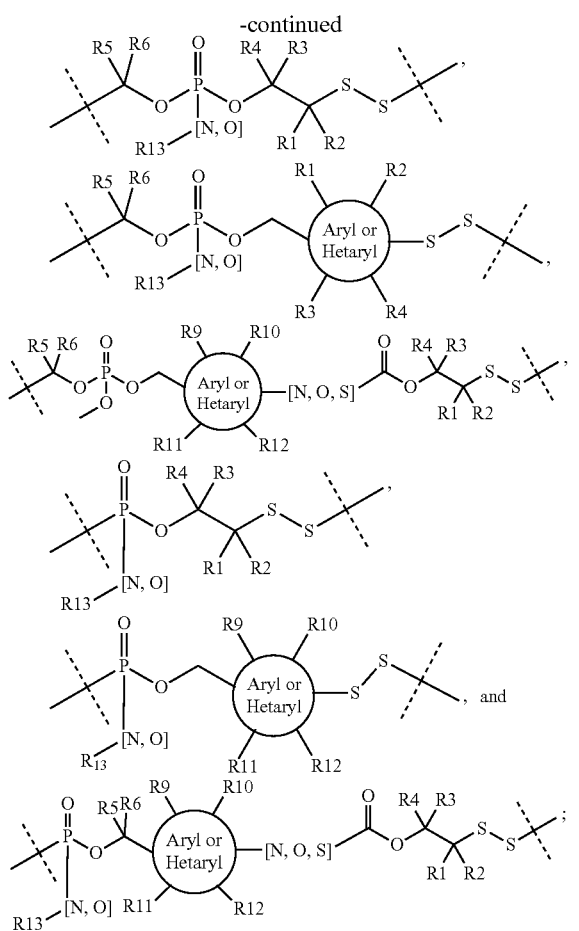

$R^1$, $R^2$, $R^3$, $R^4$, $R^5$, $R^6$, $R^9$, $R^{10}$, $R^{11}$, and $R^{12}$ are each independently selected from H, $C_{1-4}$ alkyl, $C_{1-4}$ alkenyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, or $R^1$ and $R^2$ together with the carbon atom to which they are attached form a $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^3$ together with the carbon atom to which they are attached form a $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^2$ and $R^3$ together with the carbon atom to which they are attached form a $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^3$ and $R^4$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^5$ and $R^6$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

$R^{13}$ is H or $C_{1-6}$ alkyl;

A is H or $C_{1-4}$ alkyl;

$R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH$;

is $C_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S;

[N, O, S] is NH, O, or S;

[N, O] is NH or O;

[C, N, O] is $CR^XR^Y$, NH, or O; and each $R^X$ and $R^Y$ are independently selected from H and $C_{1-4}$ alkyl.

In some embodiments, the lefthand side of Q attaches to $R^8$ and the righthand side of Q attaches to $R^7$.

In some embodiments, a sulfur atom of the disulfide moiety of Q is part of a cysteine residue of $R^7$.

As used herein, "peptide" refers to a targeting moiety comprising a 10-50 amino acid sequence, made up of naturally-occurring amino acid residues and optionally one or more non-naturally-occurring amino acids. In some embodiments, the peptide of $R^7$ is a peptide of 20 to 20 to 30 amino acids, or 30 to 40 residues. Peptides suitable for use in the compounds of the invention are those that can insert across a cell membrane via a conformational change or a change in secondary structure in response to environmental pH changes. In this way, the peptide can target acidic tissue and selectively translocate polar, cell-impermeable molecules across cell membranes in response to low extracellular pH. In some embodiments, the peptide is capable of selectively delivering a conjugated moiety (e.g., $R^8Q-$) across a cell membrane having an acidic or hypoxic mantle having a pH less than about 6.0. In some embodiments, the peptide is capable of selectively delivering a conjugated moiety (e.g., $R^8Q-$) across a cell membrane having an acidic or hypoxic mantle having a pH less than about 6.5. In some embodiments, the peptide is capable of selectively delivering a conjugated moiety (e.g., $R^8Q-$) across a cell membrane having an acidic or hypoxic mantle having a pH less than about 5.5. In some embodiments, the peptide is capable of selectively delivering a conjugated moiety (e.g., R⁸Q-) across a cell membrane having an acidic or hypoxic mantle having a pH between about 5.0 and about 6.0.

In certain embodiments, the peptide of R⁷ includes a cysteine residue which can form the site of attachment to a payload moiety (e.g., R⁸Q-) to be delivered across a cell membrane. In some embodiments, R⁷ is attached to Q through a cysteine residue of R⁷. In some embodiments, the sulfur atom of the cysteine residue can form part of the disulfide bond of the disulfide bond-containing linker Q.

Suitable peptides, that can conformationally change based on pH and insert across a cell membrane, are described, for example, in U.S. Pat. Nos. 8,076,451 and 9,289,508 (each of which is incorporated herein by reference in its entirety). Other suitable peptides are described, for example, in Weerakkody, et al., PNAS 110 (15), 5834-5839 (Apr. 9, 2013), which is also incorporated herein by reference in its entirety.

In some embodiments, R⁷ is a peptide comprising at least one of the following sequences:
ADDQNPWRAYLDLLFPTDTLLLDLLWCG (SEQ ID NO. 1; Pv1),
AEQNPIYWARYADWLFTTPLLLLDLALLVDADECG (SEQ ID NO. 2; Pv2), and
ADDQNPWRAYLDLLFPTDTLLLDLLWDADECG (SEQ ID NO. 3; Pv3);
Ac-AAEQNPIYWARYADWLFTTPLLLLDLALLVDADEGTKCG (SEQ ID NO. 4; Pv4); and
AAEQNPIYWARYADWLFTTPLLLLDLALLVDADEGTC (SEQ ID No. 5; Pv5);
wherein R⁷ is attached to Q through a cysteine residue of R⁷.

In some embodiments, R⁷ is a peptide comprising at least one of the following sequences:
ADDQNPWRAYLDLLFPTDTLLLDLLWCG (SEQ ID NO. 1; Pv1),
AEQNPIYWARYADWLFTTPLLLLDLALLVDADECG (SEQ ID NO. 2; Pv2), and
ADDQNPWRAYLDLLFPTDTLLLDLLWDADECG (SEQ ID NO. 3; Pv3),
wherein R⁷ is attached to Q through a cysteine residue of R⁷.

In some embodiments, R⁷ is a peptide comprising the sequence ADDQNPWRAYLDLLFPTDTLLLDLLWCG (SEQ ID NO. 1; Pv1).

In some embodiments, R⁷ is a peptide comprising the sequence AEQNPIYWARYADWLFTTPLLLLDLALLVDADECG (SEQ ID NO. 2; Pv2).

In some embodiments, R⁷ is a peptide comprising the sequence ADDQNPWRAYLDLLFPTDTLLLDLLWDADECG (SEQ ID NO. 3; Pv3).

In some embodiments, R⁷ is a peptide comprising the sequence Ac-AAEQNPIYWARYADWLFTTPLLLLDLALLVDADEGTKCG (SEQ ID NO. 4; Pv4).

In some embodiments, R⁷ is a peptide comprising the sequence AAEQNPIYWARYADWLFTTPLLLLDLALLVDADEGTC (SEQ ID NO. 5; Pv5).

In some embodiments, R⁷ is a peptide consisting of the sequence ADDQNPWRAYLDLLFPTDTLLLDLLWCG (SEQ ID NO. 1; Pv1).

In some embodiments, R⁷ is a peptide consisting of the sequence AEQNPIYWARYADWLFTTPLLLLDLALLVDADECG (SEQ ID NO. 2; Pv2).

In some embodiments, R⁷ is a peptide consisting of the sequence ADDQNPWRAYLDLLFPTDTLLLDLLWDADECG (SEQ ID NO. 3; Pv3).

In some embodiments, R⁷ is a peptide consisting of the sequence Ac-AAEQNPIYWARYADWLFTTPLLLLDLALLVDADEGTKCG (SEQ ID NO. 4; Pv4).

In some embodiments, R⁷ is a peptide consisting of the sequence AAEQNPIYWARYADWLFTTPLLLLDLALLVDADEGTC (SEQ ID NO. 5; Pv5).

In some embodiments, R⁷ is a peptide comprising at least one sequence selected from SEQ ID NO: 6 to SEQ ID NO: 311 as shown in Table 1.

In some embodiments, R⁷ is a peptide consisting of a sequence selected from SEQ ID NO: 6 to SEQ ID NO: 311 as shown in Table 1.

TABLE 1

Additional R⁷ Sequences

| SEQ ID NO. | Sequence |
|---|---|
| 6 | AAEQNPIYWWARYADWLFTTPLLLLDLALLVDADEGTCG |
| 7 | AEQNPIYWARYADWLFTTPLLLLDLALLVDADEGT |
| 8 | GGEQNPIYWARYADWLFTTPLLLLDLALLVDADEGT |
| 9 | AEQNPIYWARYADWLFTTPLLLLDLALLVDADEGT |
| 10 | AAEQNPIYWARYADWLFTTPLLLLDLALLVDADEGTCG |
| 11 | GGEQNPIYWARYADWLFTTPLLLLDLALLVDADEGTCG |
| 12 | ACEQNPIYWARYADWLFTTPLLLLDLALLVDADEGTG |
| 13 | ACEQNPIYWARYADWLFTTPLLLLDLALLVDADEGT |
| 14 | AKEQNPIYWARYADWLFTTPLLLLDLALLVDADEGT |
| 15 | AAEQNPIYWARYADWLFTTPLLLLDLALLVDADEGTKCG |
| 16 | AKEQNPIYWARYADWLFTTPLLLLDLALLVDADECT |
| 17 | ACEQNPIYWARYANWLFTTPLLLLNLALLVDADEGTG |
| 18 | ACEQNPIYWARYAKWLFTTPLLLLKLALLVDADEGTG |
| 19 | GGEQNPIYWARYADWLFTTPLLLLDLALLVNANQGT |
| 20 | AAEQNPIYWARYADWLFTTPLLLLALALLVDADEGT |
| 21 | AAEQNPIYWARYAAWLFTTPLLLLDLALLVDADEGT |
| 22 | AAEQNPIYWARYADWLFTTALLLLDLALLVDADEGT |
| 23 | AAEQNPIYWARYADWLFTTPLLLLELALLVDADEGT |
| 24 | AAEQNPIYWARYAEWLFTTPLLLLDLALLVDADEGT |
| 25 | AAEQNPIIYWARYADWLFTDLPLLLLDLLALLVDADEGT |
| 26 | GEQNPIYWAQYADWLFTTPLLLLDLALLVDADEGTCG |
| 27 | GGEQNPIYWARYADWLFTTPLLLLDLLALLVDADEGTCG |
| 28 | GGEQNPIYWARYADWLFTTPLLLLLDALLVDADEGTCG |
| 29 | GGEQNPIYWARYDAWLFTTPLLLLDLALLVDADEGTCG |
| 30 | GGEQNPIYWARYAWDLFTTPLLLLDLALLVDADEGTCG |
| 31 | AAEQNPIYWARYADWLFTTGLLLLDLALLVDADEGT |
| 32 | DDDEDNPIYWARYADWLFTTPLLLLHGALLVDADECT |
| 33 | DDDEDNPIYWARYAHWLFTTPLLLLHGALLVDADEGCT |
| 34 | DDDEDNPIYWARYAHWLFTTPLLLLHGALLVNADECT |
| 35 | DDDEDNPIYWARYAHWLFTTPLLLLHGALLVNANECT |
| 36 | AEQNPIYWARYADFLFTTPLLLLDLALLVDADET |

TABLE 1-continued

Additional R⁷ Sequences

| SEQ ID NO. | Sequence |
|---|---|
| 37 | AEQNPIYFARYADWLFTTPLLLLDLALLVDADEGT |
| 38 | AEQNPIYFARYADFLFTTPLLLLDLALLWDADET |
| 39 | AKEDQNPIYWARYADWLFTTPLLLLLDLALLVDG |
| 40 | ACEDQNPIYWARYADWLFTTPLLLLLDLALLVDG |
| 41 | AEDQNPIYWARYADWLFTTPLLLLLDLALLVDCG |
| 42 | AEDQNPIYWARYADWLFTTPLLLLELALLVECG |
| 43 | AKEDQNPYWRAYADLFTPLTLLDLLALWDG |
| 44 | ACEDQNPYWRAYADLFTPLTLLDLLALWDG |
| 45 | ACDDQNPWRAYLDLLFPTDTLLLDLLW |
| 46 | TEDADVLLALDLLLLPTTFLWD |
| 47 | AEQNPIYWARYADWLFTTPL |
| 48 | AEQNPIYWARYADWLFTTPCL |
| 49 | ACEQNPIYWARYADWLFTTPL |
| 50 | AEQNPIYFARYADWLFTTPL |
| 51 | KEDQNPWARYADLLFPTTLAW |
| 52 | ACEDQNPWARYADLLFPTTLAW |
| 53 | ACEDQNPWARYADWLFPTTLLLLD |
| 54 | ACEEQNPWARYAELLFPTTLAW |
| 55 | ACEEQNPWARYAEWLFPTTLLLLE |
| 56 | ACEEQNPWARYLEWLFPTETLLLEL |
| 57 | GGEQNPIY WARYADWLFTTPLLLLLDLALLV DADEGT |
| 58 | ACEQNPIY WARYADWLFTTPLLLLLDLALLV |
| 59 | WARYADWLFTTPLLLLLDLALLV DADEGTCG |
| 60 | WARYADWLFTTPLLLLLDLALLV DADEGCT |
| 61 | GGEQNPIY WARYADWLFTTPLLLLLDLALLV DADEGTCG |
| 62 | ACEQNPIY WARYADWLFTTPLLLLLDLALLV DADEGT |
| 63 | AKEQNPIY WARYADWLFTTPLLLLLDLALLV DADEGT |
| 64 | AKEQNPIY WARYADWLFTTPLLLLLDLALLV DADECT |
| 65 | AAEQNPIY WARYADWLFTTALLLLLDLALLV DADEGT |
| 66 | ACAEQNPIY WARYADWLFTTGLLLLDLALLV DADEGT |
| 67 | AEQNPIY WARYADFLFTTALLLLLDLALLV DADE_T |
| 68 | AEQNPIY FARYADWLFTTPLLLLDLALLV DADEGT |
| 69 | AEQNPIY FARYADFLFTTPLLLLDLALLW DADE_T |
| 70 | AKEDQNP_Y WARYADWLFTTPLLLLLDLALLV DG____ |
| 71 | ACEDQNP_Y WARYADWLFTTPLLLLLDLALLV DG____ |
| 72 | AEDQNP_Y WARYADWLFTTPLLLLLDLALLV DG____ |
| 73 | AEDQNP_Y WARYADWLFTTPLLLLELALLV ECG___ |
| 74 | AKEDQNP_Y WRAYAD_LFT_PLTLLDLLALW DG____ |
| 75 | ACEDQNP_Y WRAYAD_LFT_PLTLLDLLALW DG____ |
| 76 | AKEDQNDP_Y WARYADWLFTTPLLLLLDLALLV G_____ |
| 77 | TEDADVLLALDLLLLPTTFLWDAYRAWYPNQECA |
| 78 | GGEQNPIY WARYADWLFTTPLLLLLDLALLV DADEGT |
| 79 | AEQNPIY WARYADWLFTTPL |
| 80 | AEQNPIY WARYADWLFTTPCL |
| 81 | ACEQNPIY WARYADWLFTTPL |
| 82 | ACEQNPIY FARYADWLFTTPL |
| 83 | ACDDQNP WRAYLDLLFPTDTLLLDLLW |
| 84 | ACEEQNP WRAYLELLFPTETLLLELLW |
| 85 | ACDDQNP WARYLDWLFPTDTLLLDL |
| 86 | CDNNNP WRAYLDLLFPTDTLLLDW |
| 87 | ACEEQNP WARYLEWLFPTETLLLEL |
| 88 | ACEDQNP WARYADWLFPTTLLLLD |
| 89 | ACEEQNP WARYAEWLFPTTLLLLE |
| 90 | ACEDQNP WARYADLLFPTTLAW |
| 91 | ACEDQNP WARYAELLFPTTLW |
| 92 | KEDQNP WARYADLLFPTTLW |
| 93 | DDDEDNP IYWARYAHWLFTTPLLLLHGALLVDADECT |
| 94 | DDDEDNPIYWARYAHWLFTTPLLLLDGALLVDADECT |
| 95 | DDDEDNPIYWARYAHWLFTTPLLLLHGALLVNADECT |
| 96 | DDDEDNPIYWARYAHWLFTTPLLLLHGALLVNANECT |
| 97 | DDDEDNPIYWARYAHWLFTTPLLLLHGALLVDADECT |
| 98 | ACEQNPIYWARYADWLFTTPLLLLDLALLVDADEGIG |
| 99 | ACEQNPIYWARYADWLFTTPLLLLDLALLVDADET |
| 100 | ACEQNPIYWARYADWLF TTPLLLLLDLALLVDADEGT |
| 101 | GGEQNPIYWARYADWLFTTPLLLDLLALLVDADEGTCG |
| 102 | GGEQNPIYWARYADWLFTTPLLLLLDALLVDADEGTCG |
| 103 | GGEQNPIYWARYAWDLFTTPLLLLDLALLVDADEGTCG |
| 104 | AAEQNPIYWARYAEWLFTTPLLLLDLALLVDADEGTCG |
| 105 | AAEQNPIYWARYAEWLFTTPLLLLELALLVDADEGTCG |
| 106 | GGEQNPIYWARYDAWLFTTPLLLLDLALLVDADEGTCG |
| 107 | GGEQNPIYWAQYDAWLFTTPLLLLDLALLVDADEGTCG |
| 108 | GGEQNPIYWAQDYAWLFTTPLLLLDLALLVDADEGTCG |
| 109 | AAEQNPIYWARYAAWLFTTPLLLLDLALLVDADEGTCG |
| 110 | ACEQNPIYWARYANWLFTTPLLLLNLALLVDADEGTG |

TABLE 1-continued

Additional R[7] Sequences

| SEQ ID NO. | Sequence |
|---|---|
| 111 | DDDEDNPIYWARYAHWLFTTPLLLLLHGALLVNANECT |
| 112 | DDDEDNPIYWARYAHWLFTTPLLLLLHGALLVNADECT |
| 113 | DDDEDNPIYWARYADWLFTTPLLLLLHGALLVDADECT |
| 114 | DDDEDNPIYWARYAHWLFTTPLLLLLHGALLVDADECT |
| 115 | DDDEDNPIYWARYAHWLFTTPLLLLDGALLVDADECT |
| 116 | GGEQNPIYWARYADWLFTTPLLLLDLALLVNANQGT |
| 117 | AAEQNPIYWARYADWLFTTPLLLLELALLVDADEGTCG |
| 118 | AAEQNPIYWARYAEWLFTTPLLLLELALLVDADEGTCG |
| 119 | AAEQNPIYWARYADWLFTTPLLLLELALLVDADEGTKCG |
| 120 | GGEQNPIYWAQYADWLFTTPLLLLDLALLVDADEGTCG |
| 121 | GGEQNPIYWAQYDAWLFTTPLLLLDLALLVDADEGTCG |
| 122 | GGEQNPIYWAQDYAWLFTTPLLLLDLALLVDADEGTCG |
| 123 | GGEQNPIYWARYADWLFTTPLLLLDALLVNANQGT |
| 124 | DDDEDNPIYWARYAHWLFTTPLLLLLHGALLVNADECT |
| 125 | DDDEDNPIYWARYAHWLFTTPLLLLLHGALLVNANECT |
| 126 | ACEQNPIYWARYAKWLF TTPLLLLKLALLVDADEGTG |
| 127 | GGEQNPIYWAQDYAWLFTTPLLLLDLALLVDADEGTCG |
| 128 | GGEQNPIYWAQYDAWLFTTPLLLLDLALLVDADEGTCG |
| 129 | GGEQNPIYWAQYADWLFTTPLLLLDLALLVDADEGTCG |
| 130 | AAEQNPIYWARYAAWLFTTPLLLLDLALLVDADEGTCG |
| 131 | AAEQNPIYWARYADWLFTDLPLLLLDLLALLVDADEGT |
| 132 | GGEQNPIYWARYADWLFTTPLLLLLDALLVDADEGTCG |
| 133 | GGEQNPIYWARYADWLFTTPLLLLDLLALLVDADEGTCG |
| 134 | AAEQNPIYWARYADWLFTTGLLLLDLALLVDADEGT |
| 135 | AEQNPIYWARYAAWLFTTPLLLLLDLALLVDADEGTCG |
| 136 | GGEQNPIYWAQYDAWLFTTPLLLLDLALLVDADEGTCG |
| 137 | GGEQNPIYWAQDYAWLFTTPLLLLDLALLDADEGTCG |
| 138 | GGEQNPIYWARYDAWLFTTPLLLLDLALLVDADEGTCG |
| 139 | AAEQNPIYWARYADWLFTTPLLLLALALLVDADEGTCG |
| 140 | AAEQNPIYWARYADWLFTTPLLLLLDLALLVDADEGTKCG . . . EGTK(rhodamine)C(phalloidin)G |
| 141 | AAEQNPIYWARYADWLFTTPLLLLELALLDADEGTKCG |
| 142 | AAEQNPIYWARYADWLFTTPLLLLDLALLVDADEGTCG |
| 143 | AAEQNPIYWARYADWLFTTPLLLLLDLALLVDADEGTC(phalloidin)G |
| 144 | GGEQNPIYWARYADWLFTTPLLLLLDLALLVDADEGTCG |
| 145 | ACEQNPIYWARYADWLFTTPLLLLLDLALLVDADET |
| 146 | ACEQNPIYWARYADWLFTTPLLLLLDLALLVDADEGTG |
| 147 | ACEQNPIYWARYADWLFTTPLLLLDLALLVDADEGT |
| 148 | GGEQNPIYWARYADWLFTTPLLLLDLALLVNANQGT |
| 149 | DDDEDNPIYWARYAHWLFTTPLLLLLHGALLVNADECT |
| 150 | DDDEDNPIYWARYAHWLFTTPLLLLLHGALLVNANECT |
| 151 | GGEQNPIYWARYADWLFTTPLLLLDLALLVDADEGTCG |
| 152 | AAEQNPIYWARYADWLFTTPLLLLLDLALLVDADEGTC(phalloidin)G |
| 153 | AAEQNPIYWARYADWLFTTPLLLLELALLVDADEGTKCG |
| 154 | AAEQNPIYWARYADWLFTTPLLLLDLALLVDADEGTKCG |
| 155 | DDDEDNPIYWARYAHWLFTTPLLLLLBGALLVDADECT |
| 156 | DDDEDNPIYWARYAHWLFTTPLLLLLDGALLVDADECT |
| 157 | DDDEDNPIYWARYAHWLFTTPLLLLLBGALLVNADECT |
| 158 | DDDEDNPIYWARYAHWLFTTPLLLLLBGALLVNANECT |
| 159 | DDDEDNPIYWARYADWLFTTPLLLLIBGALLVDADECT |
| 160 | DDDEDNPIYWARYADWTFTTPLLLLLHGALLVDADECT |
| 161 | DDDEDNPIYWARYAHWLFTTPLLLLLDGALLVDADECT |
| 162 | DDDEDNPIYWARYAHWLFTTPLLLLLHGALLVDADECT |
| 163 | DDDEDNPIYWARYAHWLFTTPLLLLLHGALLVNADECT |
| 164 | DDDEDNPIYWARYHWLFTTPLLLLLHGALLVNANECT |
| 165 | DDDEDNPIYWARYAHWLFTTPLLLLLHGALLVNANECT |
| 166 | DDDEDNPIYWARYAHWLFTTPLLLLLHGALLVNADECT |
| 167 | DDDEDNPIYWARYADWLFTTPLLLLLHGALLVDADECT |
| 168 | DDDEDNPIYWARYAHWLFTTPLLLLLHGALLVDADECT |
| 169 | DDDEDNPIYWARYAHWLFTTPLLLLLDGALLVDADECT |
| 170 | GGEQNPIYWARYADWLFTTPLLLLDLALLVNANQGT |
| 171 | DDDEDNPIYWARYAHWLFTTPLLLLLHGALLVNADECT |
| 172 | DDDEDNPIYWARYADWLFTTPLLLLLHGALLVDADECT |
| 173 | DDDEDNPIYWARYAHWLFTTPLLLLLHGALLVDADECT |
| 174 | DDDEDNPIYWARYAHMLFTTPLLLLLDGALLVDADECT |
| 175 | DDDEDNPIYWARYAHWLFTTPLLLLLHGALLVNANECT |
| 176 | DDDEDNPIYWARYADWLFTTPLLLLLDGALLVDADECT |
| 177 | DDDEDNPIYWARYADWLFTTPLLLLLHGALLVDADECT |
| 178 | DDDEDNPIYWARYAHWLFTTPLLLLLDGALLVDADECT |
| 179 | DDDEDNPIYWARYAHWLFTTPLLLLLHGALLVNADECT |
| 180 | DDDEDNPIYWARYAHWLFTTPLLLLLHGALLVNANECT |
| 181 | AAEQNPIYWARYADWLFTTGLLLLDLALLVDADEGT |
| 182 | GGEQNPIYWARYAWDLFTTPLLLLDLALLVDADEGTCG |

TABLE 1-continued

Additional R⁷ Sequences

| SEQ ID NO. | Sequence |
|---|---|
| 183 | GGEQNPIYWARYDAWLFTTPLLLLDLALLVDADEGTCG |
| 184 | GGEQNPIYWAQYDAWLFTTPLLLLDLALLVDADEGTCG |
| 185 | GGEQNPIYWAQDYAWLFTTPLLLLDLALLVDADEGTCG |
| 186 | AAEQNPIYWARYAAWLFTTPLLLLDLALLVDADEGTCG |
| 187 | GGEQNPIYWARYADWLFTTPLLLLDALLVDADEGTCG |
| 188 | GGEQNPIYWARYADWLFTTPLLLDLLALLVDADEGTCG |
| 189 | GGEQNPIYWARYADWLFTTPLLLLDLLALLVDADEGTCG |
| 190 | GGEQNPIYWARYADWLFTTPLLLLLDALLVDADEGTCG |
| 191 | GGEQNPIYWAQYADWLFTTPLLLLDLALLVDADEGTCG |
| 192 | GGEQNPIYWAQYDAWLFTTPLLLLDLALLVDADEGTCG |
| 193 | GGEQNPIYWAQDYAWLFTTPLLLLDLALLVDADEGTCG |
| 194 | GGEQNPIYWAQYDAWLFTTPLLLLDLALLVDADEGTCG |
| 195 | GGEQNPIYWAQYDAWLFTTPLLLLLDLALLVDADEGTCG |
| 196 | GGEQNPIYWAQYDAWLFTTPLLLLDLALLVDADEGTCG |
| 197 | AAEQNPIYWARYAAWLFTTPLLLLDLALLVDADEGTCG |
| 198 | GGEQNPIYWAQDYAWLFTTPLLLLDLALLVDADEGTCG |
| 199 | GGEQNPIYWAQYDAWLFTTPLLLLDLALLVDADEGTCG |
| 200 | GGEQNPIYWAQYDAWLFTTPLLLLDLALLVDADEGTCG |
| 201 | AAEQNPIYWARYAAWLFTTPLLLLDLALLVDADEGTCG |
| 202 | AAEQNPIYWARYADWLFTTPLLLLELALLVDADEGTKCG |
| 203 | ... EGTK(rhidamine)C(phalloidin)G |
| 204 | AAEQNPIYWARYADWLFTTPLLLLDLALLVDADEGTKCG |
| 205 | ACEQNPIYWARYADWLF TTPLLLLDLALLVDADEGTG |
| 206 | AAEQNPIYWARYADWLFTTPLLLLDLALLVDADEGTC(phalloidin)G |
| 207 | AAEQNPIYWARYADWLFTTPLLLLDLALLVDADEGTKCG |
| 208 | AAEQNPIYWARYADWLFTTPLLLLELALLVDADEGTKCG |
| 209 | AAEQNPIYWARYADWLFTDLPLLLLDLLALLVDADEGT |
| 210 | AAEQNPIYWARYAAWLFTTPLLLLDLALLVDADEGTCG |
| 211 | GGEQNPIYWAQYDAWLFTTPLLLLDLALLVDADEGTCG |
| 212 | GGEQNPIYWAQDYAWLFTTPLLLLDLALLVDADEGTCG |
| 213 | GGEQNPIYWARYDAWLFTTPLLLLDLALLVDADEGTCG |
| 214 | AAEQNPIYWARYAEWLF TTPLLLLDLALLVDADEGTCG |
| 215 | AAEQNPIYWARYAEWLF TTPLLLLELALLVDADEGTCG |
| 216 | AAEQNPIYWARYADWLFTTPLLLLALALLVDADEGTCG |
| 217 | AAEQNPIYWARYADWLFTTPLLLLELALLVDADEGTCG |
| 218 | AAEQNPIYWARYAEWLF TTPLLLLELALLVDADEGTCG |
| 219 | AAEQNPIYWARYADWLFTTPLLLLELALLVDADEGTKCG |
| 220 | ACEQNPIYWARYAKWLFTTPLLLLKLALLVDADEGTG |
| 221 | ACEQNPIYWARYANWLFTTPLLLLNLALLVDADEGTG |
| 222 | AAEQNPIYWARYADWLFTTALLLLDLALLVDADEGT |
| 223 | AEQNPIYFARYADLLFPTTLAW |
| 224 | AEQNPIYWARYADLLFPTTLAF |
| 225 | AEQNPIYWARYADLLFPTTLAW |
| 226 | ACEQNPIYWARYADWLFTTPLLLLDLALLVDADET |
| 227 | GGEQNPIYWARYADWLFTTPLLLLDLALLVDADEGT |
| 228 | AAEQNPIYWARYADWLFTTPLLLLDLALLVDADEGTCG |
| 229 | AAEQNPIYWARYADWLFTTPLLLLDLALLVDADEGTKCG |
| 230 | AKEQNPIYWARYADWLFTTPLLLLDLALLVDADECT |
| 231 | CCTCTTACCTCAGTTACA |
| 232 | D-Arg8 D-Arg8-CCTCTTACCTCAGTTACA |
| 233 | D-Lys4 D-Lys4-CCTCTTACCTCAGTTACA |
| 234 | S-S-CCTCTTACCTCAGTTACA |
| 235 | S-S-CCTCTGACCTCATTTACA |
| 236 | D-Arg8-Deca D-Arg8-Deca-CCTCTTACCTCAGTTACA |
| 237 | D-Arg8-Deca-mismatch D-Arg8-Deca-CCTCTGACCTCATTTACA |
| 238 | S-S-CCTCTTACCTCAGTTACA |
| 239 | AAEQNPIYWARYADWLFTTPLLLLDLALLVDADEGTCG |
| 240 | AEDQNPYWARYDWLFTTPLLLLDLALLVDCG |
| 241 | AEDQNPYWARYADWLFTTPLLLLELALLVECG |
| 242 | AEQNPIYWARYADWLFTTPLLLLDLALLVDADEGCT |
| 243 | ACEQNPIYWARYADWLFTTPLLLLDLALLVDADET |
| 244 | AE-QN-PI YWARYADWLFTTPLLLLDLALLV DADEGT-COOH |
| 245 | AEDQN-P- YWARYADWLFTTPLLLLDLALLV D---G--COOH |
| 246 | AEDQNDP-YWARYADWLFTTPLLLLLDLALLV----G--COOH |
| 247 | AEQNPI YWARYADFLFTTPLLLLDLALLV DADET-COOH |
| 248 | AEQNPI YFARYADWLFTTPLLLLDLALLV DADET-COOH |
| 249 | AEQNPI YFARYADFLFTTPLLLLDLALLW DADET-COOH |
| 250 | AE-QN-PI YWARYADWLFTTPLLLLDLALLV DADEGCT-COOH |
| 251 | AEDQN-PI YWARYADWLFTTPLLLLDLALLV DC--G-T-COOH |
| 252 | AEDQNDPI YWARYADWLFTTPLLLLELALLV EC--G-T-COOH |
| 253 | Chelate-ACEEQNPWARYLEWLFPTETLLLEL |
| 254 | AEQNPIY WARYADWLFTTPLLLLDLALLV DADEGT-COOH |
| 255 | AKEDQNPY WARYADWLFTTPLLLLLDLALLV DG-COOH |

TABLE 1-continued

Additional R[7] Sequences

| SEQ ID NO. | Sequence |
|---|---|
| 256 | AKEDQNDPY WARYADWLFTTPLLLLDLALLV G-COOH |
| 257 | AEQNPI YWARYADWLFTTPLLLLDLALLV DADEGC-Biotin-T-COOH |
| 258 | AEDQNP YWARYADWLFTTPLLLLDLALLV DC-Biotin-G-COOH |
| 259 | AEDQNP YWARYADWLFTTPLLLLELALLV EC-Biotin-G-COOH |
| 260 | ACEQNPIY WARYADWLFTTPLLLLDLALLV DADEGT |
| 261 | ACEDQNPY WARYADWLFTTPLLLLDLALLV DG |
| 262 | ACEDQNPY WRAYADLFTPLTLLDLLALW DG |
| 263 | ACDDQNP WRAYLDLLFPTDTLLLDLLW |
| 264 | WRAYLELLFPTETLLLELLW |
| 265 | WARYLDWLFPTDTLLLDL |
| 266 | WRAYLDLLFPTDTLLLDW |
| 267 | WARYLEWLFPTETLLLEL |
| 268 | WAQYLELLFPTETLLLEW |
| 269 | WRAYLELLFPTETLLLEW |
| 270 | WARYADWLFPTTLLLLD |
| 271 | WARYAEWLFPTTLLLLE |
| 272 | ACEDQNP WARYADLLFPTTLAW |
| 273 | ACEEQNP WARYAELLFPTTLAW |
| 274 | Ac-TEDAD VLLALDLLLLPTTFLWDAYRAW YPNQECA-Am |
| 275 | CDDDDDNPNY WARYANWLFTTPLLLLNGALLV EAEET |
| 276 | CDDDDDNPNY WARYAPWLFTTPLLLLPGALLV EAEET |
| 277 | Ac-AEQNPIYWARYADWLFTTPLLLLDLALLVDADEGCT |
| 278 | Ac-AKEQNPIYWARYADWLFTTPLLLLDLALLVDADEGTG |
| 279 | ACEQNPIYWARYANWLFTTPLLLLNLALLVDADEGT |
| 280 | Ac-AAEQNPIYWARYADWLFTTPLLLLELALLVDADEGTKCG |
| 281 | DDDEDNPIYWARYADWLFTTPLLLLHGALLVDADET |
| 282 | CDDDEDNPIYWARYAHWLFTTPLLLLHGALLVDADET |
| 283 | DDDEDNPIYWARYAHWLFTTPLLLLHGALLVDADEGT |
| 284 | DDDEDNPIYWARYAHWLFTTPLLLLHGALLVNADEGT |
| 285 | DDDEDNPIYWARYAHWLFTTPLLLLHGALLVNANEGT |
| 286 | AKEDQNDPYWARYADWLFTTPLLLLDLALLVG |
| 287 | AEDQNPYWARYADWLFTTPLLLLELALLVCG |
| 288 | AKDDQNPWRAYLDLLFPTDTLLLDLLWC |
| 289 | ACEEQNPWRAYLELLFPTETLLLELLW |
| 290 | ACDDQNPWARYLDWLFPTDTLLLDL |
| 291 | CDNNNPWRAYLDLLFPTDTLLLDW |
| 292 | CEEQQPWAQYLELLFPTETLLLEW |
| 293 | EEQQPWRAYLELLFPTETLLLEW |
| 294 | CDDDDDNPNYWARYANWLFTTPLLLLNGALLVEAEET |
| 295 | CDDDDDNPNYWARYAPWLFTTPLLLLPGALLVEAEE |
| 296 | AEQNPIYFARYADLLFPTTLAW |
| 297 | AEQNPIYWARYADLLFPTTLAF |
| 298 | AEQNPIYWARYADLLFPTTLAW |
| 299 | KEDQNPWARYADLLFPTTLW |
| 300 | ACEEQNPQAEYAEWLFPTTLLLLE |
| 301 | AAEEQNPWARYLEWLFPTETLLLEL |
| 302 | AKEEQNPWARYLEWLFPTETLLLEL |
| 303 | AAEQNPIYWARYADWLFTTPLLLLDLALLVDADEGTGG |
| 304 | XXEXNPIYWAXXXXXXLFTXXLLLXXXALLVXAXXXXTXG |
| 305 | DAAEQNPIYWARYADWLFTTPLLLLDLLALLVDADEGTKGG |
| 306 | GGEQNPIYWARYADWLFTTPLLLLDLALLVDADEGTGG |
| 307 | XXEXNPIYWAXXXXXXLFTXXLLLXXXALLVXAXXXXTGG |
| 308 | DGGEQNDPIYWARYADWLFTTPLLLLDLLALLVDADEGCTXGG |
| 309 | AAEQNPIYWARYADWLFTTPLLLLDLALLVDADEGTCG |
| 310 | AEDQNPIYWARYDWLFTTPLLLLDLALLVDCG |
| 311 | GLAGLAGLLGLEGLLGLPLGLLEGLWLGLELEGN |

Any of the recited peptides useful in the present invention can be modified to include a cysteine residue by replacing a non-cysteine residue with cysteine, or appending a cysteine residue to either the N-terminus or C-terminus.

In some embodiments, the peptide of R[7] is a conformationally restricted peptide. A conformationally restricted peptide can include, for example, macrocyclic peptides and stapled peptides. A stapled peptide is a peptide constrained by a covalent linkage between two amino acid side-chains, forming a peptide macrocycle. Conformationally restricted peptides are described, for example, in Guerlavais et al., Annual Reports in Medicinal Chemistry 2014, 49, 331-345; Chang et al., Proceedings of the National Academy of Sciences of the United States of America (2013), 110(36), E3445-E3454; Tesauro et al., Molecules 2019, 24, 351-377; Dougherty et al., Journal of Medicinal Chemistry (2019), 62(22), 10098-10107; and Dougherty et al., Chemical Reviews (2019), 119(17), 10241-10287, each of which is incorporated herein by reference in its entirety.

The term "small molecule topoisomerase I targeting moiety" or "topoisomerase I inhibitor" refers to a chemical group that binds to topoisomerase I. The small molecule topoisomerase I targeting moiety can be a group derived from a compound that inhibits the activity of topoisomerase I. Topoisomerase inhibitors include camptothecin and derivatives and analogues thereof such as opotecan, irinotecan (CPT-11), silatecan (DB-67, AR-67), cositecan (BNP-1350), lurtotecan, gimatecan (ST1481), belotecan (CKD- 602), rubitecan, topotecan, deruxtecan, and exatecan. Topoisomerase inhibitors are described in, for example, Ogitani, Bioorg. Med. Chem. Lett. 26 (2016), 5069-5072; Kumazawa, E., Cancer Chemother Pharmacol 1998, 42: 210-220; Tahara, M, Mol Cancer Ther 2014, 13(5): 1170-1180; Nakada, T., Bioorganic & Medicinal Chemistry Letters 2016, 26: 1542-1545.

The moeity Q is a linking group, covalently connecting $R^7$ and $R^8$ that serves a tether between the peptide and topoisomerase I inhibitor that may be cleaved when the conjugate or portion there of is inside a cell. In some embodiments, Q is a chain of 1 to 40, 1 to 30, 1 to 25, 1 to 20, 1 to 15, 1 to 10, or 1 to 5 chain atoms, which is optionally substituted with 1-10 $R^q$ substituents, and wherein one or more chain carbon atoms of Q can be oxidized to form a carbonyl (C=O), and wherein one or more N and S chain atoms can each be optionally oxidized to form an amine oxide, sulfoxide or sulfonyl group; wherein each $R^q$ is independently selected from OH, CN, —COOH, $NH_2$, halo, $C_{1-6}$ haloalkyl, $C_{1-6}$ alkyl, $C_{1-6}$ alkoxy, $C_{1-6}$ haloalkoxy, $C_{1-6}$ alkylthio, phenyl, 5-6 membered heteroaryl, 4-6 membered heterocycloalkyl, $C_{3-6}$ cycloalkyl, $NH(C_{1-6}$ alkyl) and $N(C_{1-6}$ alkyl$)_2$, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5- or 6-membered heteroaryl or 4-6 membered heterocycloalkyl; and two $R^q$ groups together with the chain atoms to which they are attached can form a phenyl, 5-6 membered heteroaryl, 4-6 membered heterocycloalkyl, or $C_{3-6}$ cycloalkyl ring.

In some embodiments, $R^q$ is independently selected from OH, CN, —COOH, $NH_2$, halo, $C_{1-6}$ haloalkyl, $C_{1-6}$ alkyl, $C_{1-6}$ alkoxy, $C_{1-6}$ haloalkoxy, $NH(C_{1-6}$ alkyl) and $N(C_{1-6}$ alkyl$)_2$.

In some embodiments, Q is selected from:

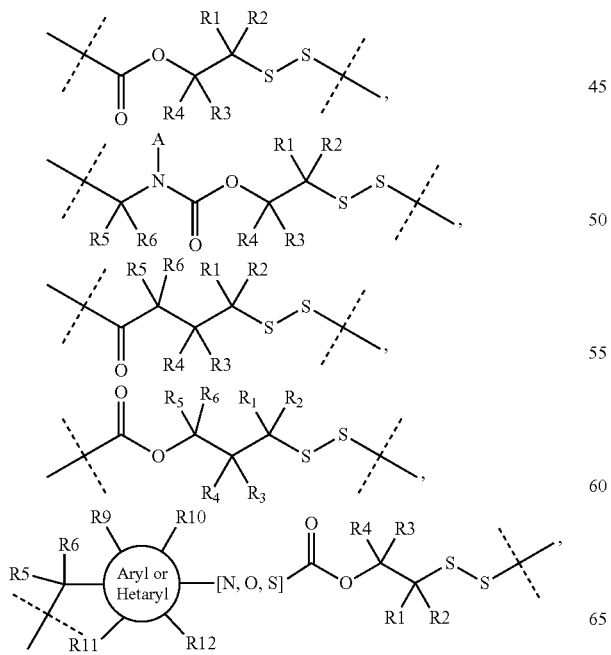

-continued

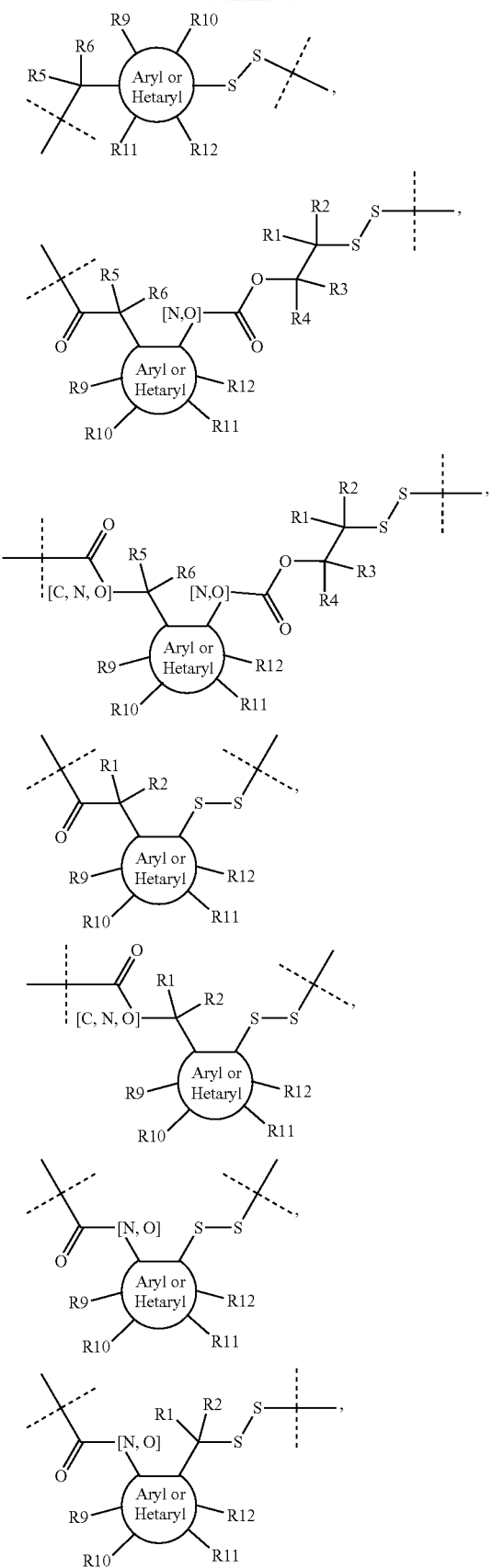

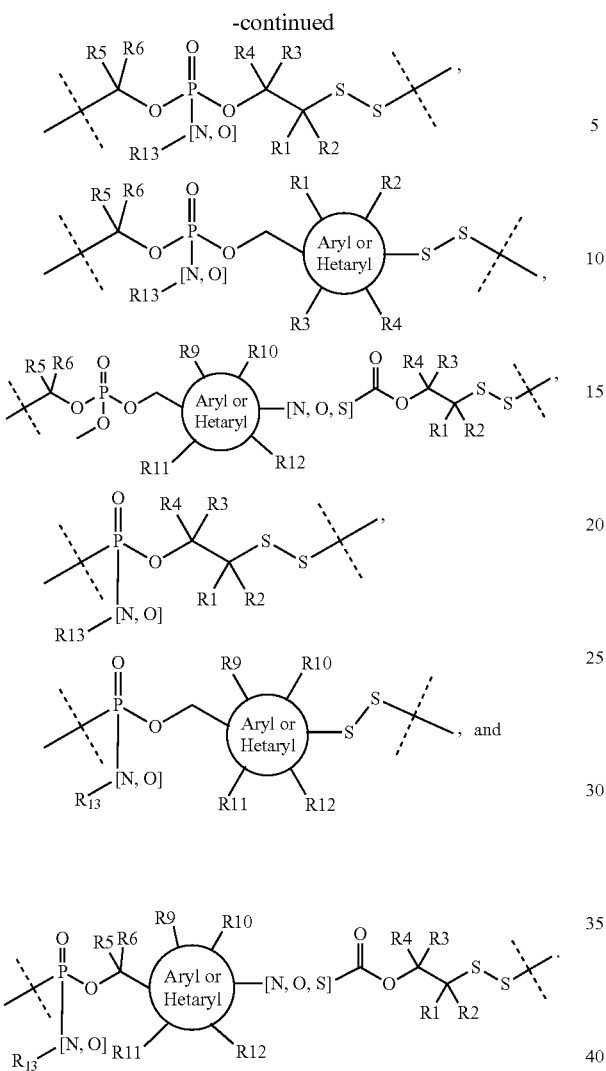

In some embodiments, Q is:

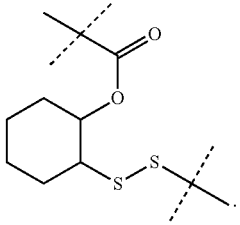

In some embodiments, Q is:


In some embodiments, Q is:


In some embodiments, Q is:

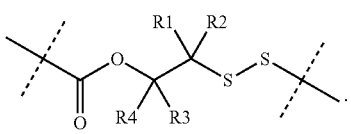

In some embodiments, Q is:

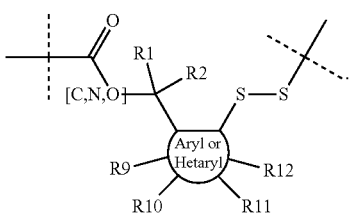

In some embodiments:

$R^1$, $R^2$, $R^3$, and $R^4$ are each independently selected from H and $C_{1-4}$ alkyl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl is optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^2$ together with the carbon atom to which they are attached form a $C_{3-10}$ cycloalkyl group or 4-10 membered heterocycloalkyl group, each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^3$ together with the carbon atom to which they are attached form a $C_{3-10}$ cycloalkyl group or 4-10 membered heterocycloalkyl group, each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^4$ together with the carbon atom to which they are attached form a $C_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^2$ and R$^3$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^2$ and R$^4$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{di}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^3$ and R$^4$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$; NR$^{c1}$C(O)R$^{b1}$; NR$^{c1}$C(O)OR$^{a1}$, and NR$^{c1}$C(O)NR$^{c1}$R$^{d1}$.

In some embodiments:
R$^1$, R$^2$, R$^3$, and R$^4$ are each independently selected from H and C$_{1-4}$ alkyl;
or R$^1$ and R$^2$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$; NR$^{c1}$C(O)R$^{b1}$; NR$^{c1}$C(O)OR$^{a1}$, and NR$^{c1}$C(O)NR$^{c1}$R$^{d1}$;

or R$^1$ and R$^3$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$; NR$^{c1}$C(O)R$^{b1}$; NR$^{c1}$C(O)OR$^{a1}$, and NR$^{c1}$C(O)NR$^{c1}$R$^{d1}$;

or R$^3$ and R$^4$ together with the carbon atom to which they are attached form a C$_{3-10}$ cycloalkyl group or 4-10 membered heterocycloalkyl group, each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$; NR$^{c1}$C(O)R$^{b1}$, NR$^{c1}$C(O)OR$^{a1}$, and NR$^{c1}$C(O)NR$^{c1}$R$^{d1}$.

In some embodiments, R$^1$ and R$^2$ are each independently selected from H and methyl, and R$^3$, R$^4$, R$^5$, and R$^6$ are each hydrogen.

In some embodiments, R$^1$, R$^2$, R$^3$, and R$^4$ are each independently selected from H and methyl, and R$^5$, and R$^6$ are each hydrogen.

In some embodiments, R$^1$ and R$^2$ are each independently selected from H and methyl.

In some embodiments, R$^3$ and R$^4$ are each independently selected from H and methyl.

In some embodiments, R$^1$ and R$^2$ are each H.

In some embodiments, R$^1$ and R$^2$ together with the carbon atom to which they are attached form a C$_{3-7}$ cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$.

In some embodiments, R$^1$ and R$^2$ together with the carbon atom to which they are attached form a C$_{3-7}$ cycloalkyl group.

In some embodiments, R$^1$ and R$^2$ together with the carbon atom to which they are attached form a cyclobutyl group.

In some embodiments, R$^3$ and R$^4$ are each H.

In some embodiments, R$^1$ and R$^3$ together with the carbon atom to which they are attached form a C$_{3-7}$ cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$.

In some embodiments, R$^1$ and R$^3$ together with the carbon atom to which they are attached form a cyclopentyl, cyclohexyl, cycloheptyl, 1,2,3,4-tetrahydronaphthyl, tetrahydrofuranyl, or tetrahydropyranyl.

In some embodiments, R$^1$ and R$^3$ together with the carbon atom to which they are attached form a C$_{3-7}$ cycloalkyl group.

In some embodiments, R$^1$ and R$^3$ together with the carbon atom to which they are attached form a cyclohexyl group.

In some embodiments, R$^2$ and R$^4$ are each H.

In some embodiments, R$^5$ and R$^6$ are each H.

In some embodiments, R$^9$, R$^{10}$, R$^{11}$, and R$^{12}$ are each independently selected from H and methyl.

In some embodiments, the compound of the invention is a compound of Formula (II):

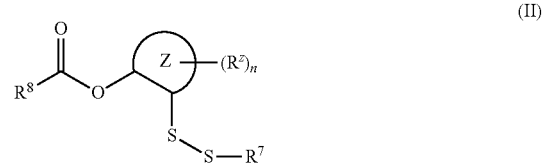

(II)

or a pharmaceutically acceptable salt thereof, wherein:
R$^7$ is a peptide;
R$^8$ is a topoisomerase I inhibitor;
Ring Z is a monocyclic C$_{5-7}$ cycloalkyl ring or a monocyclic 5-7 membered heterocycloalkyl ring;
each R$^Z$ is independently selected from C$_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$; NR$^{c1}$C(O)R$^{b1}$, NR$^{c1}$C(O)OR$^{a1}$; and NR$^{c1}$C(O)NR$^{c1}$R$^{d1}$;

or two adjacent R$^Z$ together with the atoms to which they are attached form a fused monocyclic C$_{5-7}$ cycloalkyl ring, a fused monocyclic 5-7 membered heterocycloalkyl ring, a fused C$_{6-10}$ aryl ring, or a fused 6-10 membered heteroaryl ring, each of which is optionally substituted with 1, 2, or 3 substituents independently selected from C$_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

R$^{a1}$, R$^{b1}$, R$^{c1}$, and R$^{d1}$ are each independently selected from H, C$_{1-4}$ alkyl, C$_{2-4}$ alkenyl, C$_{2-4}$ alkynyl, each optionally substituted with 1, 2, or 3 substituents independently selected from halo, OH, CN, and NO$_2$; and n is 0, 1, 2, or 3.

In some embodiments of compounds of Formula (II), R$^7$ is a peptide comprising the sequence of SEQ ID NO: 1, SEQ ID NO:2, SEQ ID NO:3, SEQ ID NO:4, or SEQ ID NO:5.

In some embodiments of compounds of Formula (II), R$^7$ is Pv1, Pv2, Pv3, Pv4, or Pv5.

In some embodiments of compounds of Formula (II), R$^7$ is attached to the core via a cysteine residue of R$^7$ wherein one of the sulfur atoms of the disulfide moiety in Formula II is derived from the cysteine residue.

In some embodiments of compounds of Formula (II), R$^8$ is camptothecin, opotecan, irinotecan (CPT-11), silatecan (DB-67, AR-67), cositecan (BNP-1350), lurtotecan, gimatecan (ST1481), belotecan (CKD-602), rubitecan, topotecan, deruxtecan, or exatecan.

In some embodiments of compounds of Formula (II), R$^8$ is exatecan.

In some embodiments of compounds of Formula (II), R$^8$ is attached to the core through an N atom.

In some embodiments of compounds of Formula (II), Ring Z is a monocyclic C$_{5-7}$ cycloalkyl ring.

In some embodiments of compounds of Formula (II), Ring Z is a cyclopentyl ring.

In some embodiments of compounds of Formula (II), Ring Z is a cyclohexyl ring.

In some embodiments of compounds of Formula (II), Ring Z is a cycloheptyl ring.

In some embodiments of compounds of Formula (II), Ring Z is a monocyclic 5-7 membered heterocycloalkyl ring.

In some embodiments of compounds of Formula (II), Ring Z is a 5-membered heterocycloalkyl ring.

In some embodiments of compounds of Formula (II), Ring Z is a 6-membered heterocycloalkyl ring.

In some embodiments of compounds of Formula (II), Ring Z is a 7-membered heterocycloalkyl ring.

In some embodiments of compounds of Formula (II), two adjacent R$^Z$ together with the atoms to which they are attached form a fused monocyclic C$_{5-7}$ cycloalkyl ring, a fused monocyclic 5-7 membered heterocycloalkyl ring, a fused C$_{6-10}$ aryl ring, or a fused 6-10 membered heteroaryl ring, each of which is optionally substituted with 1, 2, or 3 substituents independently selected from C$_{1-4}$ alkyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$.

In some embodiments of compounds of Formula (II), n is 0.

In some embodiments of compounds of Formula (II), n is 1.

In some embodiments of compounds of Formula (II), n is 2.

In some embodiments of compounds of Formula (II), n is 3.

In some embodiments, the compounds of the invention is a compound of Formula (III), Formula (IV), or Formula (V):

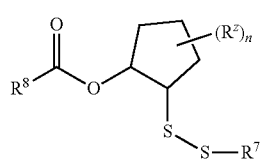

(III)

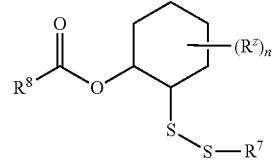

(IV)

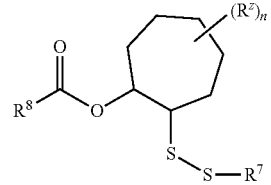

(V)

or a pharmaceutically acceptable salt thereof, wherein R$^7$, R$^8$, R$^Z$ and n are defined as in any of the embodiments above for Formula (II).

In some embodiments, the compound of formula (I) is selected from:

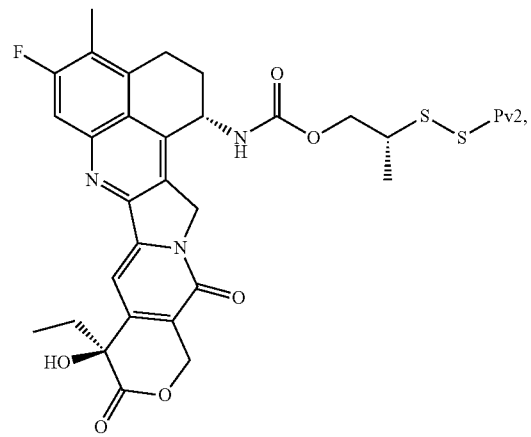

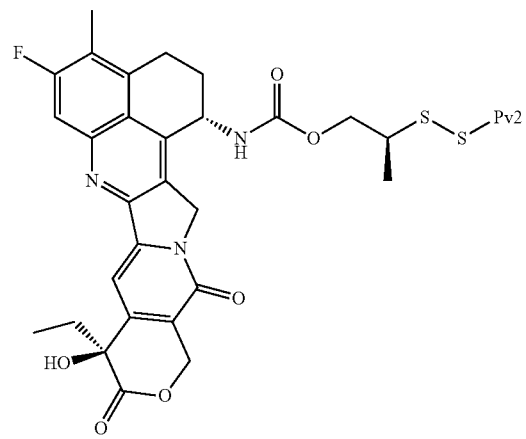

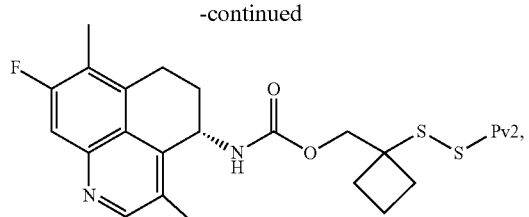
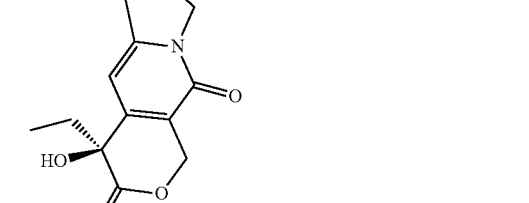
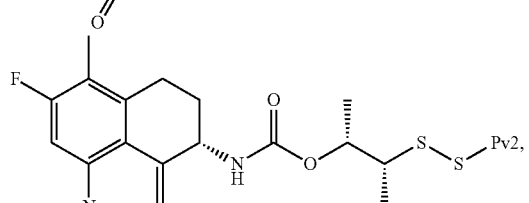
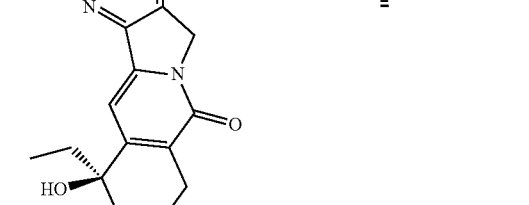
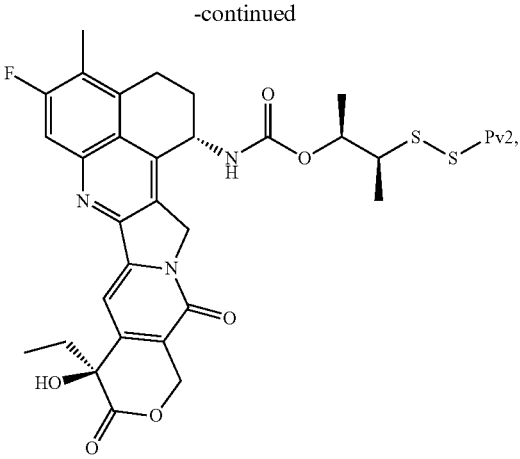
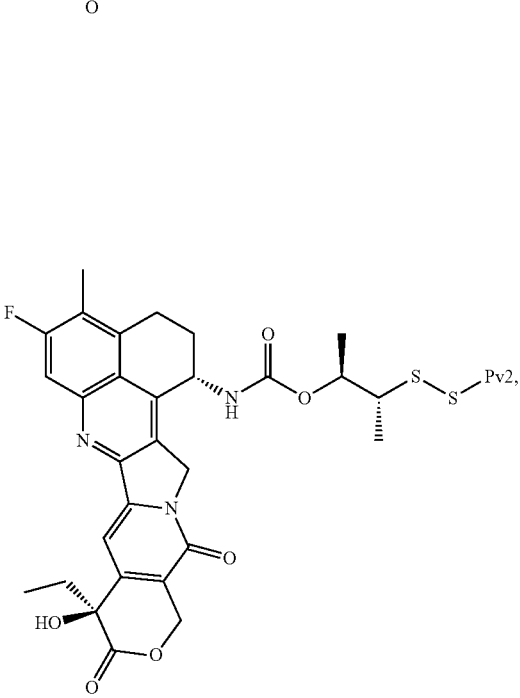
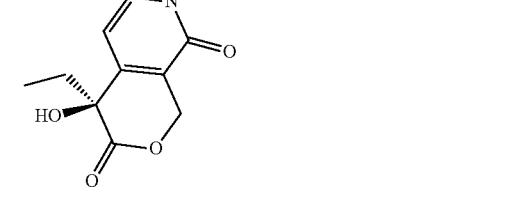

47
-continued
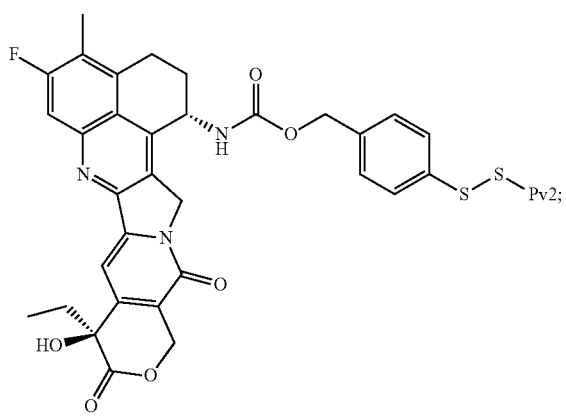
48
-continued
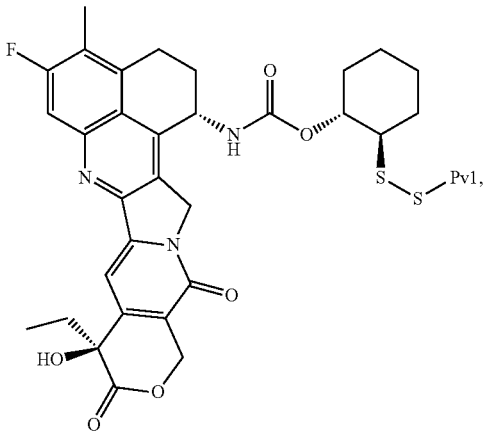
or a pharmaceutically acceptable salt of any of the aforementioned.
In some embodiments, the compound of formula (I) is selected from:
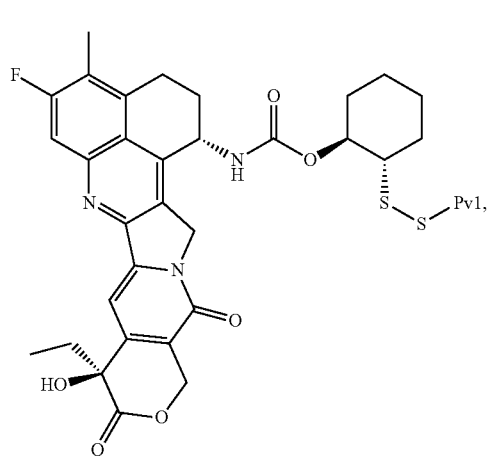
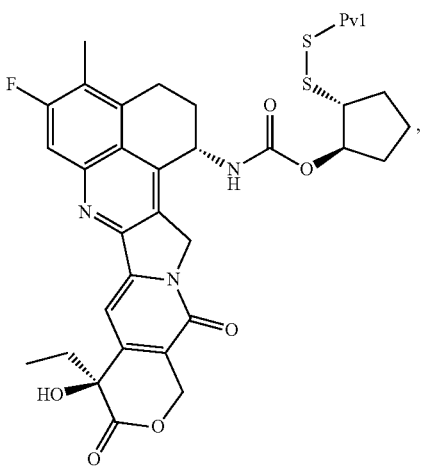
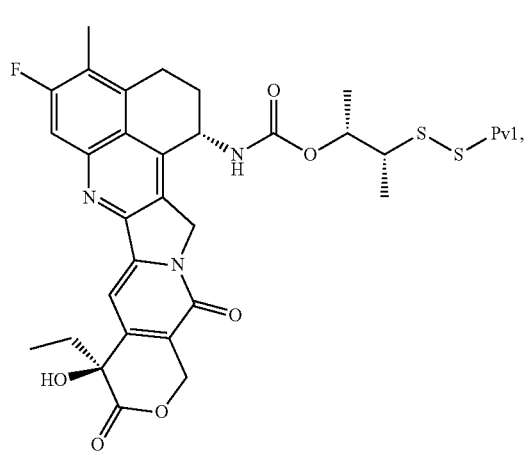
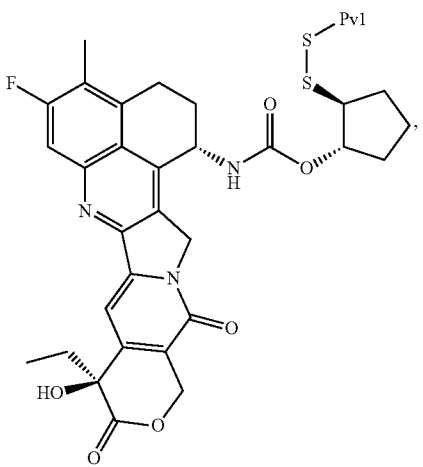

49
-continued
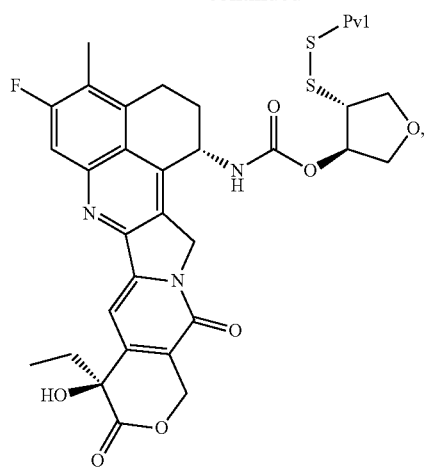
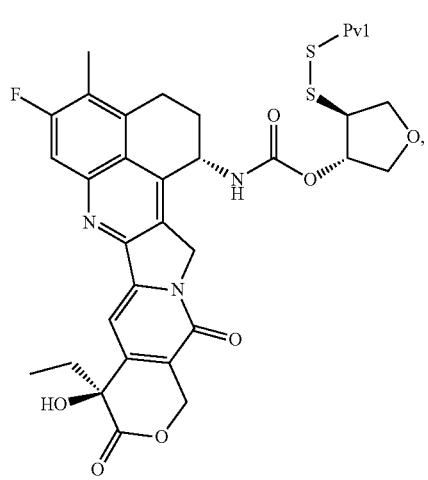
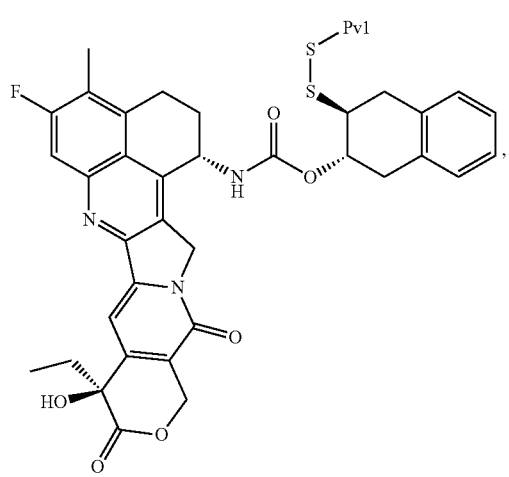
50
-continued
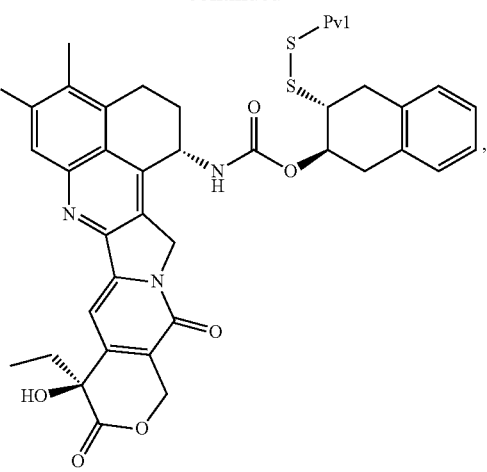
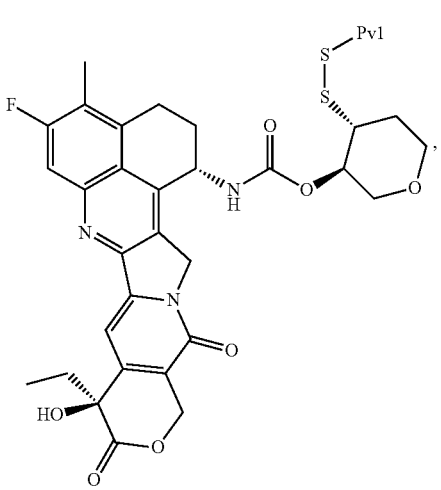
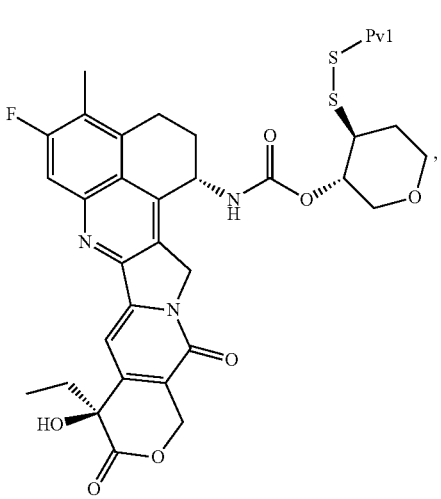

51
-continued
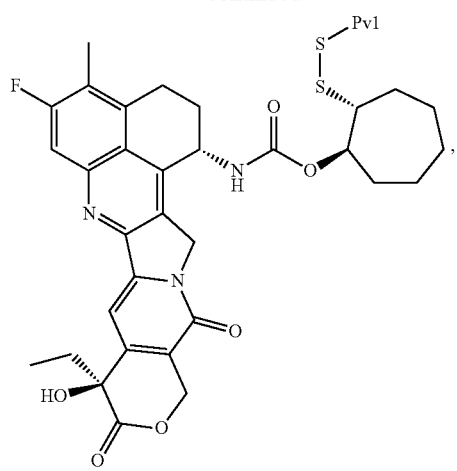
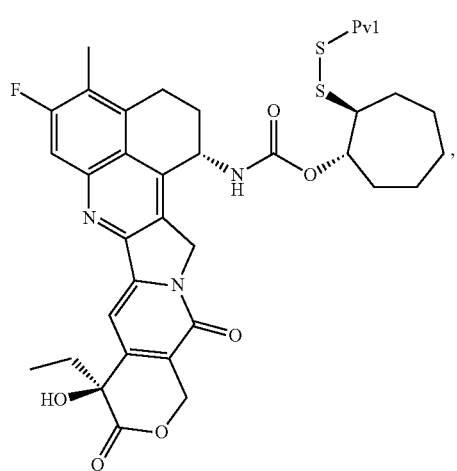
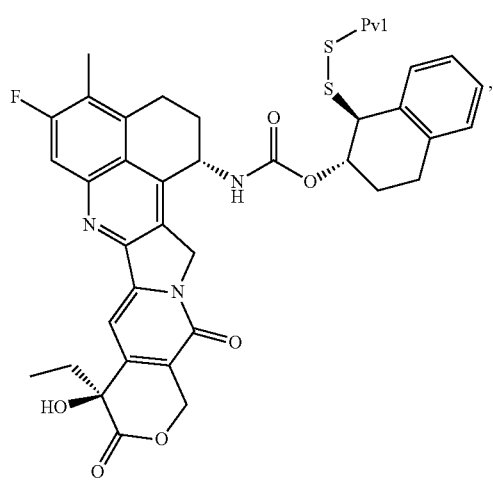
52
-continued
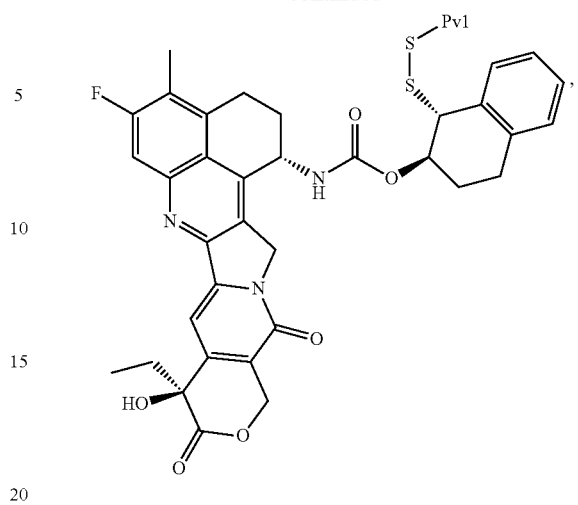
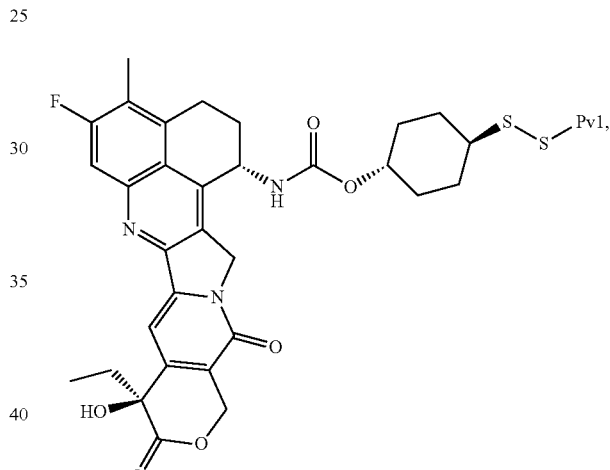
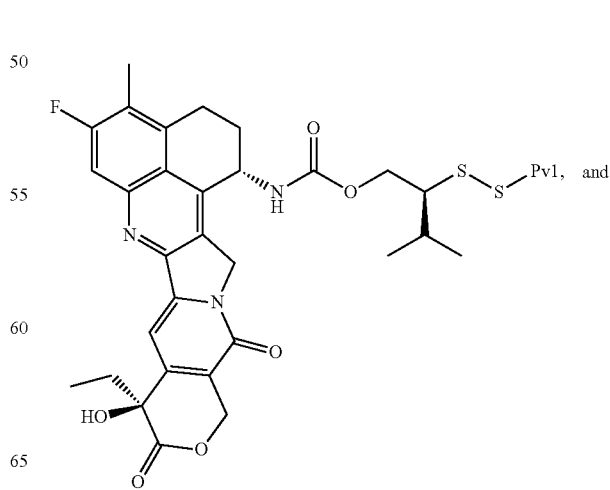

-continued

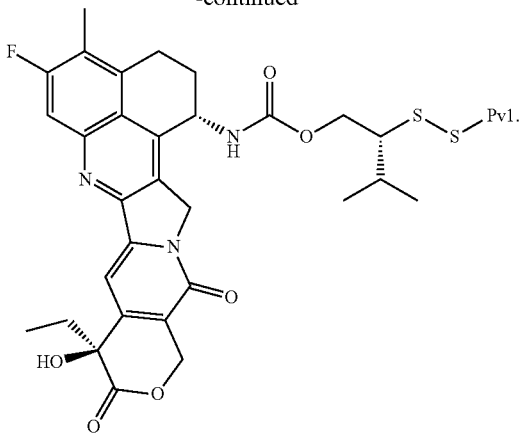

In some embodiments, provided herein is a compound having Formula (IIA):

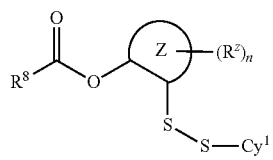

(IIA)

or a salt thereof, wherein:
- $Cy^1$ is $C_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S; and wherein said $C_{6-10}$ aryl and 5-10 membered heteroaryl are each optionally substituted with 1, 2, or 3 substituents independently selected from $C_{1-4}$ alkyl, halo, OH, $C_{1-6}$ alkoxy, CN, and $NO_2$;
- and $R^8$, Ring Z, $R^Z$, and n are as defined herein.

In some embodiments, $Cy^1$ is 5-10 membered heteroaryl. In some embodiments, $Cy^1$ is pyridinyl. In some embodiments, $Cy^1$ is phenyl.

In some embodiments, the compound of Formula (IIA) has the structure:

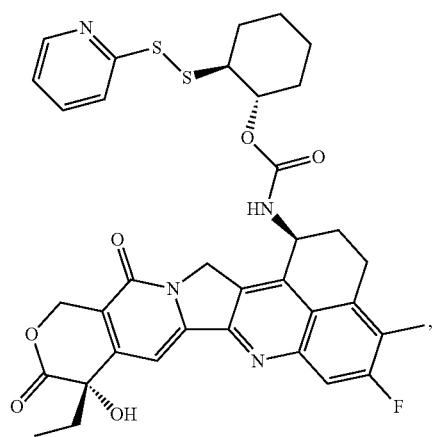 [SMILES: CC[C@@]1(O)C(=O)OCc2c1cc1n(c2=O)Cc2c-1nc1cc(F)c(C)c3c1c2[C@@H](NC(=O)O[C@H]1CCCC[C@@H]1SSc1ccccn1)CC3]

or a salt thereof.

In some embodiments, provided herein is a compound of Formula (IIA):

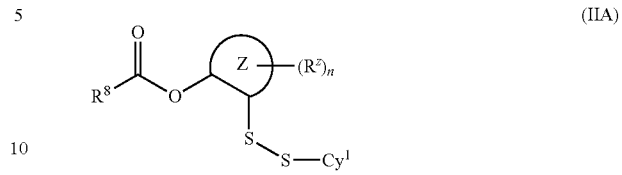

(IIA)

or a salt thereof, for use in preparing a compound of the invention (e.g., a compound of Formula (I) or Formula (II)), wherein $Cy^1$, $R^8$, Ring Z, $R^Z$, $R^{a1}$, $R^{b1}$, $R^{c1}$, $R^{d1}$, and n are as defined herein.

In some embodiments, provided herein is a compound having the structure:

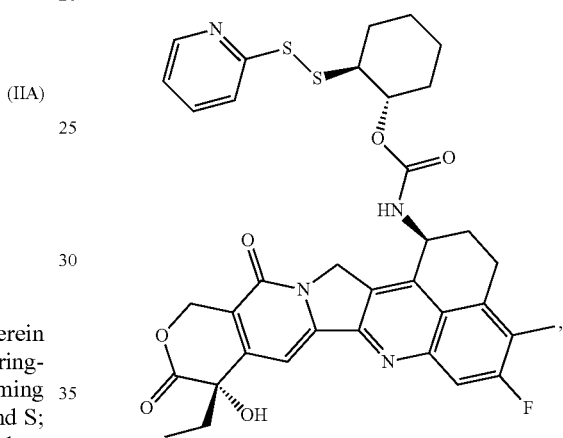

or a salt thereof, for use in preparing a compound of the invention (e.g., a compound of Formula (I) or Formula (II)).

The molecules of the invention can be tagged, for example, with a probe such as a fluorophore, radioisotope, and the like. In some embodiments, the probe is a fluorescent probe, such as LICOR. A fluorescent probe can include any moiety that can re-emit light upon light excitation (e.g., a fluorophore).

The Amino acids are represented by the IUPAC abbreviations, as follows: Alanine (Ala; A), Arginine (Arg; R), Asparagine (Asn; N), Aspartic acid (Asp; D), Cysteine (Cys; C), Glutamine (Gln; Q), Glutamic acid (Glu; E), Glycine (Gly; G), Histidine (His; H), Isoleucine (Ile; I), Leucine (Leu; L), Lysine (Lys; K), Methionine (Met; M), Phenylalanine (Phe; F), Proline (Pro; P), Serine (Ser; S), Threonine (Thr; T), Tryptophan (Trp; W), Tyrosine (Tyr; Y), Valine (Val; V).

```
The term "Pv1" means
                                  (SEQ ID NO: 1)
ADDQNPWRAYLDLLFPTDTLLLDLLWCG.

The term "Pv2" means
                                  (SEQ ID NO: 2)
AEQNPIYWARYADWLFTTPLLLLDLALLVDADECG.

The term "Pv3" means
                                  (SEQ ID NO: 3)
ADDQNPWRAYLDLLFPTDTLLLDLLWDADECG.
```

-continued

```
The term "Pv4" means
                                    (SEQ ID NO: 4)
AcAAEQNPIYWARYADWLFTTPLLLLDLALLVDADEGTKCG.

The term "Pv5" means
                                    (SEQ ID NO: 5)
AAEQNPIYWARYADWLFTTPLLLLDLALLVDADEGTC.
```

In the compounds of the invention, the peptides $R^7$ are attached to the disulfide moiety in the linker Q by an amino acid residue comprising a sulfur atom, such as a cysteine residue. Typically, the sulfur atom of the disulfide moiety in the linker Q which is the point of attachment to peptide $R^7$ is derived from an amino acid residue of the peptide, such as from a cysteine residue.

The term "acidic and/or hypoxic mantle" refers to the environment of the cell in the diseased tissue in question having a pH lower than 7.0 and preferably lower than 6.5. An acidic or hypoxic mantle more preferably has a pH of about 5.5 and most preferably has a pH of about 5.0. The compounds of formula (I) insert across a cell membrane having an acidic and/or hypoxic mantle in a pH dependent fashion to insert $R^8Q$ into the cell, whereupon the disulfide linker is cleaved to deliver free $R^8H$. Since the compounds of formula (I) are pH-dependent, they preferentially insert across a cell membrane only in the presence of an acidic or hypoxic mantle surrounding the cell and not across the cell membrane of "normal" cells, which do not have an acidic or hypoxic mantle. An example of a cell having an acidic or hypoxic mantle is a cancer cell.

The terms "pH-sensitive" or "pH-dependent" as used herein to refer to the peptide $R^7$ or to the mode of insertion of the peptide $R^7$ or of the compounds of the invention across a cell membrane, means that the peptide has a higher affinity to a cell membrane lipid bilayer having an acidic or hypoxic mantle than a membrane lipid bilayer at neutral pH. Thus, the compounds of the invention preferentially insert through the cell membrane to insert $R^8Q$ to the interior of the cell (and thus deliver $R^8H$ as described above) when the cell membrane lipid bilayer has an acidic or hypoxic mantle (a "diseased" cell) but does not insert through a cell membrane when the mantle (the environment of the cell membrane lipid bilayer) is not acidic or hypoxic (a "normal" cell). It is believed that this preferential insertion is achieved as a result of the peptide $R^7$ forming a helical configuration, which facilitates membrane insertion.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "amino" refers to a group of formula —$NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring.

A five-membered heteroaryl ring is a heteroaryl group having five ring atoms wherein one or more (e.g., 1, 2 or 3) ring atoms are independently selected from N, O and S.

A six-membered heteroaryl ring is a heteroaryl group having six ring atoms wherein one or more (e.g., 1, 2 or 3) ring atoms are independently selected from N, O and S.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2-pyrrolidinyl; morpholinul; azetidinyl; and piperazinyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (9, unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, Protecting Group Chemistry, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

Scheme 1: Synthesis of Carbonate and Carbamate Linked Compounds

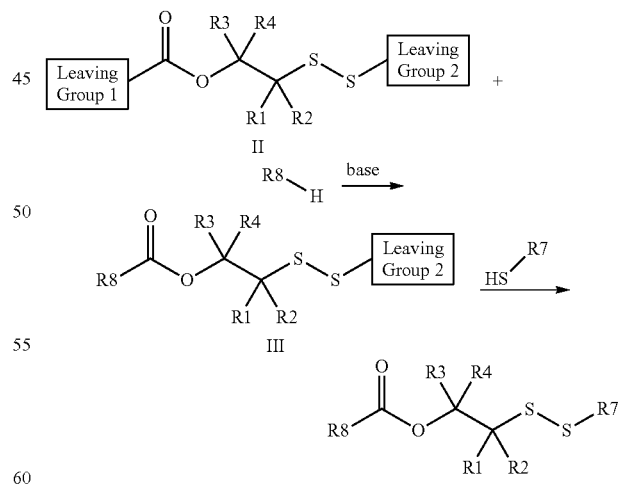

Intermediate II, which is flanked by orthogonal leaving groups, can be reacted with a nucleophilic $R^8$H compound to give Intermediate III. Intermediate III can then be reacted with a thiol containing peptide (HS—$R^7$) that participates in a disulfide exchange reaction to give the final compound. Suitable leaving groups are described below.

Scheme 2: Synthesis 1 of Thio Propionate Linked Conjugates

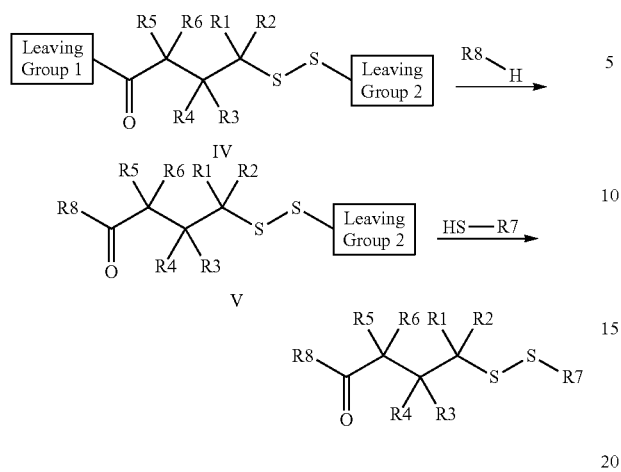

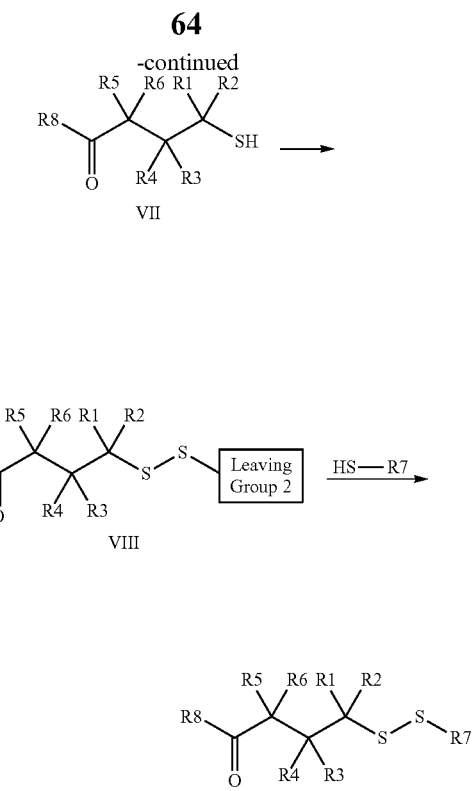

Propionate disulfide IV with previously installed Leaving Groups 1 and 2 can be reacted selectively with nucleophilic $R^8$—H to give V. This compound can then be reacted with $R^7$—SH to provide the desired conjugate.

Thionoester VI can be reacted with nucleophilic $R^8$—H to give propionate thiol VII. This compound can engage in a disulfide exchange reaction to provide Intermediate VIII. This compound can be treated with $R^7$—SH to provide the desired conjugate.

Scheme 3: Synthesis 2 of Thio Propionate Linked Conjugates

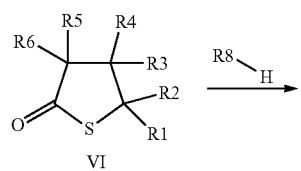

Scheme 4: Synthesis 1 of Para Benzyl-Linked Conjugates

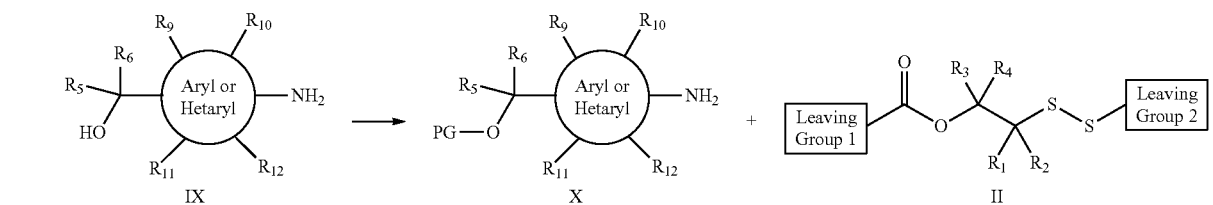

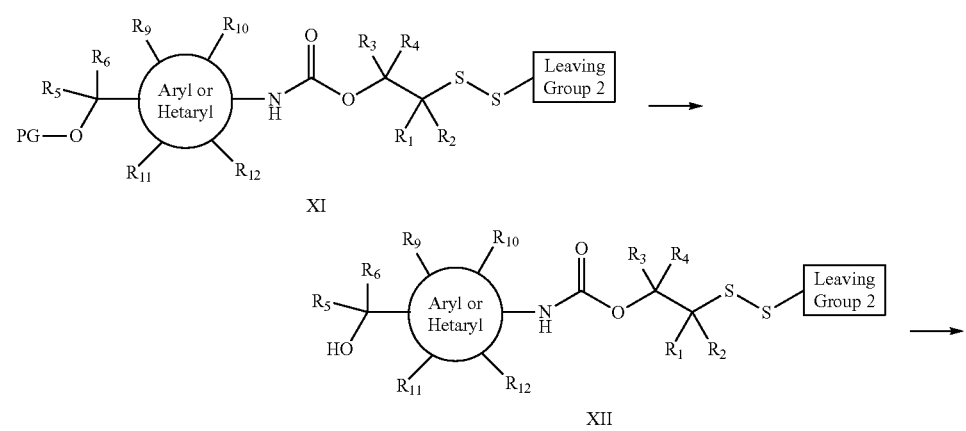

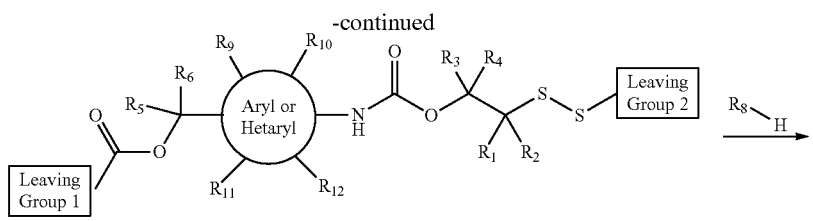

XIII

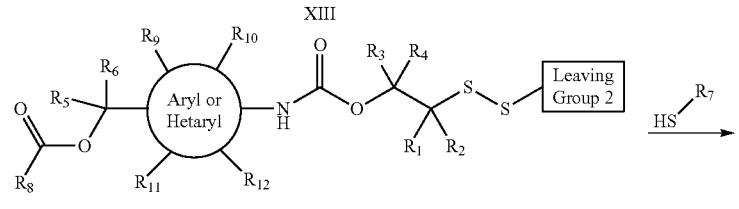

XIV

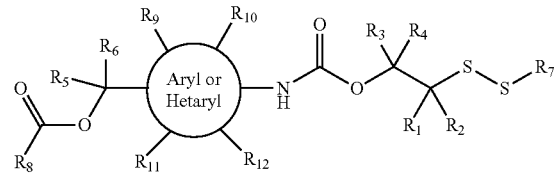

The alcohol group of para aminobenzyl alcohol IX can be selectively protected to give Intermediate X. This intermediate can then be reacted at the aniline position with Intermediate II to provide aryl carbamate XI. The protecting group can be removed giving free alcohol XII, which can be treated with an activating agent to provide Intermediate XIII, containing orthogonal leaving groups. Reaction of Intermediate XIII with $R^8$—H can provide Intermediate XIV, followed by treatment with $R^7$—SH can give the desired para benzyl-linked conjugate.

Scheme 5: Synthesis of Para Benzyl-Linked Conjugates

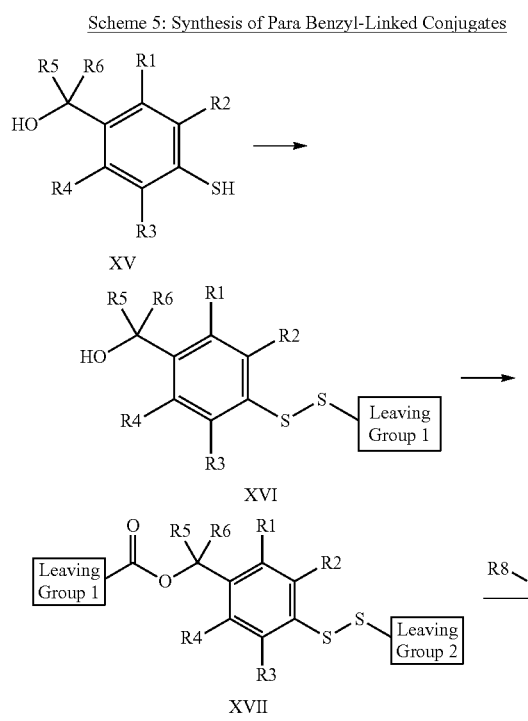

XVIII

4-Mercapto benzyl alcohol XV can be reacted in a disulfide exchange reaction to give 4-mercapto benzyl alcohol disulfide XVI containing Leaving Group 2. The remaining benzyl alcohol can be treated with an appropriate carbonyl compound to provide activated compound XVII. This intermediate can be further reacted selectively with nucleophilic $R^8$—H to provide Intermediate XVIII, which can be treated with $R^7$—SH to give the desired conjugate.

Scheme 6: Synthesis of Ortho Benzyl-Linked Conjugates

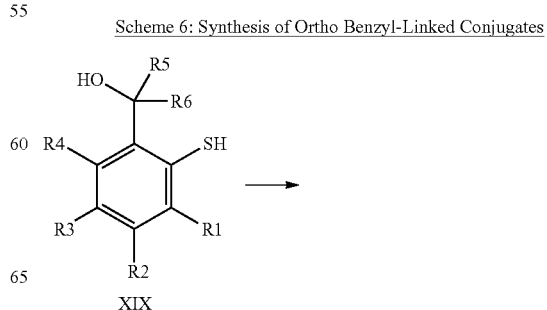

XIX

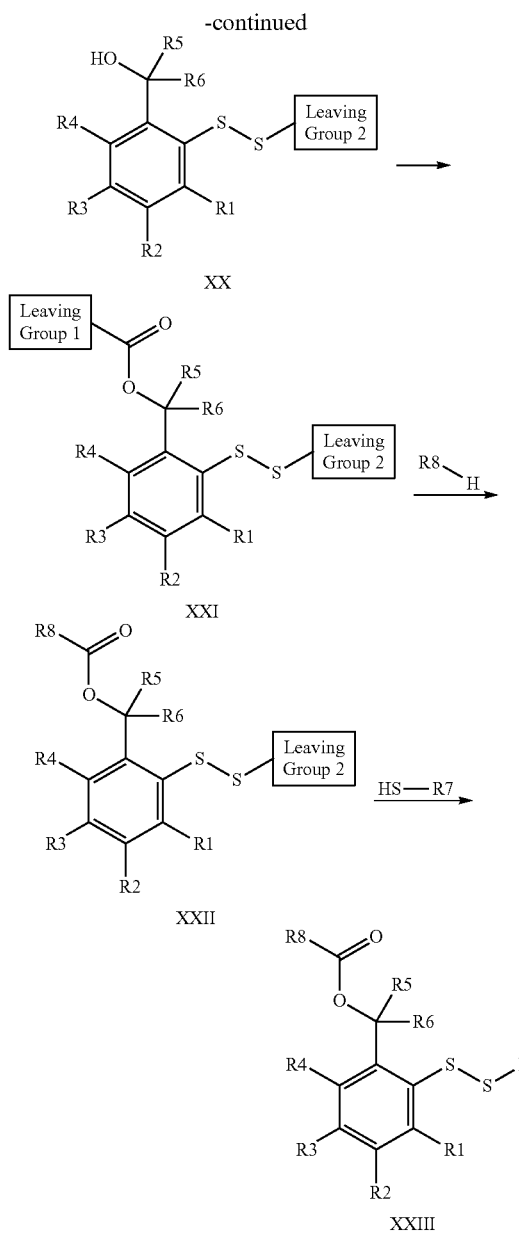

2-Mercapto benzyl alcohol XXIII can be reacted as previously described to give the desired conjugate.

Scheme 7: Cleavage of Peptide Conjugates

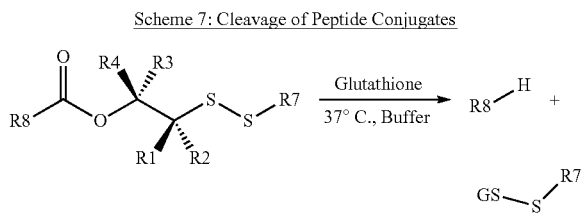

Cleavage of the final compound to release $R^8$—H can be achieved by treating the compound with an excess of glutathione (GSH) in a buffer with incubation at 37° C. Reversed phase HPLC analysis at a desired time course is used to follow the course of the cleavage.

The peptides $R^7$ may be prepared using the solid-phase synthetic method first described by Merrifield in J.A.C.S., Vol. 85, pgs. 2149-2154 (1963), although other art-known methods may also be employed. The Merrifield technique is well understood and is a common method for preparation of peptides. Useful techniques for solid-phase peptide synthesis are described in several books such as the text "Principles of Peptide Synthesis" by Bodanszky, Springer Verlag 1984. This method of synthesis involves the stepwise addition of protected amino acids to a growing peptide chain which was bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond, followed by the addition of the succeeding protected amino acids, one at a time, in a stepwise manner until the desired sequence is assembled. Finally, the protected peptide is removed from the solid resin support and the protecting groups are cleaved off.

The peptides $R^7$ may also be produced by fermentation, for example, by modification of *E. coli*. Protein production in *E. coli* can be controlled to produce recombinant polypeptides having a sequence of an $R^7$ peptide disclosed herein. Recombinant polypeptide production in *E. coli* is described in the following references: Zhao, Q., Xu, W.; Xing, L. et al. Recombinant production of medium- to large-sized peptides in *Escherichia coli* using a cleavable self-aggregating tag. *Microb Cell Fact* 15, 136 (2016); de Marco, Recombinant polypeptide production in *E. coli*: towards a rational approach to improve the yields of functional proteins; Microbial Cell Factories 2013, 12:101; and Kleiner-Grote G. M., Risse, J. M., Friehs, K, Secretion of recombinant proteins from *E. coli; Eng. Lie Sci.* 2018, 18, 532-550, each of which is incorporated by reference in its entirety.

The amino acids may be attached to any suitable polymer. The polymer must be insoluble in the solvents used, must have a stable physical form permitting ready filtration, and must contain a functional group to which the first protected amino acid can be firmly linked by a covalent bond. Various polymers are suitable for this purpose, such as cellulose, polyvinyl alcohol, polymethylmethacrylate, and polystyrene.

Methods of Use

Provided herein is the use of the compounds of formula (I) in the treatment of diseases, such as cancer or neurodegenerative disease. Another aspect of the present invention is the use of the compounds of formula (I) in the treatment of diseases involving acidic or hypoxic diseased tissue, such as cancer or neurodegenerative disease. Hypoxia and acidosis are physiological markers of many disease processes, including cancer. In cancer, hypoxia is one mechanism responsible for development of an acid environment within solid tumors. As a result, hydrogen ions must be removed from the cell (e.g., by a proton pump) to maintain a normal pH within the cell. As a consequence of this export of hydrogen ions, cancer cells often have an increased pH gradient across the cell membrane lipid bilayer and a lower pH in the extracellular milieu when compared to normal cells. One approach to improving the efficacy and therapeutic index of cytotoxic agents is to leverage this physiological characteristic to afford selective delivery of compound to hypoxic cells over healthy tissue.

In the methods of treatment of the invention, a therapeutically-effective amount of a compound of formula (I) or a pharmaceutically-acceptable salt thereof may be administered as a single agent or in combination with other forms of therapy, such as ionizing radiation or cytotoxic agents in the case of cancer. In combination therapy, the compound of formula (I) may be administered before, at the same time as, or after the other therapeutic modality, as will be appreciated by those of skill in the art. Either method of treatment (single agent or combination with other forms of therapy) may be administered as a course of treatment involving multiple doses or treatments over a period of time.

Examples of cancers that are treatable using the compounds of the present disclosure include, but are not limited to, colorectal cancer, gastric cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure include bladder cancer, bone cancer, glioma, breast cancer (e.g., triple-negative breast cancer), cervical cancer, colon cancer, colorectal cancer, endometrial cancer, epithelial cancer, esophageal cancer, Ewing's sarcoma, pancreatic cancer, gallbladder cancer, gastric cancer, gastrointestinal tumors, head and neck cancer (upper aerodigestive cancer), intestinal cancers, Kaposi's sarcoma, kidney cancer, laryngeal cancer, liver cancer (e.g., hepatocellular carcinoma), lung cancer (e.g., non-small cell lung cancer, adenocarcinoma), melanoma, prostate cancer, rectal cancer, renal clear cell carcinoma, skin cancer, stomach cancer, testicular cancer, thyroid cancer, and uterine cancer.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

The compounds of the invention (e.g., a compound of formula (I)) comprising a topoisomerase I targeting moiety derived from a topoisomerase I inhibitor (e.g., exatecan) can exhibit certain therapeutic advantages over the topoisomerase I inhibitor itself. For example, administration of a compound of formula (I) can show reduced toxicity (e.g., bone marrow or gastric toxicity) as compared with administration of the corresponding topoisomerase I inhibitor (e.g., exatecan). In some embodiments, the bone marrow toxicity is measured by total bone marrow count from samples of the subject (e.g., total bone marrow count in femurs of a mouse). In some embodiments, bone marrow toxicity is measured by PARylation in bone marrow tissue. In some embodiments, bone marrow toxicity is measured according to total nucleated bone marrow cells. In some embodiments, gastric toxicity is assessed using photographs of the stomachs of the subject (e.g., a mouse) taken both in situ and ex vivo.

In certain embodiments, a compound of formula (I) or a pharmaceutically-acceptable salt thereof may be used in combination with a chemotherapeutic agent, a targeted cancer therapy, an immunotherapy or radiation therapy. The agents can be combined with the present compounds in a single dosage form, or the agents can be administered simultaneously or sequentially as separate dosage forms. In some embodiments, the chemotherapeutic agent, targeted cancer therapy, immunotherapy or radiation therapy is less toxic to the patient, such as by showing reduced bone marrow or gastric toxicity, when administered together with a compound of formula (I), or a pharmaceutically acceptable salt thereof, as compared with when administered in combination with the corresponding topoisomerase inhibitor (e.g., $R^8$—H).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents that can be administered in combination with the compounds of the invention include, for example, navelbene, CPT-11, anastrazole, letrazole, capecitabine, reloxafine, cyclophosphamide, ifosamide, and droloxafine.

Also suitable are cytotoxic agents such as, for example, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-α, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines that can be administered in combination with the compounds of the invention include, for example, dendritic cells, synthetic peptides, DNA vaccines and recombinant viruses.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or administered in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with the compounds of the invention. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with compounds of the invention. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds of the invention. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention. A further example of a PARP inhibitor that can be combined with a compound of the invention is talazoparib.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

The phrase "therapeutically effective amount" of a compound (therapeutic agent, active ingredient, drug, etc.) refers to an amount of the compound to be administered to a subject in need of therapy or treatment which alleviates a symptom, ameliorates a condition, or slows the onset of disease conditions, according to clinically acceptable standards for the disorder or condition to be treated. For instance, a therapeutically effective amount can be an amount which has been demonstrated to have a desired therapeutic effect in an in vitro assay, an in vivo animal assay, or a clinical trial. The therapeutically effective amount can vary based on the particular dosage form, method of administration, treatment protocol, specific disease or condition to be treated, the benefit/risk ratio, etc., among numerous other factors.

Said therapeutically effective amount can be obtained from a clinical trial, an animal model, or an in vitro cell culture assay. It is known in the art that the effective amount suitable for human use can be calculated from the effective amount determined from an animal model or an in vitro cell culture assay. For instance, as reported by Reagan-Shaw et al., FASEB J. 2008: 22(3) 659-61, "µg/ml" (effective amount based on in vitro cell culture assays)="mg/kg body weight/day" (effective amount for a mouse). Furthermore, the effective amount for a human can be calculated from the effective amount for a mouse based on the fact that the metabolism rate of mice is 6 times faster than that of humans.

As an example of treatment using a compound of formula (I) in combination with a cytotoxic agent, a therapeutically-effective amount of a compound of formula (I) may be administered to a patient suffering from cancer as part of a treatment regimen also involving a therapeutically-effective amount of ionizing radiation or a cytotoxic agent. In the context of this treatment regimen, the term "therapeutically-effective" amount should be understood to mean effective in the combination therapy. It will be understood by those of skill in the cancer-treatment field how to adjust the dosages to achieve the optimum therapeutic outcome.

Similarly, the appropriate dosages of the compounds of the invention for treatment of non-cancerous diseases or conditions (such as cardiovascular diseases) may readily be determined by those of skill in the medical arts.

The term "treating" as used herein includes the administration of a compound or composition which reduces the frequency of, delays the onset of, or reduces the progression of symptoms of a disease involving acidic or hypoxic diseased tissue, such as cancer, stroke, myocardial infarction, or long-term neurodegenerative disease, in a subject relative to a subject not receiving the compound or composition. This can include reversing, reducing, or arresting the symptoms, clinical signs, or underlying pathology of a condition in a manner to improve or stabilize a subject's condition (e.g., regression of tumor growth, for cancer or decreasing or ameliorating myocardial ischemia reperfusion injury in myocardial infarction, stroke, or the like cardiovascular disease). The terms "inhibiting" or "reducing" are used for cancer in reference to methods to inhibit or to reduce tumor growth (e.g., decrease the size of a tumor) in a population as compared to an untreated control population.

All publications (including patents) mentioned herein are incorporated herein by reference for the purpose of describing and disclosing, for example, the constructs and methodologies that are described in the publications, which might be used in connection with the disclosure herein described. The publications discussed throughout the text are provided solely for their disclosure prior to the filing date of the present application.

Disclosed herein are several types of ranges. When a range of any type is disclosed or claimed, the intent is to disclose or claim individually each possible number that such a range could reasonably encompass, including end points of the range as well as any sub-ranges and combinations of sub-ranges encompassed therein. When a range of therapeutically effective amounts of an active ingredient is disclosed or claimed, for instance, the intent is to disclose or claim individually every possible number that such a range could encompass, consistent with the disclosure herein. For example, by a disclosure that the therapeutically effective amount of a compound can be in a range from about 1 mg/kg to about 50 mg/kg (of body weight of the subject).
Formulation, Dosage Forms and Administration To prepare the pharmaceutical compositions of the present invention, a compound of Formula (I) or a pharmaceutically-acceptable salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. One of skill in the pharmaceutical and medical arts will be able to readily determine a suitable dosage of the pharmaceutical compositions of the invention for the particular disease or condition to be treated.

EXAMPLES

As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997. The following definitions describe terms and abbreviations used herein:

Brine: a saturated NaCl solution in water
DCM: dichloromethane
TFA: trifluoroacetic acid
DIPEA: diisopropylethylamine
DMA: dimethylacetamide
DME: dimethoxyethane
DMF: dimethylformamide
DMSO: methylsulfoxide
DTT: dithiothreitol
MSD: mass spec detector
$Et_2O$: ethyl ether
EtOAc: ethyl acetate
EtOH: ethyl alcohol
HATU: O-(7-azabenzotriazol-1-yl)-N,N,N',N'-tetramethyluronium hexafluorophosphate
HOBt: 1-hydroxybenzotriazole
RP: reverse phase
HPLC: high performance liquid chromatography
IPA: isopropanol
LAH: lithium aluminum hydride
N-BuLi: n-butyl lithium
LC-MS: liquid chromatography-mass spectrometry
LDA: lithium diisoproylethylamide
Me: methyl
MeOH: methanol
MTBE: methyl t-butyl ether
NMP: N-methylpyrrolidine
Ph: phenyl
PNPC: para-nitrophenylchloroformate
RT or rt: room temperature SFC: supercritical fluid chromatography
TBAI: tetrabutylammonium iodide
TBME: tert-butylmethyl ether
tBu: tertiary butyl
THF: tetrahydrofuran
TEA: triethylamine
TMEDA: tetramethylethylenediamine
GSH: Glutathione
GS: Glutathione bonded at sulfur
LiOH: lithium hydroxide
DPPA: diphenyl phosphoryl azide Sn(Bu)$_2$(Laurate)$_2$: dibutyltin dilaurate
PBS: phosphate buffered saline
ACN: acetonitrile
AcOH: acetic acid
EEDQ: N-ethoxycarbonyl-2-ethoxy-1,2-dihydroquinoline
DMAP: 4-dimethylaminopyridine
EDC: 1-ethyl-3-(3-dimethylaminopropyl)carbodiimide The source of the starting materials employed in the Examples are set forth below in the following tables.

TABLE 2

| | Starting materials for R$^8$ | |
|---|---|---|
| R$^8$ Code | R$^8$H Structure | Synthesis Reference or Purchased |
| R$^8$H-1 | | Medchem Express HY-16560 |
| R$^8$H-2 | | MedKoo 406280 |
| R$^8$H-3 | | AstaTech F11420 |
| R$^8$H-4 | | AstaTech 42333 |

TABLE 2-continued

| | Starting materials for R⁸ | |
|---|---|---|
| R⁸ Code | R⁸H Structure | Synthesis Reference or Purchased |
| R⁸H-5 | | Medchem Express HY-13631A |
| R⁸H-6 | | Medchem Express HY-13631D |
| R⁸H-7 | | AstaTech 21428 |
| R⁸H-8 | | Medchem Express HY-14812 |

TABLE 2-continued

| Starting materials for R⁸ | | |
|---|---|---|
| R⁸ Code | R⁸H Structure | Synthesis Reference or Purchased |
| R⁸H-9 | | US 20030105109 A1 |
| R⁸H-10 | | WO 9902530 A1 |
| R⁸H-11 | | Medchem Express: Cat. No.: HY-16562 |

TABLE 2-continued

Starting materials for R⁸

| R⁸ Code | R⁸H Structure | Synthesis Reference or Purchased |
|---|---|---|
| R⁸H-12 | [Structure: fluorinated methyl-substituted camptothecin analog with CH₂NH₂ group] | Widdison et al., ACS Medicinal Chemistry Letters 2019 10 (10), 1386-1392 |

TABLE 3

Starting Materials for Linkers

| Linker Code | Linker Structure | Synthetic Reference or Purchased |
|---|---|---|
| L-1 | HO–CH₂–CH(CH₃)–SH | Synthesized WO2013055987A1 |
| L2 | HO–CH₂–CH(CH₃)–SH | Synthesized WO2013055987A1 |
| L3 | HO–CH₂–C(cyclobutyl)–SH | Synthesized ACS Med. Chem. Lett. 2016, 7, 988-993 |
| L4 | HO–CH(CH₃)–CH(CH₃)–SH | R, R* |
| L5 | HO–CH(CH₃)–CH(CH₃)–SH | S, S* |
| L6 | HO–CH(CH₃)–CH(CH₃)–SH | R, S* |
| L7 | HO–CH(CH₃)–CH(CH₃)–SH | S, R* |
| L8 | HO–(cyclohexyl)–SH | R, R* |
| L9 | HO–(cyclohexyl)–SH | S, S* |
| XV-1 | HO–CH₂–C₆H₄–SH (para) | Combiblocks OR-5865 |

*Absolute configuration randomly assigned

The HPLC methods employed are set forth below:

HPLC Methods

A: Sunfire C18 150×4.6 mm; H₂O/Acetonitrile w/TFA modifier (0.05%); Flow rate: 1 ml/min; Wavelength=217 nM.

B: Ace Equivalence 250×4.6 mm; H₂O/Acetonitrile w/TFA modifier (0.05%); Flow rate: 1 ml/min; Wavelength=217 nM.

C: Sunfire C18 150×30 mm; H₂O/Acetonitrile w/TFA modifier (0.05%); Flow rate: 30 ml/min; Wavelength=217 nM.

Mass Spectrometry Methods

Maldi-TOF (Matrix-assisted laser desorption/ionization-Time of Flight) mass spectrometry was measured on an Applied Biosystems Voyager System 6268. The sample was prepared as a matrix of α-cyano hydroxy cinnamic acid on an AB Science plate (Part #V700666).

ESI (Electrospray Ionization) mass spectrometry was measured on either an Agilent 1100 series LC-MS with a 1946 MSD or a Waters Xevo Qtof high-resolution MS, both providing a mass/charge species (m/z=3).

Synthesis of cis-S-(3-hydroxybutan-2-yl) ethanethioate (L-4 and L-5)

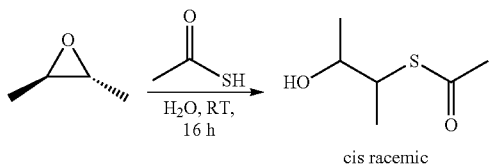

cis racemic

To a stirred solution of trans-2,3-dimethyloxirane (5.0 g, 69.3 mmol) in water (50 mL) was added thioacetic acid (5.8 mL, 76.2 mmol) at room temperature. The reaction mixture was stirred at room temperature for 16 h. The reaction mixture was quenched with sat. sodium bicarbonate solution (10 mL) and extracted with ethyl acetate (200 mL). The organic layer was dried over anhydrous sodium sulphate and then evaporated under reduced pressure to afford cis-S-(3-hydroxybutan-2-yl) ethanethioate as an oily compound (4.0 g, crude). MS m/z 149.0 [M+H]$^+$.

Synthesis of cis-3-Mercaptobutan-2-ol

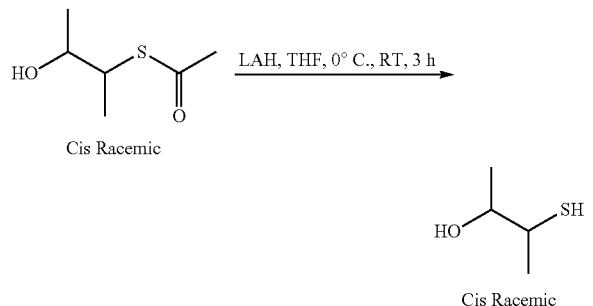

Cis Racemic

To a stirred solution of S-(3-hydroxybutan-2-yl) ethanethioate (4 g, 26.9 mmol) in THF (40 mL) was added lithium aluminum hydride (1M solution in THF) (27 mL, 26.9 mmol) drop wise at 0° C. The Reaction mixture was gradually allowed to warm to room temperature and stirred for 3 hours. The reaction mixture was quenched slowly with 1N HCl at 0° C. and pH was adjusted to 2-3. The reaction mixture was extracted in ethyl acetate (50 mL) and the organic layer was dried over anhydrous sodium sulphate and evaporated off to obtain cis-3-mercaptobutan-2-ol as a crude oily compound.

Synthesis of trans-S-(3-hydroxybutan-2-yl) ethanethioate (L-6 and L-7)

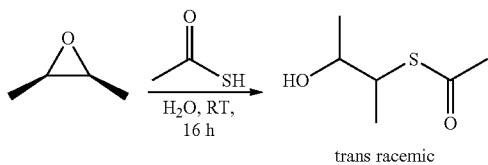

trans racemic

To a stirred solution of cis-2,3-dimethyloxirane (1.0 g, 13.9 mmol) in water (15 mL) was added thioacetic acid (1.1 mL, 15.6 mmol) at room temperature and stirred for 16 h. The reaction mixture was quenched with sodium bicarbonate solution (10 mL) and extracted with ethyl acetate (20 mL). The organic layer was dried over anhydrous sodium sulphate and then evaporated under reduced pressure to afford trans-S-(3-hydroxybutan-2-yl) ethanethioate as yellow oil (0.7 g crude).

Synthesis of trans-3-mercaptobutan-2-ol

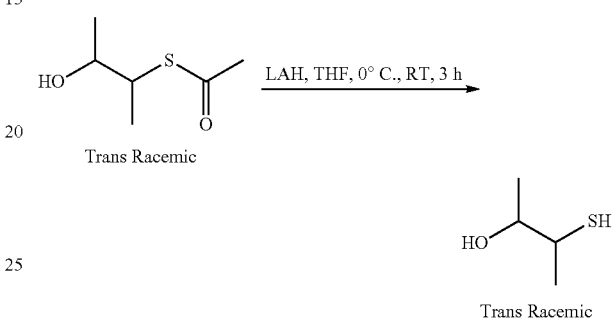

Trans Racemic

To a stirred solution of trans-S-(3-hydroxybutan-2-yl) ethanethioate (700 mg, 4.72 mmol) in THF (10 mL) was added lithium aluminum hydride (1M solution in THF) (4.8 mL, 4.72 mmol) drop wise at 0° C. and stirred at the same temperature for 3 h. The reaction mixture was quenched with 1N HCl at 0° C. then pH was adjusted to 2-3. The reaction mixture was extracted with CH$_2$Cl$_2$ (10 mL). The organic layer was dried over anhydrous sodium sulphate and taken directly for next step.

Synthesis of trans-S-(2-hydroxycyclohexyl) ethanethioate (L-8 and L-9)

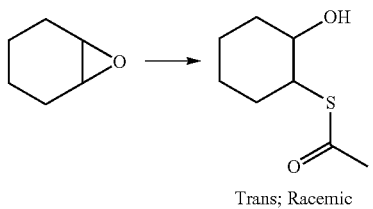

Trans; Racemic

To a stirred solution of 7-oxabicyclo[4.1.0]heptane (5.0 g, 51.0 mmol) in water (50.0 mL) was added thioacetic acid (4.92 mL, 61.0 mmol). The reaction mixture was stirred for 16 h at room temperature. Progress of the reaction was monitored by TLC (20% EtOAc/Hexane). After completion of reaction, the reaction mixture was diluted with diethyl ether. The organic layer was separated and washed with brine, dried over anhydrous sodium sulphate and concentrated under reduced pressure to afford trans-S-(2-hydroxycyclohexyl) ethanethioate as a brown color liquid (3.8 g crude).

Synthesis of trans-2-mercaptocyclohexan-1-ol

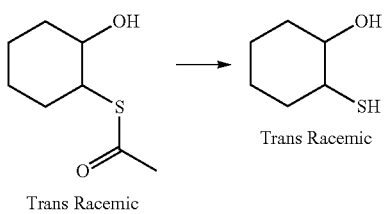

Trans Racemic → Trans Racemic

To a stirred solution of trans-S-(2-hydroxycyclohexyl) ethanethioate ate (3.8 g, 21.8 mmol) in THF (20.0 mL) was added 1M LiAH4 in THF (21.8 mL, 21.8 mmol) at 0° C. The reaction mixture was gradually allowed to warm to room temperature and stirred for 1 h. Progress of the reaction was monitored by TLC (20% EtOAc/Hex). Upon completion of the reaction, the reaction mixture was cooled to room temperature and quenched with 1.0 N HCl (30 mL). The reaction mixture was extracted in $CH_2Cl_2$ (30.0 mL). The organic layer was washed with brine solution (30.0 mL), concentrated and crude trans-2-sulfanylcyclohexanol taken for next step. (2.88 g, crude).

Synthesis of Intermediate I from L

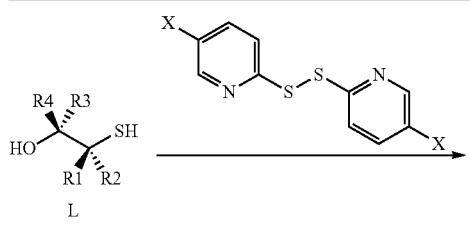

| Int. | $R^1$, $R^2$ | $R^3$, $R^4$ | X | Method/Ref. | $MH^+$ |
|---|---|---|---|---|---|
| I-1 | H, Me | H, H | H | WO2013055987A1 | 202.1 |
| I-2 | Me, H | H, H | H | WO2013055987A1 | 202.1 |
| I-3 | —$CH_2CH_2CH_2$— | H, H | $NO_2$ | ACS Med. Chem. Lett. 2016, 7, 988-993 | 272.9 |
| I-4 | H, Me | Me, H | H | | 216.1 |
| I-5 | Me, H | H, Me | H | | 216.1 |
| I-6 | Me, H | Me, H | H | | 215.9 |
| I-7 | H, Me | H, Me | H | | 216.2 |
| I-8 | $CH_2$, H / $CH_2CH_2CH_2CH_2$ | $CH_2$, H | H | | |
| I-9 | H, $CH_2$ / $CH_2CH_2CH_2CH_2$ | H, $CH_2$ | H | | |

Synthesis of Intermediate I-1: (2R)-2-(2-pyridyldisulfanyl)propan-1-ol

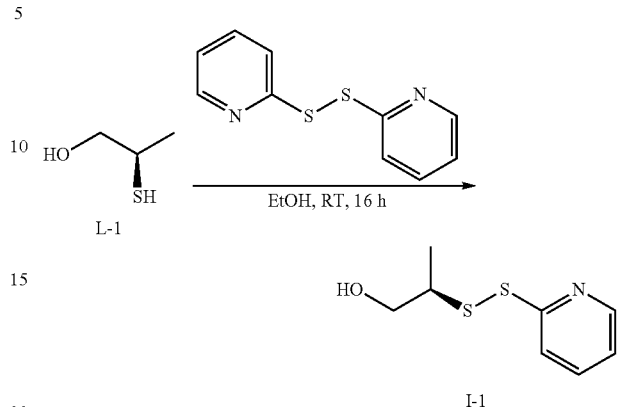

To 2-(2-pyridyldisulfanyl)pyridine (5.00 g, 22.7 mmol) in 40 ml of MeOH degassed with $N_2$ was added (2R)-2-sulfanylpropan-1-ol (0.75 g, 8.14 mmol) in a drop-wise fashion. The mixture was stirred for 2 h under Na. The mixture was concentrated to dryness and directly loaded onto a $SiO_2$ flash column and eluted with 0-50% EtOAc/Hexanes to give 1.17 g, 71% of (2R)-2-(2-pyridyldisulfanyl)propan-1-ol. MS m/z 202.1 $[M+H]^+$.

Intermediate I-2 was prepared from L-2 in an analogous manner

Synthesis of Intermediate I-3: [1-[(5-nitro-2-pyridyl)disulfanyl]cyclobutyl]methanol

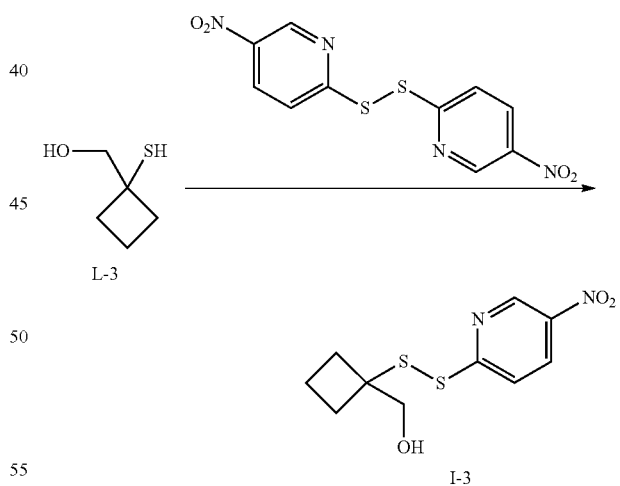

To a solution of 5-nitro-2-[(5-nitro-2-pyridyl)disulfanyl]pyridine (17.4 g, 56.0 mmol) in degassed ($N_2$) MeOH (100 mL) was added (1-mercaptocyclobutyl)methanol (8.3 mL, 70.0 mmol) (degassed with $N_2$) in a dropwise manner and stirred for 16 h at room temperature under $N_2$ atmosphere. The reaction mixture was concentrated to dryness under vacuum. The resultant crude was purified by column chromatography using 30% EtOAc/hexanes to afford [1-[(5-nitro-2-pyridyl)disulfanyl]cyclobutyl]methanol as a yellow liquid (9.0 g, 46% yield). MS m/z 272.9 $[M+H]^+$.

Synthesis of I-4 and I-5:
3-(pyridin-2-yldisulfanyl)butan-2-ol Isomer 1 and Isomer 2

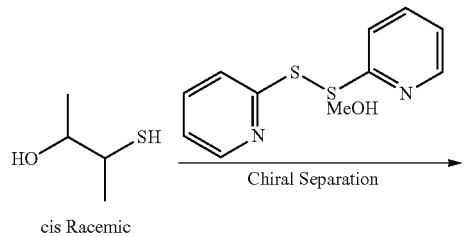

cis Racemic

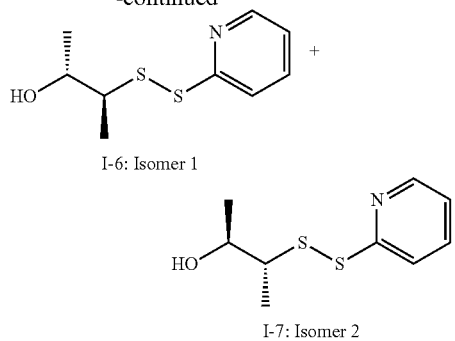

I-5: Isomer 1

I-4: Isomer 2

A stirred solution 2,2-dipyridyldisulfide (520 mg, 2.35 mmol) in MeOH (15 mL) was purged with nitrogen gas for 5 min. Nitrogen gas purged solution of cis-3-mercaptobutan-2-ol (500 mg) in $CH_2Cl_2$ (10 mL) was added to it at 0° C. The reaction mixture was gradually allowed to warm to room temperature and stirred for 16 h. The reaction mixture was concentrated under reduced pressure to afford crude material which was purified by column chromatography using 30-40% EA/hexane. The racemic product was separated with Chiral Prep HPLC (CHIRALPAK IG; 100 mm×4.6 mm×3 mic; Mobile phase: nHexane:Ethanol 80:20 with 0.1% DEA; Flow rate: 1.0 mL/min) to separate the respective enantiomers. Solvents were removed to obtain (2S,3S)-3-(2-pyridyldisulfanyl)butan-2-ol* (140 mg, Isomer-1) MS m/z 216.1 [M+H]$^+$ and (2R,3R)-3-(2-pyridyldisulfanyl)butan-2-ol (140 mg, Isomer-2). MS m/z 216.1 [M+H]$^+$.

Synthesis of I-6 and I-7:
3-(pyridin-2-yldisulfanyl)butan-2-ol Isomer 1 and Isomer 2

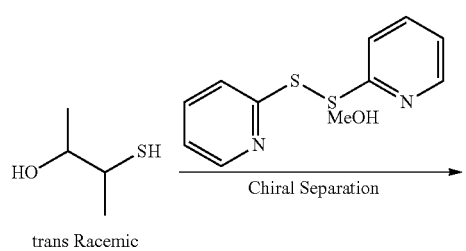

trans Racemic

I-6: Isomer 1

I-7: Isomer 2

A stirred solution 2,2-dipyridyldisulfide (520 mg, 2.35 mmol) in MeOH (15 mL) was purged with nitrogen gas for 5 min. Nitrogen gas purged solution of cis-3-mercaptobutan-2-ol (500 mg) in $CH_2Cl_2$ (10 mL) was added to it at 0° C. The reaction mixture was gradually allowed to warm to room temperature and stirred for 16 h. The reaction mixture was concentrated under reduced pressure to afford crude material which was purified by column chromatography using 30-40% EA/hexane. The racemic product was separated with Chiral Prep HPLC (Column: CHIRALPAK IG (100 mm×4.6 mm×3 mic) Mobile phase: nHexane:Ethanol with 0.1% DEA (80:20) Flow rate: 1.0 mL/min) to separate the respective enantiomers. Solvents were removed to obtain (2R,3S)-3-(2-pyridyldisulfanyl)butan-2-ol* (0.6 g, Isomer-I) MS m/z 215.9 [M+H]$^+$ and (2S,3R)-3-(2-pyridyldisulfanyl)butan-2-ol* (0.6 g, Isomer-II) MS m/z 216.2 [M+H]$^+$ as oily compounds.

Synthesis Intermediate I-6:
Trans-2-(pyridin-2-yldisulfanyl)cyclohexan-1-ol

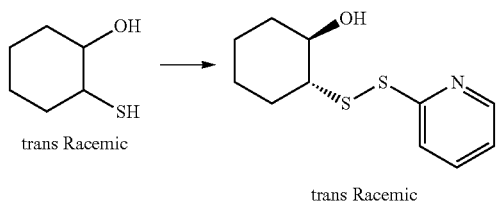 [SMILES: OC1CCCCC1S ; O[C@@H]1CCCC[C@H]1SSc1ccccn1]

trans Racemic trans Racemic

To a solution of 1,2-di(pyridin-2-yl)disulfane (2.41 g, 10.9 mmol) in MeOH (degassed with $N_2$) (30 mL) was added trans-2-sulfanylcyclohexanol (2.88 g, 21.0 mmol) (degassed with $N_2$) dropwise and stirred for 16 h at room temperature under $N_2$ atmosphere. The reaction mixture was concentrated to dryness under vacuum. The resultant crude was purified by column chromatography using 30% of EtOAc/hexanes to afford trans-2-(pyridin-2-yldisulfanyl)cyclohexan-1-ol as a yellow color liquid.

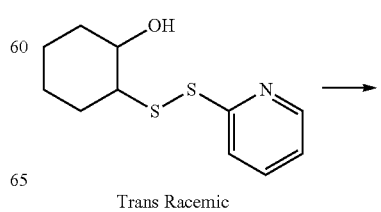

Trans Racemic

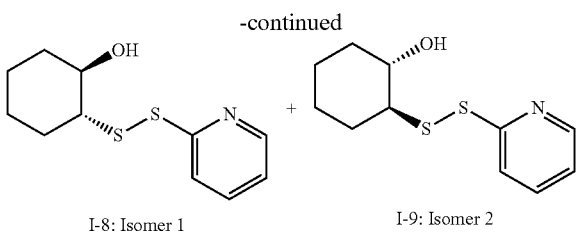

I-8: Isomer 1   I-9: Isomer 2

Chiral separation was done by chiralpak IG (100 mm×4.6 mm×3 mic) using n-hexane: IPA with 0.1% diethylamine (80:20) to afford (1R,2R)-2-(2-pyridyldisulfanyl)cyclohexanol* Isomer-1 (350 mg) and (1S,2S)-2-(2-pyridyldisulfanyl)cyclohexanol* Isomer-2 (400 mg).

Intermediate XV from XXI

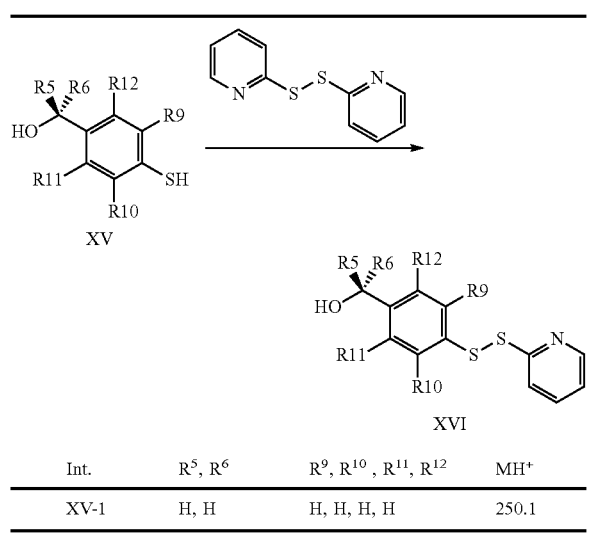

| Int. | $R^5$, $R^6$ | $R^9$, $R^{10}$, $R^{11}$, $R^{12}$ | MH+ |
|---|---|---|---|
| XV-1 | H, H | H, H, H, H | 250.1 |

Synthesis of Intermediate XV-1:
[4-(2-pyridyldisulfanyl)phenyl]methanol

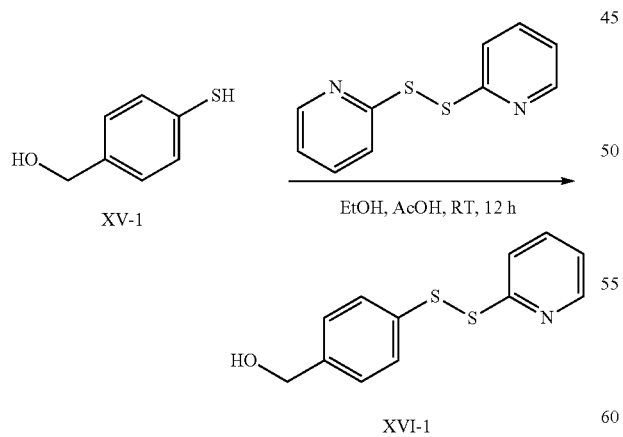

A stirred solution of 1,2-di(pyridin-2-yl)disulfane (2.68 g, 12.1 mmol) in mixture of AcOH:ethanol (5 mL, 1:10) solvent was degassed under $N_2$. This was followed by addition of 4-mercaptophenyl)methanol (0.74 g, 5.2 mmol) in mixture of AcOH/ethanol (5 mL) solvent drop-wise over 20 min and stirred for 12 h under $N_2$ atmosphere at room temperature. The reaction was concentrated under reduced pressure to afford the crude product which is purified by column chromatography ($SiO_2$, 60-70% EtOAc/hexanes) to afford [4-(2-pyridyldisulfanyl)phenyl]methanol as a colourless liquid (800 mg, 61% yield).

Carbonate Leaving Group Intermediate II from Intermediate I

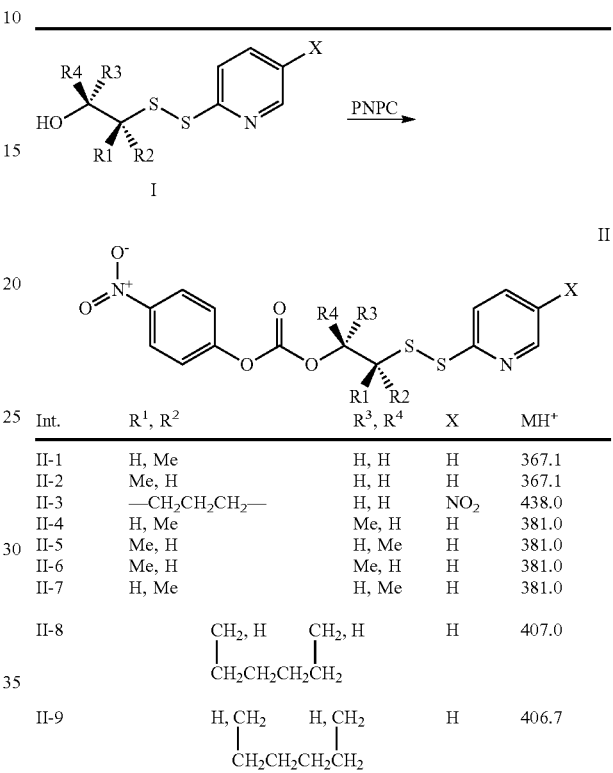

| Int. | $R^1$, $R^2$ | $R^3$, $R^4$ | X | MH+ |
|---|---|---|---|---|
| II-1 | H, Me | H, H | H | 367.1 |
| II-2 | Me, H | H, H | H | 367.1 |
| II-3 | —$CH_2CH_2CH_2$— | H, H | $NO_2$ | 438.0 |
| II-4 | H, Me | Me, H | H | 381.0 |
| II-5 | Me, H | H, Me | H | 381.0 |
| II-6 | Me, H | Me, H | H | 381.0 |
| II-7 | H, Me | H, Me | H | 381.0 |
| II-8 | $CH_2$, H $\|$ $CH_2CH_2CH_2CH_2$ | $CH_2$, H | H | 407.0 |
| II-9 | H, $CH_2$ $\|$ $CH_2CH_2CH_2CH_2$ | H, $CH_2$ | H | 406.7 |

Synthesis of II-1: (4-nitrophenyl) [(2R)-2-(2-pyridyldisulfanyl)propyl] carbonate

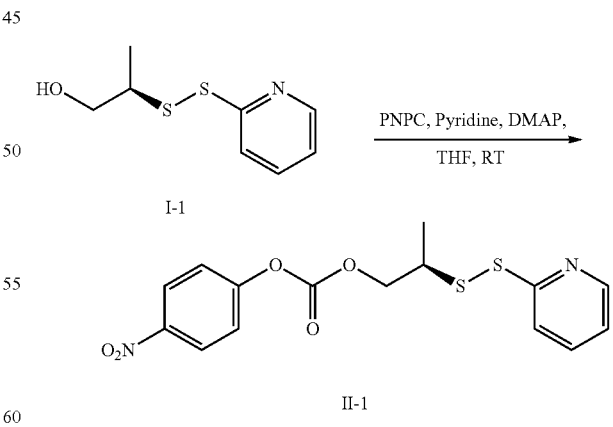

To (2R)-2-(2-pyridyldisulfanyl)propan-1-ol (0.39 g, 1.94 mmol) in THF under $N_2$ was added pyridine (0.16 mL, 1.94 mmol) and the (4-nitrophenyl) carbonochloridate (0.59 g, 2.91 mmol). The mixture was stirred for 16 h under Na. The mixture was diluted with EtOAc and quenched with 20 mL of sat. $NH_4Cl$. The mixture was washed with water and brine and the organic layer concentrated. The crude mixture was purified by column chromatography (SiO₂, 0-50% EtOAc/Hexanes) to afford 0.59 g, 83% of (4-nitrophenyl) [(2R)-2-(2-pyridyldisulfanyl)propyl] carbonate. MS m/z found 367.1 [M+H]⁺.

Intermediates II-2 and II-3 were synthesized analogously to II-1.

Synthesis of II-4: 4-nitrophenyl((2R,3R)-3-(pyridin-2-yldisulfanyl)butan-2-yl) carbonate

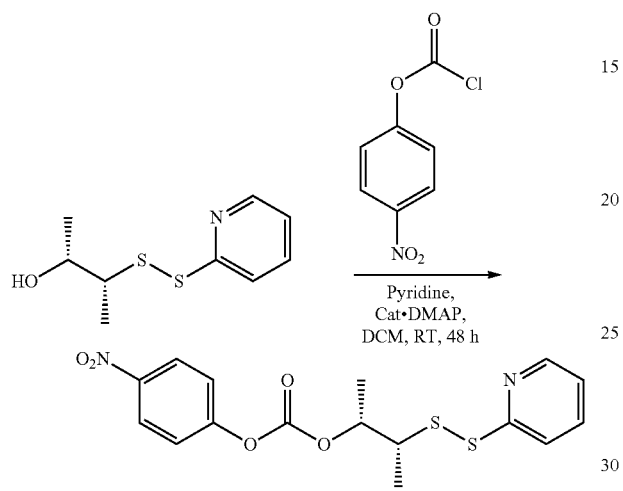

To a stirred solution of (2R,3R)-3-(pyridin-2-yldisulfanyl) butan-2-ol (140 mg, 0.651 mmol) in CH₂Cl₂ (2.0 mL) was added pyridine (0.11 mL, 1.43 mmol), 4-nitrophenyl carbonochloridate (150 mg, 0.781 mmol) and catalytic amount of 4-dimethylaminopyridine at room temperature. The reaction vessel was sealed and stirred at RT for 48 h. The reaction mixture was diluted with CH₂Cl₂ (10 mL) and then washed with water (10 mL). The organic layer was dried over anhydrous sodium sulphate and concentrated under reduced pressure to afford crude which is purified by column chromatography using 30-40% ethyl acetate/hexane. The fractions were concentrated off to obtain crude which was further purified over C18 reverse phase column. The pure fractions are concentrated to obtain 4-nitrophenyl ((2R,3R)-3-(pyridin-2-yldisulfaneyl)butan-2-yl) carbonate (70 mg, 28%) as an oily compound. MS m/z 381.0 [M+H]⁺.

Synthesis of II-5: 4-nitrophenyl((2S,3S)-3-(pyridin-2-yldisulfanyl)butan-2-yl) carbonate

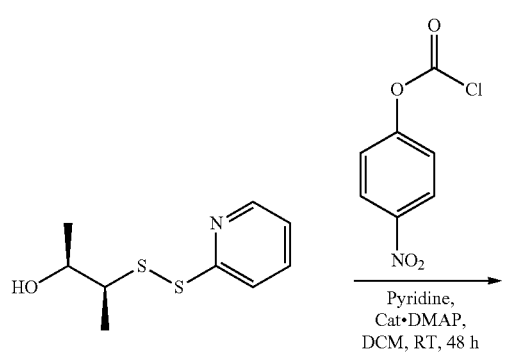

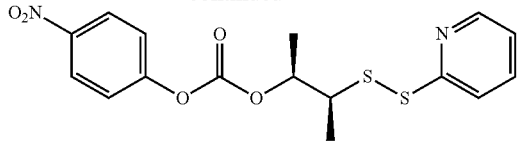

To a stirred solution of (2S,3S)-3-(pyridin-2-yldisulfanyl) butan-2-ol (80 mg, 0.372 mmol) in CH₂Cl₂ (1.0 mL) was added pyridine (0.066 mL, 0.818 mmol), 4-nitrophenylcarbonochloridate (89 mg, 0.446 mmol) and catalytic amount of 4-dimethylaminopyridine at room temperature. The reaction vessel was sealed and stirred at RT for 48 h. The reaction mixture was diluted with CH₂Cl₂ (5 mL) and then washed with water (5 mL). The organic layer was dried over anhydrous sodium sulphate and concentrated under reduced pressure to afford the crude titular product which was purified by column chromatography using 30-40% ethyl acetate/Hexane. The fractions were concentrated to obtain crude which was further purified over C18 reverse phase column. The pure fractions are concentrated to obtain 4-nitrophenyl ((2S,3S)-3-(pyridin-2-yldisulfanyl)butan-2-yl) carbonate (140 mg, 58%) as an oily compound. MS m/z 381.0 [M+H]⁺.

Synthesis of II-6: 4-nitrophenyl((2R,3S)-3-(pyridin-2-yldisulfanyl)butan-2-yl) carbonate

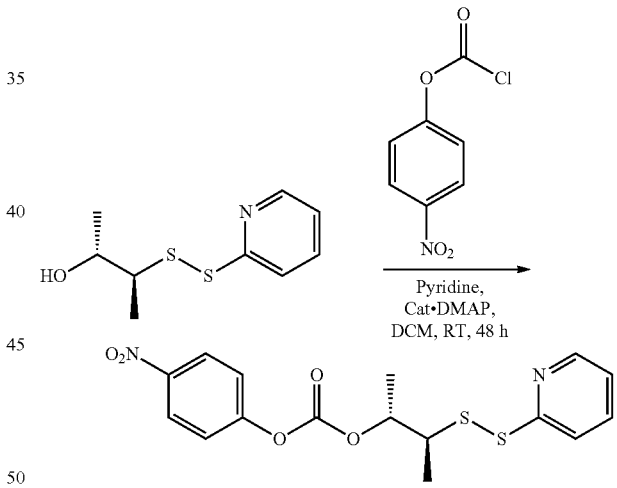

To a stirred solution of (2R,3S)-3-(pyridin-2-yldisulfanyl) butan-2-ol (0.4 g, 1.86 mmol) in CH₂CL₂ (10 mL) was added pyridine (0.36 mL, 4.09 mmol), 4-nitrophenyl carbonochloridate (0.44 g, 2.32 mmol) and catalytic amount of 4-dimethylaminopyridine at 0° C. The reaction vessel was sealed and stirred at room temperature for 48 h. The reaction mixture was diluted with CH₂Cl₂ (20 mL) and washed with water (20 mL). The organic layer was dried over anhydrous sodium sulphate and concentrated under reduced pressure to afford crude which was purified by silica gel flash column chromatography using 30-40% ethyl acetate/hexane. The compound eluted out as a mixture in 30% EtOAc:Hexane. The fractions were concentrated to obtain crude which is further purified over C18 reverse phase column. The pure fractions were evaporated off to obtain 4-nitrophenyl ((2R, 3S)-3-(pyridin-2-yldisulfanyl)butan-2-yl) carbonate (0.17 g, 24.2%) as an oily compound. MS m/z 381.0 [M+H]$^+$.

Synthesis of II-7: 4-nitrophenyl((2S,3R)-3-(pyridin-2-yldisulfanyl)butan-2-yl) carbonate

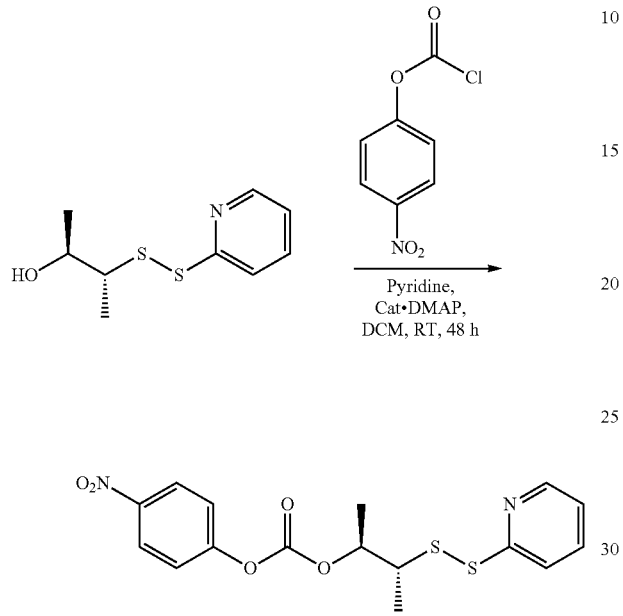

To a stirred solution of (2S,3R)-3-(pyridin-2-yldisulfanyl) butan-2-ol (0.4 g, 1.86 mmol) in $CH_2Cl_2$ (10 mL) was added pyridine (0.36 mL, 4.09 mmol), 4-nitrophenyl carbonochloridate (0.44 g, 2.32 mmol) and catalytic amount of 4-dimethylaminopyridine at 0° C. The reaction vessel was sealed and stirred at room temperature for 48 h. The reaction mixture was diluted with $CH_2Cl_2$ (20 mL) and washed with water (20 mL). The organic layer was dried over anhydrous sodium sulfate and concentrated under reduced pressure to afford crude which was purified by silica gel flash column chromatography using 30-40% ethyl acetate/hexane. The compound eluted out as a mixture in 30% EtOAc:Hexane. The fractions were concentrated to obtain crude which is further purified over C18 reverse phase column. The pure fractions were concentrated to obtain 4-nitrophenyl ((2S, 3R)-3-(pyridin-2-yldisulfanyl)butan-2-yl) carbonate (0.18 g, 26%) as an oily compound. MS m/z 381.0 [M+H]$^+$.

Synthesis of II-8: (4-nitrophenyl) [(1R,2R)-2-(2-pyridyldisulfanyl)cyclohexyl] carbonate To a solution of (1R,2R)-2-(2-pyridyldisulfanyl)cyclohexanol* (130.0 mg, 0.5 mmol) in THF (3.0 mL) was added potassium carbonate (0.20 g, 1.5 mmol), catalytic amount of DMAP and 4-nitrophenyl chloroformate (0.21 g, 0.10 mmol) at room temperature. The reaction vessel was sealed and stirred at RT for 48 h. Progress of the reaction was monitored by TLC (20% EtOAc/Hex). After completion of reaction, the reaction mixture was quenched with water (20.0 mL) and extracted with EtOAc (20.0 mL). The organic layer was separated, washed with brine, dried over anhydrous sodium sulphate and concentrated under reduced pressure to afford the crude product which was purified by column chromatography using 20-30% of EtOAc/hexanes to afford 4-nitrophenyl (4-nitrophenyl) [(1R,2R)-2-(2-pyridyldisulfanyl)cyclohexyl] carbonate* as an off white solid (89 mg, 40% yield). MS m/z 407.0 [M+H]$^+$.

Synthesis of II-9: (4-nitrophenyl) [(1S,2S)-2-(2-pyridyldisulfanyl)cyclohexyl] carbonate To a solution of (1S,2S)-2-(2-pyridyldisulfanyl)cyclohexanol* (0.42 g, 1.7 mmol) in THF (10.0 mL) was added potassium carbonate (0.70 g, 5.1 mmol), catalytic amount of DMAP and 4-nitrophenyl chloroformate (0.69 g, 3.4 mmol) at room temperature. The reaction vessel was sealed and stirred at RT for 48 h. Progress of the reaction was monitored by TLC (20% EtOAc/Hex). After completion of reaction, the reaction mixture was quenched with water (20.0 mL) and extracted with EtOAc (20.0 mL). The organic layer was separated, washed with brine, dried over anhydrous sodium sulphate and concentrated under reduced pressure to afford the crude product which was purified by column chromatography using 20-30% of EtOAc/hexanes to afford 4-nitrophenyl (4-nitrophenyl) [(1R,2R)-2-(2-pyridyldisulfanyl)cyclohexyl] carbonate* as an off white solid (250 mg, 35% yield). MS m/z 406.7 [M+H]+.

Carbonate Leaving Group Intermediate XV from XIV

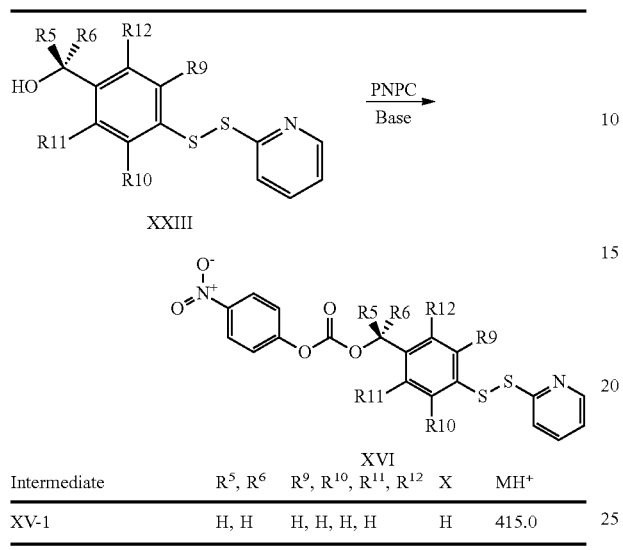

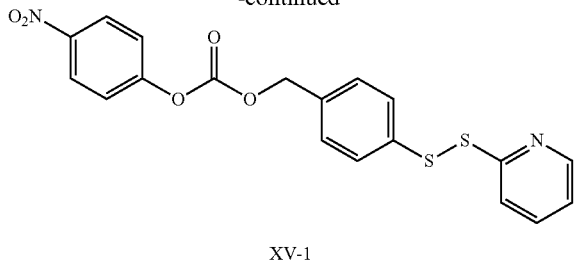

XV-1

| Intermediate | $R^5, R^6$ | $R^9, R^{10}, R^{11}, R^{12}$ | X | MH+ |
|---|---|---|---|---|
| XV-1 | H, H | H, H, H, H | H | 415.0 |

Synthesis of XV-1: (4-nitrophenyl) [4-(2-pyridyldisulfanyl)phenyl]methyl carbonate

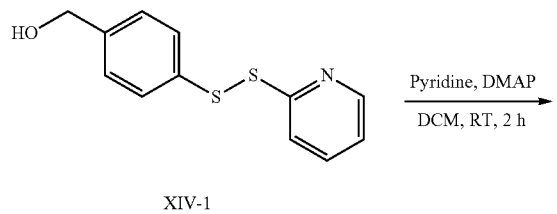

XIV-1

To a stirred solution of (4-(pyridin-2-yldisulfanyl)phenyl)methanol (0.40 g, 1.60 mmol) in $CH_2Cl_2$ (10 mL) were added 4-nitrophenyl chloroformate (0.65 g, 3.2 mmol), pyridine (0.25 mL, 3.20 mmol), catalytic amount of DMAP (0.005 g) at 0° C. The mixture was allowed to stir for 2 h at room temperature. The reaction mixture was quenched with 1.5 N HCl solution. The organic layer was separated and washed with brine, dried over anhydrous $Na_2SO_4$ and concentrated. The crude product was purified by column chromatography ($SiO_2$, 20-30% of EtOAc/hexanes) to afford (4-nitrophenyl) [4-(2-pyridyldisulfanyl)phenyl]methyl carbonate as a colourless liquid (600 mg, 91% yield); MS m/z 415.0 [M+H]+.

Carbonate and Carbamate Linked Intermediates III

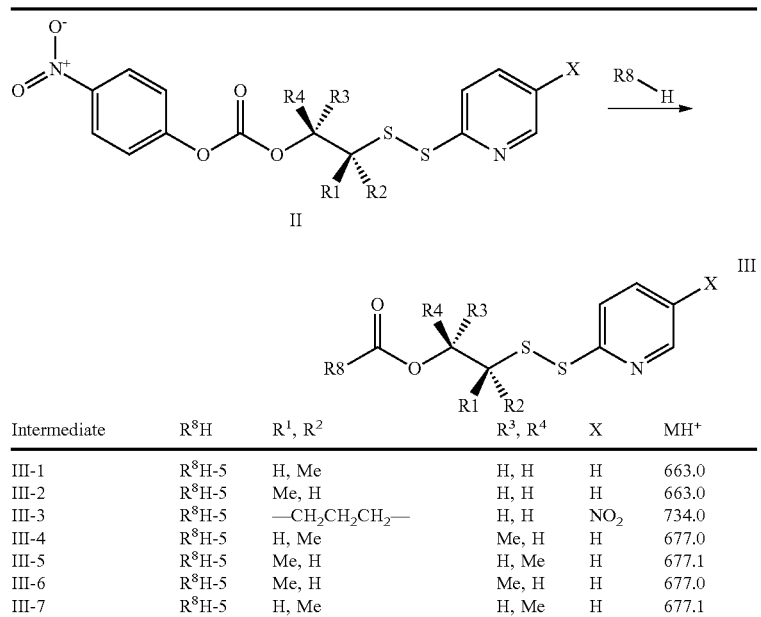

| Intermediate | $R^8H$ | $R^1, R^2$ | $R^3, R^4$ | X | MH+ |
|---|---|---|---|---|---|
| III-1 | $R^8H$-5 | H, Me | H, H | H | 663.0 |
| III-2 | $R^8H$-5 | Me, H | H, H | H | 663.0 |
| III-3 | $R^8H$-5 | —$CH_2CH_2CH_2$— | H, H | $NO_2$ | 734.0 |
| III-4 | $R^8H$-5 | H, Me | Me, H | H | 677.0 |
| III-5 | $R^8H$-5 | Me, H | H, Me | H | 677.1 |
| III-6 | $R^8H$-5 | Me, H | Me, H | H | 677.0 |
| III-7 | $R^8H$-5 | H, Me | H, Me | H | 677.1 |

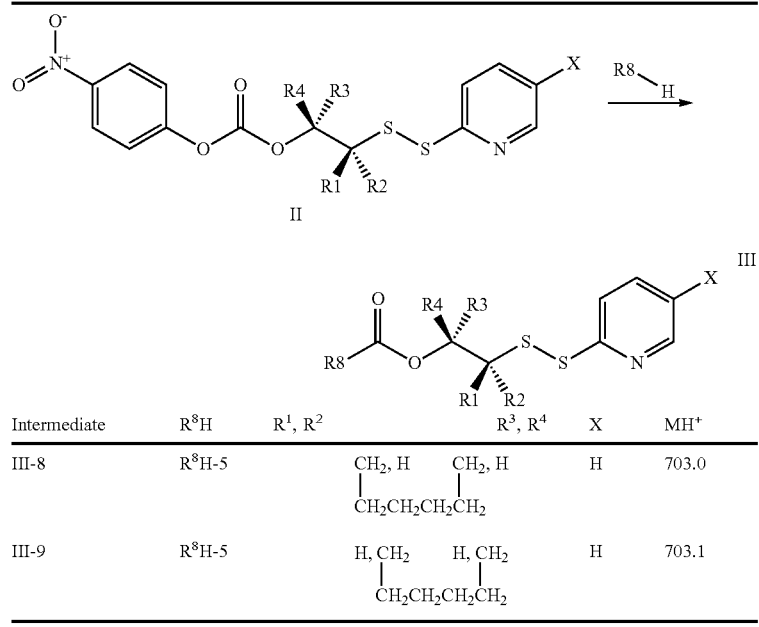

| Intermediate | R⁸H | R¹, R² | R³, R⁴ | X | MH⁺ |
|---|---|---|---|---|---|
| III-8 | R⁸H-5 | CH₂, H<br>\|<br>CH₂CH₂CH₂CH₂ | CH₂, H | H | 703.0 |
| III-9 | R⁸H-5 | H, CH₂<br>\|<br>CH₂CH₂CH₂CH₂ | H, CH₂ | H | 703.1 |

Synthesis of III-1: [(2S)-2-(2-pyridyldisulfanyl)propyl] N-[(10S,23S)-10-ethyl-18-fluoro-10-hydroxy-19-methyl-5,9-dioxo-8-oxa-4,15 diazahexacyclo[14.7.1.0²,¹⁴.0⁴,¹³.0⁶,¹¹.0²⁰,²⁴]tetracosa-1,6(11),12,14,16(24),17,19-heptaen-23-yl]carbamate

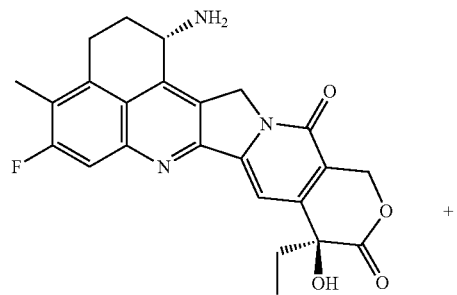

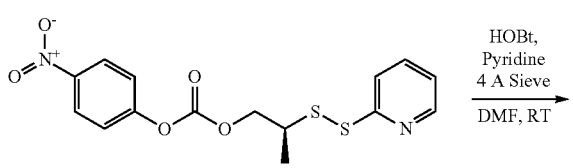

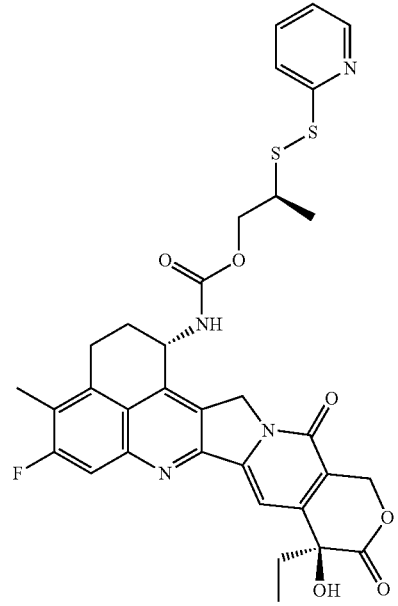

To a mixture of 1-hydroxybenzotriazole hydrate (8.64 mg, 0.0564 mmol), finely ground molecular sieve 4 Å (50 mg) (10S,23S)-23-amino-10-ethyl-18-fluoro-10-hydroxy-19-methyl-8-oxa-4,15-diazahexacyclo[14.7.1.0²,¹⁴.0⁴,¹³.0⁶,¹¹.0²⁰,²⁴]tetracosa-1,6(11),12,14,16(24),17,19-heptaene-5,9-dione; methanesulfonic acid (25.0 mg, 0.0470 mmol) and Pyridine (0.0190 mL, 0.235 mmol) in 2 mL of anhydrous DMF was added (4-nitrophenyl) [(2S)-2-(2-pyridyldisulfanyl)propyl] carbonate (19.0 mg, 0.0517 mmol). After stirring for 16 h at room temperature the mixture was filtered and the solution concentrated. The residue was purified by column chromatography (0-5% MeOH/DCM) to give [(2S)-2-(2-pyridyldisulfanyl)propyl] N-[(10S,23S)-10-ethyl-18-fluoro-10-hydroxy-19-methyl-5,9-dioxo-8-oxa-4,15 diazahexacyclo[14.7.1.0²,¹⁴.0⁴,¹³.0⁶,¹¹.0²⁰,²⁴]tetracosa-1,6

(11),12,14,16(24),17,19-heptaen-23-yl]carbamate (29.0 mg, yield: 93.0%). MS m/z 663.0 [M+H]⁺.
Intermediates III-2 through III-9 are prepared from II-2 through II-9 analogously to III-1.
Carbonate and Carbamate Linked Intermediates XVI

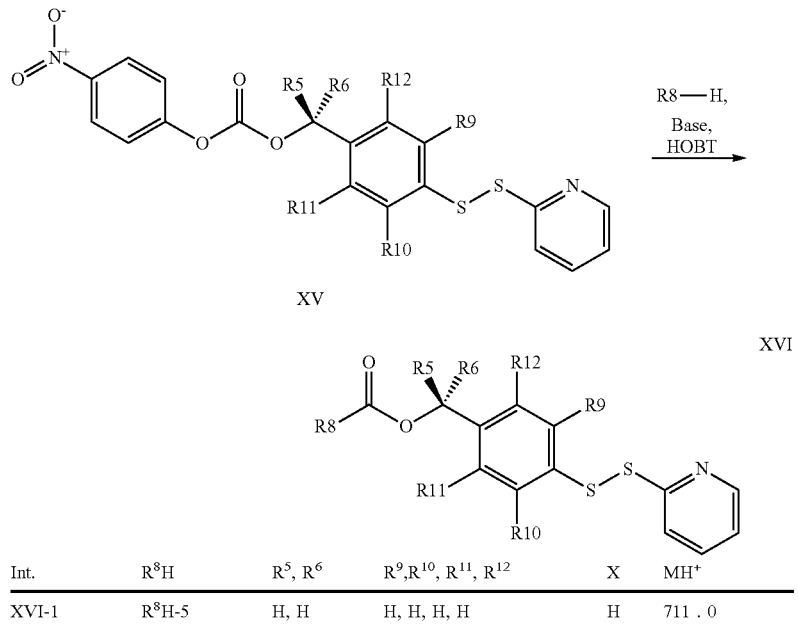

| Int. | R⁸H | R⁵, R⁶ | R⁹, R¹⁰, R¹¹, R¹² | X | MH⁺ |
|---|---|---|---|---|---|
| XVI-1 | R⁸H-5 | H, H | H, H, H, H | H | 711.0 |

Intermediate XVI-1 is prepared from XV-1 analogously to III-1.

Synthesis of 4-nitrophenyl (trans-(3RS,4RS)-4-(pyridin-2-yldisulfanyl)tetrahydrofuran-3-yl) carbonate

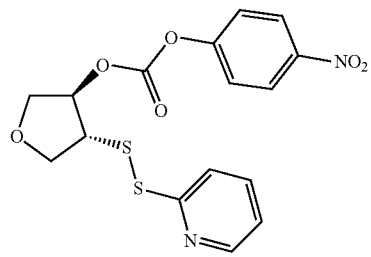 [SMILES: O=C(Oc1ccc([N+](=O)[O-])cc1)O[C@@H]1COC[C@H]1SSc1ccccn1]

Step 1: Synthesis of racemic trans-(4-hydroxytetrahydrofuran-3-yl) ethanethioate

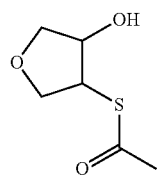

To a stirred solution of 3,6-dioxabicyclo[3.1.0]hexane (5.0 g, 0.051 mol) in water (40.0 mL) was added thioacetic acid (4.98 mL, 0.069 mol) and the resulting reaction mixture was stirred at room temperature for 16 h. Progress of the reaction was monitored by TLC (20% EtOAc/Hexane). Upon completion of the reaction, the reaction mixture was diluted with diethyl ether and washed with 10% sodium bicarbonate solution. The organic layer was separated and washed with brine, dried over anhydrous sodium sulfate, filtered and concentrated under reduced pressure to afford the crude product, which was purified by column chromatography using 20% EtOAc:n-Hexane to obtain the title product as a brown colour liquid (4.0 g, yield 42%).

¹HNMR (400 MHz, CDCl₃): δ 4.35-4.28 (m, 2H), 4.02-3.98 (m, 1H), 3.81-3.73 (m, 2H), 3.69-3.62 (m, 1H), 2.37 (s, 3H).

Step 2: Synthesis of Racemic trans-4-mercaptotetrahydrofuran-3-ol

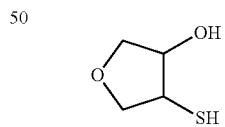

To a stirred solution of racemic trans-(4-hydroxytetrahydrofuran-3-yl) ethanethioate (4.0 g, 24.7 mmol) in dry THF (20.0 mL) under nitrogen atmosphere was added LAH (1M in THF) (27.1 mL, 27.1 mmol) in dropwise manner at 0° C. The reaction mixture was gradually allowed to warm to room temperature and stirred for 2 h. Progress of the reaction was monitored by TLC (20% EtOAc:n-Hexane). Upon completion of the reaction, the reaction mixture was cooled to room temperature and quenched with 1.0 N HCl (50 mL). The reaction mixture was extracted into DCM (3×20 mL), the organic layer was washed with brine solution (20 mL), dried over anhydrous sodium sulfate, filtered, partially distilled and taken as such to the next step. (2.9 g, crude).

Step 3: Synthesis of trans-(4RS,3RS)-4-(pyridin-2-yldisulfanyl)tetrahydrofuran-3-ol and trans-(4SR,3SR)-4-(pyridin-2-yldisulfanyl)tetrahydrofuran-3-ol

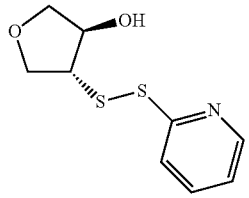

Isomer 1 trans (1RS, 2RS)

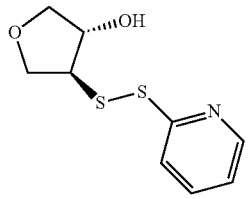

Isomer 2 trans (1SR, 2SR)

To a solution of 2-(pyridin-2-yldisulfanyl)pyridine (0.9 g, 21.7 mmol) in MeOH (degassed with $N_2$) (10 mL) was added 4-sulfanyloxolan-3-ol (2.9 g, 24.1 mmol) (degassed with $N_2$) dropwise and stirred at room temperature under nitrogen atmosphere for 16 h. The reaction mixture was concentrated to dryness under vacuum. The resultant crude was purified by flash column chromatography using 30% of EtOAc:n-Hexane to afford the title compound 4-(pyridin-2-yldisulfanyl)oxolan-3-ol (racemic mixture) as a yellow oil. The isomers were separated by Chiral preparative HPLC.

Chiral preparative HPLC Conditions:

Column: Chiralpak IA (250 mm×20 mm×5 mic)

Mobile phase: EtOH with 0.1% DEA (90:10)

Flow rate: 19 mL/min

Separated fractions of resolved isomers were collected from chiral prep. HPLC and evaporated under reduced pressure to afford the title compounds as Isomer 1 (600 mg) and Isomer 2 (620 mg).

Isomer 1: (trans-(4RS,3RS)-4-(pyridin-2-yldisulfanyl)tetrahydrofuran-3-ol): LC-MS m/z calcd. for $C_9H_{11}NO_2S_2$, 229; found 230 $[M+H]^+$. $^1$H-NMR (400 MHz, CDCl$_3$): δ 8.53-8.52 (m, 1H), 7.67-7.63 (m, 1H), 7.56 (d, J=8.0 Hz, 1H), 7.23-7.19 (m, 1H), 4.45-4.48 (m, 1H), 4.25 (t, J=8.8 Hz, 1H), 4.12 (t, J=6.8 Hz, 1H), 3.74-3.67 (m, 2H), 3.48-3.41 (m, 1H).

Isomer 2: (trans-(4SR,3SR)-4-(pyridin-2-yldisulfanyl)tetrahydrofuran-3-ol): LC-MS m/z calcd. for $C_9H_{11}NO_2S_2$, 229; found 230 $[M+H]^+$. $^1$H-NMR (400 MHz, CDCl$_3$): δ 8.54-8.53 (m, 1H), 7.68-7.64 (m, 1H), 7.56 (d, J=8.0 Hz, 1H), 7.23-7.20 (m, 1H), 4.49-4.45 (m, 1H), 4.25 (t, J=7.6 Hz, 1H), 4.12-4.10 (m, 1H), 3.74-3.67 (m, 2H), 3.47-3.44 (m, 1H).

The absolute stereochemistry of the isomers was arbitrarily assigned.

Step 4: Synthesis of 4-nitrophenyl (trans-(3RS,4RS)-4-(pyridin-2-yldisulfanyl)tetrahydrofuran-3-yl) carbonate

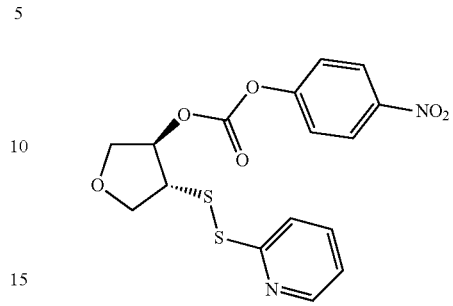

To a stirred solution of trans-(3RS,4RS)-4-(pyridin-2-yldisulfanyl)tetrahydrofuran-3-ol (0.61 g, 2.69 mmol) in DMF (10 mL) under nitrogen atmosphere was added DIPEA (1.45 mL, 8.08 mmol) and bis(4-nitrophenyl) carbonate (1.64 g, 5.38 mmol) at room temperature. The reaction vessel was sealed and stirred at room temperature for 12 h. Progress of the reaction was monitored by TLC (20% EtOAc:n-Hexane). Upon completion of the reaction, the reaction mixture was quenched with water (20 mL) and extracted with EtOAc (3×10 mL). The organic layer was separated, washed with brine, dried over anhydrous sodium sulfate, filtered and concentrated under reduced pressure to afford the crude product which was purified by flash column chromatography using 20-30% of EtOAc:n-Hexane to afford 4-nitrophenyl (trans-(3RS,4RS)-4-(pyridin-2-yldisulfanyl)tetrahydrofuran-3-yl) carbonate as an off-white solid (790 mg, 77% yield). $^1$HNMR (400 MHz, CDCl$_3$): δ 8.50 (d, J=4.4 Hz, 1H), 8.27 (d, J=8.8 Hz, 2H), 7.67-7.59 (m, 2H), 7.36 (d, J=8.8 Hz, 2H), 7.15 (t, J=5.2 Hz, 1H), 5.44-5.43 (m, 1H), 4.40-4.25 (m, 2H), 4.03 (d, J=11.2 Hz, 1H), 3.92-3.86 (m, 1H), 3.85-3.79 (m, 1H); LC-MS m/z calcd. for $C_{16}H_{14}N_2O_6S_2$, 394; found 395 $[M+H]^+$.

Synthesis of 4-nitrophenyl (trans-(3SR,4SR)-4-(pyridin-2-yldisulfanyl)tetrahydrofuran-3-yl) carbonate

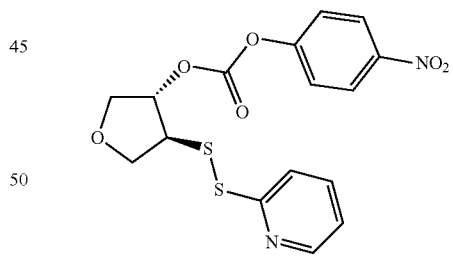

To a stirred solution of trans-(3SR,4SR)-4-(pyridin-2-yldisulfanyl)tetrahydrofuran-3-ol (550 mg, 2.46 mmol) in DMF (10.0 mL) under nitrogen was added DIPEA (1.32 mL, 7.38 mmol) and bis(4-nitrophenyl) carbonate (1.5 g, 4.92 mmol) at room temperature. The reaction vessel was sealed and stirred at room temperature for 12 h. Progress of the reaction was monitored by TLC (20% EtOAc:n-Hexane). Upon completion of the reaction, the reaction mixture was quenched with water (20 mL) and extracted with EtOAc (3×10 mL). The organic layer was separated, washed with brine, dried over anhydrous sodium sulfate, filtered and concentrated under reduced pressure to afford the crude product which was purified by flash column chromatography using 20-30% of EtOAc:n-Hexane to afford 4-nitrophenyl (trans-(3SR,4SR)-4-(pyridin-2-yldisulfanyl)tetrahydrofuran-3-yl) carbonate as an off-white solid (0.6 g, % yield). ¹HNMR (400 MHz, CDCl₃): δ 8.85 (d, J=4.4 Hz, 1H), 8.26 (d, J=8.8 Hz, 2H), 7.68-7.59 (m, 2H), 7.35 (d, J=8.8 Hz, 2H), 7.14 (t, J=5.2 Hz, 1H), 5.44-5.43 (m, 1H), 4.40-4.25 (m, 2H), 4.03 (d, J=11.2 Hz, 1H), 3.92-3.86 (m, 1H), 3.85-3.79 (m, 1H); LC-MS m/z calcd for $C_{16}H_{14}N_2O_6S_2$, 394; found 395 [M+H]⁺.

Synthesis of 4-nitrophenyl (trans-(1RS,2RS)-2-(pyridin-2-yldisulfanyl)cyclopentyl) carbonate

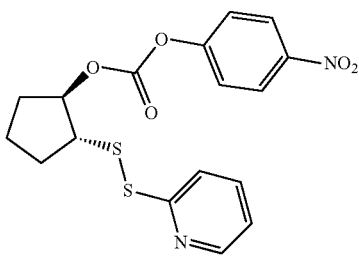 [SMILES: O=C(Oc1ccc([N+](=O)[O-])cc1)O[C@@H]1CCC[C@H]1SSc1ccccn1]

Step 1: Synthesis of racemic trans-(5-hydroxycyclopentan-1-yl) ethanethioate

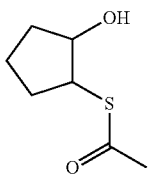

To a stirred solution of 6-oxabicyclo[3.1.0]hexane (3.0 g, mmol) in water (30 mL) was added thioacetic acid (3 mL, 39.2 mmol) at room temperature and stirred for 16 h. The reaction mixture was quenched with sat. sodium bicarbonate solution and extracted with ethyl acetate (3×10 mL). The organic layer was separated and washed with brine, dried over anhydrous sodium sulfate, filtered and concentrated under reduced pressure to afford racemic trans-(5-hydroxycyclopentan-1-yl) ethanethioate as an oily compound (2.6 g, crude). LC-MS m/z calcd for $C_7H_{12}O_2S$, 160.2; found 143.3 [M+H−17]⁺.

Step 2: Synthesis of Racemic trans-2-mercaptocyclopentan-1-ol

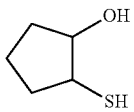

To a stirred solution of racemic trans-(5-hydroxycyclopentan-1-yl) ethanethioate (2.6 g, 16.2 mmol) in THF (20 mL) at 0° C. under nitrogen atmosphere, was added LAH (1 Min THF) (24 mL, 24.3 mmol) in dropwise manner. The reaction mixture was gradually allowed to warm to room temperature and stirred for 2 h. Progress of the reaction was monitored by TLC (20% EtOAc:n-Hexane). Upon completion of the reaction, the reaction mixture was cooled to room temperature and quenched with 1N HCl solution and extracted in DCM. The organic layer was dried over anhydrous sodium sulfate, filtered and evaporated partially and the crude racemic trans-2-mercaptocyclopentan-1-ol carried forward to the next step (1.9 g, crude).

Step 3: Synthesis of trans-(1RS, 2RS)-2-(pyridin-2-yldisulfanyl)cyclopentan-1-ol and trans-(1SR,2SR)-2-(pyridin-2-yldisulfanyl)cyclopentan-1-ol

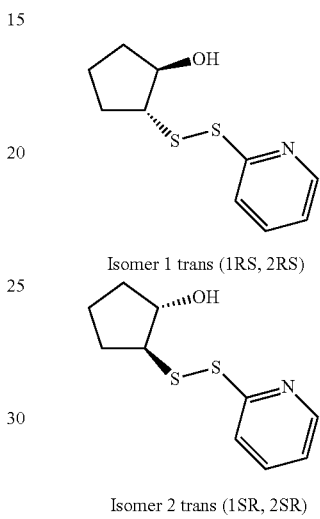

Isomer 1 trans (1RS, 2RS)

Isomer 2 trans (1SR, 2SR)

To a stirred solution of 2-(pyridin-2-yldisulfanyl)pyridine (2.1 g, 9.65 mmol) in MeOH (10 mL) under nitrogen atmosphere was added racemic trans-2-mercaptocyclopentan-1-ol (1.9 g, 16.1 mmol) in a dropwise manner at 0° C. The reaction mixture was gradually allowed to warm to room temperature and stirred for 16 h. After completion of the reaction, the reaction mixture was concentrated to dryness under vacuum. The resultant crude was purified by silica gel flash column chromatography. The compound was eluted out in 15% EtOAc:n-Hexane. Fractions containing the desired product were combined and evaporated under reduced pressure to afford the title compound (racemic mixture) as a yellow liquid. The isomers were separated by Chiral preparative HPLC.

Chiral Preparative HPLC Conditions:
Column: Chiralpak IA (250 mm×20 mm×5 mic)
Mobile phase: EtOH with 0.1% DEA (70:30)
Flow rate: 19 mL/min Separated fractions of separated isomers were collected from chiral prep. HPLC and evaporated under reduced pressure to afford the title compounds as Isomer 1 (300 mg) and Isomer 2 (300 mg) as a colourless oil.

Isomer 1 (trans-(1RS, 216)-2-(pyridin-2-yldisulfanyll)cyclopentan-1-ol): LC-MS m/z calcd for C10H13NOS2, 227.34; found 228.1 [M+H]⁺. ¹HNMR (400 MHz, CDCl₃): δ 8.51-8.50 (m, 1H), 7.61-7.57 (m, 1H), 7.48 (d, J=8.0 Hz, 1H), 7.17-7.14 (m, 1H), 4.03-3.97 (m, 1H), 3.0-2.87 (m, 1H), 2.11-2.02 (m, 3H), 1.75-1.65 (m, 4H).

Isomer 2 (trans-(1SR, 2SR)-2-(pyridin-2-yldisulfanyll) cyclopentan-1-ol): LC-MS m/z calcd for C10H13NOS2, 227.34; found 228.1 [M+H]⁺. ¹HNMR (400 MHz, CDCl₃): δ 8.51-8.50 (m, 1H), 7.61-7.57 (m, 1H), 7.48 (d, J=8.0 Hz, 1H), 7.17-7.14 (m, 1H), 4.03-3.97 (m, 1H), 3.0-2.87 (m, 1H), 2.11-2.02 (m, 3H), 1.75-1.65 (m, 4H).

The absolute stereochemistry of the isomers was arbitrarily assigned.

Step 4: Synthesis of 4-nitrophenyl ((1R,2R)-2-(pyridin-2-yldisulfanyl)cyclopentyl)carbonate

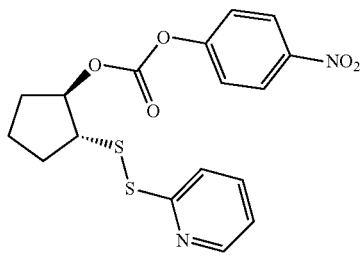 [SMILES: O=C(Oc1ccc([N+](=O)[O-])cc1)O[C@@H]1CCC[C@H]1SSc1ccccn1]

To a stirred solution of trans-(1RS,2RS)-2-(pyridin-2-yldisulfanyl)cyclopentan-1-ol (0.3 g, 1.34 mmol) in DMF (10 mL) under nitrogen atmosphere was added DIPEA (0.65 mL, 3.96 mmol) and Bis(4-nitrophenyl) carbonate (0.8 g, 2.64 mmol) at room temperature. The reaction vessel was sealed and stirred at room temperature for 16 h. The reaction mixture was quenched with water (20 mL) and extracted with EtOAc (3×10 mL). The organic layer was separated, washed with brine, dried over anhydrous sodium sulfate, filtered and concentrated under reduced pressure to afford the crude product which was purified by silica gel flash column chromatography. The compound eluted out in 10% EtOAc:n-Hexane as a mixture. The fractions were evaporated off to obtain crude compound which was purified over reverse phase column chromatography. Fractions containing the product were evaporated under reduced pressure to obtain 4-nitrophenyl (trans-(1RS,2RS)-2-(pyridin-2-yldisulfanyl)cyclopentyl) carbonate as a colourless oil (305 mg, 59%).

$^1$HNMR (400 MHz, CDCl$_3$): δ 8.46 (d, J=4.1 Hz, 1H), 8.25 (d, J=6.8 Hz, 2H), 7.66-7.62 (m, 2H), 7.34 (d, J=6.4 Hz, 2H), 7.10-7.08 (m, 1H), 5.29-5.10 (m, 1H), 3.52-3.45 (m, 1H), 2.32-2.28 (m, 2H), 1.9-1.76 (m, 4H). LC-MS m/z calcd for $C_{17}H_{16}N_2O_5S_2$, 392.44; found 393.0 [M+H]$^+$.

Synthesis of 4-nitrophenyl (trans-(1SR,2SR)-2-(pyridin-2-yldisulfanyl)cyclopentyl) carbonate

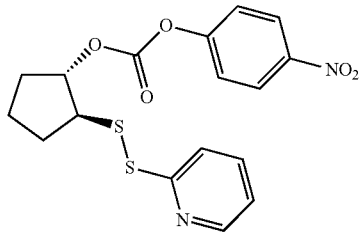 [SMILES: O=C(Oc1ccc([N+](=O)[O-])cc1)O[C@H]1CCC[C@@H]1SSc1ccccn1]

To a stirred solution of (1SR,2SR)-2-(pyridin-2-yldisulfanyl)cyclopentan-1-ol (0.26 g, 1.14 mmol) in DMF (10.0 mL) under nitrogen atmosphere was added DIPEA (0.57 mL, 3.43 mmol) and bis(4-nitrophenyl) carbonate (0.7 g, 2.29 mmol) at room temperature. The reaction vessel was sealed and stirred at room temperature for 16 h. The reaction mixture was quenched with water (20.0 mL) and extracted with EtOAc (3×10 mL). The organic layer was separated, washed with brine, dried over anhydrous sodium sulfate, filtered and concentrated under reduced pressure to afford the crude product which was purified by silica gel flash column chromatography. The compound eluted out in 10% EtOAc:n-Hexane as a mixture. The fractions were evaporated off to obtain crude compound which was purified over reverse phase column chromatography. Fractions containing the product were evaporated under reduced pressure to obtain 4-nitrophenyl (trans-(1SR,2SR)-2-(pyridin-2-yldisulfanyl)cyclopentyl) carbonate (330 mg, 73.5%) as a colorless oil. $^1$HNMR (400 MHz, CDCl$_3$): δ 8.46 (d, J=4 Hz, 1H), 8.25 (d, J=6.8 Hz, 2H), 7.66-7.62 (m, 2H), 7.34 (d, J=6.4 Hz, 2H), 7.10-7.08 (m, 1H), 5.29-5.10 (m, 1H), 3.52-3.45 (m, 1H), 2.32-2.28 (m, 2H), 1.9-1.76 (m, 4H). LC-MS m/z calcd for $C_{17}H_{16}N_2O_5S_2$, 392.44; found 393.0 [M+H]$^+$.

Synthesis 4-nitrophenyl (trans-(2RS, 3RS)-3-(pyridin-2-yldisulfanyl)-1, 2, 3, 4-tetrahydronaphthalen-2-yl) carbonate

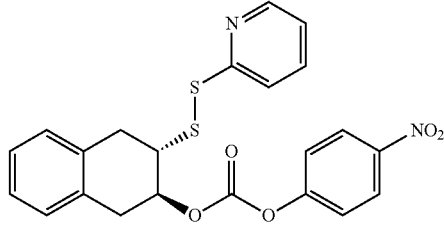 [SMILES: O=C(Oc1ccc([N+](=O)[O-])cc1)O[C@H]1Cc2ccccc2C[C@@H]1SSc1ccccn1]

Step 1: Synthesis of 1aH, 2H, 7H, 7aH-naphtho [2,3-b] oxirene

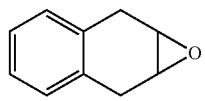 [SMILES: c1ccc2c(c1)CC1OC1C2]

To a stirred solution of 1,4-dihydronaphthalene (100 mg, 768 μmol) in dichloromethane (2.00 ml) under nitrogen atmosphere at 0° C. was added 3-chlorobenzene-1-carboperoxoic acid (199 mg, 1.5 eq., 1.15 mmol) lot wise and stirred for 16 h at RT. Progress of the reaction was monitored by TLC. After completion of the reaction, the reaction mass was filtered and extracted with dichloromethane, washed with sodium bicarbonate solution, followed by water and brine. The two layers were separated and the combined organic layer was dried over sodium sulfate, filtered and evaporated to get the crude product, which was purified by silica gel flash column chromatography. Product was eluted out in 10% EtOAc and n-Hexane, (product is UV Inactive), fractions were collected and dried under the vacuum to obtain 1aH,2H,7H,7aH-naphtho[2,3-b]oxirene (85.0 mg, 581 μmol) as an oily compound.

$^1$HNMR (400 MHz, CDCl$_3$): δ 7.14 (t, J=3.2 Hz, 2H), 7.05 (t, J=3.2 Hz, 2H), 3.48 (s, 2H), 3.32 (d, J=17.6 Hz, 2H), 3.19 (d, J=17.6 Hz, 2H).

Step 2: Synthesis of Racemic [trans-(3-hydroxy-1,2,3,4-tetrahydronaphthalen-2-yl) sulfanyl] (phenyl) methanone

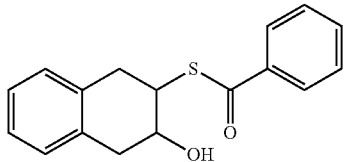 [SMILES: O=C(SC1Cc2ccccc2CC1O)c1ccccc1]

To a stirred solution of 1aH,2H,7H,7aH-naphtho[2,3-b]oxirene (100 mg, 684 μmol) in ethoxyethane (4.00 mL), under nitrogen atmosphere was added aluminium oxide (1.00 g) (acidic). The solution was cooled to 0° C. Then, thiobenzoic acid (482 mg, 5.1 eq., 3.49 mmol) was added to the reaction mixture and stirred at RT for 24 h. After completion of reaction (progress of the reaction was monitored by TLC), the reaction mixture was filtered and washed with sodium bicarbonate solution, followed by washing with water and brine solution to give the crude product. The crude product was purified by silica gel flash column chromatography using and the product was eluted out in 20% EtOAc:n-Hexane to obtain racemic [nans-(3-hydroxy-1,2,3,4-tetrahydronaphthalen-2-yl)sulfanyl](phenyl)methanone (125 mg, 440 μmol) as a colourless liquid.

$^1$HNMR (400 MHz, DMSO): δ 7.89 (d, J=7.2 Hz, 2H), 7.66 (t, 1H), 7.53 (d, J=7.2 Hz, 2H), 7.09 (m, 4H), 5.39 (s, 1H), 4.00 (s, 2H), 3.42 (d, J=17.6 Hz, 1H), 3.12 (t, J=16 Hz, 1H), 2.81 (t, J=18.4 Hz, 2H).

Step 3: Synthesis of Racemic trans-3-sulfanyl-1,2,3,4-tetrahydronaphthalen-2-ol

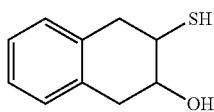 [SMILES: OC1Cc2ccccc2CC1S]

To a stirred solution of [(3-hydroxy-1,2,3,4-tetrahydronaphthalen-2-yl)sulfanyl] (phenyl) methanone (115 mg, 404 μmol) in methanol (3.00 mL) was added K$_2$CO$_3$ (113 mg, 2 eq., 809 μmol) and the reaction mixture was stirred for 0.5 h at RT. Progress of the reaction was monitored by TLC. After completion of the reaction, the reaction mass was concentrated (to remove methanol) and then acidified with 1N HCl solution until the pH reached 2-3, to obtain racemic trans-3-sulfanyl-1,2,3,4-tetrahydronaphthalen-2-ol (70.0 mg, 388 μmol) which was taken further as such for the next step.

Step 4: Synthesis of trans-(2RS, 3RS)-3-(pyridin-2-yldisulfanyl)-1, 2, 3, 4-tetrahydronaphthalen-2-ol and trans-(2SR, 3SR)-3-(pyridin-2-yldisulfanyl)-1, 2, 3, 4-tetrahydronaphthalen-2-ol

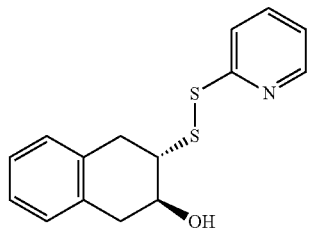

Isomer 1 trans (2RS, 3RS)

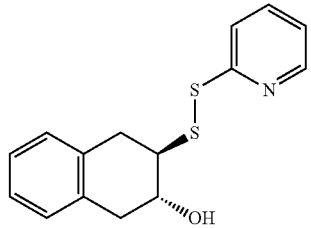

Isomer 2 trans (2SR, 3SR)

To a stirred solution of racemic trans-3-sulfanyl-1,2,3,4-tetrahydronaphthalen-2-ol (350 mg, 1.94 mmol) in methanol (2.50 ml) under nitrogen atmosphere was added 2-(pyridin-2-yldisulfanyl)pyridine (428 mg, 1 eq., 1.94 mmol) and stirred at RT for 16 h. Progress of the reaction was monitored by TLC and LC-MS. After completion of the reaction, the reaction mass was concentrated and then diluted with DCM, washed with water followed by brine and dried over sodium sulfate. The crude product obtained was purified by silica gel flash column chromatography. The desired product was eluted out in 20% EtOAc:Hexane. The product was re-purified by reverse phase column chromatography (10-20% of 0.1% Formic acid in water/Acetonitrile). Fractions containing the desired product were collected and evaporated off under vacuum to obtain 3-(pyridin-2-yldisulfanyl)-1,2,3,4-tetrahydronaphthalen-2-ol (350 mg, 1.21 mmol) as a yellow solid. The isomers were separated by chiral preparative HPLC.

$^1$HNMR (400 MHz, DMSO): δ 8.44 (d, J=4.4 Hz, 1H), 7.79 (d, J=3.2 Hz, 2H), 7.26-7.24 (m, 1H), 7.06 (s, 4H), 5.61 (s, 1H), 3.91-3.80 (m, 1H), 3.31-3.19 (m, 2H), 3.13-3.07 (m, 1H), 2.92-2.84 (m, 1H), 2.75-2.65 (m, 1H).

Prep. Conditions:

Column: CHIRALPAK IA (250 mm×420 mm×5 mic)

Mobile phase: n-Hexane:Ethanol with 0.1% DEA (50:50)

Flow rate: 19 mL/min

The isomers were separated and the respective fractions were collected from chiral prep. HPLC were combined and evaporated to afford the respective isomers. Isomer 1 was collected first and assigned as trans-(2RS, 3RS)-3-(pyridin-2-yldisulfanyl)-1, 2, 3, 4-tetrahydronaphthalen-2-ol. Isomer 2 was collected second and assigned as trans-(2SR, 3SR)-3-(pyridin-2-yldisulfanyl)-1, 2, 3, 4-tetrahydronaphthalen-2-ol. The absolute stereochemistry of the isomers was arbitrarily assigned.

Step 5: Synthesis of 4-nitrophenyl (trans-(2RS, 3RS)-3-(pyridin-2-yldisulfanyl)-1, 2, 3, 4-tetrahydronaphthalen-2-yl) carbonate To a stirred solution of trans-(2RS, 3RS)-3-(pyridin-2-yldisulfanyl)-1, 2, 3, 4-tetrahydronaphthalen-2-ol (150 mg, 518 μmol) in Dimethylformamide (3.00 ml, 38.7 mmol) was added bis(4-nitrophenyl) carbonate (315 mg, 2 eq., 1.04 mmol) followed by N,N-Diisopropylethylamine (271 μL, 3 eq., 1.55 mmol). The reaction mixture was stirred at RT for 12 h. After completion of the reaction, the reaction mass was quenched with water, extracted with DCM (3×5), combined organic phase was dried over sodium sulfate, filtered and evaporated under reduced pressure to afford crude product. The crude product was purified by silica gel flash column chromatography (0-40% EtOAc:n-Hexane) and also re-purified by reverse phase column chromatography (10-50% of 0.1% formic acid in water:ACN), to give (trans-(2RS, 3RS)-3-(pyridin-2-yldisulfanyl)-1, 2, 3, 4-tetrahydronaphthalen-2-yl) carbonate (133 mg, 293 μmol) as an off white solid.

$^1$HNMR (400 MHz, DMSO): δ 8.44 (d, 1H), 8.30 (d, J=9.2 Hz, 2H), 7.80-7.76 (m, 2H), 7.54 (d, J=9.2 Hz, 2H), 7.26-7.24 (m, 1H), 7.14-7.06 (m, 4H), 5.21-5.19 (m, 1H), 3.78-3.77 (m, 1H), 3.45-3.25 (m, 2H), 3.10-3.01 (m, 2H).

Synthesis of 4-nitrophenyl (trans-(2SR,3SR)-3-(pyridin-2-yldisulfanyl)-1, 2, 3, 4-tetrahydronaphthalen-2-yl) carbonate

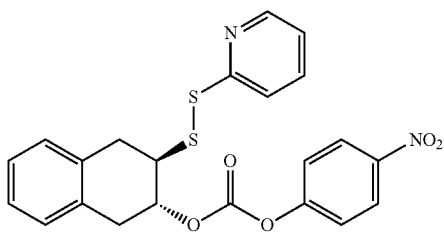 [SMILES: O=C(Oc1ccc([N+](=O)[O-])cc1)O[C@@H]1Cc2ccccc2C[C@H]1SSc1ccccn1]

To a stirred solution of trans-(2SR, 3SR)-3-(pyridin-2-yldisulfanyl)-1, 2, 3, 4-tetrahydronaphthalen-2-ol (130 mg, 449 μmol) in dimethylformamide (2.60 ml, 33.6 mmol) was added bis(4-nitrophenyl) carbonate (273 mg, 2 eq., 898 μmol) followed by diisopropylethylamine (13.0 mL, 3 eq., 74.6 mmol). The reaction mixture was stirred at RT for 12 h. After completion of the reaction (progress of the reaction was monitored by TLC), reaction mass was quenched with water, extracted with DCM (3×5), the combined organic phase was dried over sodium sulfate, filtered and evaporated under reduced pressure to afford crude product which was purified by flash column chromatography (0-40% EtOAc:n-Hexane). The product was re-purified by reverse phase column chromatography (10-50% of 0.1% formic acid in water:ACN) to give 4-nitrophenyl (trans-(2SR,3SR)-3-(pyridin-2-yldisulfanyl)-1, 2, 3, 4-tetrahydronaphthalen-2-yl) carbonate (30.0 mg, 66.0 μmol) as an off white solid.

$^1$HNMR (400 MHz, DMSO): δ 8.44 (d, 1H), 8.30 (d, J=9.2 Hz, 2H), 7.80-7.76 (m, 2H), 7.54 (d, J=9.2 Hz, 2H), 7.26-7.24 (m, 1H), 7.14-7.06 (m, 4H), 5.21-5.19 (m, 1H), 3.78-3.77 (m, 1H), 3.45-3.25 (m, 2H), 3.10-3.01 (m, 2H).

Synthesis of 4-nitrophenyl (trans-(3RS,4RS)-4-(pyridin-2-yldisulfanyl)oxan-3-yl) carbonate

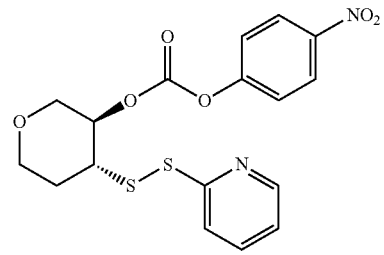 [SMILES: O=C(Oc1ccc([N+](=O)[O-])cc1)O[C@@H]1COCC[C@H]1SSc1ccccn1]

Step 1: Synthesis of 3,7-dioxabicyclo[4.1.0]heptane

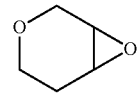

To a stirred solution of 3,6-dihydro-2H-pyran (2.0 g, 23.8 mmol) in dichloromethane (20.0 mL) at 0° C. was added 3-chlorobenzene-1-carboperoxoic acid (4.92 g, 1.2 eq., 28.5 mmol) slowly in portions and stirred under nitrogen atmosphere for 16 h at room temperature. Progress of the reaction was monitored by TLC. After completion of reaction, the reaction mass was quenched with sat. sodium bicarbonate solution, and the organic layer was separated and washed with water followed by brine solution, dried over anhydrous sodium sulfate, filtered and evaporated to give the title compound 3,7-dioxabicyclo[4.1.0]heptane (1.00 g, 9.99 mmol) as a colorless oil. $^1$H NMR (400 MHz, CDCl$_3$): 4.03-3.94 (m, 2H), 3.55-3.49 (m, 1H), 3.46-3.41 (m, 1H), 3.35 (m, 1H), 3.18 (m, 1H), 2.00 (m, 2H).

Step 2: Synthesis of Racemic [trans-(3-hydroxytetrahydropyran-4-yl)sulfanyl](phenyl)methanone

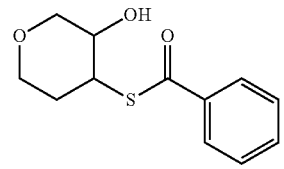 [SMILES: O=C(SC1CCOCC1O)c1ccccc1]

To a stirred solution of 3,7-dioxabicyclo[4.1.0]heptane (1.00 g, 9.99 mmol) in ethoxyethane (40 mL) at room temperature was added benzenecarbothioic S-acid (5.88 mL, 5 eq., 49.9 mmol) followed by silanedione (3.00 g, 5 eq., 49.9 mmol) and the reaction mixture was stirred at room temperature for 12 h. Progress of the reaction monitored by TLC, upon completion of the starting material, the reaction mass was quenched with sat. sodium bicarbonate solution and then extracted with ethyl acetate (2×10 mL). The combined organic layers was dried over anhydrous sodium sulfate, filtered and then evaporated under reduced pressure to afford crude product which was purified by flash column chromatography (0-30% EtOAc: n-Hexane). Compound was elutes at 20% EtOAc:n-Hexane. Pure fractions were collected and evaporated to give racemic [trans-(3-hydroxytetrahydropyran-4-yl) sulfanyl](phenyl)methanone (2.0 g, 8.39 mmol).

LC-MS m/z calculated $C_{12}H_{14}O_3S$; 238.3, found 239.1 $[M+H]^+$; $^1$H-NMR (400 MHz, $CDCl_3$): δ 7.43 (d, J=7.6 Hz, 2H), 7.09 (t, J=17.2 Hz, 1H), 6.93 (t, J=8.0 Hz, 2H), 3.55 (dd, J=4.0 Hz, 4.0 Hz, 1H), 3.37 (d, J=11.2 Hz, 1H), 3.28-3.24 (m, 1H), 3.22-3.18 (m, 1H), 3.01 (t, J=10.8 Hz, 1H), 2.83 (t, J=12.4 Hz, 1H), 1.36-1.27 (m, 1H), 1.27 (s, 2H).

Step 3: Synthesis of Racemic trans-4-sulfanyloxan-3-ol

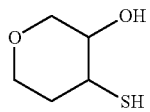

To a stirred solution of racemic [trans-3-hydroxytetrahydropyran-4-yl)sulfanyl](phenyl)methanone (2.50 g, 10.5 mmol) in dichloromethane (25 mL) at room temperature was added hydrazine hydrate (5.15 mL, 10 eq., 105 mmol) slowly and the reaction mixture was stirred for 1 h. Progress of the reaction was monitored by TLC, upon completion of the reaction, the reaction mass was quenched with 1N HCl so that the pH was adjusted to 2-3. The two layers were separated and the organic layer was dried over sodium sulphate, filtered and partially evaporated and the crude racemic trans-4-sulfanyltetrahydropyran-3-ol was taken for the next step.

Step 4: Synthesis of trans-(3RS,4RS)-4-(pyridin-2-yldisulfanyl)tetrahydropyran-3-ol and trans-(3SR,4SR)-4-(pyridin-2-yldisulfanyl)tetrahydropyran-3-ol

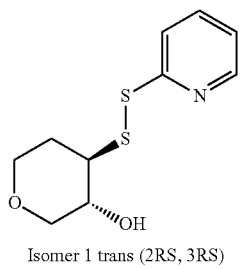

Isomer 1 trans (2RS, 3RS)

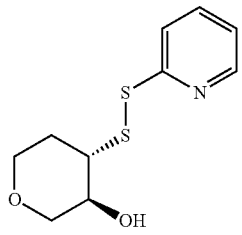

Isomer 2 trans (2SR, 3SR)

To a stirred solution of 2-(pyridin-2-yldisulfanyl)pyridine (1.85 g, 0.8 eq., 8.41 mmol) in Methanol (40 mL) was added racemic trans-4-sulfanyltetrahydropyran-3-ol of (1.41 g, 10.5 mmol) in DCM at 0° C. and then reaction mixture was stirred at room temperature for 12 h. Upon completion of the reaction, the completed reaction mass was evaporated under reduced pressure to afford crude which was purified by flash column chromatography. Product was eluted out in 20% EtOAc:n-Hexane, pure fractions were collected and evaporated to afford the tile product 4-(pyridin-2-yldisulfanyl)oxan-3-ol (racemic mixture). The isomers were separated by Chiral preparative HPLC.

Chiral Preparative HPLC Conditions:
Column: CHIRALPAK IA (250 mm×20 mm×5 mic)
Mobile phase: n-Hexane:IPA with 0.1% DEA (90:10)
Flow rate: 19 mL/min The isomers were separated and the respective fractions were collected from chiral prep. HPLC. The fractions were combined and evaporated to afford the respective isomers.

(Isomer 1-350 mg, Isomer 2-350 mg) LC-MS m/z calculated $C_{10}H_{13}NO_2S_2$; 243.34, found 244 $[M+H]^+$.

Isomer 1 (trans-(3RS,4RS)-4-(pyridin-2-yldisulfanyl)tetrahydropyran-3-ol)

$^1$H-NMR (400 MHz, DMSO): δ 8.53 (s, 1H), 7.60 (t, J=6.40 Hz, 1H), 7.40 (d, J=7.2 Hz, 1H), 7.23 (t, J=20.8 Hz, 1H), 4.28-4.06 (m, 1H), 3.94 (d, J=12 Hz, 1H), 3.54-3.40 (m, 3H), 3.33-3.21 (m, 1H), 3.07-2.74 (m, 1H), 2.04-1.94 (m, 2H).

Isomer 2 (trans-(3 SR,4SR)-4-(pyridin-2-yldisulfanyl)tetrahydropyran-3-ol)

$^1$H-NMR (400 MHz, DMSO): δ 8.52 (d, J=2.8 Hz, 1H), 7.61 (t, J=6.0 Hz, 1H), 7.39 (d, J=8.0 Hz, 1H), 7.18 (t, J=5.2 Hz, 1H), 4.12-4.09 (m, 1H), 3.94 (d, J=12 Hz, 1H), 3.53-3.47 (m, 1H), 3.47-3.37 (m, 1H), 3.25 (t, J=10.4 Hz, 1H), 2.80-2.73 (m, 1H), 1.96-1.42 (m, 1H), 1.20 (d, J=6.0 Hz, 2H).

The absolute stereochemistry of the isomers was arbitrarily assigned.

Step 5: Synthesis of 4-nitrophenyl (trans-(3RS, 4RS)-4-(pyridin-2-yldisulfanyl)tetrahydropyran-3-yl)carbonate To a stirred solution of (trans-(3RS,4RS)-4-(pyridin-2-yldisulfanyl)tetrahydropyran-3-ol) (300 mg, 1.23 mmol) in DMF (8 mL) was added bis(4-nitrophenyl) carbonate (750 mg, 2 eq., 2.47 mmol) and then followed by di-isopropylethylramine (644 μL, 3 eq., 3.70 mmol) at room temperature for 12 h. Upon completion of the reaction, the reaction mass was partitioned between water and DCM. The organic layer was separated and washed with brine solution and dried over sodium sulfate, filtered and evaporated under reduced pressure to afford crude which was purified by flash column chromatography. The desired compound elutes at 25% EtOAc:n-Hexane a s a mixture. The mixture was purified by reverse phase column chromatography (10-60% of 0.1% formic acid in water/ACN). Fractions containing the desired product were combined and evaporated to afford 4-nitrophenyl (trans-(3RS,4RS)-4-(pyridin-2-yldisulfanyl)tetrahydropyran-3-yl)carbonate (270 mg, 0.66 mmol). LC-MS m/z calculated $C_{17}H_{16}N_2O_6S_2$; 408.4, found 409.1 $[M+H]^+$; $^1$H-NMR (400 MHz, $CDCl_3$): δ 8.46 (d, 1H), 8.28 (d, J=8.8 Hz, 2H), 7.64-7.52 (m, 2H), 7.41 (d, J=8.8 Hz, 2H), 7.09 (s, 1H), 4.87 (d, J=2.8 Hz, 1H), 4.25-4.18 (m, 1H), 3.91 (d, J=11.6 Hz, 1H), 3.52-3.42 (m, 1H), 3.20 (d, J=2.8 Hz, 1H), 2.21 (d, J=12.4 Hz, 1H), 1.98 (d, J=7.6 Hz, 1H), 1.25 (s, 1H).

Synthesis of 4-nitrophenyl (trans-(3SR,4SR)-4-(pyridin-2-yldisulfanyl)tetrahydropyran-3-yl) carbonate

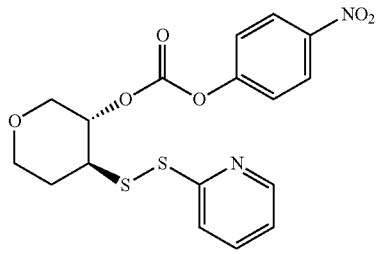 [SMILES: O=C(Oc1ccc([N+](=O)[O-])cc1)O[C@H]1COCC[C@@H]1SSc1ccccn1]

To a stirred solution of (trans-(3SR,4SR)-4-(pyridin-2-yldisulfanyl)tetrahydropyran-3-ol) (340 mg, 1.40 mmol) in DMF (8 mL) was added bis(4-nitrophenyl) carbonate (850 mg, 2 eq., 2.79 mmol) followed by di-isopropylethylamine (730 µL, 3 eq., 4.19 mmol) at room temperature for 12 h. Upon completion of the starting material, the reaction mixture was partitioned between water and DCM. The organic layer was separated and washed with brine solution, dried over sodium sulfate, filtered and evaporated under reduced pressure to afford the crude product which was purified by flash column chromatography (0-40% EtOAc:n-Hexane). The desired product was eluted out as mixture and then re-purified by reverse phase column chromatography (10-50% of 0.1% formic acid in water/ACN). Fractions containing the desired product were combined and evaporated to afford 4-nitrophenyl (trans-(3 SR,4SR)-4-(pyridin-2-yldisulfanyl)tetrahydropyran-3-yl) carbonate (300 mg, 735 µmol). LC-MS m/z calculated $C_{17}H_{16}N_2O_6S_2$; 408.4, found 409.1 [M+H]$^+$; $^1$H-NMR (400 MHz, DMSO): δ 8.46 (d, 1H), 8.28 (d, J=8.0 Hz, 2H), 7.66-7.58 (m, 2H), 7.40 (d, J=8.4 Hz, 2H), 7.09 (s, 1H), 4.87 (d, J=3.6 Hz, 1H), 4.25-4.22 (m, 1H), 3.91 (d, J=11.6 Hz, 1H), 3.52-3.42 (m, 2H), 3.20 (d, J=3.6 Hz, 1H), 2.21 (d, J=12.0 Hz, 1H), 1.98-1.95 (m, 1H).

Synthesis of 4-nitrophenyl (trans-(1RS,2RS)-2-(pyridin-2-yldisulfanyl) cycloheptyl) carbonate

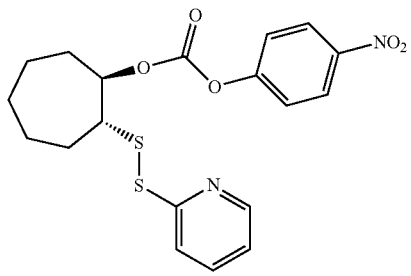 [SMILES: O=C(Oc1ccc([N+](=O)[O-])cc1)O[C@@H]1CCCCC[C@H]1SSc1ccccn1]

Step 1: Synthesis of 8-oxabicyclo[5.1.0]octane

To a stirred solution of cycloheptene (1.0 g, 10.4 mmol) in dichloromethane (10 mL) was added 3-chlorobenzene-1-carboperoxoic acid (2.15 g, 1.2 eq., 12.5 mmol) at 0° C. The reaction mixture was stirred at 0° C. for 1 h and then for 16 h at room temperature. Progress of the reaction monitored by TLC. Upon completion of the reaction, the reaction mixture was quenched slowly with aqueous sat. sodium bicarbonate solution and the mixture was stirred vigorously for about 30 min. The two layers were separated, the organic layer was dried over anhydrous sodium sulfate, filtered and evaporated under reduced pressure to afford the desired product as a colourless liquid (700 mg, 6.24 mmol). $^1$H-NMR (400 MHz, CDCl$_3$): δ 3.07 (s, 2H), 1.93-1.86 (m, 4H), 1.60-1.43 (m, 4H), 1.21-1.17 (m, 2H).

Step 2: Synthesis of Racemic [trans-(2-hydroxycycloheptyl)sulfanyl](phenyl)methanone

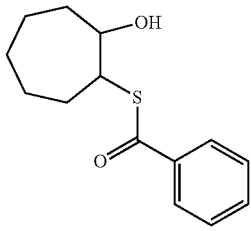 [SMILES: O=C(SC1CCCCCC1O)c1ccccc1]

To a stirred solution of 8-oxabicyclo[5.1.0]octane (3.00 g, 26.7 mmol) in toluene (60 mL) at room temperature under nitrogen atmosphere was added benzenecarbothioic S-acid (4.72 mL, 1.5 eq., 40.1 mmol), followed by 2-methylpropan-2-aminium chloride (293 mg, 0.1 eq., 2.67 mmol). The reaction mixture was stirred at 50° C. for 16 h (progress of the reaction was monitored by TLC). Upon completion of the reaction, the reaction mixture was quenched with sat. sodium bicarbonate solution and then extracted with ethyl acetate (3×20 mL). The combined organic layers were dried over anhydrous sodium sulfate, filtered and evaporated under reduced pressure to afford the crude product, which was purified by flash column chromatography. The desired product was eluted out in 20% EtOAc:n-Hexane, pure fractions were collected and evaporated to afford the title compound racemic [trans-(2-hydroxycycloheptyl)sulfanyl](phenyl)methanone (3.0 g, 12.0 mmol). LC-MS m/z calculated $C_{14}H_{18}O_2S$; 250.4, $^1$H-NMR (400 MHz, CDCl$_3$): δ 7.96 (d, J=8.0 Hz, 2H), 7.57 (t, J=6.8 Hz, 1H), 7.4 (t, J=7.6 Hz, 2H), 3.88-3.85 (m, 1H), 3.81-3.77 (m, 1H), 2.09-2.05 (m, 1H), 2.04-1.62 (m, 8H), 1.55-1.53 (m, 2H).

Step 3: Synthesis of Racemic trans-4-sulfanylcycloheptan-3-ol

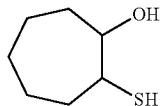

To a stirred solution of racemic [trans-(2-hydroxycycloheptyl)sulfanyl](phenyl)methanone (2.80 g, 11.2 mmol) in dichloromethane (25 mL) at room temperature, under nitrogen atmosphere was added 1,4-disulfanylbutane-2,3-diol (173 mg, 0.1 eq., 1.12 mmol), followed by hydrazine hydrate (1.37 mL, 2.5 eq., 28.0 mmol). The reaction mixture was stirred at room temperature for 3 h (progress of the reaction monitored by TLC). Upon completion of the reaction, the reaction mixture was quenched with 1N HCl and extracted with DCM (2×30 ml). The organic layers were combined and dried over sodium sulfate, filtered, the organic layer was partially evaporated and the crude racemic trans-4-sulfanylcycloheptan-3-ol directly taken for the next step.

Step 4: Synthesis of trans-(1RS, 2RS)-2-(pyridin-2-yldisulfanyl)cycloheptan-1-ol and trans-(1SR, 2SR)-2-(pyridin-2-yldisulfanyl)cycloheptan-1-ol

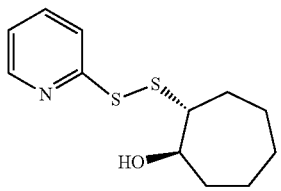

Isomer 1 trans (1RS, 2RS)

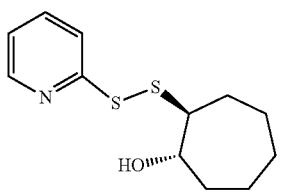

Isomer 2 trans (1SR, 2SR)

To a stirred solution of 2-(pyridin-2-yldisulfanyl)pyridine (1.73 g, 0.7 eq., 7.85 mmol) in methanol (25 mL) under nitrogen atmosphere at 0° C. was added racemic trans-4-sulfanylcycloheptan-3-ol (1.64 g, 11.2 mmol) in DCM and the reaction mixture was stirred at room temperature for 12 h. Progress of the reaction was monitored by TLC and LCMS and the reaction mass was evaporated under reduced pressure. The crude product was purified by flash column chromatography and the desired product was eluted out in 20% EtOAc:n-Hexane. As the product was collected as a mixture, it was re-purified by reverse phase column chromatography (10-50% of 0.1% formic acid in water:acetonitrile) to afford racemic trans-2-(pyridin-2-yldisulfanyl)cycloheptan-1-ol (1.5 g, 52%) (Racemic mixture). The isomers were separated by chiral preparative HPLC.

(Isomer-1: 550 mg, Isomer-2: 550 mg).

Chiral Preparative HPLC Conditions:
  Column: CHIRALPAK IA (250 mm×20 mm×5 mic)
  Mobile phase: n-Hexane:IPA with 0.1% DEA (90:10)
  Flow rate: 19 mL/min The isomers were separated and the respective fractions were collected from chiral prep. HPLC. The fractions were evaporated separately, to afford the respective isomers.

Isomer 1 (trans-(1RS, 2RS)-2-(pyridin-2-yldisulfanyl)cycloheptan-1-ol)

LC-MS m/z calculated $C_{12}H_{17}NOS_2$; 255.4, found 256.2 [M+H]$^+$; $^1$H-NMR (400 MHz, CDCl$_3$): δ 8.49 (s, 1H), 7.56 (d, J=6.8 Hz, 1H), 7.38 (d, J=8.0 Hz, 1H), 7.13 (s, 1H), 6.17 (s, 1H), 3.51 (m, 1H), 2.75-2.73 (m, 1H), 2.08-1.95 (m, 2H), 1.82-1.67 (m, 4H), 1.57-1.25 (m, 4H).

Isomer 2 (trans-(1SR, 2SR)-2-(pyridin-2-yldisulfanyl)cycloheptan-1-ol)

LC-MS m/z calculated $C_{12}H_{17}NOS_2$; 255.4, found 256.2 [M+H]$^+$; $^1$H-NMR (400 MHz, CDCl$_3$): δ 8.50 (d, J=4.40 Hz, 1H), 7.58 (t, J=8.0 Hz, 1H), 7.38 (d, J=8.40 Hz, 1H), 7.13 (t, J=6.4 Hz, 1H), 6.18 (s, 1H), 3.53-3.49 (m, 1H), 2.77-2.72 (m, 1H), 2.11-2.08 (m, 1H), 2.00-1.96 (m, 1H), 1.84-1.67 (m, 4H), 1.59-1.45 (m, 4H).

The absolute stereochemistry of the isomers was arbitrarily assigned.

Step 5: Synthesis of 4-nitrophenyl (trans-(1RS, 2RS)-2-(pyridin-2-yldisulfanyl) cycloheptyl) carbonate To a stirred solution of trans-(1RS, 2RS)-2-(pyridin-2-yldisulfanyl)cycloheptan-1-ol (500 mg, 1.96 mmol) in DMF (10 mL) under nitrogen atmosphere was added bis(4-nitrophenyl) carbonate (1.49 g, 2.5 eq., 4.89 mmol) followed by diisopropylethylamine (1.02 mL, 3 eq., 5.87 mmol) at room temperature. The reaction mixture was stirred for 12 h. Upon completion of the reaction, the reaction mixture was partitioned between water and DCM. The two layers were separated and the organic layer was washed with brine solution, dried over sodium sulfate, filtered and evaporated under reduced pressure to afford the crude product which was purified by flash column chromatography. The desired product was eluted out in 23% EtOAc:n-Hexane as a mixture. The mixture was re-purified by reverse phase column chromatography (10-60% of formic acid in water/ACN) to afford the title product 4-nitrophenyl (trans-(1RS,2RS)-2-(pyridin-2-yldisulfanyl) cycloheptyl) carbonate (450 mg, 1.07 mmol)). LC-MS m/z calculated $C_{19}H_{20}N_2O_5S_2$; 420.5, found 421.3 [M+H]$^+$; $^1$H-NMR (400 MHz, CDCl$_3$): δ 8.45 (s, 1H), 8.27 (d, J=8.8 Hz, 2H), 7.73 (d, J=7.6 Hz, 1H), 7.62 (t, J=7.6 Hz, 1H), 7.39 (d, J=8.4 Hz, 1H), 7.09 (m, 1H), 5.04-5.03 (m, 1H), 3.22 (m, 1H), 2.15-2.00 (m, 3H), 1.87-1.79 (m, 2H), 1.72-1.63 (m, 4H), 1.54-1.49 (m, 2H).

Synthesis of 4-nitrophenyl (trans-(1SR,2SR)-2-(pyridin-2-yldisulfanyl) cycloheptyl) carbonate

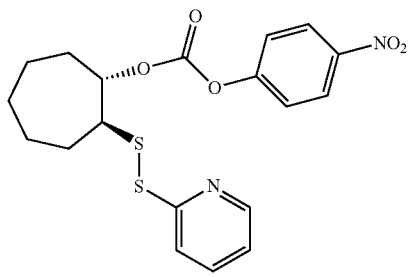 [SMILES: O=C(Oc1ccc([N+](=O)[O-])cc1)O[C@H]1CCCCC[C@@H]1SSc1ccccn1]

To a stirred solution of trans-(1SR,2SR)-2-(pyridin-2-yldisulfanyl)cycloheptan-1-ol (580 mg, 2.27 mmol) in DMF (10 mL) under nitrogen atmosphere was added bis(4-nitrophenyl) carbonate (1.73 g, 2.5 eq., 5.68 mmol) followed by di-isopropylethylamine (1.38 mL, 3.5 eq., 7.95 mmol). The reaction mixture was stirred at room temperature for 12 h. Upon completion of the reaction, monitored by TLC, the reaction mixture was partitioned between water and DCM. The two layers were separated and the combined organic layer was washed with brine solution, dried over sodium sulfate, filtered and evaporated under reduced pressure. The crude product was purified by flash column chromatography. The desired product was eluted out in 23-25% EtOAc:n-Hexane as a mixture. The product was re-purified by reverse phase column chromatography (10-60% of 0.1% formic acid in water/ACN) to afford the title compound 4-nitrophenyl (trans-(1SR,2SR)-2-(pyridin-2-yldisulfanyl) cycloheptyl) carbonate (450 mg, 1.07 mmol)). LC-MS m/z calculated $C_{19}H_{20}N_2O_5S_2$; 420.5, found 421.3 [M+H]$^+$; $^1$H-NMR (400 MHz, CDCl$_3$): δ 8.46 (s, 1H), 8.27 (d, J=8.4 Hz, 2H), 7.76 (d, J=8.0 Hz, 1H), 7.66 (t, J=7.6 Hz, 1H), 7.40 (d, J=8.4 Hz, 1H), 7.12 (m, 1H), 5.04-5.03 (m, 1H), 3.23 (m, 1H), 2.12-2.00 (m, 2H), 1.87-1.79 (m, 3H), 1.63-1.49 (m, 6H).

Synthesis of 4-nitrophenyl (trans-(1RS,2RS)-1-(pyridin-2-yldisulfanyl)-1,2,3,4-tetrahydronaphthalen-2-yl) carbonate

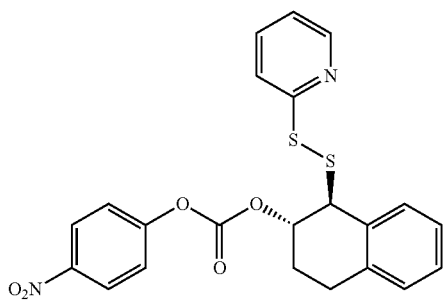 [SMILES: O=C(Oc1ccc([N+](=O)[O-])cc1)O[C@H]1CCc2ccccc2[C@@H]1SSc1ccccn1]

Step 1: Synthesis of 1aH,2H,3H,7bH-naphtho[1,2-]oxirene

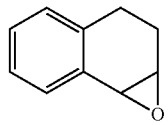 [SMILES: c1ccc2c(c1)CCC1OC21]

To a stirred solution of 1,2-dihydronaphthalene (2.0 g, 15.4 mmol) in dichloromethane (75 mL) was added a saturated solution of sat. sodium hydrogen carbonate (75 mL). The mixture was cooled to 0° C. To this mixture was added portion-wise 3-chlorobenzene-1-carboperoxoic acid (5.30 g, 2 eq., 30.7 mmol) over a period of 30 min. After the addition, the reaction mass was allowed to stir at room temperature for 16 h. The reaction was monitored by TLC. After, the reaction completion, the two layers were separated and the organic layer was dried over sodium sulfate and concentrated under reduced pressure to afford 1aH,2H,3H,7bH-naphtho[1,2-b]oxirene (2.77 g). The crude obtained was used directly for the next step without any further purification.

Step 2: Synthesis of racemic [trans-(2-hydroxy-1,2,3,4-tetrahydronaphthalen-1-yl)sulfanyl] (phenyl) methanone

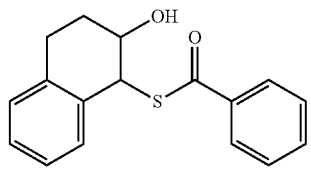 [SMILES: O=C(SC1c2ccccc2CCC1O)c1ccccc1]

To a stirred solution of 1aH,2H,3H,7bH-naphtho[1,2-b]oxirene (2.25 g, 15.4 mmol) in ethoxyethane (20 mL) was added silanedione (4.50 g, 74.9 mmol) and benzenecarbothioic S-acid drop-wise (9.06 mL, 5 eq., 77.0 mmol). The mixture was allowed to stir at room temperature for 16 h. The progress of the reaction was monitored by TLC and LCMS. After reaction completion, the reaction mixture was quenched with sat. sodium carbonate solution (25 mL) and extracted with ethyl acetate (2×20 mL). The combined organic layer was washed with water, brine and dried over sodium sulfate and concentrated under reduced pressure to obtain a crude which was purified by column chromatography to afford racemic [trans-(2-hydroxy-1,2,3,4-tetrahydronaphthalen-1-yl)sulfanyl] (phenyl) methanone as an yellow liquid (1.57 mg, 35.87%)

Step 3: Synthesis of Racemic trans-1-sulfanyl-1,2,3,4-tetrahydronaphthalen-2-ol

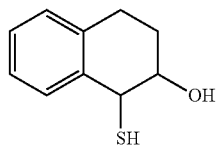 [SMILES: OC1CCc2ccccc2C1S]

To a stirred solution of racemic trans-[(2-hydroxy-1,2,3,4-tetrahydronaphthalen-1-yl)sulfanyl](phenyl)methanone (1.40 g, 4.92 mmol) in dichloromethane (25.0 mL) was added (2R,3R)-1,4-disulfanylbutane-2,3-diol (144 mg, 0.19 eq., 935 µmol) and hydrazine hydrate (60.4 eq., 1.23 mmol). The reaction mass was stirred at room temperature for 3 h. The reaction was monitored by TLC. After reaction completion, the reaction mixture was quenched with HCl solution (pH=1-2). The DCM layer was separated and dried over sodium sulfate, filtered and concentrated under reduced pressure to afford racemic trans-1-sulfanyl-1,2,3,4-tetrahydronaphthalen-2-ol which taken as such for the next step.

Step 4: Synthesis of trans-(1RS,2RS)-1-(pyridin-2-yldisulfanyl)-1,2,3,4-tetrahydronaphthalen-2-ol and trans-(1SR,2SR)-1-(pyridin-2-yldisulfanyl)-1,2,3,4-tetrahydronaphthalen-2-ol

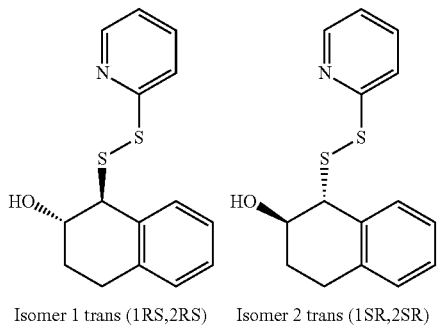

Isomer 1 trans (1RS,2RS)   Isomer 2 trans (1SR,2SR)

To a stirred solution of 2-(pyridin-2-yldisulfanyl)pyridine (867 mg, 0.8 eq., 3.94 mmol) in methanol (5 mL) at 0° C. To this, was added drop-wise racemic trans-1-sulfanyl-1,2,3,4-tetrahydronaphthalen-2-ol in DCM taken from the previous step. The reaction was allowed to stir at RT for 16 h. The reaction was monitored by LCMS and TLC. After reaction completion, the reaction mass was concentrated under reduced pressure to afford a crude which was purified by column chromatography to afford racemic 1-(pyridin-2-yldisulfanyl)-1,2,3,4-tetrahydronaphthalen-2-ol as a yellow oil which was further purified by reverse phase column chromatography to afford a colorless oil (380 mg, 26.69%). The racemic product obtained was separated by chiral chromatography to afford Isomer-1: 130 mg; Isomer-2: 190 mg.

Prep. Conditions:
Column: CHIRALPAK IA (250 mm×420 mm×5 mic)
Mobile phase: n-Hexane:Ethanol with 0.1% DEA (50:50)
Flow rate: 19 mL/min Isomer-1 (trans-(1RS,2RS)-1-(pyridin-2-yldisulfanyl)-1,2,3,4-tetrahydronaphthalen-2-ol)

LC-MS m/z calculated $C_{15}H_{15}NOS_2$; 289.4, found 290.1 [M+H]$^+$; $^1$H-NMR (400 MHz, CDCl$_3$): δ 8.07 (d, J=7.2 Hz, 2H), 7.61-7.57 (m, 1H), 7.48-7.44 (m, 2H), 7.36-7.34 (m, 1H), 7.18-7.13 (m, 3H), 4.98 (d, J=4.4 Hz, 1H), 4.24 (m, 1H), 3.07-2.99 (m, 1H), 2.91-2.80 (m, 1H).

Isomer-2(trans-(1SR, 2SR)-1-(pyridin-2-yldisulfanyl)-1, 2, 3, 4-tetrahydronaphthalen-2-ol)

LC-MS m/z calculated $C_{15}H_{15}NOS_2$; 289.4, found 290.1 [M+H]$^+$; $^1$H-NMR (400 MHz, CDCl$_3$): δ 8.55 (d, J=4.0 Hz, 1H), 7.77 (d, J=8.0 Hz, 1H), 7.58 (t, J=7.6 Hz, 1H), 7.37 (d, J=8.4 Hz, 1H), 7.26-7.17 (m, 3H), 7.08 (d, J=7.2 Hz, 1H), 4.15 (d, J=8.0 Hz, 1H), 3.97-3.93 (m, 1H), 2.89 (d, J=4.8 Hz, 2H), 2.32-2.28 (m, 1H), 1.97-1.87 (m, 2H).

The absolute stereochemistry of the isomers was arbitrarily assigned.

Step 5. Synthesis of 4-nitrophenyl (trans-(1RS, 2RS)-1-(pyridin-2-yldisulfanyl)-1,2,3,4-tetrahydronaphthalen-2-yl) carbonate To a stirred solution of trans-(1RS,2RS)-1-(pyridin-2-yldisulfanyl)-1,2,3,4-tetrahydronaphthalen-2-ol (170 mg, 587 µmol) in N,N-dimethylformamide (2.50 mL) was added bis(4-nitrophenyl) carbonate (447 mg, 2.5 eq., 1.47 mmol) followed by diisopropylethylamine (307 µL, eq., 1.76 mmol) drop-wise at RT. The reaction mixture was stirred at RT for 12 h in a sealed tube. The reaction was monitored by TLC and LCMS. After reaction completion, the reaction mass was partitioned between water (5 mL) and DCM (5 mL). The organic layer was dried over sodium sulfate and evaporated under reduced pressure to afford crude, which was purified by flash column chromatography (0-40% EA in hexane) and also re-purified by reverse phase column chromatography (10-70% of 0.1% formic acid in water/ACN) to give 4-nitrophenyl (trans-(1RS,2RS)-1-(pyridin-2-yldisulfanyl)-1,2,3,4-tetrahydronaphthalen-2-yl) carbonate (70.0 mg, 154 µmol) as a colorless gummy solid (70 mg, 26.22%). LC-MS m/z calculated $C_{22}H_{18}N_2O_4S_2$; 454.5 found 455.3 [M+H]$^+$; $^1$H-NMR (400 MHz, CDCl$_3$): δ 8.73 (d, J=20.4 Hz, 1H), 8.22 (d, J=8.4 Hz, 2H), 7.67 (s, 2H), 7.50 (m, 1H), 7.32 (d, J=8.4 Hz, 2H), 7.25-7.16 (m, 4H), 5.51 (s, 1H), 4.52 (s, 1H), 3.01-2.85 (m, 2H), 2.63 (m, 1H), 2.26-2.22 (m, 1H).

Synthesis of 4-nitrophenyl (trans-(1SR,2SR)-1-(pyridin-2-yldisulfanyl)-1,2,3,4-tetrahydronaphthalen-2-yl) carbonate

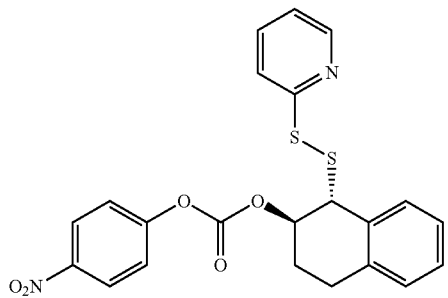 [SMILES: O=C(Oc1ccc([N+](=O)[O-])cc1)O[C@@H]1CCc2ccccc2[C@H]1SSc1ccccn1]

To a stirred solution of trans-(1SR,2SR)-1-(pyridin-2-yldisulfanyl)-1,2,3,4-tetrahydronaphthalen-2-ol (120 mg, 415 µmol) in N,N-dimethylformamide (1.50 mL) was added bis(4-nitrophenyl) carbonate (315 mg, 2.5 eq., 1.04 mmol) followed by diisopropylethylamine (217 µL, eq., 1.24 mmol) drop-wise at RT. The reaction mixture was stirred at RT for 12 h in a sealed tube. The progress of the reaction was monitored by TLC and LCMS. After reaction completion, the reaction mass was partitioned between water (5 mL) and DCM (5 mL), the organic layer was dried over sodium sulfate and evaporated under reduced pressure to afford crude which was purified by flash column chromatography (0-40% EA in hexane) and also re-purified by reverse phase column chromatography (10-70% of 0.1% formic acid in water/ACN) to give 4-nitrophenyl (trans-(1SR,2SR)-1-(pyridin-2-yldisulfanyl)-1,2,3,4-tetrahydronaphthalen-2-yl) carbonate (65.0 mg, 143 µmol)) as a colorless gummy solid (65 mg, 34.49%). LC-MS m/z calculated $C_{22}H_{18}N_2O_4S_2$; 454.5 found 455.3 [M+H]$^+$; $^1$H-NMR (400 MHz, CDCl$_3$): δ 8.55 (m, 1H), 8.22 (d, J=7.6 Hz, 2H), 7.69 (s, 2H), 7.51 (m, 1H), 7.32 (d, J=7.6 Hz, 2H), 7.25-7.16 (m, 4H), 5.51 (s, 1H), 4.52 (s, 1H), 3.01-2.86 (m, 2H), 2.62 (m, 1H), 2.26 (m, 1H).

Synthesis of 4-nitrophenyl (trans-4-(pyridin-2-yldisulfanyll)cyclohexyl) carbonate

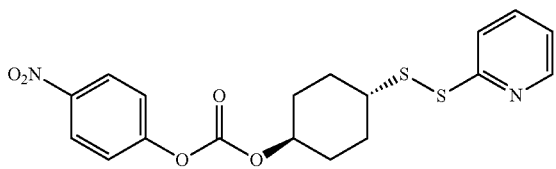 [SMILES: O=C(Oc1ccc([N+](=O)[O-])cc1)O[C@H]1CC[C@H](SSc2ccccn2)CC1]

Step 1: Synthesis of trans-4-mercaptocyclohexan-1-ol

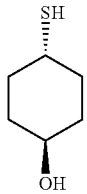

To a stirred solution of 7-oxabicyclo[2.2.1]heptane (1.00 g, 10.2 mmol) in ethanol (10 mL) was added 4-methylbenzene-1-sulfonic acid (2.63 g, 1.5 eq., 15.3 mmol), thiourea (1.16 g, 1.5 eq., 15.3 mmol) and the reaction mass was heated to 80° C. for 24 h. Then, the reaction mass was cooled to room temperature and 50% aqueous sodium hydroxide solution (1.30 g, 3.2 eq., 32.6 mmol) was added to the reaction mass and heated at 100° C. for 2 h. After completion of the reaction, the reaction mass was cooled to room temperature, concentrated under reduced pressure and acidify with 10% H$_2$SO$_4$ solution. Then, the reaction mass was extracted with DCM and taken-up for the next step as such.

Step 2: Synthesis of trans-4-(pyridin-2-yldisulfanyl)cyclohexan-1-ol

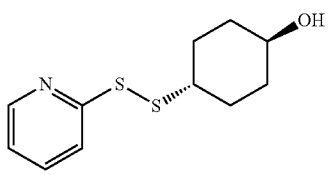 [SMILES: O[C@H]1CC[C@H](SSc2ccccn2)CC1]

A stirred solution of 2-(pyridin-2-yldisulfanyl)pyridine (1.60 g, 0.8 eq., 7.26 mmol) in methanol (10.0 mL) at 0° C. was added the organic layer from (step 1) 4-sulfanylcyclohexan-1-ol (1.20 g, 9.08 mmol). Upon completing the addition, the reaction mass allowed to stir at room temperature for 16 h. After completion of the reaction, the reaction mass was concentrated and the crude product was purified by column chromatography (using 0-40% EtOAc:n-Hexane) to give the desired product. The product was re-purified by reverse phase column chromatography using 0.1% Formic acid and ACN. Fractions containing the desired product were collected and concentrated under reduced pressure the afford the title product as a yellow oil (1.60 g, 73% yield). LC-MS m/z calculated for $C_{11}H_{15}NOS_2$, 241; found 242 [M+H]$^+$.

Step 3: Synthesis of 4-nitrophenyl (trans-4-(pyridin-2-yldisulfanyl)cyclohexyl) carbonate To a stirred solution of trans-4-(pyridin-2-yldisulfanyl)cyclohexan-1-ol (400 mg, 1.66 mmol) in N,N-dimethylformamide (3 mL) under Nitrogen atmosphere was added bis(4-nitrophenyl) carbonate (907 mg, 1.8 eq., 2.98 mmol), ethylbis(propan-2-yl)amine (892 µL, 3 eq., 4.97 mmol) and stirred for at room temperature for 16 h. Progress of the reaction was monitored by TLC. After completion of the reaction, the reaction mass was quenched with water (15 mL) and extracted with DCM (3×10 mL). The two layers were separated and the combined organic layer was washed with water fallowed by brine solution, dried over sodium sulfate, filtered and concentrated under reduced pressure. The crude product obtained was purified by flash column chromatography (0-30% EtOAc:n-Hexane). The product was re-purified by reverse phase column chromatography using 0.1% formic acid and ACN. Fractions containing the desired product were collected and concentrated under reduced pressure the afford 4-nitrophenyl (Mans-4-(pyridin-2-yldisulfanyl)cyclohexyl) carbonate as a yellow oil (0.3 g, 73% yield). LC-MS m/z calculated for $C_{18}H_{18}N_2O_5S_2$, 407; found 407 [M+H]$^+$; $^1$HNMR (400 MHz, CDCl$_3$): δ 8.49-8.42 (m, 1H), 8.26 (d, J=8.0 Hz, 2H), 7.71 (d, J=8.0 Hz, 1H), 7.65-7.60 (m, 1H), 7.35 (d, J=8.4 Hz, 2H), 7.12-7.05 (m, 1H), 4.75-4.65 (m, 1H), 2.98-2.87 (m, 1H), 2.28-2.18 (m, 4H), 1.68-1.50 (m, 4H).

Synthesis of (2R)-3-methyl-2-(pyridin-2-yldisulfanyl) butyl 4-nitrophenyl carbonate

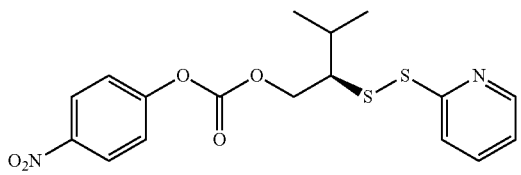 [SMILES: CC(C)[C@H](COC(=O)Oc1ccc([N+](=O)[O-])cc1)SSc1ccccn1]

Step 1. Synthesis of Cesium Benzoylsulfanide

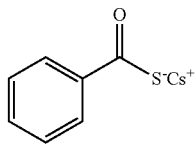

To a stirred solution of benzenecarbothioic S-acid (5.00 g, 36.2 mmol) in methanol (40.0 mL) was added cesium carbonate (7.72 g, 1.1 eq., 39.8 mmol) in portions over 10-15 min, under nitrogen atmosphere. The reaction mixture was stirred at RT for 2 h. After completion of the reaction (as judged by TLC), the reaction mixture was concentrated under reduced pressure. The solid residue was diluted with 10 mL of acetone and the white solid (CsHCO3) was filtered off. This process was repeated two times to ensure all CsHCO3 was removed. Acetone was then concentrated to afford cesium benzoylsulfanide (9.50 g, 35.2 mmol) as a colorless solid. $^1$HNMR (400 MHz, CD3OD): δ 8.08 (d, J=6.8 Hz, 2H), 7.37-7.27 (m, 3H).

Step 2. Synthesis of (2R)-2-(benzoylsulfanyl)-3-methylbutanoic acid

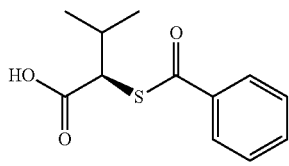 [SMILES: CC(C)[C@@H](SC(=O)c1ccccc1)C(=O)O]

To a stirred solution of (2S)-2-bromo-3-methylbutanoic acid (2.00 g, 11.0 mmol) in N,N-dimethylformamide (14.0 mL) was added cesium benzoylsulfanide (2.98 g, 11.0 mmol). The reaction mixture was stirred at RT for 20 h. Progress of the reaction was monitored by TLC, after completion of the reaction, the reaction mixture was diluted with di ethyl ether (3×15 mL) and washed with water (3×15 mL). The ethereal layer was separated, dried over sodium sulfate, and concentrated under reduced pressure. The residue obtained was recrystallized from n-hexanes to afford (2R)-2-(benzoylsulfanyl)-3-methylbutanoic acid (2.50 g, 10.5 mmol) as an oily compound. $^1$HNMR (400 MHz, DMSO-d6): δ 12.93 (s, 1H), 7.92 (d, J=7.2 Hz, 2H), 7.69 (t, J=7.6 Hz, 1H), 7.55 (t, J=7.2 Hz, 2H), 4.14 (d, J=6.8 Hz, 1H), 2.30-2.22 (m, 1H), 1.01-0.89 (m, 6H).

Step 3. Synthesis of (2R)-3-methyl-2-sulfanylbutan-1-ol

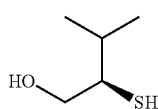

To a stirred solution of (2R)-2-(benzoylsulfanyl)-3-methylbutanoic acid (2.50 g, 10.5 mmol) in ethoxyethane (50.0 mL) at 0° C. was added lithiumaluminiumhydride (52.5 mL, 5 eq., 52.5 mmol) in drop wise manner under nitrogen atmosphere. After completion off the addition, the ice-bath was removed and the reaction mixture was stirred at room temperature for 2 h. Progress of the reaction was monitored by TLC. After the completion of the starting material, the reaction mixture was cooled in an ice-bath and quenched with 1.0 N HCl (30 mL) at 0° C. The reaction mixture was extracted with DCM (20 mL) and the remaining gel-like material from the LAH reduction was washed with diethyl ether (10 mL). The combined organic layer was dried over sodium sulfate, filtered and carried out further to the next step.

Step 4. Synthesis of (2R)-3-methyl-2-(pyridin-2-yldisulfanyl) butan-1-ol

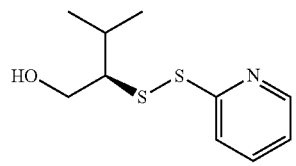

To a stirred solution of (2R)-3-methyl-2-sulfanylbutan-1-ol (1.20 g, 9.98 mmol) in MeOH (5 mL) was added 2-(pyridin-2-yldisulfanyl)pyridine (1.76 g, 0.8 eq., 7.99 mmol) under nitrogen atmosphere and stirred at room temperature for 16 h. Progress of the reaction was monitored by TLC and LC-MS. After completion of reaction, the reaction mass was concentrated, and then extracted with DCM. The two layers were separated and the combined organic layer was washed with water followed by brine and dried over sodium sulfate, filtered and evaporated. The crude product was purified by silica gel flash column chromatography (using 12 g column), which was eluted out in 50% EtOAc: n-Hexanes and also re-purified by reverse phase column chromatography (10-20% of 0.1% formic acid in water/Acetonitrile). Fractions containing the product were collected and evaporated off under vacuum to obtain the title product. The product was re-purified by Prep. HPLC.

Prep. HPLC Conditions:
Column: X-BridgeC-18 (250 mm×4.6 mm×5 mic)
Mobile phase(A): 0.1% Ammonia in water
Mobile phase(B): Acetonitrile
Flow rate: 19 mL/min
Gradient B: 0/10,12/60,22/95,25/95,27/10,30/10

Fractions collected from Prep. HPLC were combined and evaporated to afford the tile product 3-(pyridin-2-yldisulfanyl)-1,2,3,4-tetrahydronaphthalen-2-ol (350 mg, 1.21 mmol) as a yellow solid. $^1$HNMR (400 MHz, CDCl$_3$): δ 8.49 (d, J=4 Hz, 1H), 7.55-7.54 (m, 1H), 7.36 (d, J=8.4 Hz, 1H), 7.13 (t, J=6.4 Hz, 1H), 3.82 (dd, J=12.4 Hz, 1H), 3.66-3.60 (m, 1H), 2.75-2.70 (m, 1H), 2.01-1.92 (m, 1H), 1.10-1.01 (m, 7H).

Step 5. Synthesis of (2R)-3-methyl-2-(pyridin-2-yldisulfanyl) butyl 4-nitrophenyl carbonate To a stirred solution of (2R)-3-methyl-2-(pyridin-2-yldisulfanyl)butan-1-ol (800 mg, 3.49 mmol) in N,N-dimethylformamide (2.50 mL) was added bis(4-nitrophenyl) carbonate (2.12 g, 2 eq., 6.98 mmol) followed by diisopropylethylamine (1.82 mL, 3 eq., 10.5 mmol) at room temperature. The reaction mixture was stirred at room temperature for 12 h. After the reaction was completed, the reaction mass was partitioned between water and DCM. The two layers were separated and the organic layer was dried over sodium sulfate, filtered and evaporated under reduced pressure to afford the crude product, which was purified by flash column chromatography (0-40% EtOAc:n-Hexanes). The product was re-purified by reverse phase chromatography (10-70% of 0.1% formic acid in water/ACN) to obtain the title product (2R)-3-methyl-2-(pyridin-2-yldisulfanyl) butyl 4-nitrophenyl carbonate (600 mg, 1.52 mmol) as a colorless gum. $^1$HNMR (400 MHz, CDCl$_3$): δ 8.45 (d, J=4.0 Hz, 1H), 8.26 (d, J=9.2 Hz, 2H), 7.72 (d, J=8.4 Hz, 1H), 7.63

(t, J=7.2 Hz, 1H), 7.35 (d, J=9.2 Hz, 2H), 7.08 (t, J=6.8 Hz, 1H), 4.59-4.48 (m, 2H), 3.08 (q, J=6.0 Hz, 1H), 2.21-2.13 (m, 1H), 1.14-1.06 (m, 6H).

From step 2, same procedure was followed to synthesize (2S)-3-methyl-2-(pyridin-2-yldisulfanyl) butyl 4-nitrophenyl carbonate using (2R)-2-bromo-3-methylbutanoic acid.

Synthesis of the Compound of Example 2 from Intermediate III-2

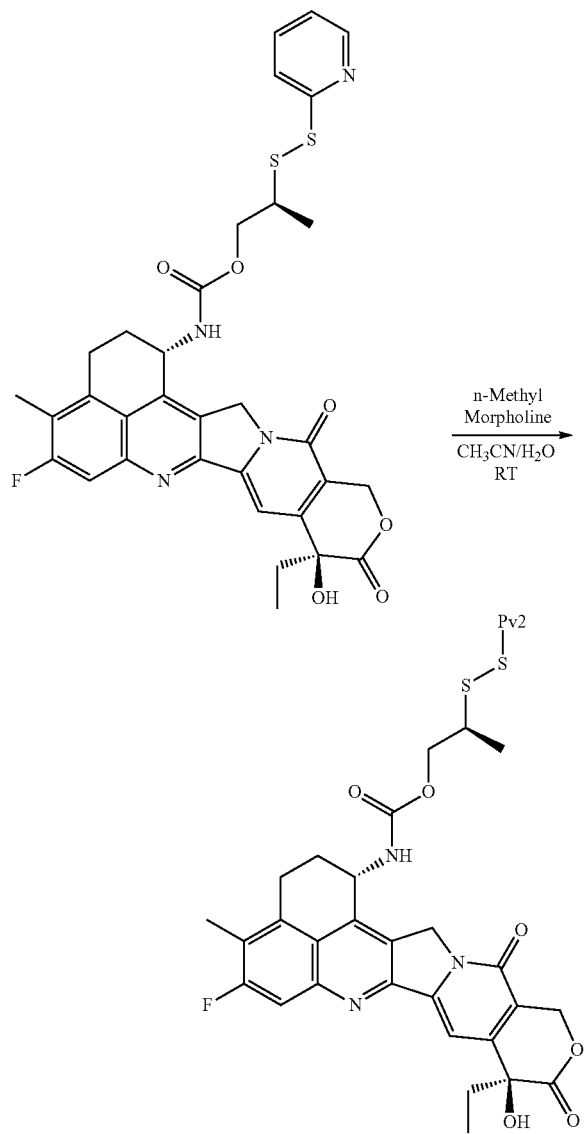

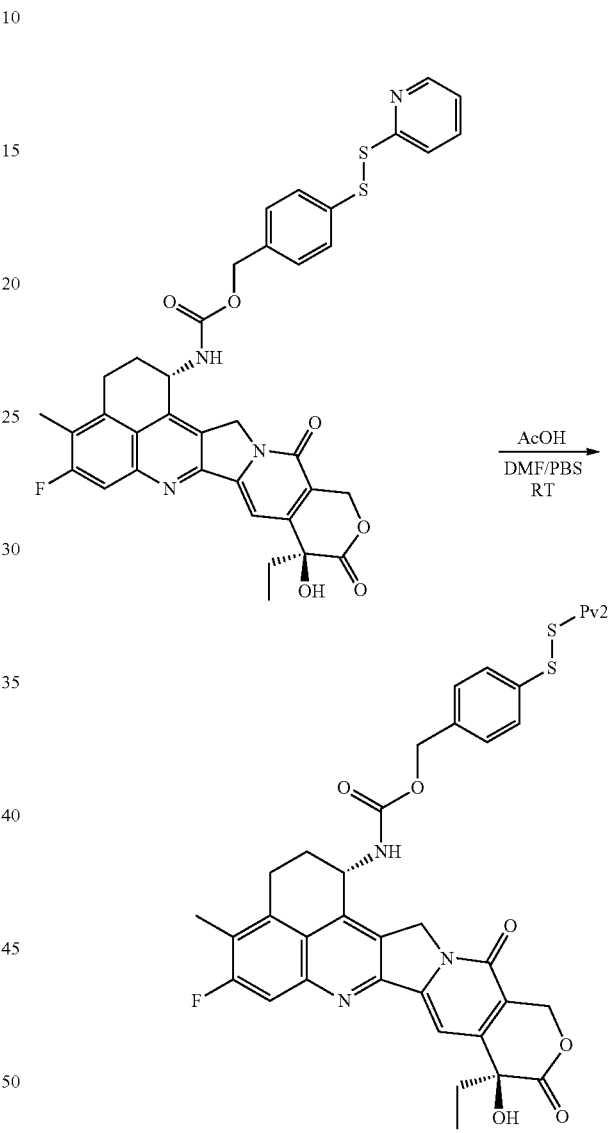

CH₃CN/H2O+0.05% TFA, 15 min) to give the desired product (13.0 mg, yield: 47.0%).

The compounds of Examples 1 and 3-9 (see Table 4 below) were synthesized analogously as the compound of Example 2, from Intermediates III-1 and III-3 to III-9, respectively.

Synthesis of the Compound of Example 10 from Intermediate XVI-1

In a vial with Pv2 (25.0 mg, 0.061 mmol; as a free flowing solid), [(2S)-2-(2-pyridyldisulfanyl)propyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl] carbamate (6.03 mg, 0.091 mmol), was added 1 mL of CH₃CN and 0.5 mL of water. To this was added N-Methyl morpholine (22.7 mg, 0.224 mmol). The mixture was stirred overnight at RT. LC-MS indicated a complete reaction. The reaction mixture was purified directly by reverse phase HPLC (Waters SunfirePrep C18, PrepSlope_4 min, 20-85%

DMF and PBS were degassed using a N₂ stream for 30 min. In a separate vial was placed Pv2 (25.0 mg, 0.061 mmol; as a free flowing solid), [4-(2-pyridyldisulfanyl) phenyl]methyl N-[(10S,23S)-10-ethyl-18-fluoro-10-hydroxy-19-methyl-5,9-dioxo-8-oxa-4,15-diazahexacyclo [14.7.1.02,14.04,13.06,11.020,24]tetracosa-1,6(11),12,14, 16(24),17,19-heptaen-23-yl]carbamate (6.5 mg, 0.09 mmol), 1.5 mL of DMF and mL of PBS. To this was added CH₃CO₂H (0.0347 mL, 0.606 mmol). The mixture was stirred at RT overnight. LC-MS indicated a complete reaction. The reaction mixture was purified by reverse phase HPLC (PrepSlope_4 min, 30-100% CH₃CN/H₂O+0.05% TFA, 18 min) to give the desired product (3.0 mg, yield: 10.7%).

Compounds of the invention and analytical data are presented below.
TABLE 4
Example Compounds
| Example | Structure | MS<br>A: Maldi-TOF (M+)<br>B: ESI (m/z = 3) | Column<br>%ACN/H₂O<br>Run Time<br>Retention Time |
|---|---|---|---|
| 1 | 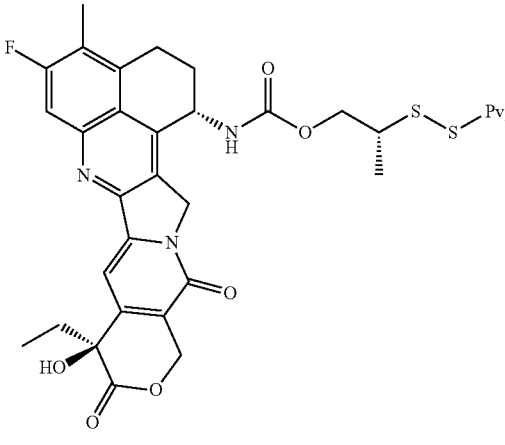 | B: 1521.3 | A<br>2-95%<br>11 min<br>7.4 min |
| 2 | 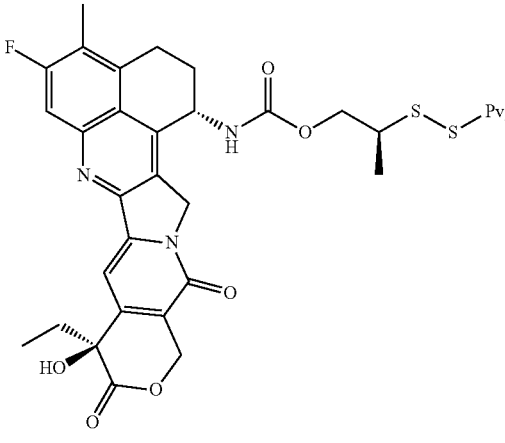 | B: 1521.7 | A<br>2-95%<br>11 min<br>7.4 min |
| 3 | 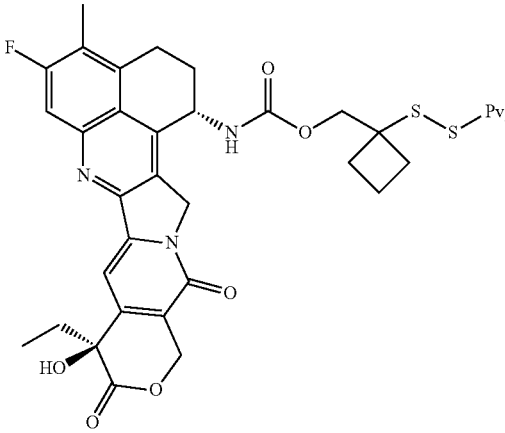 | B: 1530.6 | A<br>2-95%<br>11 min<br>7.5 min |

TABLE 4-continued

Example Compounds

| Example | Structure | MS<br>A: Maldi-TOF (M+)<br>B: ESI (m/z = 3) | Column<br>%ACN/H₂O<br>Run Time<br>Retention Time |
|---|---|---|---|
| 4 | 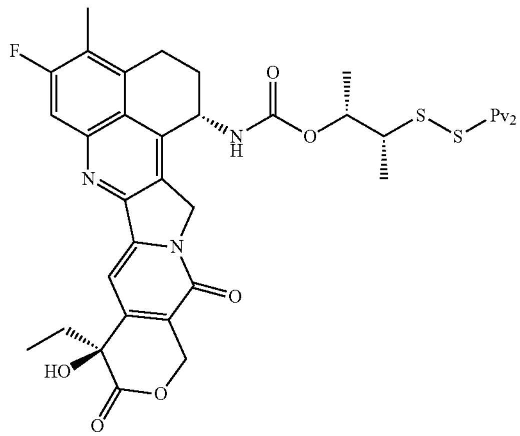 | B: 1526.5 | A<br>2-95%<br>11 min<br>7.5 mm |
| 5 | 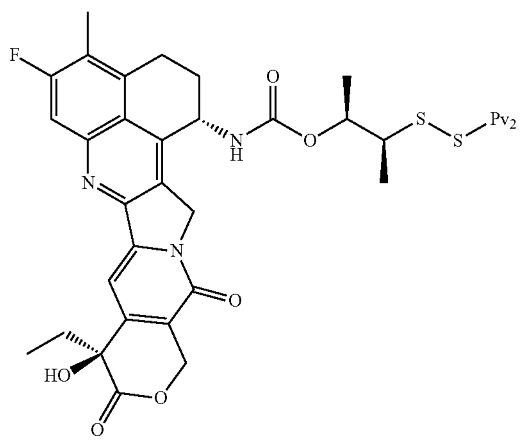 | B: 1526.1 | A<br>2-95%<br>11 min<br>7.5 min |
| 6 | 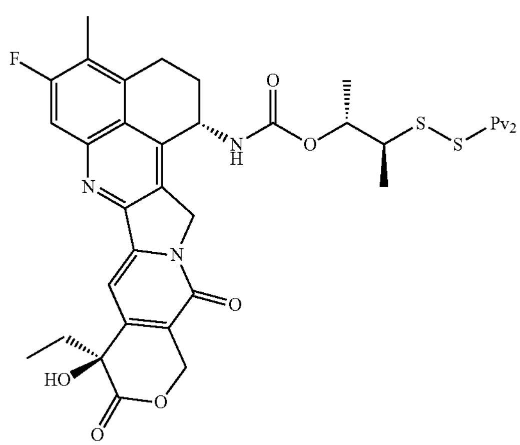 | B: 1525.8 | A<br>2-95%<br>11 min<br>7.4 min |

TABLE 4-continued

Example Compounds

| Example | Structure | MS
A: Maldi-TOF (M+)
B: ESI
(m/z = 3) | Column
%ACN/H₂O
Run Time
Retention Time |
|---|---|---|---|
| 7 | | B: 1526.4 | A
2-95%
11 min
7.5 min |
| 8 | | B: 1534.8 | A
2-95%
11 min
7.6 min |
| 9 | | B: 1534.6 | A
2-95%
11 min
7.7 min |

TABLE 4-continued

Example Compounds

| Example | Structure | MS<br>A: Maldi-TOF (M+)<br>B: ESI (m/z = 3) | Column<br>%ACN/H$_2$O<br>Run Time<br>Retention Time |
|---|---|---|---|
| 10 | 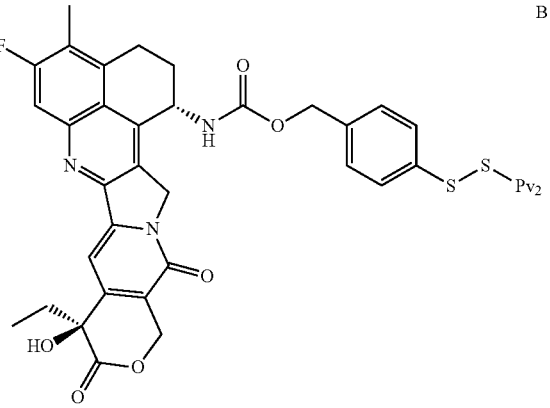 | B: 1537.6 | A<br>2-95%<br>11 min<br>7.5 min |

Example 11: Synthesis of Compound 11

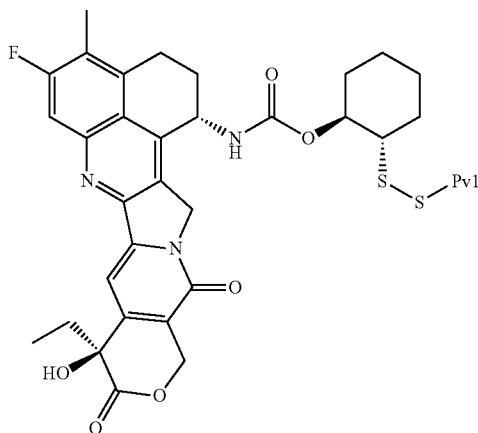

Step 1. Synthesis of 2-(pyridine-2-yldisulfanyl)cyclohexan-1-ol

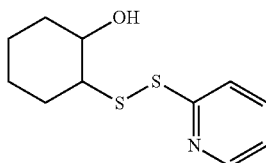

To a solution of 1,2-di(pyridine-2-yl)disulfane (15.2 g, 68.9 mmol) in MeOH (degassed with N$_2$) (30 mL) was added (1-mercaptocyclobutyl)methanol (11.4 g, 86.2 mmol) (degassed with N$_2$) dropwise and stirred for 16 h at room temperature under an N$_2$ atmosphere. The reaction mixture was concentrated to dryness under vacuum. The resultant crude material was purified by column chromatography using 30% EtOAC/hexanes to afford the title compound as a yellow liquid. $^1$HNMR (400 MHz, CDCl$_3$): δ 8.54-8.53 (m, 1H), 7.60-7.56 (m, 1H), 7.40-7.38 (m, 1H), 7.17-7.14 (m, 1H), 3.38-3.34 (m, 1H), 2.62-2.57 (m, 1H), 2.11-2.02 (m, 1H), 1.75-1.74 (m, 2H), 1.61-1.60 (m, 1H), 1.42-1.24 (m, 4H).

The title compound was subjected to chiral preparative HPLC conditions (Chiralpak IG: 250 mm×20 mm×5 mic; n-Hexane: IPA with 0.1% Diethylamine (80:20); 19 mL/min; 25° C. (Room Temperature). (1R,2R)-2-(pyridin-2-yldisulfanyl)cyclohexan-1-ol (4.5 g, 18.6 mmol) eluted first (retention time: 3.9 minutes), followed by (1S,2S)-2-(pyridin-2-yldisulfanyl)cyclohexan-1-ol (retention time: 11.3 minutes). The absolute stereochemistry was confirmed by comparison of the product of Step 2 with chiral material having a reported absolute stereochemistry (see Monaco, M. R.; J. Am. Chem. Soc. 2014, 136, 49, 16982-16985).

Step 2. Synthesis of 4-nitrophenyl ((1S,2S)-2-(pyridin-2-yldisulfanyl)cyclohexyl) carbonate

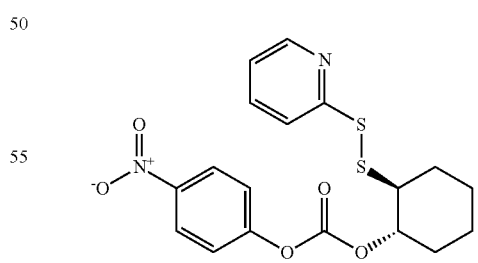

To a solution of (1R,2R)-2-(pyridin-2-yldisulfanyl)cyclohexan-1-ol (4.5 g, 18.6 mmol) in DMF (90.0 mL) was added DIPEA (10.3 mL, 56.0 mmol) and bis(4-nitrophenyl) carbonate (11.35 g, 27.3 mmol) at room temperature. The reaction vessel was sealed and stirred at room temperature for 12 h. Progress of the reaction was monitored by TLC (20% EtOAc/hexanes). After completion of the reaction, the reaction mixture was quenched with water (20.0 mL) and extracted with EtOAc (20.0 mL). The organic layer was separated, washed with brine, dried over anhydrous sodium sulfate and concentrated under reduced pressure to afford the crude product, which was purified by column chromatography using 20-30% EtOAc/hexanes to afford the title product as an off-white solid (5.0 g, 66% yield). $^1$HNMR (400 MHz, CDCl$_3$): δ 8.44 (d, J=4 Hz, 1H), 8.28 (d, J=8.8 Hz, 2H), 7.72 (d, J=8.4 Hz, 1H), 7.61-7.57 (t, J=7.6 Hz, 1H), 7.41 (d, J=9.6 Hz, 2H), 7.08-7.05 (t, J=5.2 Hz, 1H), 4.85-4.74 (m, 1H), 3.03-2.92 (m, 1H), 2.28 (d, J=9.6 Hz, 1H), 2.20-2.12 (m, 1H), 1.85-1.62 (m, 3H), 1.45-1.25 (m, 3H). LC-MS m/z calculated: 406.7; found: 407.4 [M+H]$^+$.

Step 3. Synthesis of [(1S,2S)-2-(2-pyridyldisulfanyl)cyclohexyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl] carbamate

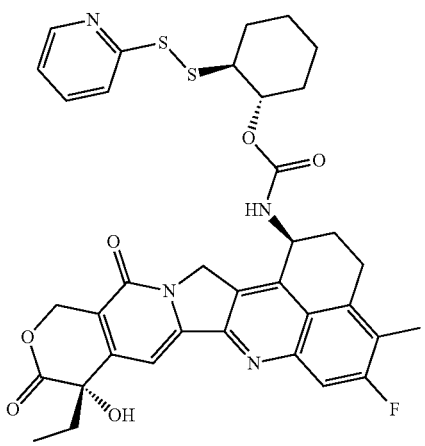 [SMILES: CC[C@@]1(O)C(=O)OCc2c1cc1n(c2=O)Cc2c-1nc1cc(F)c(C)c3c1c2[C@@H](NC(=O)O[C@H]1CCCC[C@@H]1SSc1ccccn1)CC3]

To (10S,23S)-23-amino-10-ethyl-18-fluoro-10-hydroxy-19-methyl-8-oxa-4,15-diazahexacyclo[14.7.1.02,14.04,13.06,11.020,24]tetracosa-1,6(11),12,14,16(24),17,19-heptaene-methanesulfonic acid (250 mg, 0.470 mmol) in 10 mL of dry DMF was added 4-nitrophenyl ((1S,2S)-2-(pyridin-2-yldisulfanyl)cyclohexyl) carbonate (from Step 2; 191 mg, mmol), N,N-diisopropylethylamine (122 mg, 0.941 mmol) and DMAP (115 mg, 0.941 mmol). The mixture was stirred at room temperature overnight. LC-MS indicated that the desired coupling product had formed. The reaction mixture was then diluted with EtOAc, washed with saturated aqueous NH$_4$Cl, H$_2$O, and brine. The mixture was dried over sodium sulfate, filtered, and concentrated. The crude residue was purified by column chromatography using 0-5% MeOH/dichloromethane to give 240 mg of the desired product in 72.6% yield (240 mg).

Step 4. Coupling with Pv1 (Compound 11)

In a vial was added Pv1 (275 mg, 0.0811 mmol), the compound of Step 3 (74.1 mg, 0.105 mmol), acetonitrile (10 mL) and water (5 mL). n-Methylmorpholine (0.303 g, 0.0030 mol) was added to this mixture. The mixture was stirred at room temperature overnight. LC-MS indicated that the desired coupled product had been formed.

The reaction mixture was purified directly by reverse phase HPLC (20-85% acetonitrile/water, 0.5% acetic acid on a Sunfire Prep C18 column (10 μm, 50×150 mm), retention time: 7.022 min) to give 213 mg of the desired product in 68% yield (213 mg). ESI (M+3H/3)$^{3+}$: 1291.6

Example 12: Synthesis of Compound 12

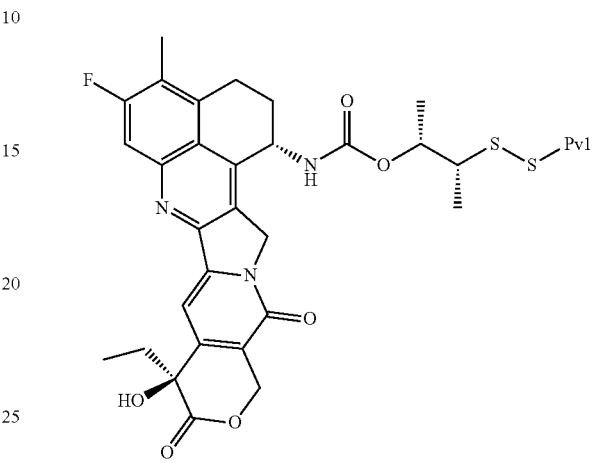

Step 1. Synthesis of [(1R,2R)-1-methyl-2-(2-pyridyldisulfanyl)propyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl] carbamate To a mixture of 1-hydroxybenzotriazole hydrate (8.64 mg, 0.0564 mmol), finely ground molecular sieve 4 Å (50 mg), and (10S,23S)-23-amino-10-ethyl-18-fluoro-10-hydroxy-19-methyl-8-oxa-4,15-diazahexacyclo[14.7.1.02,14.04,13.06,11.020,24]tetracosa-1,6(11),12,14,16(24),17,19-heptaene-5,9-dione; methanesulfonic acid (25.0 mg, 0.0470 mmol) and pyridine (0.0190 mL, 0.235 mmol) in 2 mL of anhydrous DMF was added [(1R,2R)-1-methyl-2-(2-pyridyldisulfanyl)propyl] (4-nitrophenyl) carbonate (19.7 mg, 0.470 mmol) (see Synthesis of II-4: 4-nitrophenyl((2R,3R)-3-(pyridin-2-yldisulfanyl)butan-2-yl) carbonate). After stirring for 16 h at room temperature the mixture was filtered, and the solution was concentrated. The residue was then purified by column chromatography (0-5% MeOH/DCM) to give the title compound (35.0 mg, 0.0517 mmol, yield: 110%).

Step 2. Coupling with Peptide Pv1 (Compound 12)

In a vial was placed peptide Pv1 (50.0 mg, 14.7e-5 mol), [(1R,2R)-1-methyl-2-(2-pyridyldisulfanyl)propyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl] carbamate (0.013 g, 1.92e-5 mol), 2 mL of ACN and 1 mL of water. To this was added N-methylmorpholine (0.060 mL, 0.000545 mol). The mixture was stirred overnight at RT. LC-MS indicated a complete reaction. The reaction mixture was purified directly by reverse phase HPLC (Waters SunfirePrep C18, PrepSlope 4 min, 20-85% ACN/H2O+0.05%

TFA, 13 min; retention time: 6.95 min) to give Compound 12 (0.0350 g, 9.10e-6 mol, yield: 61.8%). ESI (M+3H/3)$^{3+}$: 1281.9

Example 13: Synthesis of Compound 13

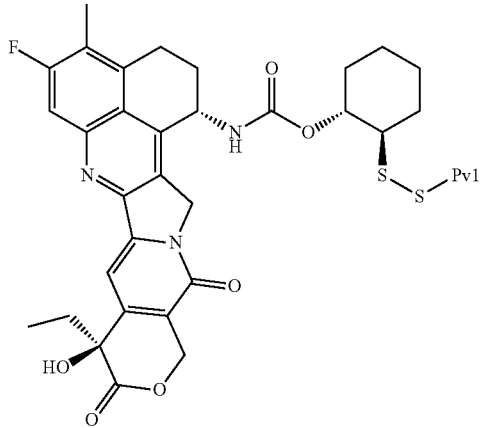

Compound 13 was made in an analagous fashion to Compound 11, replacing ((1S,2S)-2-(pyridin-2-yldisulfanyl) cyclohexyl) carbonate with ((1R,2R)-2-(pyridin-2-yldisulfanyl)cyclohexyl) carbonate in Step 2. Sunfire Prep C18 column (10 μm, 50×150 mm) (20-85% acetonitrile/water, 0.5% acetic acid); retention time: 6.609 minutes. ESI (M+3H/3)$^{3+}$: 1290.3

Example 14: Synthesis of Compound 14

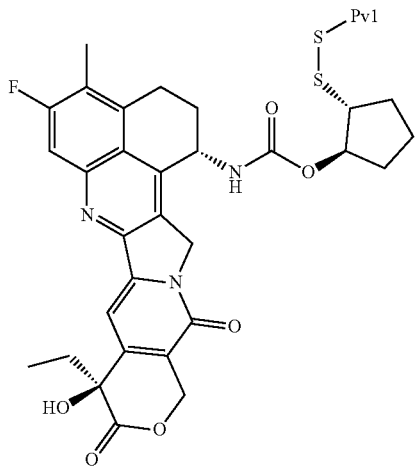

Step 1. Synthesis of (4-Nitrophenyl) [trans-(1RS, 2RS)-2-(2-pyridyldisulfanyl)cyclopentyl] carbonate The title compound was synthesized according to analagous synthetic methods described in the synthesis of Compound 11, using the first stereoisomer to be eluted from the chiral chromatography separation of racemic trans-2-(2-pyridyldisulfanyl)cyclopentyl assigned as trans-(1RS,2RS)-2-(2-pyridyldisulfanyl)cyclopentan-1-ol.

Step 2. Synthesis of [trans-(1RS,2RS)-2-(2-pyridyldisulfanyl)cyclopentyl] N-[(10S,23S)-10-ethyl-18-fluoro-10-hydroxy-19-methyl-5,9-dioxo-8-oxa-4,15-diazahexacyclo[14.7.1.02,14.04,13.06, 11.020,24] tetracosa-1,6(11),12,14,16(24),17,19-heptaen-23-yl] carbamate To a mixture of exatecan mesylate [CAS: 169869-90-3] (50 mg, 0.0941 mmol), DMAP (23.0 mg, 0.188 mmol), and (4-nitrophenyl) [trans-(1RS,2RS)-2-(2-pyridyldisulfanyl)cyclopentyl] carbonate (40.6 mg, 0.103 mmol) in 2 mL of anhydrous DMF was added N,N-diisopropylethylamine (35 μL, 0.188 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-5% MeOH/DCM) to give the title compound (33.0 mg, 0.0479 mmol, yield: 50.9%).

Step 3. Coupling with Peptide Pv1 (Compound 14)

In a vial was placed peptide Pv1 (50.0 mg, 1.47e-5 mol), [trans-(1RS,2RS)-2-(2-pyridyldisulfanyl)cyclopentyl] N-[(10S,23S)-10-ethyl-18-fluoro-10-hydroxy-19-methyl-5, 9-dioxo-8-oxa-4,15-diazahexacyclo[14.7.1.02,14.04,13.06, 11.020,24]tetracosa-1,6(11),12,14,16(24),17,19-heptaen-23-yl]carbamate (0.0124 g, 1.80e-5 mol), 2 mL of ACN and 1 mL of water. To this was added N-methylmorpholine (0.060 mL, 0.000545 mol). The mixture was stirred overnight at RT. LC-MS indicated a complete reaction. The reaction mixture was purified directly by reverse phase HPLC (Waters SunfirePrep C18, PrepSlope_4 min, 20-90% ACN/H2O+0.05% TFA, 16 min; retention time: 6.761 min) to give Compound 14 (0.0360 g, 9.34e-6 mol, yield: 63.3%). ESI (M+3H/3)$^{3+}$: 1286.3.

Example 15: Synthesis of Compound 15

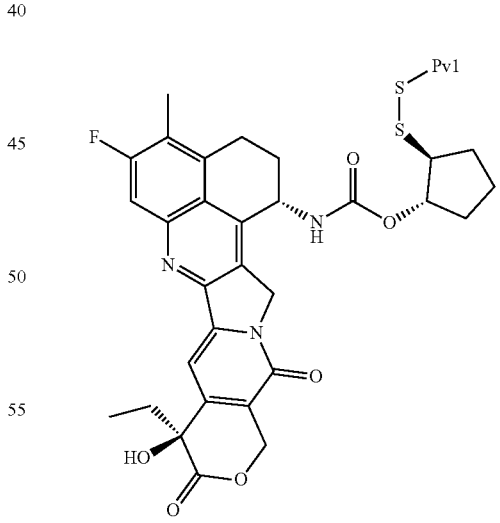

Step 1. Synthesis of (4-nitrophenyl) [trans-(1SR, 2SR)-2-(2-pyridyldisulfanyl)cyclopentyl] carbonate The title compound was synthesized from the second stereoisomer to be eluted from the chiral chromatography separation of racemic trans-2-(2-pyridyldisulfanyl)cyclopentyl, assigned as trans-(1SR,2SR)-2-(2-pyridyldisulfanyl)cyclopentan-1-ol, using analogous synthetic methods described in the synthesis of Compound 11.

Step 2. Synthesis of [trans-(1SR,2SR)-2-(2-pyridyldisulfanyl)cyclopentyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24] tetracosa-1,6(11),12,14,16(24),17,19-heptaen-23-yl]carbamate To a mixture of exatecan mesylate [CAS: 169869-90-3] (50 mg, 0.0941 mmol), DMAP (23.0 mg, 0.188 mmol), and (4-nitrophenyl) [trans-(1SR,2SR)-2-(2-pyridyldisulfanyl)cyclopentyl] carbonate (38.2 mg, 0.0974 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated NH₄Cl, 30 mL of water, and 20 mL of brine. The organic layer was concentrated and the residue was purified by column chromatography (0-5% MeOH/DCM) to give the title compound (29.0 mg, 0.0421 mmol, yield: 44.8%).

Step 3. Coupling with Peptide Pv1 (Compound 15)

In a vial was placed peptide Pv1 (50.0 mg, 1.47e-5 mol), trans-[(1SR,2SR)-2-(2-pyridyldisulfanyl)cyclopentyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.0124 g, 1.80e-5 mol), 2 mL of ACN and 1 mL of water. To this was added N-methylmorpholine (0.060 mL, 0.000545 mol). The mixture was stirred overnight at RT. LC-MS indicated a complete reaction. The reaction mixture was purified directly by reverse phase HPLC (Waters SunfirePrep C18, PrepSlope 4 min, 20-90% ACN/H2O+0.05% TFA, 16 min; retention time: 6.883 min) to give Compound 15 (0.0280 g, 7.26e-6 mol, yield: 49.3%). ESI (M+3H/3)³⁺: 1285.9.

Example 16: Synthesis of Compound 16

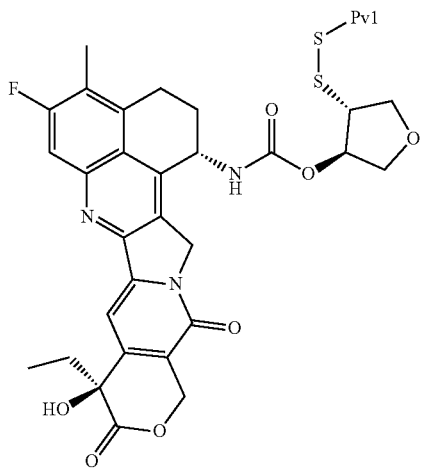

Step 1. Synthesis of (4-nitrophenyl) [trans-(3RS,4RS)-4-(2-pyridyldisulfanyl)tetrahydrofuran-3-yl] carbonate The title compound was synthesized from the first stereoisomer to be eluted from the chiral chromatography separation of racemic trans-4-(2-pyridyldisulfanyl)tetrahydrofuran-3-ol, assigned as trans-(3RS,4RS)-4-(2-pyridyldisulfanyl)tetrahydrofuran-3-ol, using analogous synthetic methods described in the synthesis of Compound 11.

Step 2. Synthesis of [trans-(3RS,4RS)-4-(2-pyridyldisulfanyl)tetrahydrofuran-3-yl] N-[(10S,23S)-diazahexacyclo[14.7.1.02,14.04,13.06,11.020,24]tetracosa-1,6(11),12,14,16(24),17,19-heptaen-23-yl]carbamate To a mixture of exatecan mesylate [CAS: 169869-90-3] (50 mg, 0.0941 mmol), DMAP (23.0 mg, 0.188 mmol), and (4-nitrophenyl) [trans-(3RS,4RS)-4-(2-pyridyldisulfanyl)tetrahydrofuran-3-yl]carbonate (38.2 mg, 0.0969 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated NH₄Cl, 30 mL of water, and 20 mL of brine. The organic layer was concentrated and the residue was purified by column chromatography (0-5% MeOH/DCM) to give the title compound (40.0 mg, 0.0579 mmol, yield: 61.6%).

Step 3. Coupling with Peptide Pv1 (Compound 16)

In a vial was placed peptide Pv1 (50.0 mg, 1.47e-5 mol), [trans-(3RS,4RS)-4-(2-pyridyldisulfanyl)tetrahydrofuran-3-yl] N-[(10S,23S)-10-ethyl-18-fluoro-10-hydroxy-19-methyl-1,6(11),12,14,16(24),17,19-heptaen-23-yl]carbamate (0.0124 g, 1.80e-5 mol), 2 mL of ACN and 1 mL of water. To this was added N-Methylmorpholine (0.060 mL, 0.000545 mol). The mixture was stirred overnight at RT. LC-MS indicated a complete reaction. The reaction mixture was purified directly by reverse phase HPLC (Waters SunfirePrep C18, PrepSlope_4 min, 20-80% ACN/H2O+0.05% TFA, 15 min; retention time: 6.633 min) to give Compound 16 (0.0290 g, 7.52e-6 mol, yield: 51.0%). ESI (M+3H/3)³⁺: 1286.4.

Example 17: Synthesis of Compound 17

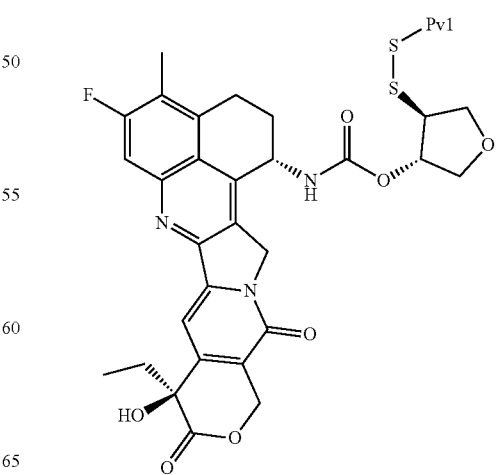

141

Step 1. Synthesis of (4-nitrophenyl) [trans-(3SR, 4SR)-4-(2-pyridyldisulfanyl)tetrahydrofuran-3-yl] carbonate The title compound was synthesized from the second stereoisomer to be eluted from the chiral chromatography separation of racemic trans-4-(2-pyridyldisulfanyl)tetrahydrofuran-3-ol, assigned as trans-(3SR,4SR)-4-(2-pyridyldisulfanyl)tetrahydrofuran-3-ol, using analagous synthetic methods described in the synthesis of Compound 11.

Step 2. Synthesis of [trans-(3SR,4SR)-4-(2-pyridyldisulfanyl)tetrahydrofuran-3-yl] N-[(10S, 23S)-diazahexacyclo[14.7.1.02,14.04,13.06,11.020, 24]tetracosa-1,6(11),12,14,16(24),17,19-heptaen-23-yl]carbamate To a mixture of exatecan mesylate [CAS: 169869-90-3] (50 mg, 0.0941 mmol), DMAP (23.0 mg, 0.188 mmol), and (4-nitrophenyl) [trans-(3SR,4SR)-4-(2-pyridyldisulfanyl)tetrahydrofuran-3-yl]carbonate (38.2 mg, 0.0969 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated $NH_4Cl$, 30 mL of water, and 20 mL of brine. The organic layer was concentrated and the residue was purified by column chromatography (0-5% MeOH/DCM) to give [trans-(3 SR,4SR)-4-(2-pyridyldisulfanyl)tetrahydrofuran-3-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6 (11),12,14,16(24),17,19-heptaen-23-yl]carbamate (31.0 mg, 0.0449 mmol, yield: 47.7%).

Step 3. Coupling with Peptide Pv1 (Compound 17)

In a vial was placed peptide Pv1 (50.0 mg, 1.47e-5 mol), [trans-(3 SR,4SR)-4-(2-pyridyldisulfanyl)tetrahydrofuran-3-yl] N-[(10S,23S)-10-ethyl-18-fluoro-10-hydroxy-19-methyl-1,6(11),12,14,16(24),17,19-heptaen-23-yl]carbamate (0.0124 g, 1.80e-5 mol), 2 mL of ACN and 1 mL of water. To this was added N-methylmorpholine (0.060 mL, 0.000545 mol). The mixture was stirred overnight at RT. LC-MS indicated a complete reaction. The reaction mixture was purified directly by reverse phase HPLC (Waters SunfirePrep C18, PrepSlope_4 min, 20-85% ACN/H2O+0.05% TFA, 13 min; retention time: 6.670 min) to give Compound 17 (0.0170 g, 4.41e-6 mol, yield: 29.9%). ESI $(M+3H/3)^{3+}$: 1286.7.

142

Example 18: Synthesis of Compound 18

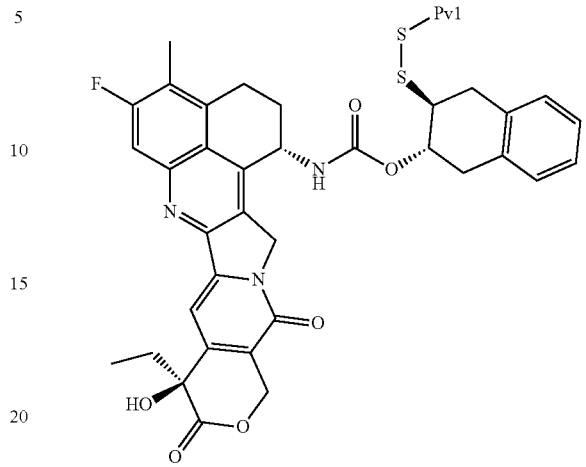

Step 1. Synthesis of (4-nitrophenyl) [trans-(2RS, 3RS)-3-(2-pyridyldisulfanyl)tetralin-2-yl] carbonate The title compound was synthesized from the first stereoisomer to be eluted from the chiral chromatography separation of racemic trans-3-(2-pyridyldisulfanyl)tetralin-2-ol, assigned as trans-(2RS,3RS)-3-(2-pyridyldisulfanyl)tetralin-2-ol, using analagous synthetic methods described in the synthesis of Compound 11.

Step 2. Synthesis of [trans-(2RS,3RS)-3-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06, 11.020,24]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(2RS,3RS)-3-(2-pyridyldisulfanyl)tetralin-2-yl] carbonate (32.1 mg, 0.0705 mmol) in 2 mL of anhydrous DMF was added N,N-diisopropylethylamine (18 µL, 0.941 mmol). After stirring for 16 h at room temperature the mixture was diluted with EtOAc (50 mL), washed with 30 mL of saturated $NH_4Cl$, 30 mL of water, and 20 mL of brine. The organic layer was concentrated and the residue was purified by column chromatography (0-3% MeOH/DCM) to give the title compound (26.0 mg, 0.0346 mmol, yield: 73.6%).

Step 3. Coupling with Peptide Pv1 (Compound 18)

In a vial was placed peptide Pv1 (25.0 mg, 7.37e-6 mol), [trans-(2RS,3RS)-3-(2-pyridyldisulfanyl)tetralin-2-yl] N-[(10S,23S)-10-ethyl-18-fluoro-10-hydroxy-19-methyl-5, 9-dioxo-8-oxa-4,15-diazahexacyclo[14.7.1.02,14.04,13.06, 11.020,24]tetracosa-1,6(11),12,14,16(24),17,19-heptaen-23-yl]carbamate (0.00719 g, 9.58e-6 mol), 1 mL of ACN and 0.5 mL of water. To this was added N-methylmorpholine (0.030 mL, 0.000273 mol). The mixture was stirred for 65h at RT. LC-MS indicated a complete reaction. The reaction mixture was purified directly by reverse phase HPLC (Waters SunfirePrep C18, PrepSlope_4 min, 20-95% ACN/

H2O+0.05% TFA, 20 min; retention time: 6.851 min) to give Compound 18 (0.0080 g, 2.04e-6 mol, yield: 27.7%). ESI (M+3H/3)$^{3+}$: 1307.4.

Example 19: Synthesis of Compound 19

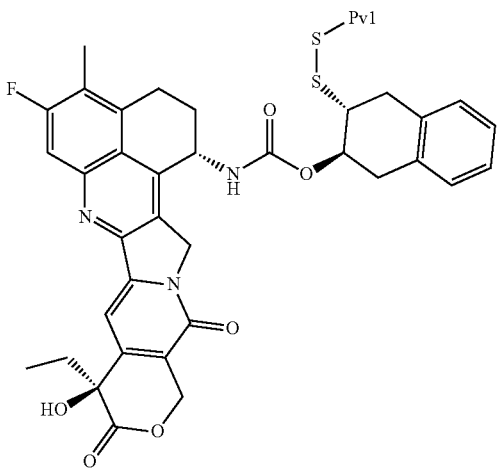

Step 1. Synthesis of (4-nitrophenyl) [trans-(2SR, 3SR)-3-(2-pyridyldisulfanyl)tetralin-2-yl] carbonate The title compound was synthesized from the second stereoisomer to be eluted from the chiral chromatography separation of racemic trans-3-(2-pyridyldisulfanyl)tetralin-2-ol, assigned as trans-(2SR,3SR)-3-(2-pyridyldisulfanyl) tetralin-2-ol, using analagous synthetic methods described in the synthesis of Compound 11.

Step 2. Synthesis of [trans-(2SR,3SR)-3-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(2SR,3SR)-3-(2-pyridyldisulfanyl)tetralin-2-yl]carbonate (32.1 mg, 0.0705 mmol) in 2 mL of anhydrous DMF was added N,N-diisopropylethylamine (18 µL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give [trans-(2SR,3SR)-3-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (10.0 mg, 0.0133 mmol, yield: 28.3%).

Step 3. Coupling with Peptide Pv1 (Compound 19)

In a vial was placed peptide Pv1 (25.0 mg, 7.37e-6 mol), [trans-(2SR,3SR)-3-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.010 g, 1.33e-5 mol), 1 mL of ACN and 1 mL of water. To this was added N-methylmorpholine (0.030 mL, 0.000273 mol). The mixture was stirred for 65 h at RT. LC-MS indicated a complete reaction.

The reaction mixture was purified directly by reverse phase HPLC (Waters SunfirePrep C18, PrepSlope_4 min, 20-95% ACN/H2O+0.05% TFA, 20 min; retention time: 6.855) to give Compound 19 (0.0060 g, 1.33e-5 mol, yield: 20.8%). ESI (M+3H/3)$^{3+}$: 1307.6.

Example 20: Synthesis of Compound 20

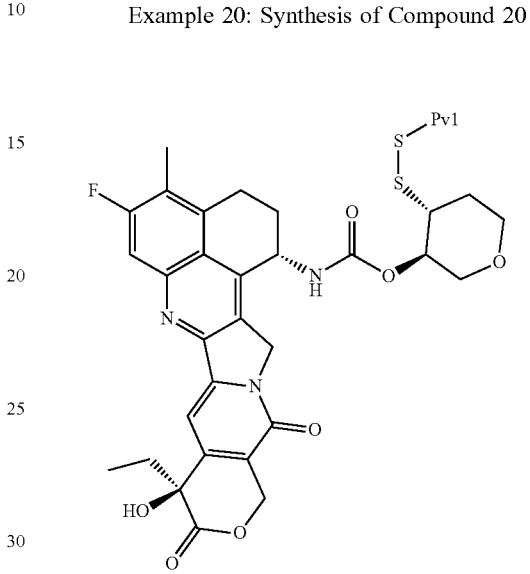

Step 1. Synthesis of (4-nitrophenyl) [trans-(3RS, 4RS)-4-(2-pyridyldisulfanyl)tetrahydropyran-3-yl] carbonate The title compound was synthesized from the first stereoisomer to be eluted from the chiral chromatography separation of racemic trans-4-(2-pyridyldisulfanyl)tetrahydropyran-3-ol, assigned as trans-(2RS,3RS)-4-(2-pyridyldisulfanyl)tetrahydropyran-3-ol, using analagous synthetic methods described in the synthesis of Compound 11.

Step 2. Synthesis of [trans-(3RS,4RS)-4-(2-pyridyldisulfanyl)tetrahydropyran-3-yl] N-[(10S, 23S)-10-ethyl-18-fluoro-10-hydroxy-19-methyl-5,9-dioxo-8-oxa-4,15-diazahexacyclo[14.7.1.02,14.04, 13.06,11.020,24]tetracosa-1,6(11),12,14,16(24),17, 19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(3RS,4RS)-4-(2-pyridyldisulfanyl) tetrahydropyran-3-yl]carbonate (23.1 mg, 0.0564 mmol) in 2 mL of anhydrous DMF was added N,N-diisopropylethylamine (18 µL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give [trans-(3RS,4RS)-4-(2-pyridyldisulfanyl)tetrahydropyran-3-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (30.0 mg, 0.0426 mmol, yield: 90.5%).

Step 3. Coupling with Peptide Pv1 (Compound 20)

In a vial was placed peptide Pv1 (25.0 mg, 7.37e-6 mol), [trans-(3RS,4RS)-4-(2-pyridyldisulfanyl)tetrahydropyran-3-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.00779 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 30-85% ACN/H2O+0.05% TFA, 13 min; retention time: 6.380) to give Compound 20 (0.0060 g, 1.55e-6 mol, yield: 21.0%). ESI (M+3H/3)$^{3+}$: 1292.3.

Example 21: Synthesis of Compound 21

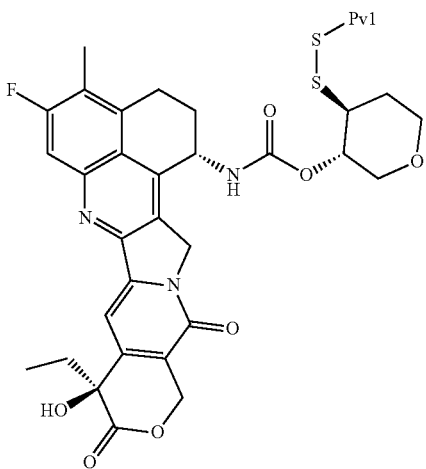

Step 1. Synthesis of (4-nitrophenyl) [trans-(3SR, 4SR)-4-(2-pyridyldisulfanyl)tetrahydropyran-3-yl] carbonate The title compound was synthesized from the second stereoisomer to be eluted from the chiral chromatography separation of racemic trans-4-(2-pyridyldisulfanyl)tetrahydropyran-3-ol, assigned as trans-(2SR,3 SR)-4-(2-pyridyldisulfanyl)tetrahydropyran-3-ol, using analagous synthetic methods described in the synthesis of Compound 11.

Step 2. Synthesis of [trans-(3SR,4SR)-4-(2-pyridyldisulfanyl)tetrahydropyran-3-yl] N-[(10S, 23S)-10-ethyl-18-fluoro-10-hydroxy-19-methyl-5,9-dioxo-8-oxa-4,15-diazahexacyclo[14.7.1.02,14.04, 13.06,11.020,24]tetracosa-1,6(11),12,14,16(24),17, 19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(3SR,4SR)-4-(2-pyridyldisulfanyl)tetrahydropyran-3-yl]carbonate (23.1 mg, 0.0564 mmol) in 2 mL of anhydrous DMF was added N,N-Diisopropylethylamine (18 μL, 0.941 mmol). After stirring for 16 h at room temperature the mixture was diluted with EtOAc (50 mL), washed with 30 mL of saturated NH4Cl, 30 mL of water, and 20 mL of brine. The organic layer was concentrated and the residue was purified by column chromatography (0-3% MeOH/DCM) to give [trans-(3SR,4SR)-4-(2-pyridyldisulfanyl)tetrahydropyran-3-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (25.0 mg, 0.0355 mmol, yield: 75.4%).

Step 3. Coupling with Peptide Pv1 (Compound 21)

In a vial was placed peptide Pv1 (25.0 mg, 7.37e-6), [trans-(3SR,4SR)-4-(2-pyridyldisulfanyl)tetrahydropyran-3-yl] N-[(10S,23S)-10-ethyl-18-fluoro-10-hydroxy-19-methyl-5,9-dioxo-8-oxa-4,15-diazahexacyclo[14.7.1.02, 14.04,13.06,11.020,24]tetracosa-1,6(11),12,14,16(24),17, 19-heptaen-23-yl]carbamate (0.00779 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-70% ACN/H2O+0.05% TFA, 17 min; retention time: 6.765 min) to give Compound 21 (0.021 g, 5.42e-6 mol, yield: 73.6%). ESI (M+3H/3)$^{3+}$: 1291.1.

Example 22: Synthesis of Compound 22

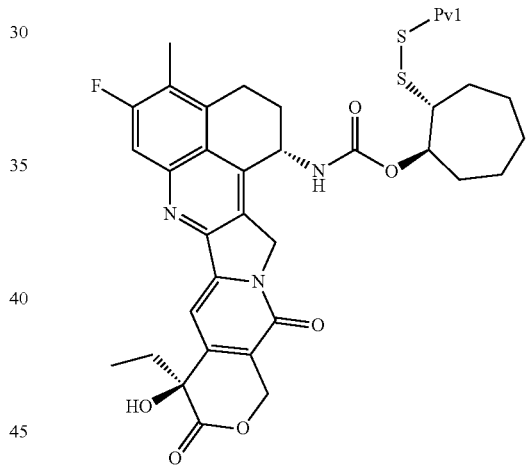

Step 1. Synthesis of (4-nitrophenyl) [trans-(1RS, 2RS)-2-(2-pyridyldisulfanyl)cycloheptyl] carbonate The title compound was synthesized from the first stereoisomer to be eluted from the chiral chromatography separation of racemic trans-2-(2-pyridyldisulfanyl)cycloheptan-1-ol, assigned as trans-(1RS,2RS)-2-(2-pyridyldisulfanyl)cycloheptan-1-ol, using analagous synthetic methods described in the synthesis of Compound 11.

Step 2. Synthesis of [trans-(1RS,2RS)-2-(2-pyridyldisulfanyl)cycloheptyl] N-[(10S,23S)-10-ethyl-18-fluoro-10-hydroxy-19-methyl-5,9-dioxo-8-oxa-4,15-diazahexacyclo[14.7.1.02,14.04,13.06, 11.020,24]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(1RS,2RS)-2-(2-pyridyldisulfanyl)cycloheptyl] carbonate (23.7 mg, 0.0564 mmol) in 2 mL of anhydrous DMF was added N,N-diisopropylethylamine (18 μL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give the title compound (29.0 mg, 0.0405 mmol, yield: 86.0%).

Step 3. Coupling with Peptide Pv1 (Compound 22)

In a vial was placed peptide Pv1 (25.0 mg, 7.37e-6), [trans-(1RS,2RS)-2-(2-pyridyldisulfanyl)cycloheptyl] N-[(10S,23S)-10-ethyl-18-fluoro-10-hydroxy-19-methyl-5,9-dioxo-8-oxa-4,15-diazahexacyclo[14.7.1.0$^{2,14}$.0$^{4,13}$.0$^{6,11}$.0$^{20,24}$]tetracosa-1,6(11),12,14,16(24),17,19-heptaen-23-yl]carbamate (0.00792 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-70% ACN/H2O+0.05% TFA, 17 min; retention time: 6.868 min) to give Compound 22 (0.020 g, mol, yield: 69.9%). ESI (M+3H/3)$^{3+}$: 1296.3.

Example 23: Synthesis of Compound 23

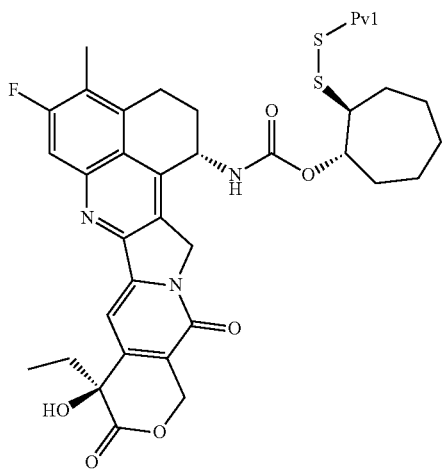

Step 1. Synthesis of (4-nitrophenyl) [trans-(1SR,2SR)-2-(2-pyridyldisulfanyl)cycloheptyl] carbonate The title compound was synthesized from the second stereoisomer to be eluted from the chiral chromatography separation of racemic trans-2-(2-pyridyldisulfanyl)cycloheptan-1-ol, assigned as trans-(1SR,2SR)-2-(2-pyridyldisulfanyl)cycloheptan-1-ol, using analagous synthetic methods described in the synthesis of Compound 11.

Step 2. Synthesis of [trans-(1SR,2SR)-2-(2-pyridyldisulfanyl)cycloheptyl] N-[(10S,23S)-10-ethyl-18-fluoro-10-hydroxy-19-methyl-5,9-dioxo-8-oxa-4,15-diazahexacyclo[14.7.1.0$^{2,14}$.0$^{4,13}$.0$^{6,11}$.0$^{20,24}$]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(1SR,2SR)-2-(2-pyridyldisulfanyl)cycloheptyl] carbonate (23.7 mg, 0.0564 mmol) in 2 mL of anhydrous DMF was added N,N-diisopropylethylamine (18 μL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give the title compound (31.0 mg, 0.0432 mmol, yield: 91.9%).

Step 3. Coupling with Peptide Pv1 (Compound 23)

In a vial was placed peptide Pv1 (25.0 mg, 7.37e-6), [trans-(1SR,2SR)-2-(2-pyridyldisulfanyl)cycloheptyl] N-[(10S,23S)-10-ethyl-18-fluoro-10-hydroxy-19-methyl-5,9-dioxo-8-oxa-4,15-diazahexacyclo[14.7.1.0$^{2,14}$.0$^{4,13}$.0$^{6,11}$.0$^{20,24}$]tetracosa-1,6(11),12,14,16(24),17,19-heptaen-23-yl]carbamate (0.00792 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-88% ACN/H2O+0.05% TFA, 17 min; retention time 7.178 min) to give Compound 23 (0.020 g, 5.15e-6 mol, yield: 69.9%). ESI (M+3H/3)$^{3+}$: 1296.0.

Example 24: Synthesis of Compound 24

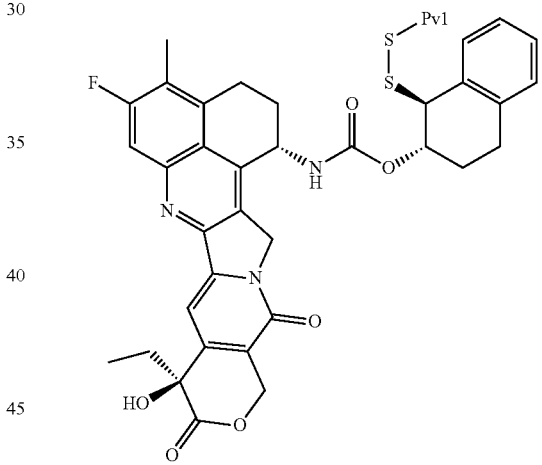

Step 1. Synthesis of (4-nitrophenyl) [trans-1-(1RS,2RS)-1-(2-pyridyldisulfanyl)tetralin-2-yl] carbonate The title compound was synthesized from the first stereoisomer to be eluted from the chiral chromatography separation of racemic trans-1-(2-pyridyldisulfanyl)tetralin-2-ol, assigned as trans-(1RS,2RS)-1-(2-pyridyldisulfanyl)tetralin-2-ol, using analagous synthetic methods described in the synthesis of Compound 11.

Step 2. Synthesis of [trans-(1RS,2RS)-1-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.0$^{2,14}$.0$^{4,13}$.0$^{6,11}$.0$^{20,24}$]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-1-(1RS,2RS)-2-pyridyldisulfanyl)tetralin-2-yl] carbonate (32.1 mg, 0.0705 mmol) in 2 mL of anhydrous DMF was added N,N-diisopropylethylamine (18 µL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give the title compound (20.0 mg, 0.0266 mmol, yield: 56.6%).

Step 3. Coupling with Peptide Pv1 (Example 24)

In a vial was placed peptide Pv1 (25.0 mg, 7.37e-6), [trans-1-(1RS,2RS)-1-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.0083 g, 1.11e-5 mol), 1 mL of ACN and mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-95% ACN/H2O+0.05% TFA, 20 min; retention time 6.968) to give Compound 24 (0.012 g, 3.06e-6 mol, yield: 41.6%). ESI (M+3H/3)$^{3+}$: 1307.2

Example 25: Synthesis of Compound 25

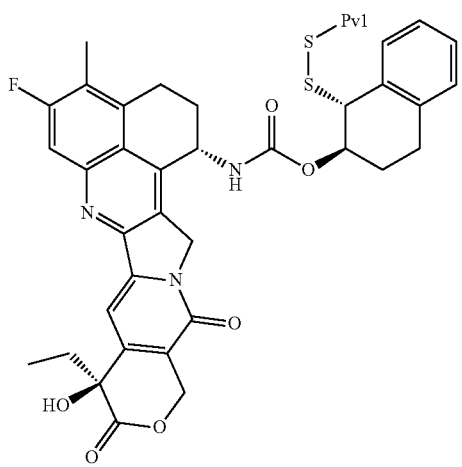

Step 1. Synthesis of (4-nitrophenyl) [trans-(1SR,2SR)-1-(2-pyridyldisulfanyl)tetralin-2-yl] carbonate The title compound was synthesized from the second stereoisomer to be eluted from the chiral chromatography separation of racemic trans-1-(2-pyridyldisulfanyl)tetralin-2-ol, assigned as trans-(1SR,2SR)-1-(2-pyridyldisulfanyl)tetralin-2-ol, using analagous synthetic methods described in the synthesis of Compound 11.

Step 2. Synthesis of [trans-(1SR,2SR)-1-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate To a mixture of exatecan mesylate [CAS: 169869-90-3] (25 mg, 0.0470 mmol), DMAP (11.5 mg, 0.0941 mmol), and (4-nitrophenyl) [trans-(1SR,2SR)-1-(2-pyridyldisulfanyl)tetralin-2-yl] carbonate (32.1 mg, 0.0705 mmol) in 2 mL of anhydrous DMF was added N,N-diisopropylethylamine (18 µL, 0.941 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give the title compound (22.0 mg, 0.0293 mmol, yield: 62.3%).

Step 3. Coupling with Peptide Pv1 (Compound 25)

In a vial was placed peptide Pv1 (25.0 mg, 7.37e-6), [trans-(1SR,2SR)-1-(2-pyridyldisulfanyl)tetralin-2-yl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.0083 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction.

The reaction mixture was purified directly by reverse phase HPLC (Waters SunfirePrep C18, PrepSlope_4 min, 20-95% ACN/H2O+0.05% TFA, 20 min; retention time: 6.944) to give Compound 25 (0.013 g, 3.32e-6 mol, yield: 45.0%). ESI (M+3H/3)$^{3+}$: 1307.0

Example 26: Synthesis of Compound 26

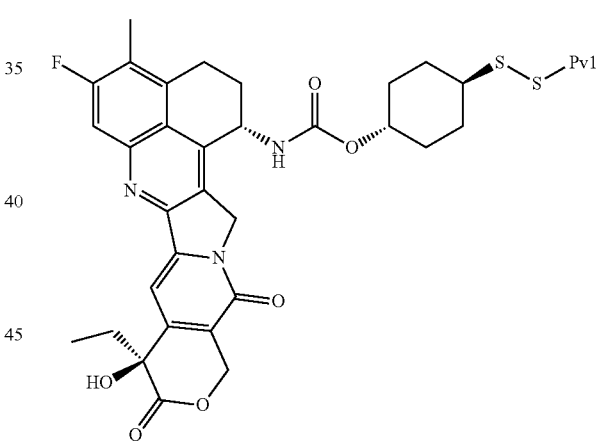

Step 1. Synthesis of [trans-4-(2-pyridyldisulfanyl)cyclohexyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24] tetracosa-1,6(11),12,14,16(24),17,19-heptaen-23-yl]carbamate To a mixture of exatecan mesylate [CAS: 169869-90-3] (50 mg, 0.0941 mmol) and (4-nitrophenyl) [4-(2-pyridyldisulfanyl)cyclohexyl] carbonate (synthesized from commercial trans-4-mercaptocyclohexan-1-ol) (42.1 mg, 0.103 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated NH$_4$Cl, 30 mL of water, and 20 mL of brine. The organic layer was concentrated and the residue was purified by column chromatography (0-3% MeOH/DCM) to give the title compound (45.0 mg, 0.0640 mmol, yield: 68.1%).

Step 2. Coupling with Peptide Pv1 (Compound 26)

In a vial was placed peptide Pv1 (25.0 mg, 7.37e-6), [trans-4-(2-pyridyldisulfanyl)cyclohexyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.00777 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction.
The reaction mixture was purified directly by reverse phase HPLC (Waters SunfirePrep C18, PrepSlope_4 min, 20-95% ACN/H2O+0.05% TFA, 20 min; retention time: 6.593 min) to give Compound 26 (0.028 g, 7.23e-6 mol, yield: 98.2%). ESI (M+3H/3)$^{3+}$: 1291.0.

Example 27: Synthesis of Compound 27

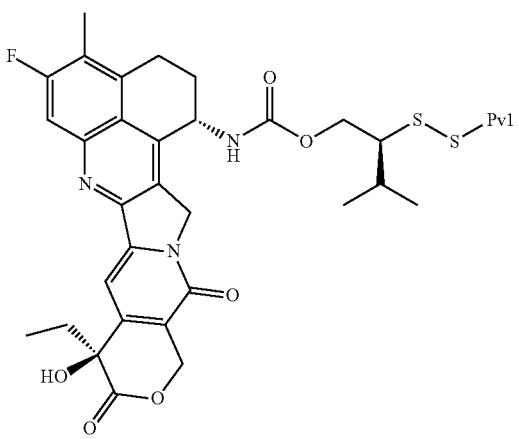

Step 1. Synthesis of [(2S)-3-methyl-2-(2-pyridyldisulfanyl)butyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate To a mixture of exatecan mesylate [CAS: 169869-90-3] (50 mg, 0.0941 mmol) and [(2S)-3-methyl-2-(2-pyridyldisulfanyl)butyl] (4-nitrophenyl) carbonate (synthesized from L-valine, cf J. Org. Chem. 1990,55, 2286-2288) (40.8 mg, 0.103 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated NH4Cl, 30 mL of water, and 20 mL of brine. The organic layer was concentrated and the residue was purified by column chromatography (0-3% MeOH/DCM) to give the title compound (48.0 mg, 0.0695 mmol, yield: 73.9%).

Step 2. Coupling with Peptide Pv1 (Compound 27)

In a vial was placed peptide Pv1 (25.0 mg, 7.37e-6 mol), [(2S)-3-methyl-2-(2-pyridyldisulfanyl)butyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.00764 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-95% ACN/H2O+0.05% TFA, 20 min; retention time: 6.773 min) to give Compound 27 (0.024 g, 6.22e-6 mol, yield: 84.4%). ESI (M+3H/3)$^{3+}$: 1286.8.

Example 28: Synthesis of Compound 28

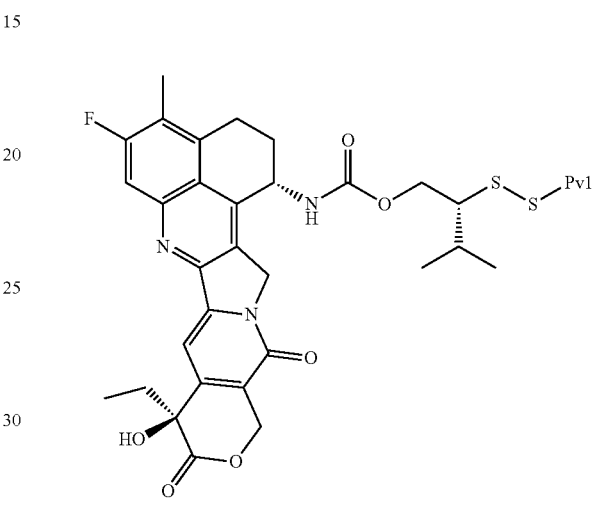

Step 1. Synthesis of [(2R)-3-methyl-2-(2-pyridylisulfanyl)butyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24), 17,19-heptaen-23-yl]carbamate To a mixture of exatecan mesylate [CAS: 169869-90-3] (50 mg, 0.0941 mmol) and (4-nitrophenyl) (2R)-3-methyl-2-(2-pyridyldisulfanyl)butyl] carbonate (synthesized from D-valine, cf J. Org. Chem. 1990,55, 2286-2288) (40.8 mg, 0.103 mmol) in 2 mL of anhydrous DMF was added N,N-diisopropylethylamine (35 µL, 0.188 mmol). After stirring for 16 h at room temperature the mixture was diluted with EtOAc (50 mL), washed with 30 mL of saturated NH4Cl, 30 mL of water, and 20 mL of brine. The organic layer was concentrated and the residue was purified by column chromatography (0-3% MeOH/DCM) to give the title compound (41.0 mg, 0.0594 mmol, yield: 63.1%).

Step 2. Coupling with Peptide Pv1 (Compound 28)

In a vial was placed peptide Pv1 (25.0 mg, 7.37e-6), [(2R)-3-methyl-2-(2-pyridyldisulfanyl)butyl] N-[(10S,23S)-10-ethyl-18-fluoro-10-hydroxy-19-methyl-5,9-dioxo-8-oxa-4,15-diazahexacyclo[14.7.1.02,14.04,13.06,11.020,24]tetracosa-1,6(11),12,14,16(24),17,19-heptaen-23-yl]carbamate (0.00764 g, 1.11e-5 mol), 1 mL of ACN and 0.5 mL of water. To this was added N-methylmorpholine (0.030 mL, 0.000273 mol). The mixture was stirred for 65 h at RT. LC-MS indicated a complete reaction. The reaction mixture was purified directly by reverse phase HPLC (Waters SunfirePrep C18, PrepSlope_4 min, 20-95% ACN/H2O+0.05% TFA, 20 min; retention time: 6.708 min) to give Compound 28 (0.012 g, 3.08e-6 mol, yield: 41.8%). ESI (M+3H/3)$^{3+}$: 1287.8.

Example 29: Synthesis of Compound 29

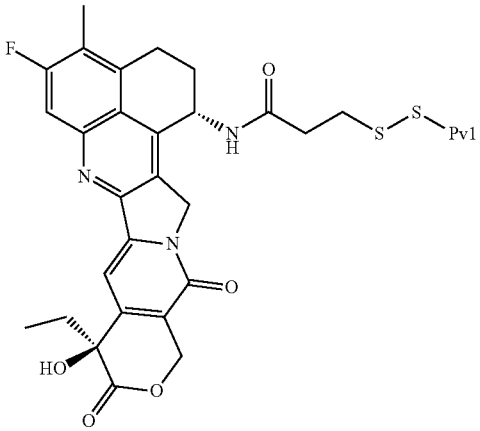

Analytical methods: Chromatographic purities were determined on an Agilent 1200 Series, 1100 Series or 6130 Series LC/MS system using a Merck Chromolith RP-18e analytical HPLC column (monolithic, 50×2 mm) and the following analytical HPLC method: injection volume 5 µL; flow rate 1 mL/min; 5→95% acetonitrile in water with 0.05% AcOH (Method A) or 0.05% TFA (Method B) over 5 mins; Agilent diode array detector at 1=254, 220 or 195 nm; room temperature.

Step 1. Preparation of N-((1S,9S)-9-ethyl-5-fluoro-9-hydroxy-4-methyl-10,13-dioxo-2,3,9,10,13,15-hexahydro-1H,12H-benzo[de]pyrano[3'4':6,7]indolizino[1,2-b]quinolin-1-yl)-3-(pyridin-2-yldisulfaneyl)propanamide A solution of 2,5-dioxopyrrolidin-1-yl 3-(pyridin-2-yldisulfaneyl)propanoate (180 mg, mmol), in DMF (4 mL) was added to solid exatecan mesylate [CAS: 169869-90-3] (80 mg, 0.150 mmol) then added aqueous PBS buffer (4 mL, pH=7.4, 50 mM) and sonicated ~5 minutes. The cloudy mixture was stirred at ambient temperature for 2 hours, and the reaction was determined to be about 25% complete. Ammonium acetate (11 mg, 0.143 mmol) was added with an additional 2 mL of DMF, and the resultant mixture was stirred at ambient temperature for 18 hours. The mixture was made acidic with TFA (80 mL, 0.98 mmol), and divided into 2 equal portions. Each individual portion was purified on a Redi-Sep C$_{18}$ 50 g cartridge and eluted with a gradient of acetonitrile (5% to 95%) in water with TFA (0.05% v/v). Combined fractions were frozen and lyophilized to afford the title compound as a pale yellow solid (42 mg, 44%). HPLC purity at 254 nm: 97%. Retention time: 2.50 min (Method A). MS data, 633.2 (M+H)$^+$.

Step 2. Coupling with Peptide Pv1 (Compound 29)

Solid peptide Pv1 (168.4 mg, 0.0480 mmol) was added to solid N-(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-(pyridin-2-yldisulfaneyl)propanamide (30.5 mg, 0.0482 mmol) and dissolved in DMF (2 mL) with sonication (~1 minute) and flushed with nitrogen. 4-Methylmorpholine (20 mL, 0.182 mmol) was added and the solution kept at ambient temperature for 18 h. The solution was made acidic with acetic acid (17 mL, 0.296 mmol), applied to a Biotage C$_{18}$ 300 A 25 g reverse phase column, and eluted with a gradient of acetonitrile (25% to 95%) in water with TFA (0.05% v/v). Combined fractions were frozen and lyophilized to afford a pale yellow solid. The product was dissolved in DMSO (3 mL) and 1 mL portions of the solution were individually purified on a Biotage C$_{18}$ 300 A 25 g reverse phase column, eluted with a gradient (25% to 95%) of a solution (acetonitrile/water/2-propanol, 3/2/1) in water with ammonium acetate (10 mM). Combined fractions were frozen and lyophilized to afford a pale yellow solid, which was dissolved in water/acetonitrile (2/1) with 0.4% TFA, transferred into a tared vial and lyophilized to a solid, Compound 29 (128 mg, 66%). HPLC purity at 254 nm: >95%. Retention time: 3.19 min (Method B) MS data: 1900.6 (M+2H/2)$^{2+}$, 1267.3 (M+3H/3)$^{3+}$.

Example A. Growth Delay Assay

Cells were plated in 96 well black walled-clear bottom plates (Griener), DLD-1 WT cells at 2500 cells per well, FaDu, and HeLa cells at 5000 cells per well, and HCT116 at 3000 cells per well, in growth media containing 10% FBS. Cells were allowed to adhere at room temperature for 60 minutes before returning to a 37 C, 5% CO$_2$ incubator. After 24 hours, media was removed and replaced with fresh growth media containing various drug concentrations. Each drug concentration was added in triplicate. Non-drug treated controls contained growth media only. Cells were returned to the incubator. Ninety-six hours after addition of drug, cells were fixed with 4% paraformaldehyde for 20 minutes and stained with Hoechst at 1 ug/mL. The plates were imaged on a Cytation 5 auto imager (BioTek) and cells were counted using CellProfiler (http://cellprofiler.org). The percent cell growth delay was calculated and data plotted using GraphPad Prism

| Compound | DLD-1 (IC50, nM) | HCT116 (IC50, nM) | FaDu (IC50, nM) | HeLa (IC50, nM) |
|---|---|---|---|---|
| R$^8$H-5 | 0.13 | 0.05 | 0.04 | 0.12 |
| 1 | 1.8 | 0.38 | 0.21 | 0.3 |
| 2 | 4.0 | 0.66 | 0.39 | 0.51 |
| 3 | IC* | 8.33 | 5.9 | 7.6 |
| 6 | 13.9 | 1.0 | 0.76 | 0.62 |
| 5 | 0.83 | 0.12 | 0.06 | 0.07 |
| 4 | 0.80 | 0.10 | 0.06 | 0.07 |

*IC = Incomplete curve.

| Compound | HCT-116 (IC50, nM) |
|---|---|
| 11 | 22.6 |
| 12 | 2.6 |
| 13 | 21.0 |
| 14 | 4.7 |
| 15 | 1.7 |
| 16 | 1.7 |
| 17 | 0.7 |
| 18 | 2.9 |
| 19 | 1.8 |

-continued

| Compound | HCT-116 (IC50, nM) |
| --- | --- |
| 20 | 7.9 |
| 21 | 3.1 |
| 22 | 5.9 |
| 23 | 11.9 |
| 24 | 3.4 |
| 25 | 2.9 |
| 26 | 87.0 |
| 27 | 0.7 |
| 28 | 1.1 |
| 29 | 69.0 |

Example B: Plasma Pharmacokinetics of Compound 11 in a Rat Model

Animal Dosing

Male Sprague Dawley rats underwent jugular vein cannulation and insertion of a vascular access button (VAB, Instech Labs Cat #VABR1B/22) at Envigo Labs prior to shipment. Magnetic, aluminum caps (Instech Labs Cat #Cat #VABRC) were used to protect the access port for the jugular catheters allowing the animals to be housed 2 per cage on corn cob bedding for 4-5 days prior to the study. Rats were administered a single intravenous dose of 5 mg/kg Compound 11 prepared in a vehicle of 5% mannitol in citrate buffer. At 1, 2, 4, 8, 24 and 30 hours following compound administration, blood (250 µL) was collected into K2EDTA filled microtainers from fed rats. Plasma was isolated by centrifugation and 100 µL aliquots were transferred to 96-well polypropylene plates on dry ice. Samples were stored at −80° C. until processed for quantification of total peptide by ELISA and released exatecan by LC-MS/MS.

ELISA Measurement of Total Peptide Plasma Concentrations

96-Well plates were coated with 100 µL/well of 0.1 µM BSA-labelled peptide prepared in 0.2 M Carbonate-Bicarbonate Buffer, pH 9.4 and incubated overnight at 4° C. Plates were washed 4× with an ELISA wash buffer (PBS+0.05% Tween 20), incubated for 2 hours at room temperature with Blocking Buffer (PBS+5% dry milk+0.05% Tween 20) (300 µL/well) and washed again 4× with ELISA wash buffer. Concurrently, 2× Compound 11 standards in control plasma and study plasma samples were pre-incubated with 1-10 ng/mL of a primary antibody specific for the Pv1 peptide for 30 minutes at room temperature. Pre-incubated samples were added to pre-coated, pre-blocked assay plates at 100 µL/well and incubated for 1 hour at room temperature. Plates were washed 4× with ELISA wash buffer and incubated with 100 µL/well of a secondary goat anti-mouse IgG HRP antibody (1:5,000 in antibody diluent) for 1 hour at room temperature. Plates were washed 4× with ELISA wash buffer and incubated with 100 µL/well of SuperSignal substrate at room temperature with gentle shaking for 1 minute. Luminescence was read from the plate on a BioTek Cytation 5 plate reader.

LC-MS/MS Measurement of Exatecan Plasma Concentrations

For quantification of exatecan, a 20 µL plasma sample was added to a polypropylene autosampler vial. 20 µL PPT-IS (ACN:H20 (50:50)+0.5% FA containing 1000 ng/mL internal standard) and 20 µL diluent (ACN:H20 (50:50)+0.5% FA) was added to each sample. Followed by addition of 120 µl of ACN+5% FA. The vials were capped and vortexed for 2 minutes. The samples were centrifuged for 5-10 minutes at 3700 rpm then analyzed via liquid chromatography tandem mass spectrometry (LC-MS/MS).

FIG. 1 shows a plot of the plasma concentration of Compound 11 and released exatecan after a single IV dose of 5 mg/kg of Compound 11 in a rat (data are expressed as means±SEM). As shown in FIG. 1, less than 0.002% of the exatecan warhead was released after 30h in circulation. FIG. 1 demonstrates that Compound 11 is stable in plasma for at least 30 h.

Example C: Tumor and Bone Marrow Pharmacokinetics of Compound 11 in a Mouse Model Animal Dosing Six-week-old female athymic nude Foxn$^{nu}$ mice were obtained from Taconic Labs (Cat #NCRNU-F) and were housed 5 per cage on Alpha-Dri bedding in a disposable caging system (Innovive). Human HCT116 cancer cells derived from colorectal carcinoma were diluted 1:1 in Phenol Red-free Matrigel and subcutaneously implanted into the left flank of each mouse at a density of 2.5×10$^6$ cells in 100 µL. When xenografts reached a minimal volume of 300 mm$^3$, mice were administered a single intraperitoneal injection of 10 mg/kg Compound 11 prepared in a vehicle of 5% mannitol in citrate. Tumor and bone marrow samples were collected from fed, anesthetized mice at 1, 2, 4, 8, 16, 24, 32 and 48 hours after compound administration. Total peptide concentrations in tumor and bone marrow were determined via ELISA.

ELISA Measurement of Total Peptide Tissue Concentrations 96-well plates were coated with 100 µL/well of 0.1 µM BSA-labelled peptide prepared in 0.2 M Carbonate-Bicarbonate Buffer, pH 9.4 and incubated overnight at 4° C. Plates were washed 4× with an ELISA wash buffer (PBS+0.05% Tween 20), incubated for 2 hours at room temperature with Blocking Buffer (PBS+5% dry milk+0.05% Tween 20) (300 µL/well) and washed again 4× with ELISA wash buffer. Concurrently, 2× Compound 11 standards (in respective tissue matrix) or sample tumor homogenates or bone marrow samples diluted with antibody diluent (PBS+2% dry milk+0.05% Tween 20), were pre-incubated with 1-10 ng/mL of a primary antibody specific for the Pv1 peptide for 30 minutes at room temperature. Pre-incubated samples were added to pre-coated, pre-blocked assay plates at 100 µL/well and incubated for 1 hour at room temperature. Plates were washed 4× with ELISA wash buffer and incubated with 100 µL/well of a secondary goat anti-mouse IgG HRP antibody (1:5,000 in antibody diluent) for 1 hour at room temperature. Plates were washed 4× with ELISA wash buffer and incubated with 100 µL/well of SuperSignal substrate at room temperature with gentle shaking for 1 minute. Luminescence was read from the plate on a BioTek Cytation 5 plate reader.

Figure 2:
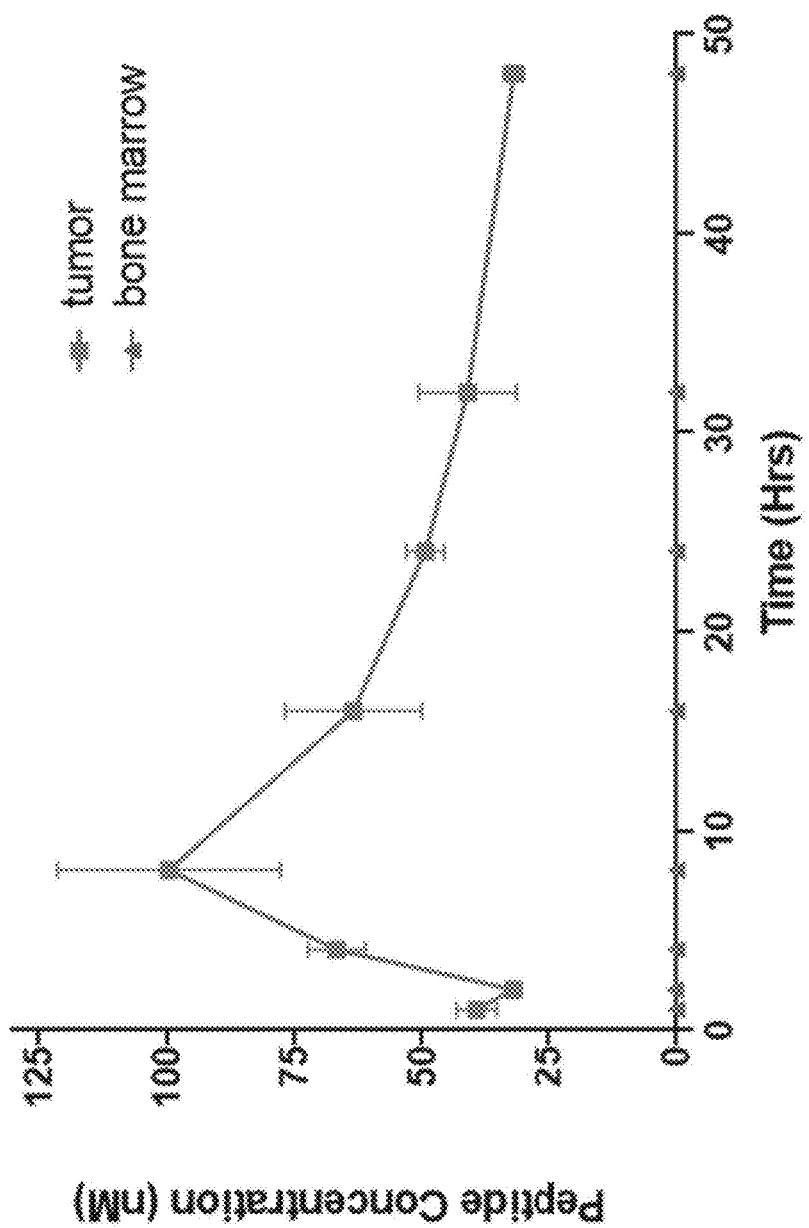
FIG. 2 shows a plot of the peptide concentration in tumor and bone marrow after a single IP dose of 10 mg/kg of Compound 11 in a mouse (data are expressed as means±SEM).

FIG. 2 shows a plot of the peptide concentration in tumor and bone marrow after a single IP dose of 10 mg/kg of Compound 11 in a mouse (data are expressed as means±SEM). FIG. 2 demonstrates Compound 11 effectively targets tumors.

Example D: Bone Marrow Toxicity Study in a Mouse Model

Animal Dosing

Six-week-old female athymic nude Foxn$^{nu}$ mice were obtained from Taconic Labs (Cat #NCRNU-F) and were housed 5 per cage on Alpha-Dri bedding in a disposable caging system (Innovive). Human HCT116 cancer cells derived from colorectal carcinoma were diluted 1:1 in Phenol Red-free Matrigel and subcutaneously implanted into the left flank of each mouse at a density of $2.5 \times 10^6$ cells in 100 µL. When xenografts reached a minimal volume of 200 mm$^3$, mice were administered intraperitoneal doses of vehicle or 2.6 or 5.2 µmoles/kg of either unconjugated exatecan (equivalent to 1.15 or 2.3 mg/kg exatecan, respectively) or Compound 11 (equivalent to 10 or 20 mg/kg Compound 11, respectively). Compounds were administered once daily for 4 days.

Bone Marrow Collection

Tumor bearing mice were euthanized by cervical dislocation 6 hours after the last dose. Femurs were removed, and bone marrow was extruded into 50 mL conical tubes by flushing the bones with a 23-gauge needle fitted on a 5 cc syringe containing PBS+2% fetal bovine serum. Bone marrow was homogenized by gentle pipetting and filtered through 100 µm nylon mesh filters and cells were pelleted by centrifugation at 1200 rpm for 5 minutes at 4° C. Red blood cells were lysed with 3 mL of lysis buffer for 2 minutes at room temperature. PBS was added to a volume of 25 mL and cells were re-pelleted by centrifugation as described above. Cell pellets were suspended in 5 mL of PBS and cell count was assessed by trypan blue exclusion. The cell counts from four independent studies were averaged and plotted.

Figure 3:
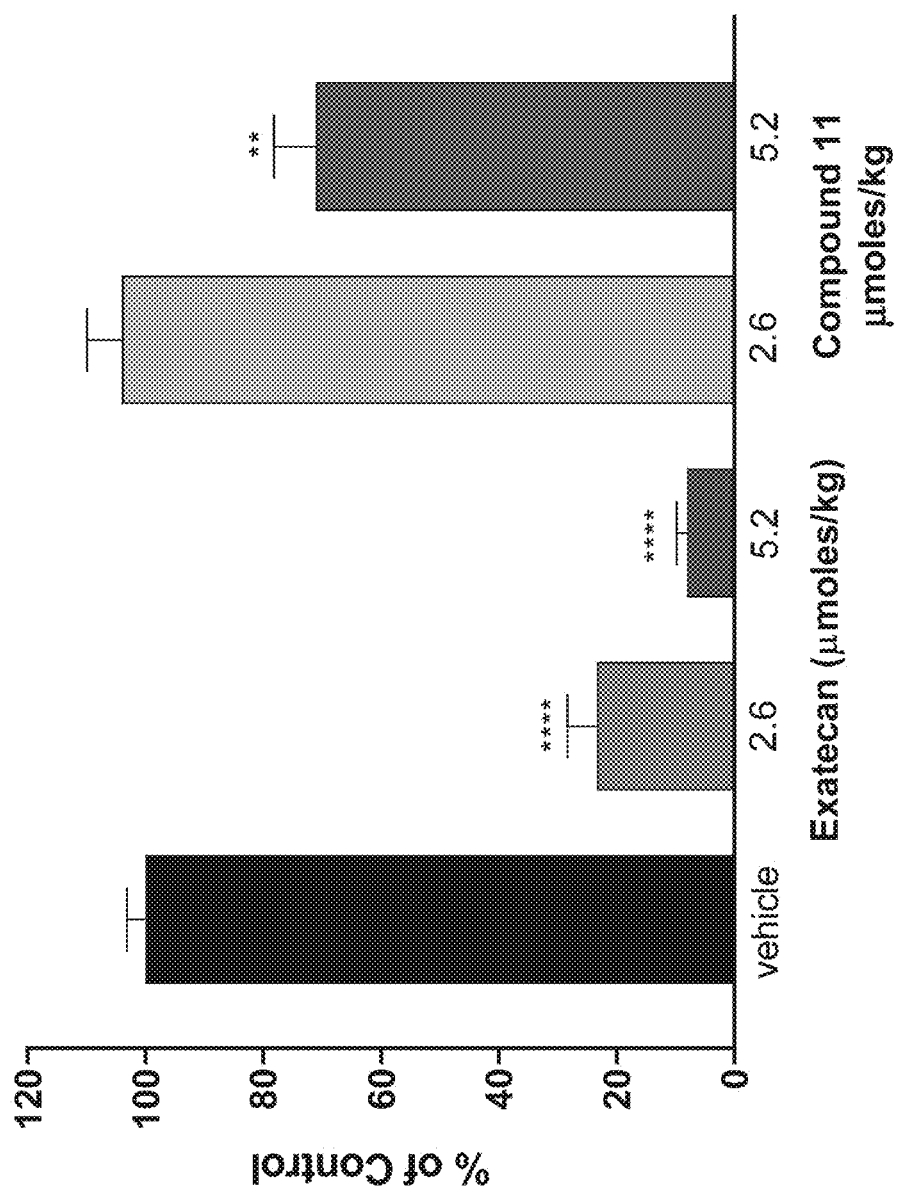
FIG. 3 shows a graph of the total bone marrow counts from the femurs of tumor bearing nude mice after dosing of 2.6 and 5.2 µmoles/kg of either Compound 11 (equivalent to 10, 20 mg/kg conjugate) or free exatecan (equivalent to 1.15 and 2.3 mg/kg exatecan) dosed once daily for four days (data are expressed as means±SEM).

FIG. 3 shows a graph of the total bone marrow counts from the femurs of tumor bearing nude mice after dosing of 2.6 and 5.2 µmoles/kg of either Compound 11 (equivalent to 10, 20 mg/kg conjugate) or free exatecan (equivalent to 1.15 and 2.3 mg/kg exatecan) dosed once daily for four days. (data are expressed as means±SEM). Compound 11 did not display the bone marrow toxicity that limits the clinical utility of exatecan.

Example E: Gastric Toxicity Study in a Mouse Model

Animal Dosing and Stomach Imaging

Six-week-old female athymic nude Foxn$^{nu}$ mice were obtained from Taconic Labs (Cat #NCRNU-F) and were housed 5 per cage on Alpha-Dri bedding in a disposable caging system (Innovive). Human HCT116 cells derived from colorectal carcinoma were diluted 1:1 in Phenol Red-free Matrigel and subcutaneously implanted into the left flank of each mouse at a density of $2.5 \times 10^6$ cells in 100 µL. When xenografts reached a minimal volume of 300 mm$^3$, mice were administered intraperitoneal doses of vehicle, or 5.2 µmoles/kg of either unconjugated exatecan (equivalent to 2.3 mg/kg exatecan) or Compound 11 (equivalent to 20 mg/kg Compound 11). Compounds were administered once daily for 4 days. At 6 hours after administration of the last dose, mice were euthanized by cervical dislocation and gross necropsy was conducted. Photographs were taken of the stomachs both in situ and ex vivo.

Figure 4A:
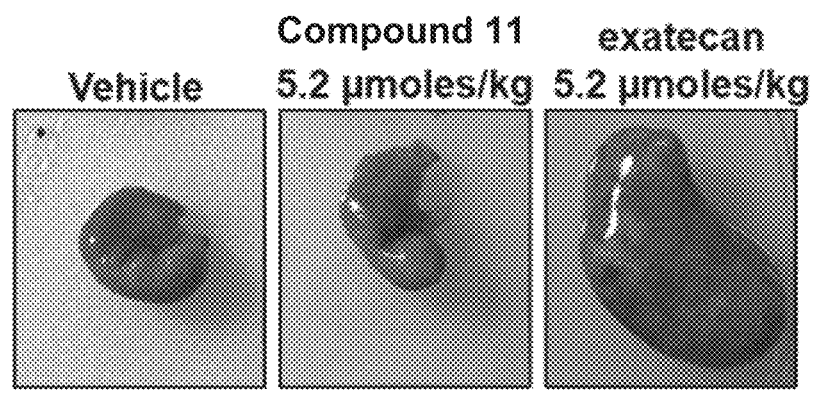
FIG. 4A shows the stomachs of tumor bearing nude mice excised after dosing of vehicle or 5.2 µmoles/kg of either Compound 11 (equivalent to 20 mg/kg conjugate) or free exatecan (equivalent to 2.3 mg/kg exatecan) dosed once daily for four days.
Figure 4B:
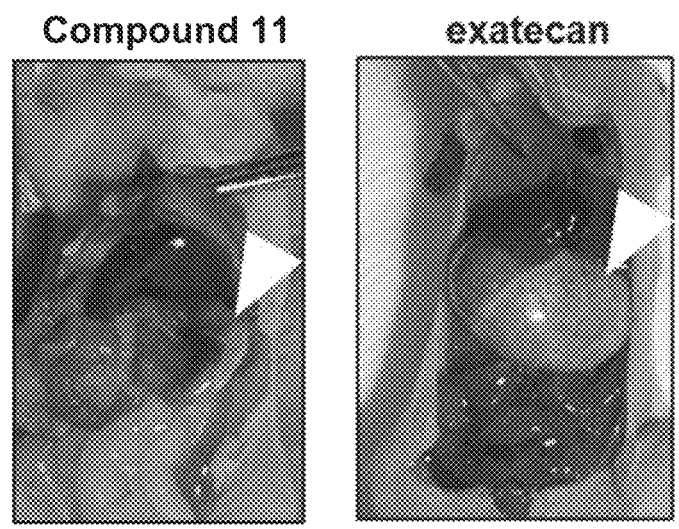
FIG. 4B shows the stomachs of tumor bearing nude mice in situ after dosing of 5.2 µmoles/kg of either Compound 11 (equivalent to 20 mg/kg conjugate) or free exatecan (equivalent to 2.3 mg/kg exatecan) dosed once daily for four days.

FIG. 4A shows the stomachs of tumor bearing nude mice excised after dosing of vehicle or 5.2 µmoles/kg of either Compound 11 (equivalent to 20 mg/kg conjugate) or free exatecan (equivalent to 2.3 mg/kg exatecan) dosed QD×4. FIG. 4B shows the stomachs of tumor bearing nude mice in situ after dosing of 5.2 µmoles/kg of either Compound 11 (equivalent to 20 mg/kg conjugate) or free exatecan (equivalent to 2.3 mg/kg exatecan) dosed once daily for four days. Compound 11 did not display the gastric toxicity that limits the clinical utility of exatecan.

Example F: Efficacy of Compound 11 in a HCT116 Colorectal Cancer Model

Six-week-old female athymic nude Foxn$^{nu}$ mice were obtained from Taconic Labs (Cat #NCRNU-F) and were housed 5 per cage on Alpha-Dri bedding in a disposable caging system. Human HCT116 cells derived from colorectal carcinoma were diluted 1:1 in Phenol Red-free Matrigel and subcutaneously implanted into the left flank of each mouse at a density of $2.5 \times 10^6$ cells in 100 µL. When xenografts reached a mean volume of 100-200 mm$^3$, mice were randomized into groups and treated as detailed in the table below. Mice were administered intraperitoneal (IP) doses of vehicle or 2.6 or 5.2 µmole/kg of either unconjugated exatecan (equivalent to 1.15 or 2.3 mg/kg exatecan, respectively) or Compound 11 (equivalent to 10 or 20 mg/kg Compound 11, respectively). Doses were prepared by diluting 0.1 mg/µL DMSO stocks in 5% mannitol in citrate buffer and were administered QD×4/week for three weeks at a volume of 12 mL/kg (300 µL per 25 g mouse). Xenograft tumors were measured by calipers and volume was calculated using the equation for ellipsoid volume: Volume=$\pi/6 \times$ (length)×(width)$^2$. Animals were removed from the study due to death, tumor size exceeding 2000 mm$^3$ or loss of >20% body weight. The below table shows the dosing schedule of various treatment groups.

| Group | Treatment | Dose | Dosing Schedule | Administration Route | Number of Mice |
|---|---|---|---|---|---|
| 1 | Vehicle (5% mannitol in citrate buffer) | NA | QD × 4/ wk × 3 | i.p. | 8 |
| 2 | Compound 11 | 10 mg/kg | QD × 4/ wk × 3 | i.p. | 8 |
| 3 | Compound 11 | 20 mg/kg | QD × 4/ wk × 3 | i.p. | 8 |
| 4 | exatecan | 1.15 mg/kg | QD × 4/ wk × 3 | i.p. | 8 |
| 5 | exatecan | 2.3 mg/kg | QD × 4/ wk × 3 | i.p. | 8 |

Figure 5A:
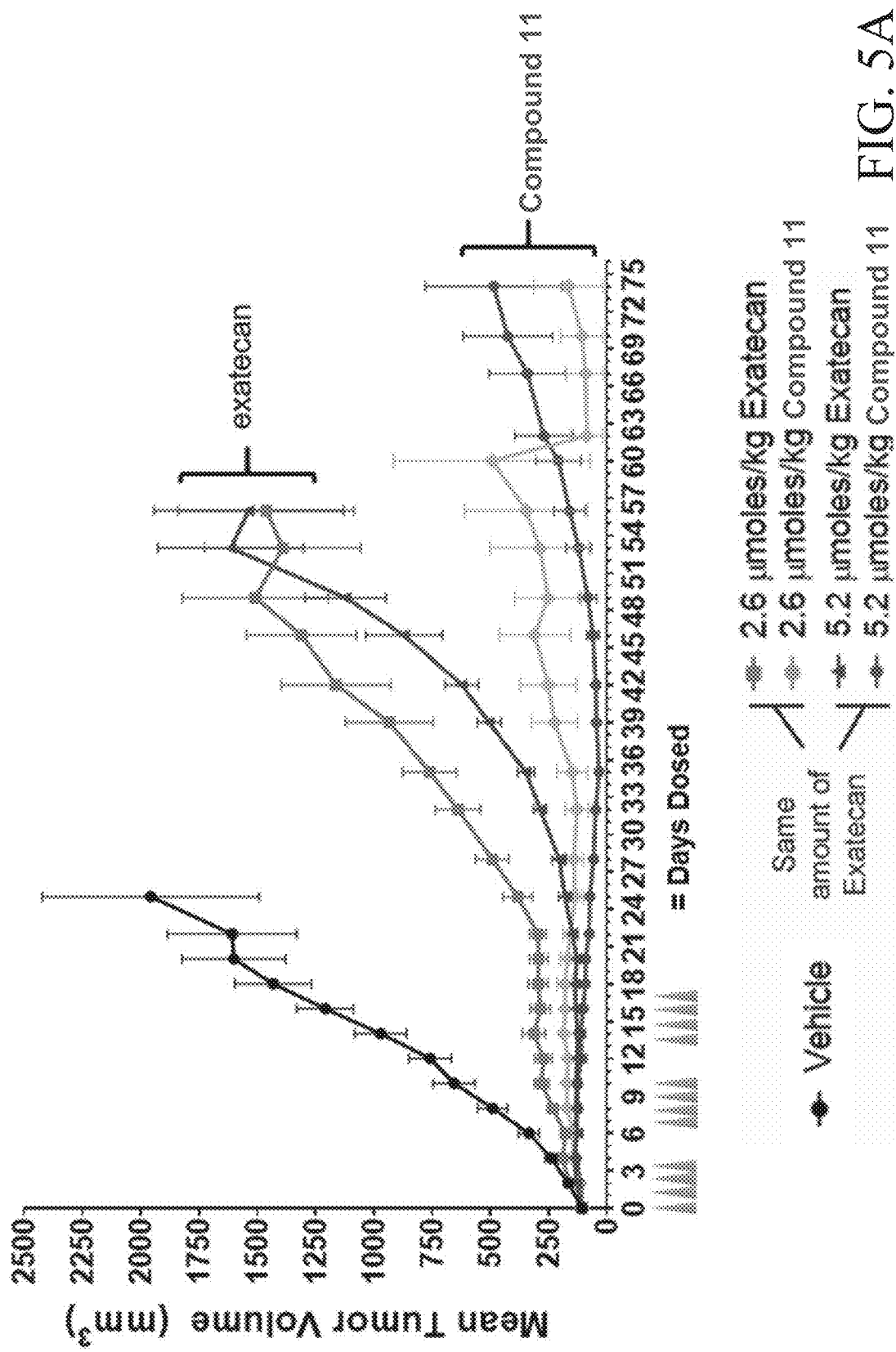
FIG. 5A shows a plot of the mean tumor volume resulting from dosing equimolar amounts of either free exatecan or Compound 11 in nude mice bearing HCT116 colorectal flank tumors. Animals were dosed once daily four times per week intraparenterally for three weeks.
Figure 5B:
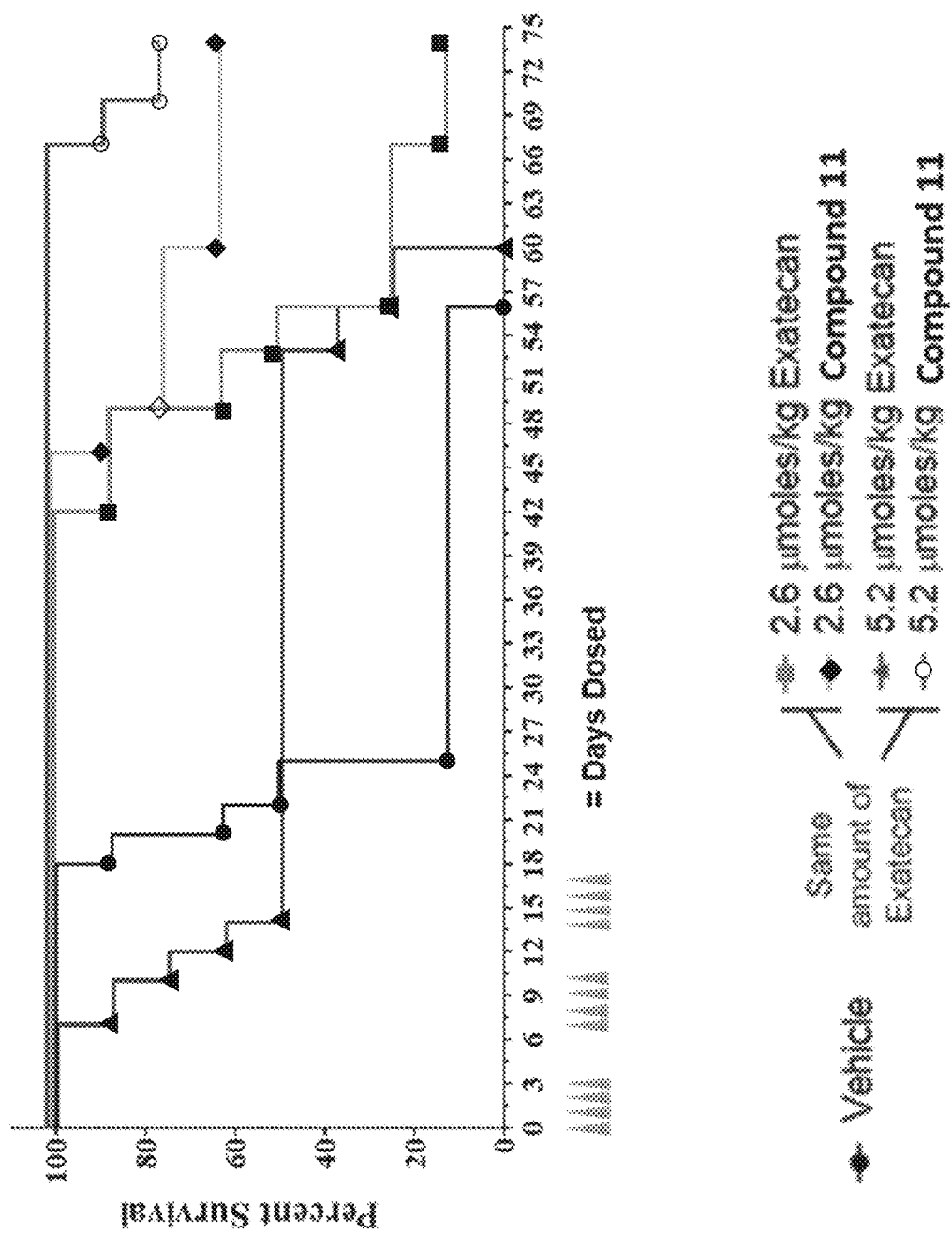
FIG. 5B displays a Kaplan Meier survival curve for dosing equimolar amounts of either free exatecan or Compound 11 in nude mice bearing HCT116 colorectal flank tumors.

FIG. 5A shows a plot of the mean tumor volume resulting from dosing equimolar amounts of either free exatecan or Compound 11 in nude mice bearing HCT116 colorectal flank tumors. Animals were dosed once daily four times per week intraparenterally for three weeks. FIG. 5B displays a Kaplan Meier survival curve for dosing equimolar amounts of either free exatecan or Compound 11 in nude mice bearing HCT116 colorectal flank tumors. Data are expressed as means±SEM. These data demonstrate that Compound 11 demonstrates potent anti-tumor activity in a pre-clinical colorectal cancer model.

Example G: Efficacy of Compound 11 in a MKN45 HER2 Negative Gastric Cancer Model Six-week-old female athymic nude Foxn$^{nu}$ mice were obtained from Taconic Labs (Cat #NCRNU-F) and were housed 5 per cage on Alpha-Dri bedding in a disposable caging system. Human MKN45 cells derived from gastric carcinoma were diluted 1:1 in Phenol Red-free Matrigel and subcutaneously implanted into the left flank of each mouse at a density of $2 \times 10^6$ cells in 100 µL. When xenografts reached a mean volume of 100-200 mm$^3$, mice were randomized into groups and treated as detailed in the table below. Mice were administered intraperitoneal (IP) doses of vehicle or 2.6 or 5.2 μmole/kg of either unconjugated exatecan (equivalent to 1.15 or 2.3 mg/kg exatecan, respectively) or Compound 11 (equivalent to 10 or 20 mg/kg Compound 11, respectively). Doses were prepared by diluting 0.1 mg/μL DMSO stocks in 5% mannitol in citrate buffer and were administered QD×4/week for two weeks at a volume of 12 mL/kg (300 μL per 25 g mouse). Xenograft tumors were measured by calipers and volume was calculated using the equation for ellipsoid volume: Volume=π/6× (length)×(width). Animals were removed from the study due to death, tumor size exceeding 2000 mm$^3$, or loss of >20% body weight. The following table shows the dosing schedule of the various treatment groups.

| Group | Treatment | Dose | Dosing Schedule | Administration Route | Number of Mice |
|---|---|---|---|---|---|
| 1 | Vehicle (5% mannitol in citrate buffer) | NA | QD × 4/ wk × 2 | i.p. | 8 |
| 2 | Compound 11 | 2.5 mg/kg | QD × 4/ wk × 2 | i.p. | 8 |
| 3 | Compound 11 | 5 mg/kg | QD × 4/ wk × 2 | i.p. | 8 |
| 4 | Compound 11 | 10 mg/kg | QD × 4/ wk × 2 | i.p. | 8 |
| 5 | Compound 11 | 20 mg/kg | QD × 4/ wk × 2 | i.p. | 8 |
| 6 | exatecan | 1.15 mg/kg | QD × 4/ wk × 2 | i.p. | 8 |
| 7 | exatecan | 2.3 mg/kg | QD × 4/ wk × 2 | i.p. | 8 |

Figure 6A:
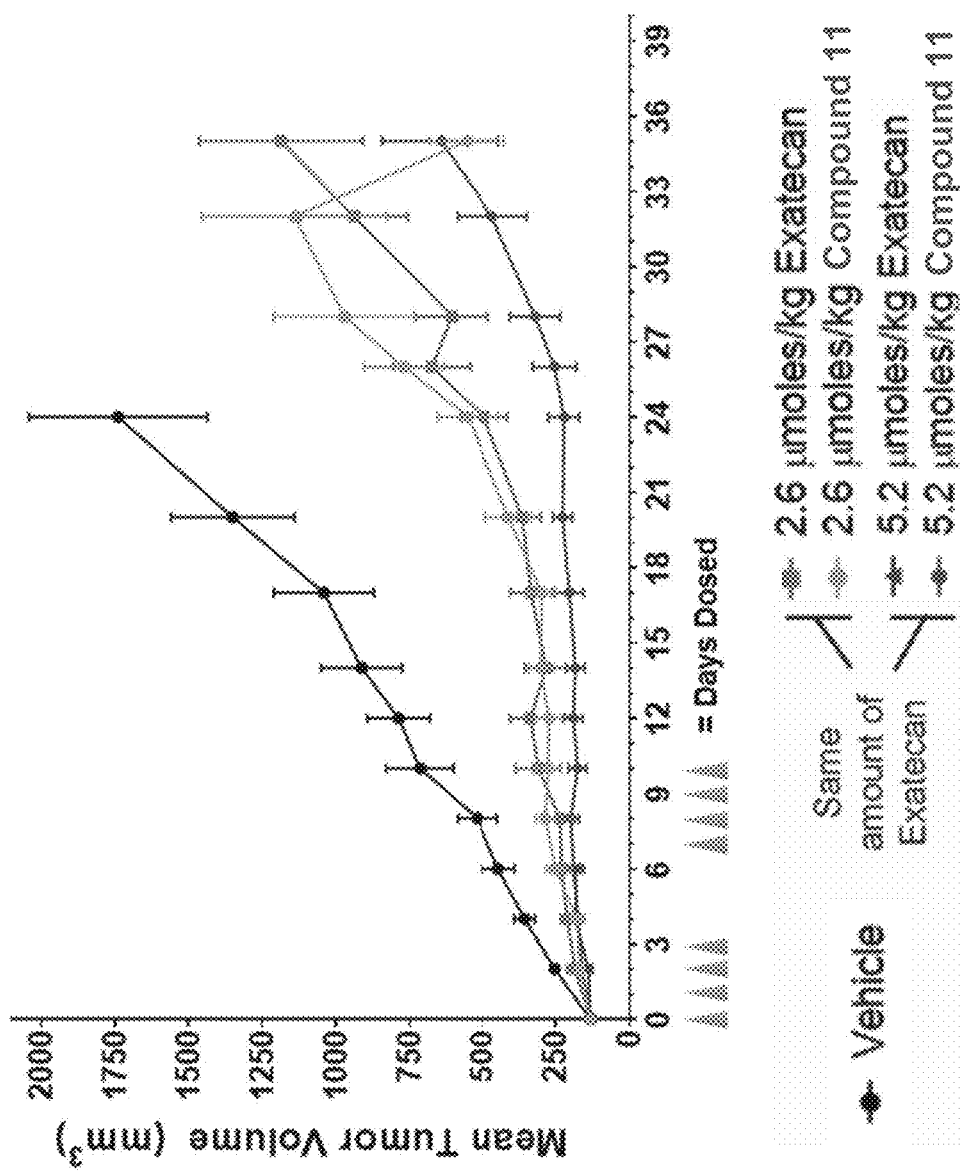
FIG. 6A shows the single agent efficacy of Compound 11 in nude mice bearing MKN45 HER2 negative gastric cancer flank tumors. Animals were dosed once daily four times per week intraparenterally for two weeks.
Figure 6B:
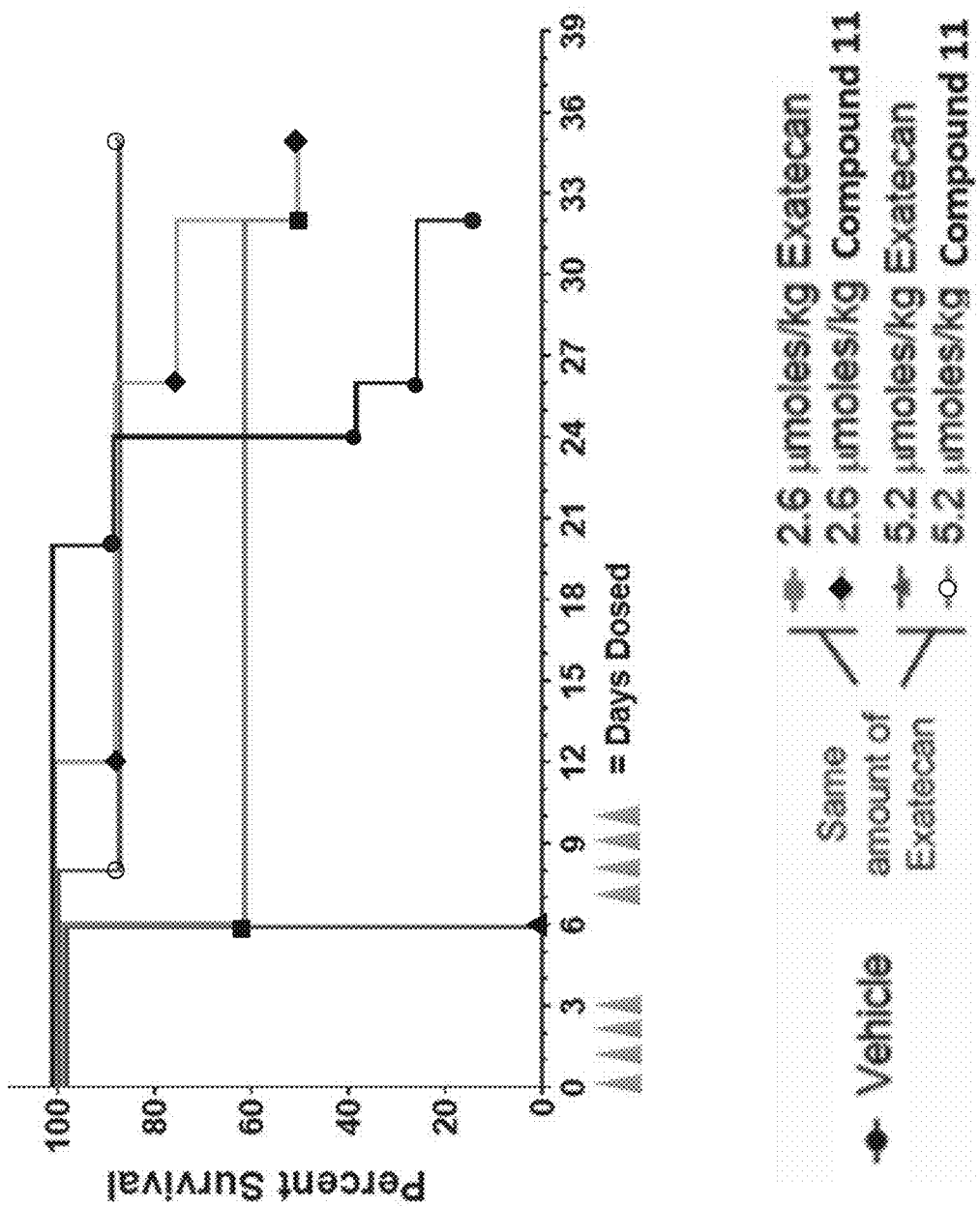
FIG. 6B displays a Kaplan Meier survival curve for dosing equimolar amounts of either free exatecan or Compound 11 in nude mice bearing MKN45 HER2 negative gastric cancer flank tumors.

FIG. 6A shows the single agent efficacy of Compound 11 in nude mice bearing MKN45 HER2 negative gastric cancer flank tumors. Animals were dosed once daily four times per week intraparenterally for two weeks. FIG. 6B displays a Kaplan Meier survival curve for dosing equimolar amounts of either free exatecan or Compound 11 in nude mice bearing MKN45 HER2 negative gastric cancer flank tumors. Data are expressed as means±SEM. These data demonstrate that Compound 11 demonstrates potent anti-tumor activity in a pre-clinical gastric cancer model.

FIG. 6B. Kaplan-Meier analysis was used to evaluate survival rate based on death or removal from study.

Example H: Efficacy of Compound 11 in a JIMT-1 HER2 Intermediate Breast Cancer Model Five to six-week-old female NOD.SCID mice were obtained from Beijing Anikeeper Biotech Co., Ltd (Beijing, China). Human J1MT-1 cells derived from breast carcinoma were diluted 1:1 in Phenol Red-free Matrigel and subcutaneously implanted into the left flank of each mouse at a density of 5×10$^6$ cells in 100 μL. When xenografts reached a mean volume of 100 mm$^3$, mice were randomized into groups and treated as detailed in the table below. Mice were administered intraperitoneal (IP) doses of vehicle or 2.6 or 5.2 μmole/kg of Compound 11 (equivalent to 10 or 20 mg/kg Compound 11, respectively). Doses were prepared by diluting 0.1 mg/μL DMSO stocks in 5% mannitol in citrate buffer and were administered QD×4/week for three weeks at a volume of 12 mL/kg (300 μL per 25 g mouse). Xenograft tumors were measured by calipers and volume was calculated using the equation for ellipsoid volume: Volume=π/6× (length)×(width). Body weight of animals was measured at the same time as tumor volume assessment. Animals were removed from the study due to death, tumor size exceeding 2000 mm$^3$, or loss of >20% body weight. The following table shows the dosing schedule for various treatment groups.

| Group | Treatment | Dose | Dosing Schedule | Administration Route | Number of Mice |
|---|---|---|---|---|---|
| 1 | Vehicle (5% mannitol in citrate buffer) | NA | QD × 4/ wk × 3 | i.p. | 8 |
| 2 | Compound 11 | 10 mg/kg | QD × 4/ wk × 3 | i.p. | 8 |
| 3 | Compound 11 | 20 mg/kg | QD × 4/ wk × 3 | i.p. | 8 |

Figure 7A:
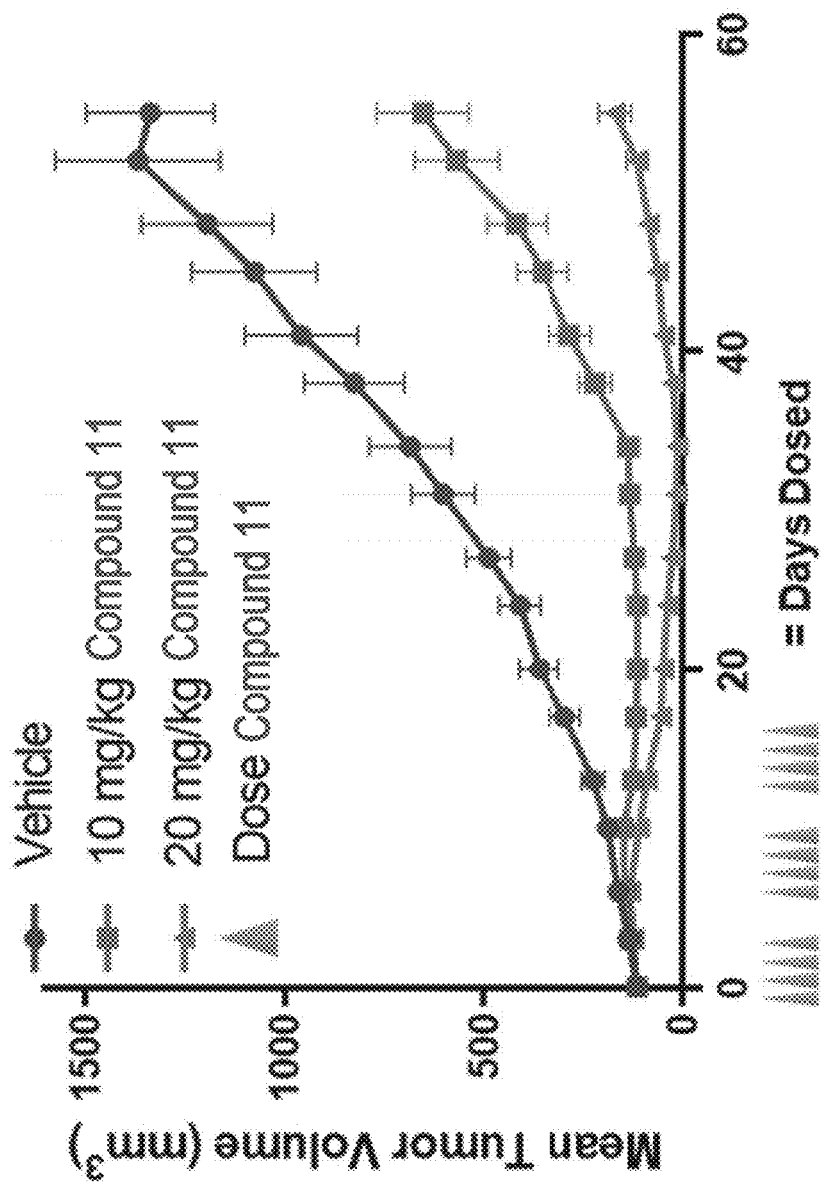
FIG. 7A shows a plot of the mean tumor volume resulting from dosing Compound 11 in SCID mice bearing JIMT-1 HER2 intermediate breast cancer flank tumors. Animals were dosed once daily four times per week intraparenterally for three weeks.
Figure 7B:
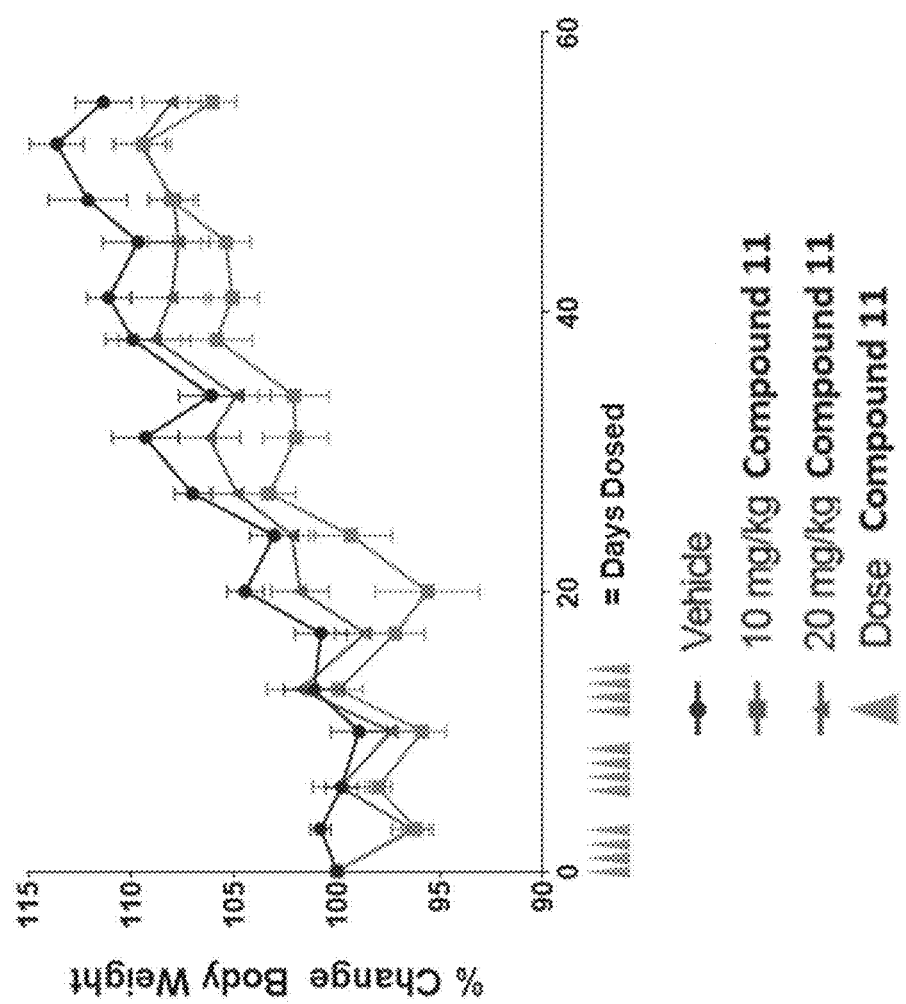
FIG. 7B shows a plot of the percent change in body weight in SCID mice bearing JIMT-1 HER2 intermediate breast cancer flank tumors dosed with Compound 11.

FIG. 7A shows a plot of the mean tumor volume resulting from dosing Compound 11 in SCID mice bearing JIMT-1 HER2 intermediate breast cancer flank tumors. Animals were dosed once daily four times per week intraparenterally for three weeks. FIG. 7B shows a plot of the percent change in body weight in SCID mice bearing JIMT-1 HER2 intermediate breast cancer flank tumors dosed with Compound 11. Data are expressed as means±SEM. These data demonstrate that Compound 11 demonstrates potent anti-tumor activity in a pre-clinical breast cancer model.

Example I: Efficacy of Compound 11 in a MDA-MB-231 Triple Negative Breast Cancer Model Three to four-week-old female athymic nude Foxn$^{nu}$ mice were obtained from Envigo Labs. Human MDA-MB-231 cells derived from breast adenocarcinoma were diluted 1:1 in Phenol Red-free Matrigel and subcutaneously implanted into the left flank of each mouse at a density of 2×10$^6$ cells in 100 μL. When xenografts reached a mean volume of 50-100 mm$^3$, mice were randomized into groups and treated as detailed in the table below. Mice were administered intraperitoneal (IP) doses of vehicle or 5, 10, or 20 mg/kg Compound 11. Doses were prepared by diluting 0.1 mg/μL DMSO stocks in 5% mannitol in citrate buffer and were administered QD×4/week for three weeks at a volume of 12 mL/kg (300 μL per 25 g mouse). Xenograft tumors were measured by calipers and volume was calculated using the equation for ellipsoid volume: Volume=π/6×(length)× (width). Body weight of animals was measured at the same time as tumor volume assessment. Animals were removed from the study due to either death, tumor size exceeding 2000 mm$^3$ or due to loss of >20% body weight. The following table shows the dosing schedule of various treatment groups.

| Group | Treatment | Dose | Dosing Schedule | Administration Route | Number of Mice |
|---|---|---|---|---|---|
| 1 | Vehicle (5% mannitol in citrate buffer) | NA | NA | i.p. | 8 |

-continued

| Group | Treatment | Dose | Dosing Schedule | Administration Route | Number of Mice |
|---|---|---|---|---|---|
| 2 | Compound 11 | 5 mg/kg | QD × 4/wk × 3 | i.p. | 9 |
| 3 | Compound 11 | 10 mg/kg | QD × 4/wk × 3 | i.p. | 9 |
| 4 | Compound 11 | 20 mg/kg | QD × 4/wk × 3 | i.p. | 9 |

Figure 8A:
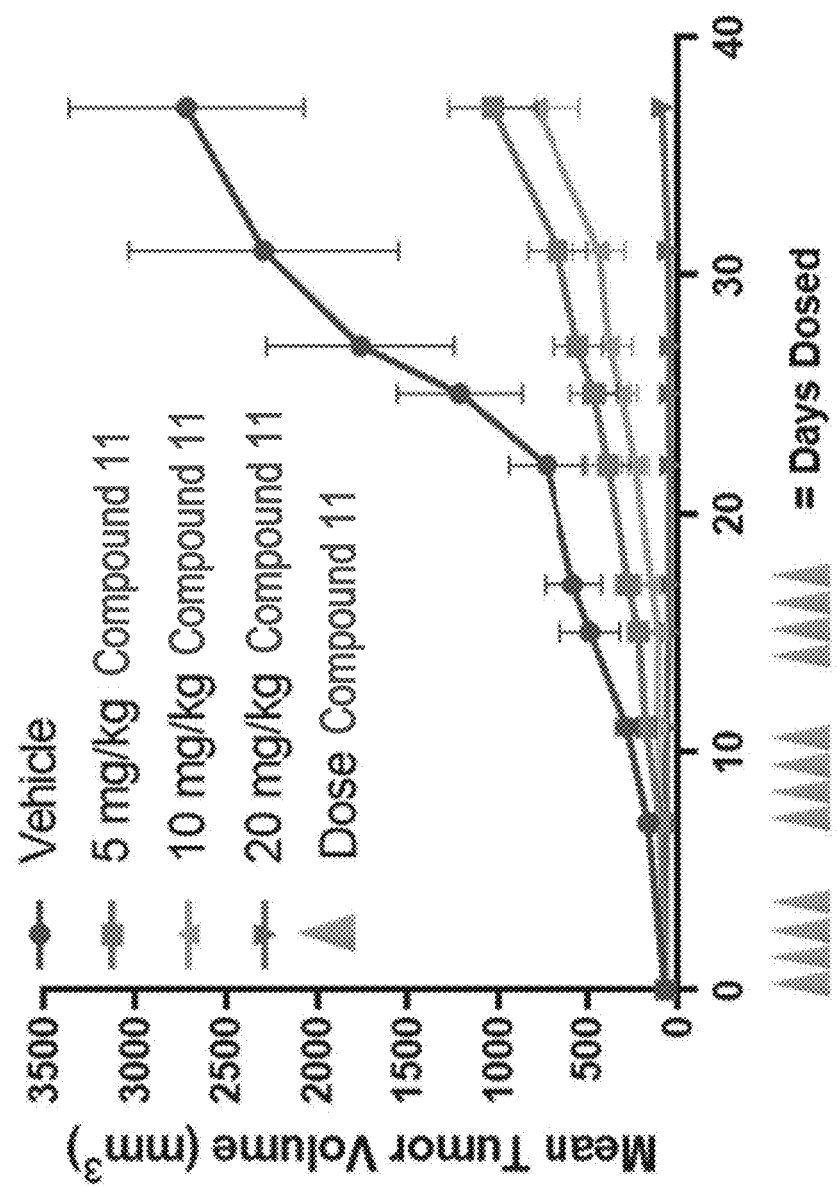
FIG. 8A shows a plot of the mean tumor volume in nude mice bearing MDA-MB-231 triple negative breast cancer flank tumors dosed with Compound 11. Animals were dosed once daily four times per week intraparenterally for three weeks.
Figure 8B:
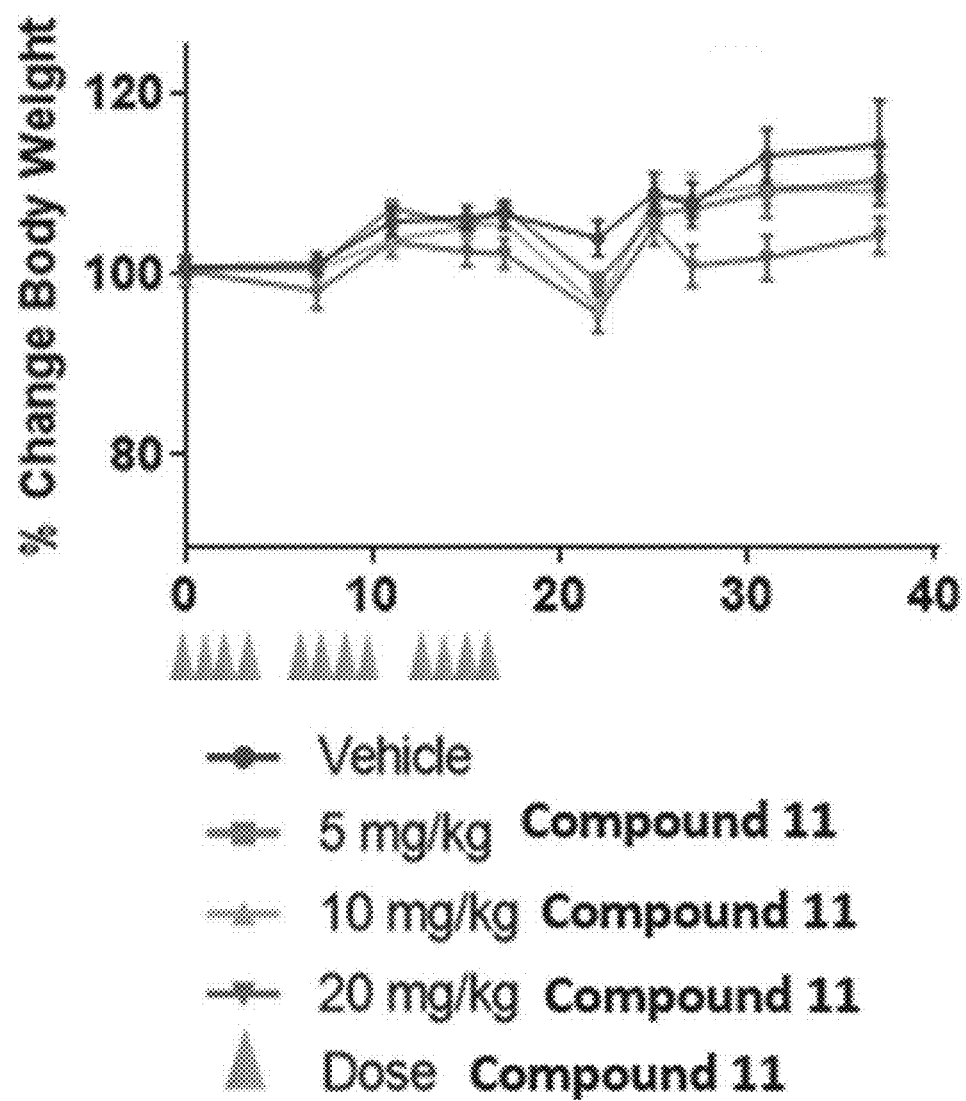
FIG. 8B shows a plot of the percent change in body weight relative to day 0 in nude mice bearing MDA-MB-231 triple negative breast cancer flank tumors dosed with Compound 11.

FIG. 8A shows the a plot of the mean tumor volume in nude mice bearing MDA-MB-231 triple negative breast cancer flank tumors dosed with Compound 11. Animals were dosed once daily four times per week intraparenterally for three weeks. FIG. 8B shows a plot of the percent change in body weight relative to day 0 in nude mice bearing MDA-MB-231 triple negative breast cancer flank tumors dosed with Compound 11. Data are expressed as means±SEM. These data demonstrate that Compound 11 demonstrates potent anti-tumor activity in a pre-clinical breast cancer model.

Example J: Combination Efficacy of Compound 11 and Talazoparib in a MDA-MB-231 Triple Negative Breast Cancer Model Three to four-week-old female athymic nude Foxn$^{nu}$ mice were obtained from Envigo Labs. Human MDA-MB-231 cells derived from breast adenocarcinoma were diluted 1:1 in Phenol Red-free Matrigel and subcutaneously implanted into the left flank of each mouse at a density of 2×10$^6$ cells in 100 µL. When xenografts reached a mean volume of 50-100 mm$^3$, mice were randomized into groups and treated as detailed in the table below. Mice were administered intraperitoneal (IP) doses of vehicle or 5 mg/kg Compound 11 alone or in combination with an oral (PO) dose of 0.33 mg/kg talazoparib. Doses were prepared by diluting 0.1 mg/µL DMSO stocks in 5% mannitol in citrate buffer. Compound 11 was administered QD×4/week for three weeks at a volume of 12 mL/kg (300 µL per 25 g mouse) and talazoparib was administered once daily for 15 days. Xenograft tumors were measured by calipers and volume was calculated using the equation for ellipsoid volume: Volume=π/6×(length)×(width). Body weight of animals was measured at the same time as tumor volume assessment. Animals were removed from the study due to either death, tumor size exceeding 2000 mm$^3$ or due to loss of >20% body weight. The following table shows the dosing schedule of various treatment groups.

| Group | Treatment | Dose | Dosing Schedule | Administration Route | Number of Mice |
|---|---|---|---|---|---|
| 1 | None | NA | NA | NA | 9 |
| 2 | Talazoparib | 0.33 mg/kg | QD × 15 | p.o. | 9 |
| 3 | Compound 11 | 5 mg/kg | QD × 4/wk × 3 | i.p. | 10 |
| 4 | Talazoparib | 0.33 mg/kg | QD × 15 | p.o. | 8 |
|   | Compound 11 | 5 mg/kg | QD × 4/wk × 3 | i.p. |   |

Figure 9A:
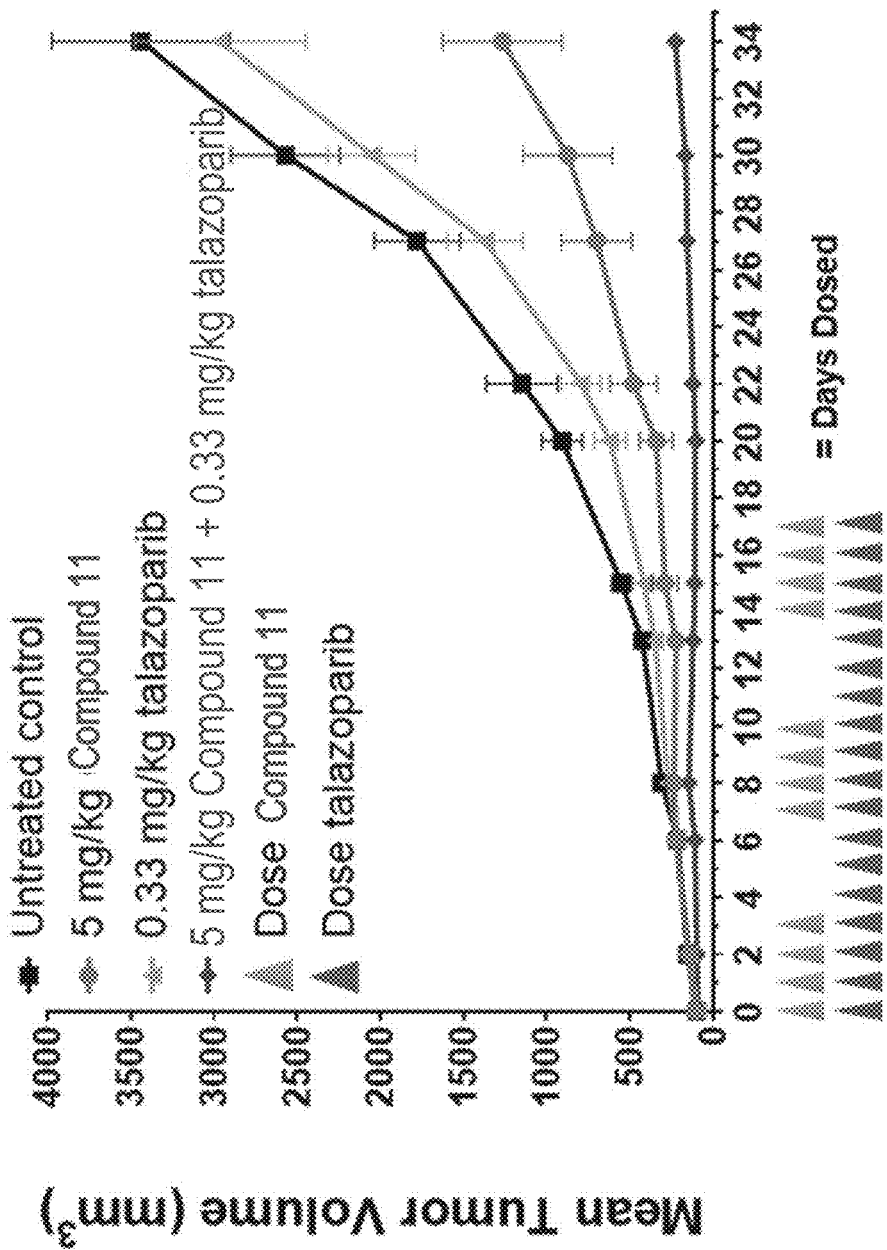
FIG. 9A shows a plot of the mean tumor volume of nude mice bearing MDA-MB-231 triple negative breast cancer flank tumors dosed with Compound 11 and talazoparib. Animals were dosed once daily four times per week intraparenterally for three weeks with Compound 11 and once daily for 18 days orally with talazoparib.
Figure 9B:
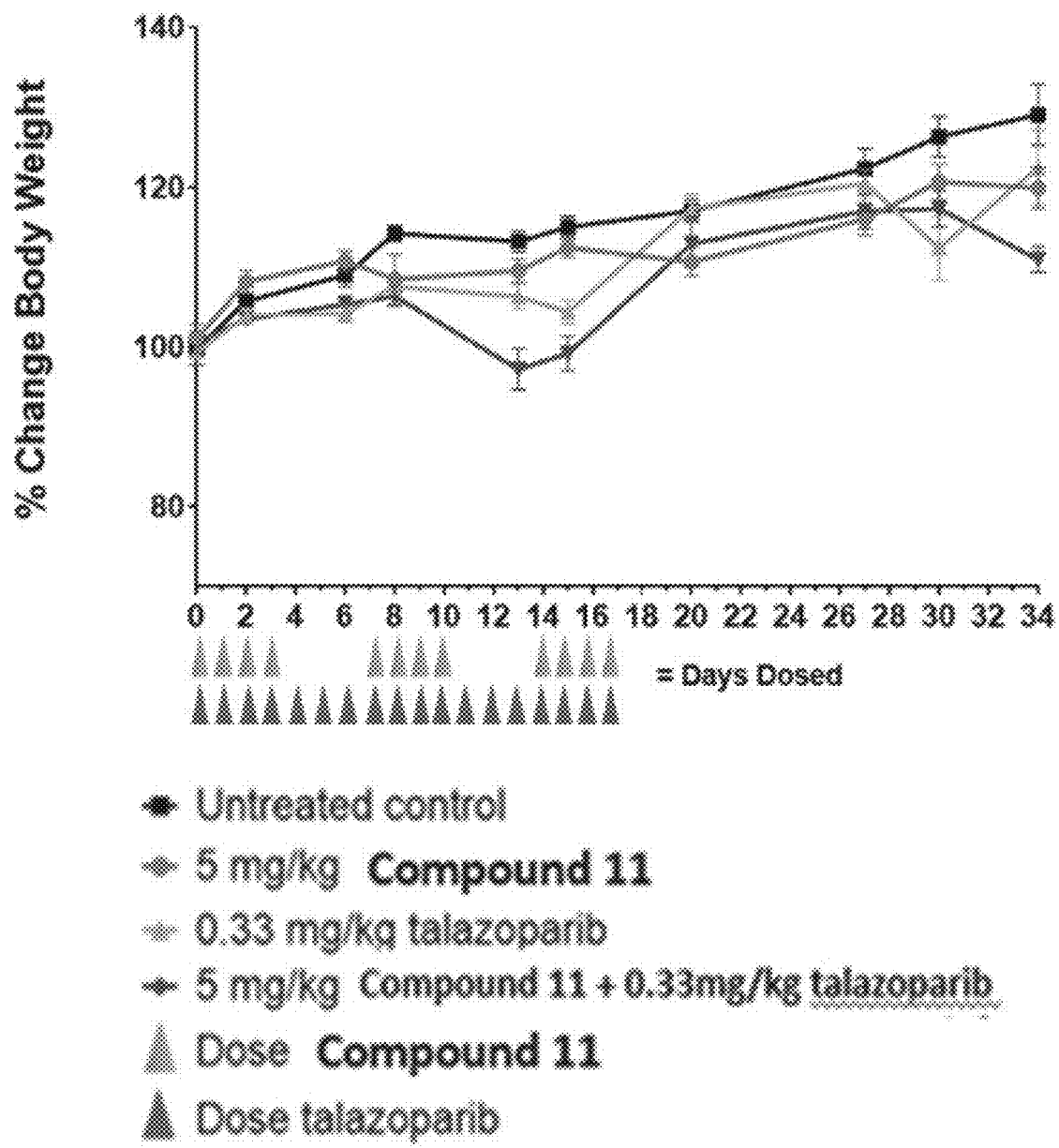
FIG. 9B shows a plot of the percent change in body weight relative to day 0 of nude mice bearing MDA-MB-231 triple negative breast cancer flank tumors dosed with Compound 11 and talazoparib.

FIG. 9A shows a plot of the mean tumor volume of nude mice bearing MDA-MB-231 triple negative breast cancer flank tumors dosed with Compound 11 and talazoparib. Animals were dosed once daily four times per week intraparenterally for three weeks with Compound 11 and once daily for 18 days orally with talazoparib. FIG. 9B shows a plot of the percent change in body weight relative to day 0 of nude mice bearing MDA-MB-231 triple negative breast cancer flank tumors dosed with Compound 11 and talazoparib.

Example K: Glutathione Cleavage Study

A 20 mM stock of conjugate was prepared in 100% DMSO. The stocks were subsequently diluted in 100 mM Tris, pH 7.5, to yield an intermediate dilution of 500 µM followed by an additional dilution of 1:5 in 100 mM Tris, pH 7.5 to give a final concentration of 100 µM of conjugate. 100 mM glutathione was prepared immediately prior to use in H$_2$O and diluted 1:10 in challenge samples for a final glutathione challenge concentration of 10 mM. Samples were mixed by inversion and incubated at 37° C. for up to 24 hrs. 50 µL samples were aliquoted into siliconized microfuge tubes at time 0, 4, and 24 hours and immediately frozen at −80° C.

Samples were thawed and extracted as follows: 8 µL of 25% phosphoric acid followed by 117 µL of 100% acetonitrile/0.1% TFA were added to each sample, mixed and centrifuged at 13000×G for 10 minutes. The supernatant was pipetted into 0.2 mL HPLC vials and placed on a Perkin Elmer Flexar HPLC autosampler. The following table summarizes HPLC conditions:

| | |
|---|---|
| HPLC | Perkin Elmer Flexar Binary pump, auto sampler, UV detector |
| Column | Waters BioResolve RP mAb Polyphenyl Column, 450 Å, 2.7 µm, 4.6 mm × 150 mm |
| Guard Coulmn | Waters BioResolve RP mAb Polyphenyl VanGuard Cartridge w/holder, 450 Å, 2.7 µm, 3.9 mm × 5 mm |
| Detection Wavelength | 217 nm |
| Column temperature | 37° C. |
| Pressure Limits | Min: 0 PSI, Max: 3050 PSI |
| Mobile phase | |
| Mobile phase A | 0.05% TFA in water |
| Mobile phase B | 0.05% TFA in Acetonitrile |
| Flow rate | 0.8 mL/min |
| Injection volume | 10.0 µL |
| Run time | 14.0 minutes |

| | Time (minutes) | % A | % B |
|---|---|---|---|
| Gradient program | 0.0 | 80 | 20 |
| | 0.5 | 80 | 20 |
| | 10.0 | 0 | 100 |
| | 11.0 | 80 | 20 |
| | 14.0 | 80 | 20 |

Data was analyzed by calculating the percentage reduction of compound (area of retention time peak of cleaved conjugate/area of retention time peak of conjugate at time 0)×100.

Figure 10:
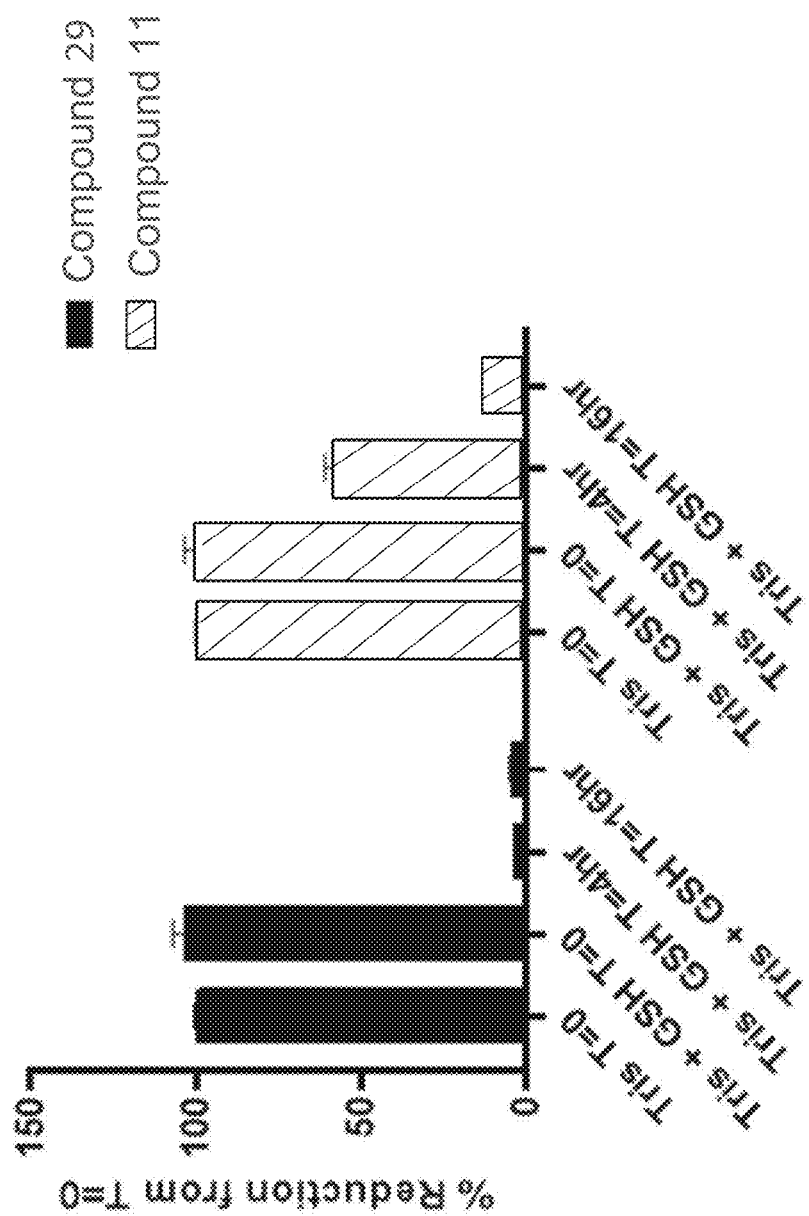
FIG. 10 shows a graph of the degradation of Compound 11 and Compound 29 resulting from treatment with 10 mM glutathione over 16 h.

FIG. 10 shows a graph of the degradation of Compound 11 and Compound 29 resulting from treatment with 10 mM glutathione over 16 h. As shown in FIG. 10, Compound 29 is released much faster than Compound 11 under similar gluathione exposure.

The table below summarizes the degradation data for the 10 mM glutathione exposure conditions described above for Compounds 11 to Compound 29 measured at 4 h and 24 h.

| Glutathione Challenge (10 mM) | | |
|---|---|---|
| Compound | % Remaining at 4 h | % Remaining at 24 h |
| 11 | 50.1 | 10.2 |
| 12 | ND | ND |
| 13 | ND | ND |
| 14 | 14.9 | 6.5 |
| 15 | 19.4 | 8.3 |
| 16 | 3.4 | 2.0 |
| 17 | 3.4 | 1.7 |
| 18 | 60.1 | 13.0 |
| 19 | ND | ND |
| 20 | 5.2 | 8.0 |
| 21 | 9.5 | 12.6 |
| 22 | 65.8 | 12.3 |
| 23 | 61.4 | 13.2 |
| 24 | 20.8 | 4.2 |
| 25 | 42.0 | 4.1 |
| 26 | 75.8 | 32.1 |
| 27 | 18.0 | 0.0 |
| 28 | 40.5 | 0.0 |
| 29 | 3.1 | 5.9 |

Example L: Plasma Stability Studies

A 20 mM stock of conjugate was prepared in 100% DMSO. The stocks were subsequently diluted in 100 mM Tris, pH 7.5 to yield an intermediate dilution of 500 µM and then diluted 1:5 directly into rat plasma to yield a final concentration of 100 µM of conjugate. Samples were mixed by inversion and incubated at 37° C. for up to 24 h. 50 µL samples were aliquoted into siliconized microfuge tubes at time 0, 4, and 24 h and immediately frozen at −80° C.

Samples were thawed and extracted as follows: 8 µL of 25% phosphoric acid followed by 117 µL of 100% Acetonitrile/0.1% TFA was added to each sample, mixed and centrifuged at 13000×G for 10 minutes. The supernatant was pipetted into 0.2 mL HPLC vials and placed on a Perkin Elmer Flexar HPLC autosampler. The following table summarizes HPLC conditions:

| HPLC | Perkin Elmer Flexar Binary pump, auto sampler, UV detector |
|---|---|
| Column | Waters BioResolve RP mAb Polyphenyl Column, 450 Å, 2.7 µm, 4.6 mm × 150 mm |
| Guard Coulmn | Waters BioResolve RP mAb Polyphenyl VanGuard Cartridge w/holder, 450 Å, 2.7 µm, 3.9 mm × 5 mm |
| Detection Wavelength | 217 nm |
| Column temperature | 37° C. |
| Pressure Limits | Min: 0 PSI, Max: 3050 PSI |
| Mobile phase | |
| Mobile phase A | 0.05% TFA in water |
| Mobile phase B | 0.05% TFA in Acetonitrile |
| Flow rate | 0.8 mL/min |
| Injection volume | 10.0 µL |
| Run time | 14.0 minutes |

| | Time (minutes) | % A | % B |
|---|---|---|---|
| Gradient program | 0.0 | 80 | 20 |
| | 0.5 | 80 | 20 |
| | 10.0 | 0 | 100 |
| | 11.0 | 80 | 20 |
| | 14.0 | 80 | 20 |

Data was analyzed by calculating the percentage reduction of compound (area of retention time peak of incubated conjugate/area of retention time peak of conjugate at time 0)×100. The results of the study are shown in the table below.

| Plasma Stability | | |
|---|---|---|
| Compound | % Remaining at 4 hrs | % Remaining at 24 hrs |
| 11 | 108.2 | 107.2 |
| 12 | ND | ND |
| 13 | ND | ND |
| 14 | 106.1 | 105.9 |
| 15 | 104.9 | 103.3 |
| 16 | 115.6 | 106.1 |
| 17 | 106.8 | 105.0 |
| 18 | 104.0 | 93.0 |
| 19 | ND | ND |
| 20 | 98.7 | 95.8 |
| 21 | 101.0 | 98.2 |
| 22 | 106.0 | 105.0 |
| 23 | 92.0 | 92.0 |
| 24 | 87.0 | 87.0 |
| 25 | 103.0 | 104.0 |
| 26 | 105.0 | 112.0 |
| 27 | 117.0 | 109.0 |
| 28 | 106.0 | 106.0 |
| 29 | 116.0 | 110.0 |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of treating cancer in a patient in need thereof, comprising administering to the patient a therapeutically effective amount of a compound of Formula (I):

$$R^8\text{-}Q\text{-}R^7 \quad (I)$$

or a pharmaceutically acceptable salt thereof, wherein:

$R^7$ is a peptide;

$R^8$ is:

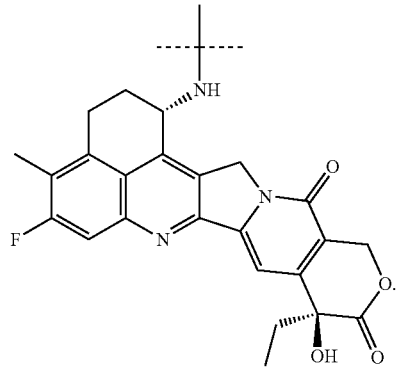

Q is:

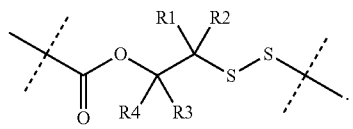

$R^1$ and $R^3$ together with the carbon atoms to which they are attached form a $C_{3\text{-}14}$ cycloalkyl group or 4-14 membered heterocycloalkyl group, each optionally substituted with 1, 2, or 3 substituents independently selected from $C_{1\text{-}4}$ alkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

$R^2$ and $R^4$ are each independently selected from H, $C_{1\text{-}4}$ alkyl, $C_{1\text{-}4}$ alkenyl, $C_{6\text{-}10}$ aryl, $C_{3\text{-}10}$ cycloalkyl, 5-10 membered heteroaryl, 4-10 membered heterocycloalkyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1\text{-}4}$ alkyl, $C_{1\text{-}4}$ alkenyl, $C_{6\text{-}10}$ aryl, $C_{3\text{-}10}$ cycloalkyl, 5-10 membered heteroaryl, and 4-10 membered heterocycloalkyl, are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, and $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH_3$.

2. The method of claim 1, wherein the cancer is selected from bladder cancer, bone cancer, glioma, breast cancer, cervical cancer, colon cancer, colorectal cancer, endometrial cancer, epithelial cancer, esophageal cancer, Ewing's sarcoma, pancreatic cancer, gallbladder cancer, gastric cancer, gastrointestinal tumors, head and neck cancer, intestinal cancers, Kaposi's sarcoma, kidney cancer, laryngeal cancer, liver cancer, lung cancer, melanoma, prostate cancer, rectal cancer, renal clear cell carcinoma, skin cancer, stomach cancer, testicular cancer, thyroid cancer, and uterine cancer.

3. The method of claim 1, wherein the cancer is selected from breast cancer, colorectal cancer, and gastric cancer.

4. The method of claim 2, wherein the breast cancer is triple-negative breast cancer.

5. The method of claim 1, wherein the cancer is ovarian cancer.

6. The method of claim 1, wherein $R^7$ is a peptide capable of selectively delivering $R^8Q$-across a cell membrane having an acidic or hypoxic mantle having a pH less than about 6.0.

7. The method of claim 1, wherein $R^7$ is a peptide comprising at least one of the following sequences:
ADDQNPWRAYLDLLFPTDTLLLDLLWCG (SEQ ID NO: 1; Pv1);
AEQNPIYWARYADWLFTTPLLLLDLALLVDA-DECG (SEQ ID NO: 2; Pv2);
ADDQNPWRAYLDLLFPTDTLLLDLLWDADECG (SEQ ID NO: 3; Pv3);
Ac-AAEQNPIYWARYADWLFTTPLLLLDLALLVDA-DEGTKCG (SEQ ID NO: 4; Pv4); and
AAEQNPIYWARYADWLFTTPLLLLDLALLVDADE-GTC (SEQ ID No. 5; Pv5);
and wherein $R^7$ is attached to Q through a cysteine residue of $R^7$.

8. The method of claim 1, wherein $R^7$ is a peptide comprising at least one of the following sequences:
ADDQNPWRAYLDLLFPTDTLLLDLLWCG (SEQ ID NO: 1; Pv1),
AEQNPIYWARYADWLFTTPLLLLDLALLVDA-DECG (SEQ ID NO: 2; Pv2), and
ADDQNPWRAYLDLLFPTDTLLLDLLWDADECG (SEQ ID NO: 3; Pv3),
and wherein $R^7$ is attached to Q through a cysteine residue of $R^7$.

9. The method of claim 1, wherein $R^7$ is a peptide comprising the sequence: ADDQNPWRAYLDLL-FPTDTLLLDLLWCG (SEQ ID NO: 1; Pv1).

10. The method of claim 1, wherein $R^7$ is a peptide comprising the sequence: AEQNPIYWARY-ADWLFTTPLLLLDLALLVDADECG (SEQ ID NO: 2; Pv2).

11. The method of claim 1, wherein $R^1$ and $R^3$ together with the carbon atom to which they are attached form a cyclopentyl, cyclohexyl, cycloheptyl, 1,2,3,4-tetrahydronaphthyl, tetrahydrofuranyl, or tetrahydropyranyl.

12. The method of claim 1, wherein $R^1$ and $R^3$ together with the carbon atom to which they are attached form a $C_{3-7}$ cycloalkyl group.

13. The method of claim 1, wherein $R^1$ and $R^3$ together with the carbon atom to which they are attached form a cyclohexyl group.

14. The method of claim 1, wherein Q is:

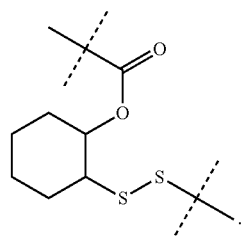

15. The method of claim 1, wherein $R^2$ and $R^4$ are each H.

16. The method of claim 1, wherein the compound is selected from:

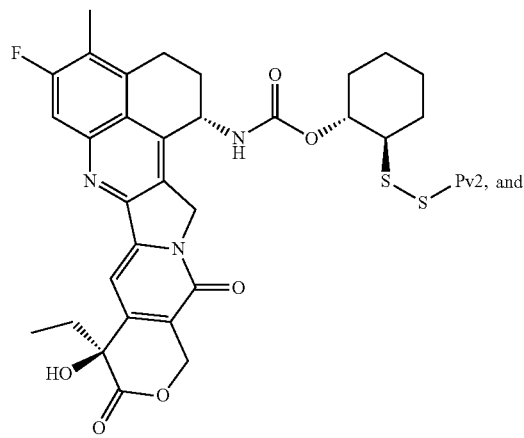

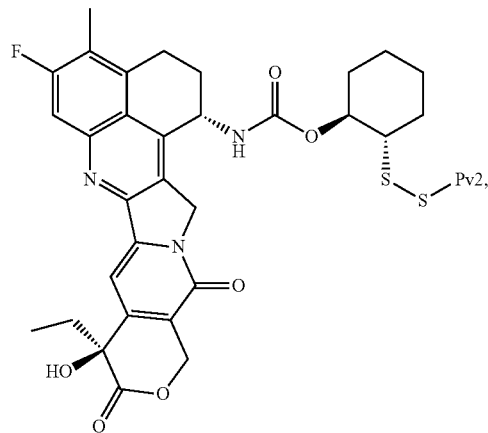

wherein Pv2 is a peptide comprising the sequence:

(SEQ ID NO: 2)
AEQNPIYWARYADWLFTTPLLLLDLALLVDADECG.

17. The method of claim 1, wherein the compound is selected from:
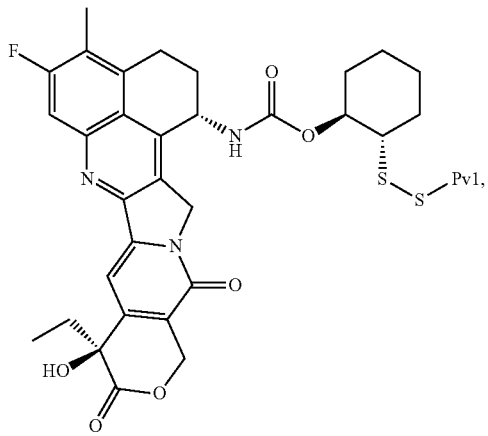
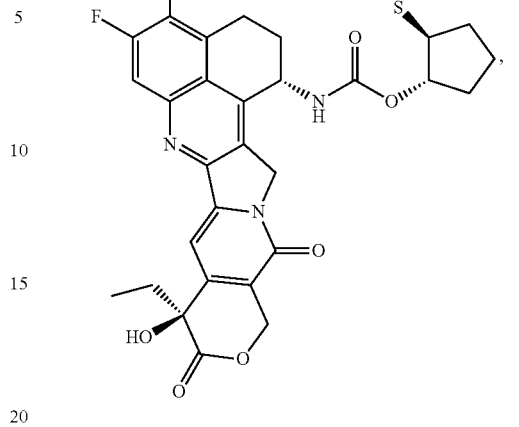
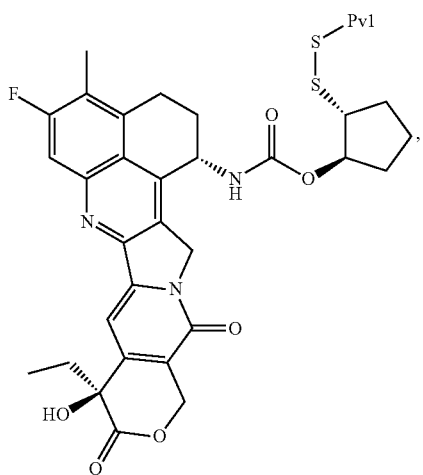
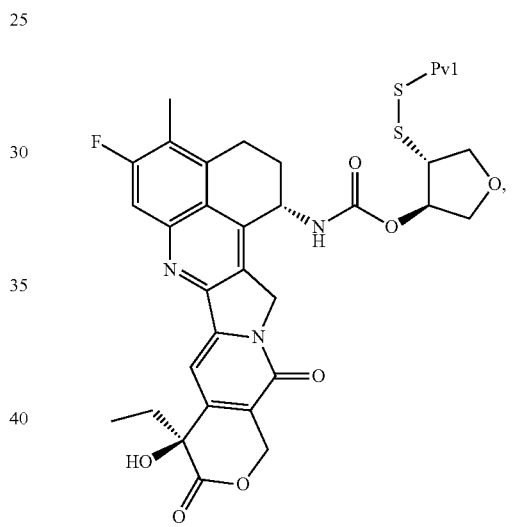
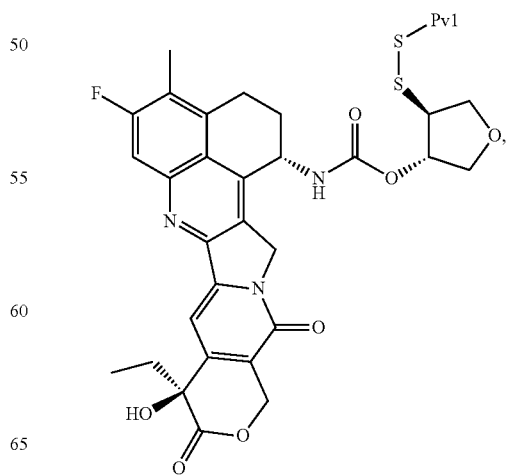

237
-continued
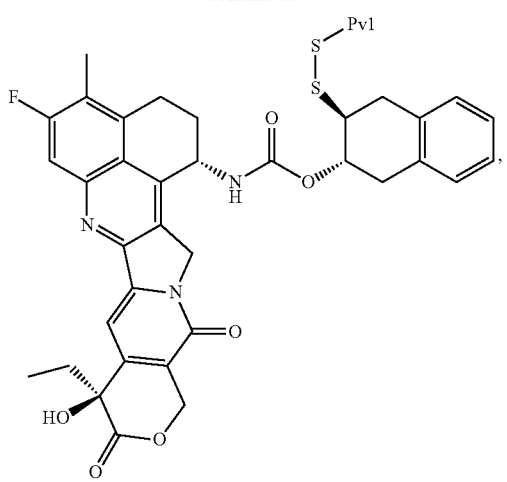
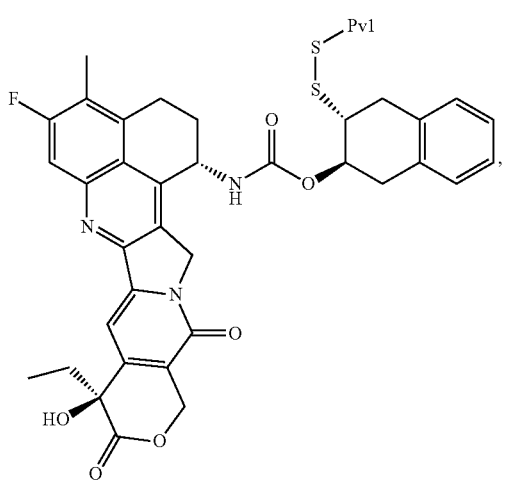
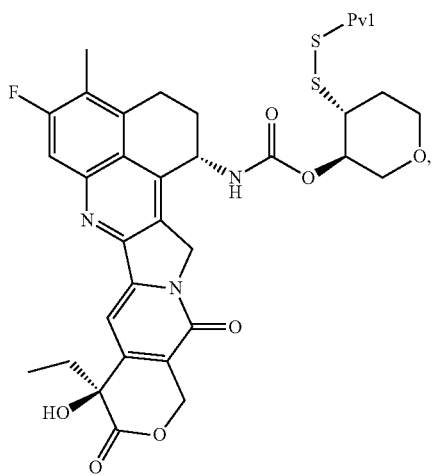
238
-continued
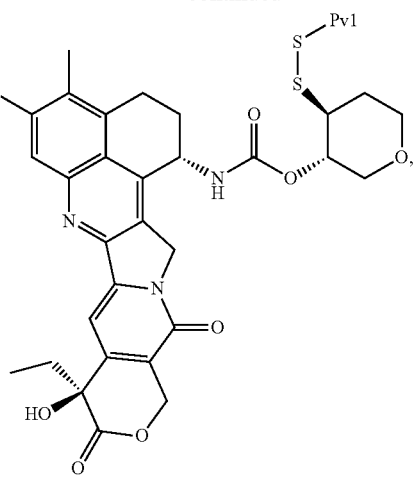
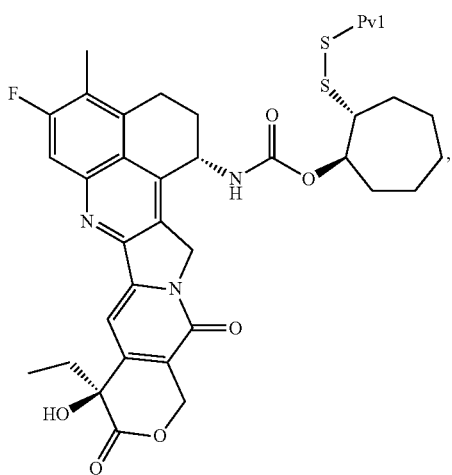
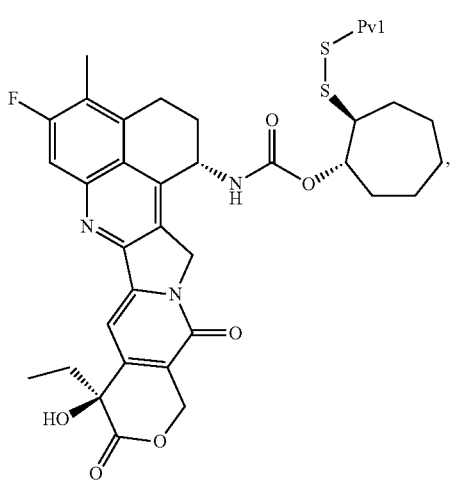

-continued

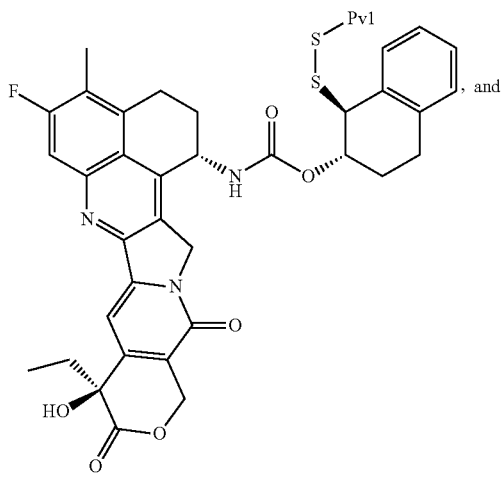, and

18. The method of claim 1, wherein the compound is:

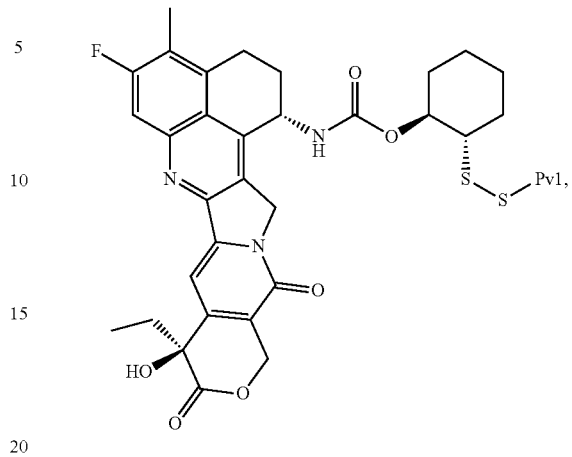

wherein Pv1 is a peptide comprising the sequence:

ADDQNPWRAYLDLLFPTDTLLLDLLWCG. (SEQ ID NO: 1)

19. The method of claim 1, wherein the compound is:

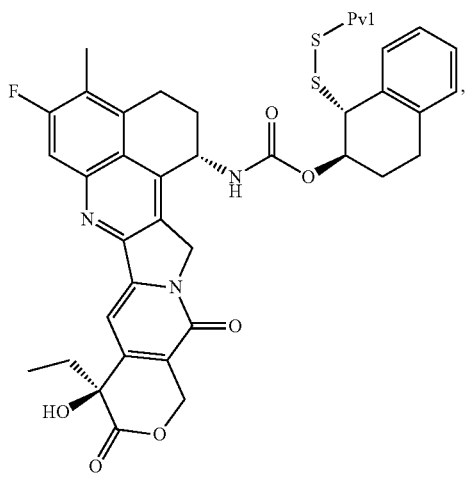

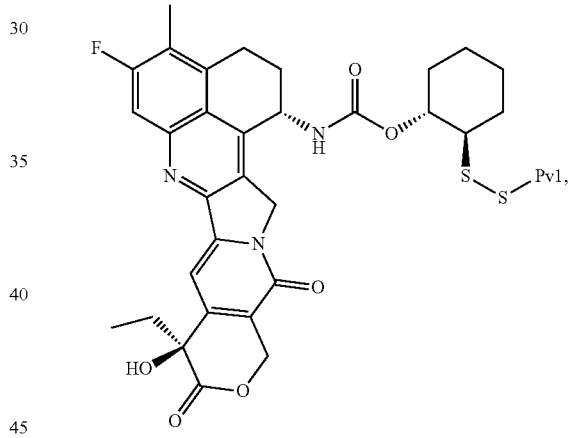

wherein Pv1 is a peptide comprising the sequence:

ADDQNPWRAYLDLLFPTDTLLLDLLWCG. (SEQ ID NO: 1)

wherein Pv1 is a peptide comprising the sequence:

ADDQNPWRAYLDLLFPTDTLLLDLLWCG. (SEQ ID NO: 1)

* * * * *

SEQUENCE LISTING

```
Sequence total quantity: 311
SEQ ID NO: 1            moltype = AA  length = 28
FEATURE                 Location/Qualifiers
source                  1..28
                        mol_type = protein
                        organism = synthetic construct
SEQUENCE: 1
ADDQNPWRAY LDLLFPTDTL LLDLLWCG                                         28

SEQ ID NO: 2            moltype = AA  length = 35
```

```
FEATURE                    Location/Qualifiers
source                     1..35
                           mol_type = protein
                           organism = synthetic construct
SEQUENCE: 2
AEQNPIYWAR YADWLFTTPL LLLDLALLVD ADECG                                35

SEQ ID NO: 3               moltype = AA  length = 32
FEATURE                    Location/Qualifiers
source                     1..32
                           mol_type = protein
                           organism = synthetic construct
SEQUENCE: 3
ADDQNPWRAY LDLLFPTDTL LLDLLWDADE CG                                   32

SEQ ID NO: 4               moltype = AA  length = 39
FEATURE                    Location/Qualifiers
MOD_RES                    1
                           note = acetylated
source                     1..39
                           mol_type = protein
                           organism = synthetic construct
SEQUENCE: 4
AAEQNPIYWA RYADWLFTTP LLLLDLALLV DADEGTKCG                            39

SEQ ID NO: 5               moltype = AA  length = 37
FEATURE                    Location/Qualifiers
source                     1..37
                           mol_type = protein
                           organism = synthetic construct
SEQUENCE: 5
AAEQNPIYWA RYADWLFTTP LLLLDLALLV DADEGTC                              37

SEQ ID NO: 6               moltype = AA  length = 39
FEATURE                    Location/Qualifiers
source                     1..39
                           mol_type = protein
                           organism = synthetic construct
SEQUENCE: 6
AAEQNPIYWW ARYADWLFTT PLLLLDLALL VDADEGTCG                            39

SEQ ID NO: 7               moltype = AA  length = 35
FEATURE                    Location/Qualifiers
source                     1..35
                           mol_type = protein
                           organism = synthetic construct
SEQUENCE: 7
AEQNPIYWAR YADWLFTTPL LLLDLALLVD ADEGT                                35

SEQ ID NO: 8               moltype = AA  length = 36
FEATURE                    Location/Qualifiers
source                     1..36
                           mol_type = protein
                           organism = synthetic construct
SEQUENCE: 8
GGEQNPIYWA RYADWLFTTP LLLLDLALLV DADEGT                               36

SEQ ID NO: 9               moltype = AA  length = 35
FEATURE                    Location/Qualifiers
source                     1..35
                           mol_type = protein
                           organism = synthetic construct
SEQUENCE: 9
AEQNPIYWAR YADWLFTTPL LLLDLALLVD ADEGT                                35

SEQ ID NO: 10              moltype = AA  length = 38
FEATURE                    Location/Qualifiers
source                     1..38
                           mol_type = protein
                           organism = synthetic construct
SEQUENCE: 10
AAEQNPIYWA RYADWLFTTP LLLLDLALLV DADEGTCG                             38

SEQ ID NO: 11              moltype = AA  length = 38
FEATURE                    Location/Qualifiers
source                     1..38
                           mol_type = protein
                           organism = synthetic construct
SEQUENCE: 11
```

GGEQNPIYWA RYADWLFTTP LLLLDLALLV DADEGTCG                                38

SEQ ID NO: 12           moltype = AA  length = 37
FEATURE                 Location/Qualifiers
source                  1..37
                        mol_type = protein
                        organism = synthetic construct
SEQUENCE: 12
ACEQNPIYWA RYADWLFTTP LLLLDLALLV DADEGTG                                 37

SEQ ID NO: 13           moltype = AA  length = 36
FEATURE                 Location/Qualifiers
source                  1..36
                        mol_type = protein
                        organism = synthetic construct
SEQUENCE: 13
ACEQNPIYWA RYADWLFTTP LLLLDLALLV DADEGT                                  36

SEQ ID NO: 14           moltype = AA  length = 36
FEATURE                 Location/Qualifiers
source                  1..36
                        mol_type = protein
                        organism = synthetic construct
SEQUENCE: 14
AKEQNPIYWA RYADWLFTTP LLLLDLALLV DADEGT                                  36

SEQ ID NO: 15           moltype = AA  length = 39
FEATURE                 Location/Qualifiers
source                  1..39
                        mol_type = protein
                        organism = synthetic construct
SEQUENCE: 15
AAEQNPIYWA RYADWLFTTP LLLLDLALLV DADEGTKCG                               39

SEQ ID NO: 16           moltype = AA  length = 36
FEATURE                 Location/Qualifiers
source                  1..36
                        mol_type = protein
                        organism = synthetic construct
SEQUENCE: 16
AKEQNPIYWA RYADWLFTTP LLLLDLALLV DADECT                                  36

SEQ ID NO: 17           moltype = AA  length = 37
FEATURE                 Location/Qualifiers
source                  1..37
                        mol_type = protein
                        organism = synthetic construct
SEQUENCE: 17
ACEQNPIYWA RYANWLFTTP LLLLNLALLV DADEGTG                                 37

SEQ ID NO: 18           moltype = AA  length = 37
FEATURE                 Location/Qualifiers
source                  1..37
                        mol_type = protein
                        organism = synthetic construct
SEQUENCE: 18
ACEQNPIYWA RYAKWLFTTP LLLLKLALLV DADEGTG                                 37

SEQ ID NO: 19           moltype = AA  length = 36
FEATURE                 Location/Qualifiers
source                  1..36
                        mol_type = protein
                        organism = synthetic construct
SEQUENCE: 19
GGEQNPIYWA RYADWLFTTP LLLLDLALLV NANQGT                                  36

SEQ ID NO: 20           moltype = AA  length = 36
FEATURE                 Location/Qualifiers
source                  1..36
                        mol_type = protein
                        organism = synthetic construct
SEQUENCE: 20
AAEQNPIYWA RYADWLFTTP LLLLALALLV DADEGT                                  36

SEQ ID NO: 21           moltype = AA  length = 36
FEATURE                 Location/Qualifiers
source                  1..36
                        mol_type = protein
                        organism = synthetic construct

```
SEQUENCE: 21
AAEQNPIYWA RYAAWLFTTP LLLLDLALLV DADEGT                                   36

SEQ ID NO: 22           moltype = AA  length = 36
FEATURE                 Location/Qualifiers
source                  1..36
                        mol_type = protein
                        organism = synthetic construct
SEQUENCE: 22
AAEQNPIYWA RYADWLFTTA LLLLDLALLV DADEGT                                   36

SEQ ID NO: 23           moltype = AA  length = 36
FEATURE                 Location/Qualifiers
source                  1..36
                        mol_type = protein
                        organism = synthetic construct
SEQUENCE: 23
AAEQNPIYWA RYADWLFTTP LLLLELALLV DADEGT                                   36

SEQ ID NO: 24           moltype = AA  length = 36
FEATURE                 Location/Qualifiers
source                  1..36
                        mol_type = protein
                        organism = synthetic construct
SEQUENCE: 24
AAEQNPIYWA RYAEWLFTTP LLLLDLALLV DADEGT                                   36

SEQ ID NO: 25           moltype = AA  length = 39
FEATURE                 Location/Qualifiers
source                  1..39
                        mol_type = protein
                        organism = synthetic construct
SEQUENCE: 25
AAEQNPIIYW ARYADWLFTD LPLLLLDLLA LLVDADEGT                                39

SEQ ID NO: 26           moltype = AA  length = 37
FEATURE                 Location/Qualifiers
source                  1..37
                        mol_type = protein
                        organism = synthetic construct
SEQUENCE: 26
GEQNPIYWAQ YADWLFTTPL LLLDLALLVD ADEGTCG                                  37

SEQ ID NO: 27           moltype = AA  length = 38
FEATURE                 Location/Qualifiers
source                  1..38
                        mol_type = protein
                        organism = synthetic construct
SEQUENCE: 27
GGEQNPIYWA RYADWLFTTP LLLDLLALLV DADEGTCG                                 38

SEQ ID NO: 28           moltype = AA  length = 38
FEATURE                 Location/Qualifiers
source                  1..38
                        mol_type = protein
                        organism = synthetic construct
SEQUENCE: 28
GGEQNPIYWA RYADWLFTTP LLLLLDALLV DADEGTCG                                 38

SEQ ID NO: 29           moltype = AA  length = 38
FEATURE                 Location/Qualifiers
source                  1..38
                        mol_type = protein
                        organism = synthetic construct
SEQUENCE: 29
GGEQNPIYWA RYDAWLFTTP LLLLDLALLV DADEGTCG                                 38

SEQ ID NO: 30           moltype = AA  length = 38
FEATURE                 Location/Qualifiers
source                  1..38
                        mol_type = protein
                        organism = synthetic construct
SEQUENCE: 30
GGEQNPIYWA RYAWDLFTTP LLLLDLALLV DADEGTCG                                 38

SEQ ID NO: 31           moltype = AA  length = 36
FEATURE                 Location/Qualifiers
source                  1..36
                        mol_type = protein
```

```
                        organism = synthetic construct
SEQUENCE: 31
AAEQNPIYWA RYADWLFTTG LLLLDLALLV DADEGT                              36

SEQ ID NO: 32           moltype = AA   length = 37
FEATURE                 Location/Qualifiers
source                  1..37
                        mol_type = protein
                        organism = synthetic construct
SEQUENCE: 32
DDDEDNPIYW ARYADWLFTT PLLLLHGALL VDADECT                             37

SEQ ID NO: 33           moltype = AA   length = 38
FEATURE                 Location/Qualifiers
source                  1..38
                        mol_type = protein
                        organism = synthetic construct
SEQUENCE: 33
DDDEDNPIYW ARYAHWLFTT PLLLLHGALL VDADEGCT                            38

SEQ ID NO: 34           moltype = AA   length = 37
FEATURE                 Location/Qualifiers
source                  1..37
                        mol_type = protein
                        organism = synthetic construct
SEQUENCE: 34
DDDEDNPIYW ARYAHWLFTT PLLLLHGALL VNADECT                             37

SEQ ID NO: 35           moltype = AA   length = 37
FEATURE                 Location/Qualifiers
source                  1..37
                        mol_type = protein
                        organism = synthetic construct
SEQUENCE: 35
DDDEDNPIYW ARYAHWLFTT PLLLLHGALL VNANECT                             37

SEQ ID NO: 36           moltype = AA   length = 34
FEATURE                 Location/Qualifiers
source                  1..34
                        mol_type = protein
                        organism = synthetic construct
SEQUENCE: 36
AEQNPIYWAR YADFLFTTPL LLLDLALLVD ADET                                34

SEQ ID NO: 37           moltype = AA   length = 35
FEATURE                 Location/Qualifiers
source                  1..35
                        mol_type = protein
                        organism = synthetic construct
SEQUENCE: 37
AEQNPIYFAR YADWLFTTPL LLLDLALLVD ADEGT                               35

SEQ ID NO: 38           moltype = AA   length = 34
FEATURE                 Location/Qualifiers
source                  1..34
                        mol_type = protein
                        organism = synthetic construct
SEQUENCE: 38
AEQNPIYFAR YADFLFTTPL LLLDLALLWD ADET                                34

SEQ ID NO: 39           moltype = AA   length = 32
FEATURE                 Location/Qualifiers
source                  1..32
                        mol_type = protein
                        organism = synthetic construct
SEQUENCE: 39
AKEDQNPYWA RYADWLFTTP LLLLDLALLV DG                                  32

SEQ ID NO: 40           moltype = AA   length = 32
FEATURE                 Location/Qualifiers
source                  1..32
                        mol_type = protein
                        organism = synthetic construct
SEQUENCE: 40
ACEDQNPYWA RYADWLFTTP LLLLDLALLV DG                                  32

SEQ ID NO: 41           moltype = AA   length = 32
FEATURE                 Location/Qualifiers
source                  1..32
```

```
                        mol_type = protein
                        organism = synthetic construct
SEQUENCE: 41
AEDQNPYWAR YADWLFTTPL LLLDLALLVD CG                                  32

SEQ ID NO: 42           moltype = AA  length = 32
FEATURE                 Location/Qualifiers
source                  1..32
                        mol_type = protein
                        organism = synthetic construct
SEQUENCE: 42
AEDQNPYWAR YADWLFTTPL LLLELALLVE CG                                  32

SEQ ID NO: 43           moltype = AA  length = 30
FEATURE                 Location/Qualifiers
source                  1..30
                        mol_type = protein
                        organism = synthetic construct
SEQUENCE: 43
AKEDQNPYWR AYADLFTPLT LLDLLALWDG                                     30

SEQ ID NO: 44           moltype = AA  length = 30
FEATURE                 Location/Qualifiers
source                  1..30
                        mol_type = protein
                        organism = synthetic construct
SEQUENCE: 44
ACEDQNPYWR AYADLFTPLT LLDLLALWDG                                     30

SEQ ID NO: 45           moltype = AA  length = 27
FEATURE                 Location/Qualifiers
source                  1..27
                        mol_type = protein
                        organism = synthetic construct
SEQUENCE: 45
ACDDQNPWRA YLDLLFPTDT LLLDLLW                                        27

SEQ ID NO: 46           moltype = AA  length = 34
FEATURE                 Location/Qualifiers
source                  1..34
                        mol_type = protein
                        organism = synthetic construct
SEQUENCE: 46
TEDADVLLAL DLLLLPTTFL WDAYRAWYPN QECA                                34

SEQ ID NO: 47           moltype = AA  length = 20
FEATURE                 Location/Qualifiers
source                  1..20
                        mol_type = protein
                        organism = synthetic construct
SEQUENCE: 47
AEQNPIYWAR YADWLFTTPL                                                20

SEQ ID NO: 48           moltype = AA  length = 21
FEATURE                 Location/Qualifiers
source                  1..21
                        mol_type = protein
                        organism = synthetic construct
SEQUENCE: 48
AEQNPIYWAR YADWLFTTPC L                                              21

SEQ ID NO: 49           moltype = AA  length = 21
FEATURE                 Location/Qualifiers
source                  1..21
                        mol_type = protein
                        organism = synthetic construct
SEQUENCE: 49
ACEQNPIYWA RYADWLFTTP L                                              21

SEQ ID NO: 50           moltype = AA  length = 20
FEATURE                 Location/Qualifiers
source                  1..20
                        mol_type = protein
                        organism = synthetic construct
SEQUENCE: 50
AEQNPIYFAR YADWLFTTPL                                                20

SEQ ID NO: 51           moltype = AA  length = 21
FEATURE                 Location/Qualifiers
```

```
source                  1..21
                        mol_type = protein
                        organism = synthetic construct
SEQUENCE: 51
KEDQNPWARY ADLLFPTTLA W                                         21

SEQ ID NO: 52           moltype = AA   length = 22
FEATURE                 Location/Qualifiers
source                  1..22
                        mol_type = protein
                        organism = synthetic construct
SEQUENCE: 52
ACEDQNPWAR YADLLFPTTL AW                                        22

SEQ ID NO: 53           moltype = AA   length = 24
FEATURE                 Location/Qualifiers
source                  1..24
                        mol_type = protein
                        organism = synthetic construct
SEQUENCE: 53
ACEDQNPWAR YADWLFPTTL LLLD                                      24

SEQ ID NO: 54           moltype = AA   length = 22
FEATURE                 Location/Qualifiers
source                  1..22
                        mol_type = protein
                        organism = synthetic construct
SEQUENCE: 54
ACEEQNPWAR YAELLFPTTL AW                                        22

SEQ ID NO: 55           moltype = AA   length = 24
FEATURE                 Location/Qualifiers
source                  1..24
                        mol_type = protein
                        organism = synthetic construct
SEQUENCE: 55
ACEEQNPWAR YAEWLFPTTL LLLE                                      24

SEQ ID NO: 56           moltype = AA   length = 25
FEATURE                 Location/Qualifiers
source                  1..25
                        mol_type = protein
                        organism = synthetic construct
SEQUENCE: 56
ACEEQNPWAR YLEWLFPTET LLLEL                                     25

SEQ ID NO: 57           moltype = AA   length = 36
FEATURE                 Location/Qualifiers
source                  1..36
                        mol_type = protein
                        organism = synthetic construct
SEQUENCE: 57
GGEQNPIYWA RYADWLFTTP LLLLDLALLV DADEGT                         36

SEQ ID NO: 58           moltype = AA   length = 35
FEATURE                 Location/Qualifiers
source                  1..35
                        mol_type = protein
                        organism = synthetic construct
SEQUENCE: 58
ACEQNPIYWA RYADWLFTTP LLLLDLALLV DADET                          35

SEQ ID NO: 59           moltype = AA   length = 38
FEATURE                 Location/Qualifiers
source                  1..38
                        mol_type = protein
                        organism = synthetic construct
SEQUENCE: 59
AAEQNPIYWA RYADWLFTTP LLLLDLALLV DADEGTCG                       38

SEQ ID NO: 60           moltype = AA   length = 36
FEATURE                 Location/Qualifiers
source                  1..36
                        mol_type = protein
                        organism = synthetic construct
SEQUENCE: 60
AEQNPIYWAR YADWLFTTPL LLLDLALLVD ADEGCT                         36

SEQ ID NO: 61           moltype = AA   length = 38
```

```
FEATURE                 Location/Qualifiers
source                  1..38
                        mol_type = protein
                        organism = synthetic construct
SEQUENCE: 61
GGEQNPIYWA RYADWLFTTP LLLLDLALLV DADEGTCG                              38

SEQ ID NO: 62           moltype = AA   length = 36
FEATURE                 Location/Qualifiers
source                  1..36
                        mol_type = protein
                        organism = synthetic construct
SEQUENCE: 62
ACEQNPIYWA RYADWLFTTP LLLLDLALLV DADEGT                                36

SEQ ID NO: 63           moltype = AA   length = 36
FEATURE                 Location/Qualifiers
source                  1..36
                        mol_type = protein
                        organism = synthetic construct
SEQUENCE: 63
AKEQNPIYWA RYADWLFTTP LLLLDLALLV DADEGT                                36

SEQ ID NO: 64           moltype = AA   length = 36
FEATURE                 Location/Qualifiers
source                  1..36
                        mol_type = protein
                        organism = synthetic construct
SEQUENCE: 64
AKEQNPIYWA RYADWLFTTP LLLLDLALLV DADECT                                36

SEQ ID NO: 65           moltype = AA   length = 36
FEATURE                 Location/Qualifiers
source                  1..36
                        mol_type = protein
                        organism = synthetic construct
SEQUENCE: 65
AAEQNPIYWA RYADWLFTTA LLLLDLALLV DADEGT                                36

SEQ ID NO: 66           moltype = AA   length = 37
FEATURE                 Location/Qualifiers
source                  1..37
                        mol_type = protein
                        organism = synthetic construct
SEQUENCE: 66
ACAEQNPIYW ARYADWLFTT GLLLLDLALL VDADEGT                               37

SEQ ID NO: 67           moltype = AA   length = 34
FEATURE                 Location/Qualifiers
source                  1..34
                        mol_type = protein
                        organism = synthetic construct
SEQUENCE: 67
AEQNPIYWAR YADFLFTTPL LLLDLALLVD ADET                                  34

SEQ ID NO: 68           moltype = AA   length = 35
FEATURE                 Location/Qualifiers
source                  1..35
                        mol_type = protein
                        organism = synthetic construct
SEQUENCE: 68
AEQNPIYFAR YADWLFTTPL LLLDLALLVD ADEGT                                 35

SEQ ID NO: 69           moltype = AA   length = 34
FEATURE                 Location/Qualifiers
source                  1..34
                        mol_type = protein
                        organism = synthetic construct
SEQUENCE: 69
AEQNPIYFAR YADFLFTTPL LLLDLALLWD ADET                                  34

SEQ ID NO: 70           moltype = AA   length = 32
FEATURE                 Location/Qualifiers
source                  1..32
                        mol_type = protein
                        organism = synthetic construct
SEQUENCE: 70
AKEDQNPYWA RYADWLFTTP LLLLDLALLV DG                                    32
```

```
SEQ ID NO: 71            moltype = AA   length = 32
FEATURE                  Location/Qualifiers
source                   1..32
                         mol_type = protein
                         organism = synthetic construct
SEQUENCE: 71
ACEDQNPYWA RYADWLFTTP LLLLDLALLV DG                                         32

SEQ ID NO: 72            moltype = AA   length = 31
FEATURE                  Location/Qualifiers
source                   1..31
                         mol_type = protein
                         organism = synthetic construct
SEQUENCE: 72
AEDQNPYWAR YADWLFTTPL LLLDLALLVD G                                          31

SEQ ID NO: 73            moltype = AA   length = 32
FEATURE                  Location/Qualifiers
source                   1..32
                         mol_type = protein
                         organism = synthetic construct
SEQUENCE: 73
AEDQNPYWAR YADWLFTTPL LLLELALLVE CG                                         32

SEQ ID NO: 74            moltype = AA   length = 30
FEATURE                  Location/Qualifiers
source                   1..30
                         mol_type = protein
                         organism = synthetic construct
SEQUENCE: 74
AKEDQNPYWR AYADLFTPLT LLDLLALWDG                                            30

SEQ ID NO: 75            moltype = AA   length = 30
FEATURE                  Location/Qualifiers
source                   1..30
                         mol_type = protein
                         organism = synthetic construct
SEQUENCE: 75
ACEDQNPYWR AYADLFTPLT LLDLLALWDG                                            30

SEQ ID NO: 76            moltype = AA   length = 32
FEATURE                  Location/Qualifiers
source                   1..32
                         mol_type = protein
                         organism = synthetic construct
SEQUENCE: 76
AKEDQNDPYW ARYADWLFTT PLLLLDLALL VG                                         32

SEQ ID NO: 77            moltype = AA   length = 34
FEATURE                  Location/Qualifiers
source                   1..34
                         mol_type = protein
                         organism = synthetic construct
SEQUENCE: 77
TEDADVLLAL DLLLLPTTFL WDAYRAWYPN QECA                                       34

SEQ ID NO: 78            moltype = AA   length = 36
FEATURE                  Location/Qualifiers
source                   1..36
                         mol_type = protein
                         organism = synthetic construct
SEQUENCE: 78
GGEQNPIYWA RYADWLFTTP LLLLDLALLV DADEGT                                     36

SEQ ID NO: 79            moltype = AA   length = 20
FEATURE                  Location/Qualifiers
source                   1..20
                         mol_type = protein
                         organism = synthetic construct
SEQUENCE: 79
AEQNPIYWAR YADWLFTTPL                                                       20

SEQ ID NO: 80            moltype = AA   length = 21
FEATURE                  Location/Qualifiers
source                   1..21
                         mol_type = protein
                         organism = synthetic construct
SEQUENCE: 80
AEQNPIYWAR YADWLFTTPC L                                                     21
```

```
SEQ ID NO: 81          moltype = AA  length = 21
FEATURE                Location/Qualifiers
source                 1..21
                       mol_type = protein
                       organism = synthetic construct
SEQUENCE: 81
ACEQNPIYWA RYADWLFTTP L                                                 21

SEQ ID NO: 82          moltype = AA  length = 21
FEATURE                Location/Qualifiers
source                 1..21
                       mol_type = protein
                       organism = synthetic construct
SEQUENCE: 82
ACEQNPIYFA RYADWLFTTP L                                                 21

SEQ ID NO: 83          moltype = AA  length = 27
FEATURE                Location/Qualifiers
source                 1..27
                       mol_type = protein
                       organism = synthetic construct
SEQUENCE: 83
ACDDQNPWRA YLDLLFPTDT LLLDLLW                                           27

SEQ ID NO: 84          moltype = AA  length = 27
FEATURE                Location/Qualifiers
source                 1..27
                       mol_type = protein
                       organism = synthetic construct
SEQUENCE: 84
ACEEQNPWRA YLELLFPTET LLLELLW                                           27

SEQ ID NO: 85          moltype = AA  length = 25
FEATURE                Location/Qualifiers
source                 1..25
                       mol_type = protein
                       organism = synthetic construct
SEQUENCE: 85
ACDDQNPWAR YLDWLFPTDT LLLDL                                             25

SEQ ID NO: 86          moltype = AA  length = 24
FEATURE                Location/Qualifiers
source                 1..24
                       mol_type = protein
                       organism = synthetic construct
SEQUENCE: 86
CDNNNPWRAY LDLLFPTDTL LLDW                                              24

SEQ ID NO: 87          moltype = AA  length = 25
FEATURE                Location/Qualifiers
source                 1..25
                       mol_type = protein
                       organism = synthetic construct
SEQUENCE: 87
ACEEQNPWAR YLEWLFPTET LLLEL                                             25

SEQ ID NO: 88          moltype = AA  length = 24
FEATURE                Location/Qualifiers
source                 1..24
                       mol_type = protein
                       organism = synthetic construct
SEQUENCE: 88
ACEDQNPWAR YADWLFPTTL LLLD                                              24

SEQ ID NO: 89          moltype = AA  length = 24
FEATURE                Location/Qualifiers
source                 1..24
                       mol_type = protein
                       organism = synthetic construct
SEQUENCE: 89
ACEEQNPWAR YAEWLFPTTL LLLE                                              24

SEQ ID NO: 90          moltype = AA  length = 22
FEATURE                Location/Qualifiers
source                 1..22
                       mol_type = protein
                       organism = synthetic construct
SEQUENCE: 90
```

```
ACEDQNPWAR YADLLFPTTL AW                                                 22

SEQ ID NO: 91            moltype = AA   length = 21
FEATURE                  Location/Qualifiers
source                   1..21
                         mol_type = protein
                         organism = synthetic construct
SEQUENCE: 91
ACEDQNPWAR YAELLFPTTL W                                                  21

SEQ ID NO: 92            moltype = AA   length = 20
FEATURE                  Location/Qualifiers
source                   1..20
                         mol_type = protein
                         organism = synthetic construct
SEQUENCE: 92
KEDQNPWARY ADLLFPTTLW                                                    20

SEQ ID NO: 93            moltype = AA   length = 37
FEATURE                  Location/Qualifiers
source                   1..37
                         mol_type = protein
                         organism = synthetic construct
SEQUENCE: 93
DDDEDNPIYW ARYAHWLFTT PLLLLHGALL VDADECT                                 37

SEQ ID NO: 94            moltype = AA   length = 37
FEATURE                  Location/Qualifiers
source                   1..37
                         mol_type = protein
                         organism = synthetic construct
SEQUENCE: 94
DDDEDNPIYW ARYAHWLFTT PLLLLDGALL VDADECT                                 37

SEQ ID NO: 95            moltype = AA   length = 37
FEATURE                  Location/Qualifiers
source                   1..37
                         mol_type = protein
                         organism = synthetic construct
SEQUENCE: 95
DDDEDNPIYW ARYAHWLFTT PLLLLHGALL VNADECT                                 37

SEQ ID NO: 96            moltype = AA   length = 37
FEATURE                  Location/Qualifiers
source                   1..37
                         mol_type = protein
                         organism = synthetic construct
SEQUENCE: 96
DDDEDNPIYW ARYAHWLFTT PLLLLHGALL VNANECT                                 37

SEQ ID NO: 97            moltype = AA   length = 37
FEATURE                  Location/Qualifiers
source                   1..37
                         mol_type = protein
                         organism = synthetic construct
SEQUENCE: 97
DDDEDNPIYW ARYADWLFTT PLLLLHGALL VDADECT                                 37

SEQ ID NO: 98            moltype = AA   length = 37
FEATURE                  Location/Qualifiers
source                   1..37
                         mol_type = protein
                         organism = synthetic construct
SEQUENCE: 98
ACEQNPIYWA RYADWLFTTP LLLLDLALLV DADEGTG                                 37

SEQ ID NO: 99            moltype = AA   length = 35
FEATURE                  Location/Qualifiers
source                   1..35
                         mol_type = protein
                         organism = synthetic construct
SEQUENCE: 99
ACEQNPIYWA RYADWLFTTP LLLLDLALLV DADET                                   35

SEQ ID NO: 100           moltype = AA   length = 36
FEATURE                  Location/Qualifiers
source                   1..36
                         mol_type = protein
                         organism = synthetic construct
```

```
SEQUENCE: 100
ACEQNPIYWA RYADWLFTTP LLLLDLALLV DADEGT                              36

SEQ ID NO: 101          moltype = AA  length = 38
FEATURE                 Location/Qualifiers
source                  1..38
                        mol_type = protein
                        organism = synthetic construct
SEQUENCE: 101
GGEQNPIYWA RYADWLFTTP LLLDLLALLV DADEGTCG                            38

SEQ ID NO: 102          moltype = AA  length = 38
FEATURE                 Location/Qualifiers
source                  1..38
                        mol_type = protein
                        organism = synthetic construct
SEQUENCE: 102
GGEQNPIYWA RYADWLFTTP LLLLLDALLV DADEGTCG                            38

SEQ ID NO: 103          moltype = AA  length = 38
FEATURE                 Location/Qualifiers
source                  1..38
                        mol_type = protein
                        organism = synthetic construct
SEQUENCE: 103
GGEQNPIYWA RYAWDLFTTP LLLLDLALLV DADEGTCG                            38

SEQ ID NO: 104          moltype = AA  length = 38
FEATURE                 Location/Qualifiers
source                  1..38
                        mol_type = protein
                        organism = synthetic construct
SEQUENCE: 104
AAEQNPIYWA RYAEWLFTTP LLLLDLALLV DADEGTCG                            38

SEQ ID NO: 105          moltype = AA  length = 38
FEATURE                 Location/Qualifiers
source                  1..38
                        mol_type = protein
                        organism = synthetic construct
SEQUENCE: 105
AAEQNPIYWA RYAEWLFTTP LLLLELALLV DADEGTCG                            38

SEQ ID NO: 106          moltype = AA  length = 38
FEATURE                 Location/Qualifiers
source                  1..38
                        mol_type = protein
                        organism = synthetic construct
SEQUENCE: 106
GGEQNPIYWA RYDAWLFTTP LLLLDLALLV DADEGTCG                            38

SEQ ID NO: 107          moltype = AA  length = 38
FEATURE                 Location/Qualifiers
source                  1..38
                        mol_type = protein
                        organism = synthetic construct
SEQUENCE: 107
GGEQNPIYWA QYDAWLFTTP LLLLDLALLV DADEGTCG                            38

SEQ ID NO: 108          moltype = AA  length = 38
FEATURE                 Location/Qualifiers
source                  1..38
                        mol_type = protein
                        organism = synthetic construct
SEQUENCE: 108
GGEQNPIYWA QDYAWLFTTP LLLLDLALLV DADEGTCG                            38

SEQ ID NO: 109          moltype = AA  length = 38
FEATURE                 Location/Qualifiers
source                  1..38
                        mol_type = protein
                        organism = synthetic construct
SEQUENCE: 109
AAEQNPIYWA RYAAWLFTTP LLLLDLALLV DADEGTCG                            38

SEQ ID NO: 110          moltype = AA  length = 37
FEATURE                 Location/Qualifiers
source                  1..37
                        mol_type = protein
```

```
                        organism = synthetic construct
SEQUENCE: 110
ACEQNPIYWA RYANWLFTTP LLLLNLALLV DADEGTG                              37

SEQ ID NO: 111          moltype = AA  length = 37
FEATURE                 Location/Qualifiers
source                  1..37
                        mol_type = protein
                        organism = synthetic construct
SEQUENCE: 111
DDDEDNPIYW ARYAHWLFTT PLLLLHGALL VNANECT                              37

SEQ ID NO: 112          moltype = AA  length = 37
FEATURE                 Location/Qualifiers
source                  1..37
                        mol_type = protein
                        organism = synthetic construct
SEQUENCE: 112
DDDEDNPIYW ARYAHWLFTT PLLLLHGALL VNADECT                              37

SEQ ID NO: 113          moltype = AA  length = 37
FEATURE                 Location/Qualifiers
source                  1..37
                        mol_type = protein
                        organism = synthetic construct
SEQUENCE: 113
DDDEDNPIYW ARYADWLFTT PLLLLHGALL VDADECT                              37

SEQ ID NO: 114          moltype = AA  length = 37
FEATURE                 Location/Qualifiers
source                  1..37
                        mol_type = protein
                        organism = synthetic construct
SEQUENCE: 114
DDDEDNPIYW ARYAHWLFTT PLLLLHGALL VDADECT                              37

SEQ ID NO: 115          moltype = AA  length = 37
FEATURE                 Location/Qualifiers
source                  1..37
                        mol_type = protein
                        organism = synthetic construct
SEQUENCE: 115
DDDEDNPIYW ARYAHWLFTT PLLLLDGALL VDADECT                              37

SEQ ID NO: 116          moltype = AA  length = 36
FEATURE                 Location/Qualifiers
source                  1..36
                        mol_type = protein
                        organism = synthetic construct
SEQUENCE: 116
GGEQNPIYWA RYADWLFTTP LLLLDLALLV NANQGT                               36

SEQ ID NO: 117          moltype = AA  length = 38
FEATURE                 Location/Qualifiers
source                  1..38
                        mol_type = protein
                        organism = synthetic construct
SEQUENCE: 117
AAEQNPIYWA RYADWLFTTP LLLLELALLV DADEGTCG                             38

SEQ ID NO: 118          moltype = AA  length = 38
FEATURE                 Location/Qualifiers
source                  1..38
                        mol_type = protein
                        organism = synthetic construct
SEQUENCE: 118
AAEQNPIYWA RYAEWLFTTP LLLLELALLV DADEGTCG                             38

SEQ ID NO: 119          moltype = AA  length = 39
FEATURE                 Location/Qualifiers
source                  1..39
                        mol_type = protein
                        organism = synthetic construct
SEQUENCE: 119
AAEQNPIYWA RYADWLFTTP LLLLELALLV DADEGTKCG                            39

SEQ ID NO: 120          moltype = AA  length = 38
FEATURE                 Location/Qualifiers
source                  1..38
```

```
                            mol_type = protein
                            organism = synthetic construct
SEQUENCE: 120
GGEQNPIYWA QYADWLFTTP LLLLDLALLV DADEGTCG                             38

SEQ ID NO: 121              moltype = AA   length = 38
FEATURE                     Location/Qualifiers
source                      1..38
                            mol_type = protein
                            organism = synthetic construct
SEQUENCE: 121
GGEQNPIYWA QYDAWLFTTP LLLLDLALLV DADEGTCG                             38

SEQ ID NO: 122              moltype = AA   length = 38
FEATURE                     Location/Qualifiers
source                      1..38
                            mol_type = protein
                            organism = synthetic construct
SEQUENCE: 122
GGEQNPIYWA QDYAWLFTTP LLLLDLALLV DADEGTCG                             38

SEQ ID NO: 123              moltype = AA   length = 36
FEATURE                     Location/Qualifiers
source                      1..36
                            mol_type = protein
                            organism = synthetic construct
SEQUENCE: 123
GGEQNPIYWA RYADWLFTTP LLLLDLALLV NANQGT                               36

SEQ ID NO: 124              moltype = AA   length = 37
FEATURE                     Location/Qualifiers
source                      1..37
                            mol_type = protein
                            organism = synthetic construct
SEQUENCE: 124
DDDEDNPIYW ARYAHWLFTT PLLLLHGALL VNADECT                              37

SEQ ID NO: 125              moltype = AA   length = 37
FEATURE                     Location/Qualifiers
source                      1..37
                            mol_type = protein
                            organism = synthetic construct
SEQUENCE: 125
DDDEDNPIYW ARYAHWLFTT PLLLLHGALL VNANECT                              37

SEQ ID NO: 126              moltype = AA   length = 37
FEATURE                     Location/Qualifiers
source                      1..37
                            mol_type = protein
                            organism = synthetic construct
SEQUENCE: 126
ACEQNPIYWA RYAKWLFTTP LLLLKLALLV DADEGTG                              37

SEQ ID NO: 127              moltype = AA   length = 38
FEATURE                     Location/Qualifiers
source                      1..38
                            mol_type = protein
                            organism = synthetic construct
SEQUENCE: 127
GGEQNPIYWA QDYAWLFTTP LLLLDLALLV DADEGTCG                             38

SEQ ID NO: 128              moltype = AA   length = 38
FEATURE                     Location/Qualifiers
source                      1..38
                            mol_type = protein
                            organism = synthetic construct
SEQUENCE: 128
GGEQNPIYWA QYDAWLFTTP LLLLDLALLV DADEGTCG                             38

SEQ ID NO: 129              moltype = AA   length = 38
FEATURE                     Location/Qualifiers
source                      1..38
                            mol_type = protein
                            organism = synthetic construct
SEQUENCE: 129
GGEQNPIYWA QYADWLFTTP LLLLDLALLV DADEGTCG                             38

SEQ ID NO: 130              moltype = AA   length = 38
FEATURE                     Location/Qualifiers
```

```
source                  1..38
                        mol_type = protein
                        organism = synthetic construct
SEQUENCE: 130
AAEQNPIYWA RYAAWLFTTP LLLLDLALLV DADEGTCG                              38

SEQ ID NO: 131          moltype = AA  length = 38
FEATURE                 Location/Qualifiers
source                  1..38
                        mol_type = protein
                        organism = synthetic construct
SEQUENCE: 131
AAEQNPIYWA RYADWLFTDL PLLLLDLLAL LVDADEGT                              38

SEQ ID NO: 132          moltype = AA  length = 38
FEATURE                 Location/Qualifiers
source                  1..38
                        mol_type = protein
                        organism = synthetic construct
SEQUENCE: 132
GGEQNPIYWA RYDWLFTTP LLLLLDALLV DADEGTCG                               38

SEQ ID NO: 133          moltype = AA  length = 38
FEATURE                 Location/Qualifiers
source                  1..38
                        mol_type = protein
                        organism = synthetic construct
SEQUENCE: 133
GGEQNPIYWA RYADWLFTTP LLLDLLALLV DADEGTCG                              38

SEQ ID NO: 134          moltype = AA  length = 36
FEATURE                 Location/Qualifiers
source                  1..36
                        mol_type = protein
                        organism = synthetic construct
SEQUENCE: 134
AAEQNPIYWA RYADWLFTTG LLLLDLALLV DADEGT                                36

SEQ ID NO: 135          moltype = AA  length = 38
FEATURE                 Location/Qualifiers
source                  1..38
                        mol_type = protein
                        organism = synthetic construct
SEQUENCE: 135
AAEQNPIYWA RYAAWLFTTP LLLLDLALLV DADEGTCG                              38

SEQ ID NO: 136          moltype = AA  length = 38
FEATURE                 Location/Qualifiers
source                  1..38
                        mol_type = protein
                        organism = synthetic construct
SEQUENCE: 136
GGEQNPIYWA QYDAWLFTTP LLLLDLALLV DADEGTCG                              38

SEQ ID NO: 137          moltype = AA  length = 38
FEATURE                 Location/Qualifiers
source                  1..38
                        mol_type = protein
                        organism = synthetic construct
SEQUENCE: 137
GGEQNPIYWA QDYAWLFTTP LLLLDLALLV DADEGTCG                              38

SEQ ID NO: 138          moltype = AA  length = 38
FEATURE                 Location/Qualifiers
source                  1..38
                        mol_type = protein
                        organism = synthetic construct
SEQUENCE: 138
GGEQNPIYWA RYDAWLFTTP LLLLDLALLV DADEGTCG                              38

SEQ ID NO: 139          moltype = AA  length = 38
FEATURE                 Location/Qualifiers
source                  1..38
                        mol_type = protein
                        organism = synthetic construct
SEQUENCE: 139
AAEQNPIYWA RYADWLFTTP LLLLALALLV DADEGTCG                              38

SEQ ID NO: 140          moltype = AA  length = 39
```

```
FEATURE              Location/Qualifiers
MOD_RES              37
                     note = Lys(rhodamine)
MOD_RES              38
                     note = Cys(phalloidin)
source               1..39
                     mol_type = protein
                     organism = synthetic construct
SEQUENCE: 140
AAEQNPIYWA RYADWLFTTP LLLLDLALLV DADEGTKCG                          39

SEQ ID NO: 141       moltype = AA  length = 39
FEATURE              Location/Qualifiers
MOD_RES              37
                     note = Lys(rhodamine)
MOD_RES              38
                     note = Cys(phalloidin)
source               1..39
                     mol_type = protein
                     organism = synthetic construct
SEQUENCE: 141
AAEQNPIYWA RYADWLFTTP LLLLELALLV DADEGTKCG                          39

SEQ ID NO: 142       moltype = AA  length = 38
FEATURE              Location/Qualifiers
MOD_RES              37
                     note = Cys(phalloidin)
source               1..38
                     mol_type = protein
                     organism = synthetic construct
SEQUENCE: 142
AAEQNPIYWA RYADWLFTTP LLLLDLALLV DADEGTCG                           38

SEQ ID NO: 143       moltype = AA  length = 38
FEATURE              Location/Qualifiers
MOD_RES              37
                     note = Cys(phalloidin)
source               1..38
                     mol_type = protein
                     organism = synthetic construct
SEQUENCE: 143
AAEQNPIYWA RYADWLFTTP LLLLDLALLV DADEGTCG                           38

SEQ ID NO: 144       moltype = AA  length = 38
FEATURE              Location/Qualifiers
source               1..38
                     mol_type = protein
                     organism = synthetic construct
SEQUENCE: 144
GGEQNPIYWA RYADWLFTTP LLLLDLALLV DADEGTCG                           38

SEQ ID NO: 145       moltype = AA  length = 35
FEATURE              Location/Qualifiers
source               1..35
                     mol_type = protein
                     organism = synthetic construct
SEQUENCE: 145
ACEQNPIYWA RYADWLFTTP LLLLDLALLV DADET                              35

SEQ ID NO: 146       moltype = AA  length = 37
FEATURE              Location/Qualifiers
source               1..37
                     mol_type = protein
                     organism = synthetic construct
SEQUENCE: 146
ACEQNPIYWA RYADWLFTTP LLLLDLALLV DADEGTG                            37

SEQ ID NO: 147       moltype = AA  length = 36
FEATURE              Location/Qualifiers
source               1..36
                     mol_type = protein
                     organism = synthetic construct
SEQUENCE: 147
ACEQNPIYWA RYADWLFTTP LLLLDLALLV DADEGT                             36

SEQ ID NO: 148       moltype = AA  length = 36
FEATURE              Location/Qualifiers
source               1..36
                     mol_type = protein
```

```
                      organism = synthetic construct
SEQUENCE: 148
GGEQNPIYWA RYADWLFTTP LLLLDLALLV NANQGT                                36

SEQ ID NO: 149          moltype = AA  length = 37
FEATURE                 Location/Qualifiers
source                  1..37
                        mol_type = protein
                        organism = synthetic construct
SEQUENCE: 149
DDDEDNPIYW ARYAHWLFTT PLLLLHGALL VNADECT                               37

SEQ ID NO: 150          moltype = AA  length = 37
FEATURE                 Location/Qualifiers
source                  1..37
                        mol_type = protein
                        organism = synthetic construct
SEQUENCE: 150
DDDEDNPIYW ARYAHWLFTT PLLLLHGALL VNANECT                               37

SEQ ID NO: 151          moltype = AA  length = 38
FEATURE                 Location/Qualifiers
source                  1..38
                        mol_type = protein
                        organism = synthetic construct
SEQUENCE: 151
GGEQNPIYWA RYADWLFTTP LLLLDLALLV DADEGTCG                               38

SEQ ID NO: 152          moltype = AA  length = 38
FEATURE                 Location/Qualifiers
MOD_RES                 37
                        note = Cys(phalloidin)
source                  1..38
                        mol_type = protein
                        organism = synthetic construct
SEQUENCE: 152
AAEQNPIYWA RYADWLFTTP LLLLDLALLV DADEGTCG                               38

SEQ ID NO: 153          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 153
AAEQNPIYWA RYADWLFTTP LLLLELALLV DADEGTKCG                              39

SEQ ID NO: 154          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 154
AAEQNPIYWA RYADWLFTTP LLLLDLALLV DADEGTKCG                              39

SEQ ID NO: 155          moltype = AA  length = 37
FEATURE                 Location/Qualifiers
source                  1..37
                        mol_type = protein
                        organism = synthetic construct
SEQUENCE: 155
DDDEDNPIYW ARYAHWLFTT PLLLLHGALL VDADECT                               37

SEQ ID NO: 156          moltype = AA  length = 37
FEATURE                 Location/Qualifiers
source                  1..37
                        mol_type = protein
                        organism = synthetic construct
SEQUENCE: 156
DDDEDNPIYW ARYAHWLFTT PLLLLDGALL VDADECT                               37

SEQ ID NO: 157          moltype = AA  length = 37
```

```
FEATURE                 Location/Qualifiers
source                  1..37
                        mol_type = protein
                        organism = synthetic construct
SEQUENCE: 157
DDDEDNPIYW ARYAHWLFTT PLLLLHGALL VNADECT                         37

SEQ ID NO: 158          moltype = AA   length = 37
FEATURE                 Location/Qualifiers
source                  1..37
                        mol_type = protein
                        organism = synthetic construct
SEQUENCE: 158
DDDEDNPIYW ARYAHWLFTT PLLLLHGALL VNANECT                         37

SEQ ID NO: 159          moltype = AA   length = 37
FEATURE                 Location/Qualifiers
source                  1..37
                        mol_type = protein
                        organism = synthetic construct
SEQUENCE: 159
DDDEDNPIYW ARYADWLFTT PLLLLHGALL VDADECT                         37

SEQ ID NO: 160          moltype = AA   length = 37
FEATURE                 Location/Qualifiers
source                  1..37
                        mol_type = protein
                        organism = synthetic construct
SEQUENCE: 160
DDDEDNPIYW ARYADWLFTT PLLLLHGALL VDADECT                         37

SEQ ID NO: 161          moltype = AA   length = 37
FEATURE                 Location/Qualifiers
source                  1..37
                        mol_type = protein
                        organism = synthetic construct
SEQUENCE: 161
DDDEDNPIYW ARYAHWLFTT PLLLLDGALL VDADECT                         37

SEQ ID NO: 162          moltype = AA   length = 37
FEATURE                 Location/Qualifiers
source                  1..37
                        mol_type = protein
                        organism = synthetic construct
SEQUENCE: 162
DDDEDNPIYW ARYAHWLFTT PLLLLHGALL VDADECT                         37

SEQ ID NO: 163          moltype = AA   length = 37
FEATURE                 Location/Qualifiers
source                  1..37
                        mol_type = protein
                        organism = synthetic construct
SEQUENCE: 163
DDDEDNPIYW ARYAHWLFTT PLLLLHGALL VNADECT                         37

SEQ ID NO: 164          moltype = AA   length = 37
FEATURE                 Location/Qualifiers
source                  1..37
                        mol_type = protein
                        organism = synthetic construct
SEQUENCE: 164
DDDEDNPIYW ARYAHWLFTT PLLLLHGALL VNANECT                         37

SEQ ID NO: 165          moltype = AA   length = 37
FEATURE                 Location/Qualifiers
source                  1..37
                        mol_type = protein
                        organism = synthetic construct
SEQUENCE: 165
DDDEDNPIYW ARYAHWLFTT PLLLLHGALL VNANECT                         37

SEQ ID NO: 166          moltype = AA   length = 37
FEATURE                 Location/Qualifiers
source                  1..37
                        mol_type = protein
                        organism = synthetic construct
SEQUENCE: 166
DDDEDNPIYW ARYAHWLFTT PLLLLHGALL VNADECT                         37
```

```
SEQ ID NO: 167          moltype = AA  length = 37
FEATURE                 Location/Qualifiers
source                  1..37
                        mol_type = protein
                        organism = synthetic construct
SEQUENCE: 167
DDDEDNPIYW ARYADWLFTT PLLLLHGALL VDADECT                              37

SEQ ID NO: 168          moltype = AA  length = 37
FEATURE                 Location/Qualifiers
source                  1..37
                        mol_type = protein
                        organism = synthetic construct
SEQUENCE: 168
DDDEDNPIYW ARYAHWLFTT PLLLLHGALL VDADECT                              37

SEQ ID NO: 169          moltype = AA  length = 37
FEATURE                 Location/Qualifiers
source                  1..37
                        mol_type = protein
                        organism = synthetic construct
SEQUENCE: 169
DDDEDNPIYW ARYAHWLFTT PLLLLDGALL VDADECT                              37

SEQ ID NO: 170          moltype = AA  length = 36
FEATURE                 Location/Qualifiers
source                  1..36
                        mol_type = protein
                        organism = synthetic construct
SEQUENCE: 170
GGEQNPIYWA RYADWLFTTP LLLLDLALLV NANQGT                               36

SEQ ID NO: 171          moltype = AA  length = 37
FEATURE                 Location/Qualifiers
source                  1..37
                        mol_type = protein
                        organism = synthetic construct
SEQUENCE: 171
DDDEDNPIYW ARYAHWLFTT PLLLLHGALL VNADECT                              37

SEQ ID NO: 172          moltype = AA  length = 37
FEATURE                 Location/Qualifiers
source                  1..37
                        mol_type = protein
                        organism = synthetic construct
SEQUENCE: 172
DDDEDNPIYW ARYADWLFTT PLLLLHGALL VDADECT                              37

SEQ ID NO: 173          moltype = AA  length = 37
FEATURE                 Location/Qualifiers
source                  1..37
                        mol_type = protein
                        organism = synthetic construct
SEQUENCE: 173
DDDEDNPIYW ARYAHWLFTT PLLLLHGALL VDADECT                              37

SEQ ID NO: 174          moltype = AA  length = 37
FEATURE                 Location/Qualifiers
source                  1..37
                        mol_type = protein
                        organism = synthetic construct
SEQUENCE: 174
DDDEDNPIYW ARYAHWLFTT PLLLLDGALL VDADECT                              37

SEQ ID NO: 175          moltype = AA  length = 37
FEATURE                 Location/Qualifiers
source                  1..37
                        mol_type = protein
                        organism = synthetic construct
SEQUENCE: 175
DDDEDNPIYW ARYAHWLFTT PLLLLHGALL VNANECT                              37

SEQ ID NO: 176          moltype = AA  length = 37
FEATURE                 Location/Qualifiers
source                  1..37
                        mol_type = protein
                        organism = synthetic construct
SEQUENCE: 176
DDDEDNPIYW ARYAHWLFTT PLLLLDGALL VDADECT                              37
```

```
SEQ ID NO: 177          moltype = AA   length = 37
FEATURE                 Location/Qualifiers
source                  1..37
                        mol_type = protein
                        organism = synthetic construct
SEQUENCE: 177
DDDEDNPIYW ARYADWLFTT PLLLLHGALL VDADECT                                  37

SEQ ID NO: 178          moltype = AA   length = 37
FEATURE                 Location/Qualifiers
source                  1..37
                        mol_type = protein
                        organism = synthetic construct
SEQUENCE: 178
DDDEDNPIYW ARYAHWLFTT PLLLLHGALL VDADECT                                  37

SEQ ID NO: 179          moltype = AA   length = 37
FEATURE                 Location/Qualifiers
source                  1..37
                        mol_type = protein
                        organism = synthetic construct
SEQUENCE: 179
DDDEDNPIYW ARYAHWLFTT PLLLLHGALL VNADECT                                  37

SEQ ID NO: 180          moltype = AA   length = 37
FEATURE                 Location/Qualifiers
source                  1..37
                        mol_type = protein
                        organism = synthetic construct
SEQUENCE: 180
DDDEDNPIYW ARYAHWLFTT PLLLLHGALL VNANECT                                  37

SEQ ID NO: 181          moltype = AA   length = 36
FEATURE                 Location/Qualifiers
source                  1..36
                        mol_type = protein
                        organism = synthetic construct
SEQUENCE: 181
AAEQNPIYWA RYADWLFTTG LLLLDLALLV DADEGT                                   36

SEQ ID NO: 182          moltype = AA   length = 38
FEATURE                 Location/Qualifiers
source                  1..38
                        mol_type = protein
                        organism = synthetic construct
SEQUENCE: 182
GGEQNPIYWA RYAWDLFTTP LLLLDLALLV DADEGTCG                                 38

SEQ ID NO: 183          moltype = AA   length = 38
FEATURE                 Location/Qualifiers
source                  1..38
                        mol_type = protein
                        organism = synthetic construct
SEQUENCE: 183
GGEQNPIYWA RYDAWLFTTP LLLLDLALLV DADEGTCG                                 38

SEQ ID NO: 184          moltype = AA   length = 38
FEATURE                 Location/Qualifiers
source                  1..38
                        mol_type = protein
                        organism = synthetic construct
SEQUENCE: 184
GGEQNPIYWA QYDAWLFTTP LLLLDLALLV DADEGTCG                                 38

SEQ ID NO: 185          moltype = AA   length = 38
FEATURE                 Location/Qualifiers
source                  1..38
                        mol_type = protein
                        organism = synthetic construct
SEQUENCE: 185
GGEQNPIYWA QDYAWLFTTP LLLLDLALLV DADEGTCG                                 38

SEQ ID NO: 186          moltype = AA   length = 38
FEATURE                 Location/Qualifiers
source                  1..38
                        mol_type = protein
                        organism = synthetic construct
SEQUENCE: 186
```

```
AAEQNPIYWA RYAAWLFTTP LLLLLDLALLV DADEGTCG                                   38

SEQ ID NO: 187          moltype = AA  length = 38
FEATURE                 Location/Qualifiers
source                  1..38
                        mol_type = protein
                        organism = synthetic construct
SEQUENCE: 187
GGEQNPIYWA RYADWLFTTP LLLLLDALLV DADEGTCG                                    38

SEQ ID NO: 188          moltype = AA  length = 38
FEATURE                 Location/Qualifiers
source                  1..38
                        mol_type = protein
                        organism = synthetic construct
SEQUENCE: 188
GGEQNPIYWA RYADWLFTTP LLLDLLALLV DADEGTCG                                    38

SEQ ID NO: 189          moltype = AA  length = 38
FEATURE                 Location/Qualifiers
source                  1..38
                        mol_type = protein
                        organism = synthetic construct
SEQUENCE: 189
GGEQNPIYWA RYADWLFTTP LLLDLLALLV DADEGTCG                                    38

SEQ ID NO: 190          moltype = AA  length = 38
FEATURE                 Location/Qualifiers
source                  1..38
                        mol_type = protein
                        organism = synthetic construct
SEQUENCE: 190
GGEQNPIYWA RYADWLFTTP LLLLLDALLV DADEGTCG                                    38

SEQ ID NO: 191          moltype = AA  length = 38
FEATURE                 Location/Qualifiers
source                  1..38
                        mol_type = protein
                        organism = synthetic construct
SEQUENCE: 191
GGEQNPIYWA QYADWLFTTP LLLLDLALLV DADEGTCG                                    38

SEQ ID NO: 192          moltype = AA  length = 38
FEATURE                 Location/Qualifiers
source                  1..38
                        mol_type = protein
                        organism = synthetic construct
SEQUENCE: 192
GGEQNPIYWA QYDAWLFTTP LLLLDLALLV DADEGTCG                                    38

SEQ ID NO: 193          moltype = AA  length = 38
FEATURE                 Location/Qualifiers
source                  1..38
                        mol_type = protein
                        organism = synthetic construct
SEQUENCE: 193
GGEQNPIYWA QDYAWLFTTP LLLLDLALLV DADEGTCG                                    38

SEQ ID NO: 194          moltype = AA  length = 38
FEATURE                 Location/Qualifiers
source                  1..38
                        mol_type = protein
                        organism = synthetic construct
SEQUENCE: 194
GGEQNPIYWA QYDAWLFTTP LLLLDLALLV DADEGTCG                                    38

SEQ ID NO: 195          moltype = AA  length = 38
FEATURE                 Location/Qualifiers
source                  1..38
                        mol_type = protein
                        organism = synthetic construct
SEQUENCE: 195
GGEQNPIYWA QDYAWLFTTP LLLLDLALLV DADEGTCG                                    38

SEQ ID NO: 196          moltype = AA  length = 38
FEATURE                 Location/Qualifiers
source                  1..38
                        mol_type = protein
                        organism = synthetic construct
```

```
SEQUENCE: 196
GGEQNPIYWA QYADWLFTTP LLLLDLALLV DADEGTCG                            38

SEQ ID NO: 197          moltype = AA  length = 38
FEATURE                 Location/Qualifiers
source                  1..38
                        mol_type = protein
                        organism = synthetic construct
SEQUENCE: 197
AAEQNPIYWA RYAAWLFTTP LLLLDLALLV DADEGTCG                            38

SEQ ID NO: 198          moltype = AA  length = 38
FEATURE                 Location/Qualifiers
source                  1..38
                        mol_type = protein
                        organism = synthetic construct
SEQUENCE: 198
GGEQNPIYWA QDYAWLFTTP LLLLDLALLV DADEGTCG                            38

SEQ ID NO: 199          moltype = AA  length = 38
FEATURE                 Location/Qualifiers
source                  1..38
                        mol_type = protein
                        organism = synthetic construct
SEQUENCE: 199
GGEQNPIYWA QYDAWLFTTP LLLLDLALLV DADEGTCG                            38

SEQ ID NO: 200          moltype = AA  length = 38
FEATURE                 Location/Qualifiers
source                  1..38
                        mol_type = protein
                        organism = synthetic construct
SEQUENCE: 200
GGEQNPIYWA QYADWLFTTP LLLLDLALLV DADEGTCG                            38

SEQ ID NO: 201          moltype = AA  length = 38
FEATURE                 Location/Qualifiers
source                  1..38
                        mol_type = protein
                        organism = synthetic construct
SEQUENCE: 201
AAEQNPIYWA RYAAWLFTTP LLLLDLALLV DADEGTCG                            38

SEQ ID NO: 202          moltype = AA  length = 39
FEATURE                 Location/Qualifiers
source                  1..39
                        mol_type = protein
                        organism = synthetic construct
SEQUENCE: 202
AAEQNPIYWA RYADWLFTTP LLLLELALLV DADEGTKCG                           39

SEQ ID NO: 203          moltype = AA  length = 6
FEATURE                 Location/Qualifiers
MOD_RES                 4
                        note = Lys(rhodamine)
MOD_RES                 5
                        note = Cys(phalloidin)
source                  1..6
                        mol_type = protein
                        organism = synthetic construct
SEQUENCE: 203
EGTKCG                                                                6

SEQ ID NO: 204          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 204
AAEQNPIYWA RYADWLFTTP LLLLDLALLV DADEGTKCG                           39

SEQ ID NO: 205          moltype = AA  length = 37
FEATURE                 Location/Qualifiers
source                  1..37
                        mol_type = protein
```

```
                        organism = synthetic construct
SEQUENCE: 205
ACEQNPIYWA RYADWLFTTP LLLLDLALLV DADEGTG                          37

SEQ ID NO: 206          moltype = AA  length = 38
FEATURE                 Location/Qualifiers
MOD_RES                 37
                        note = Cys(phalloidin)
source                  1..38
                        mol_type = protein
                        organism = synthetic construct
SEQUENCE: 206
AAEQNPIYWA RYADWLFTTP LLLLDLALLV DADEGTCG                         38

SEQ ID NO: 207          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 207
AAEQNPIYWA RYADWLFTTP LLLLDLALLV DADEGTKCG                        39

SEQ ID NO: 208          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 208
AAEQNPIYWA RYADWLFTTP LLLLELALLV DADEGTKCG                        39

SEQ ID NO: 209          moltype = AA  length = 38
FEATURE                 Location/Qualifiers
source                  1..38
                        mol_type = protein
                        organism = synthetic construct
SEQUENCE: 209
AAEQNPIYWA RYADWLFTDL PLLLLDLLAL LVDADEGT                         38

SEQ ID NO: 210          moltype = AA  length = 38
FEATURE                 Location/Qualifiers
source                  1..38
                        mol_type = protein
                        organism = synthetic construct
SEQUENCE: 210
AAEQNPIYWA RYAAWLFTTP LLLLDLALLV DADEGTCG                         38

SEQ ID NO: 211          moltype = AA  length = 38
FEATURE                 Location/Qualifiers
source                  1..38
                        mol_type = protein
                        organism = synthetic construct
SEQUENCE: 211
GGEQNPIYWA QYDAWLFTTP LLLLDLALLV DADEGTCG                         38

SEQ ID NO: 212          moltype = AA  length = 38
FEATURE                 Location/Qualifiers
source                  1..38
                        mol_type = protein
                        organism = synthetic construct
SEQUENCE: 212
GGEQNPIYWA QDYAWLFTTP LLLLDLALLV DADEGTCG                         38

SEQ ID NO: 213          moltype = AA  length = 38
FEATURE                 Location/Qualifiers
source                  1..38
                        mol_type = protein
                        organism = synthetic construct
SEQUENCE: 213
GGEQNPIYWA RYDAWLFTTP LLLLDLALLV DADEGTCG                         38

SEQ ID NO: 214          moltype = AA  length = 38
```

```
FEATURE                 Location/Qualifiers
source                  1..38
                        mol_type = protein
                        organism = synthetic construct
SEQUENCE: 214
AAEQNPIYWA RYAEWLFTTP LLLLDLALLV DADEGTCG                           38

SEQ ID NO: 215          moltype = AA  length = 38
FEATURE                 Location/Qualifiers
source                  1..38
                        mol_type = protein
                        organism = synthetic construct
SEQUENCE: 215
AAEQNPIYWA RYAEWLFTTP LLLLELALLV DADEGTCG                           38

SEQ ID NO: 216          moltype = AA  length = 38
FEATURE                 Location/Qualifiers
source                  1..38
                        mol_type = protein
                        organism = synthetic construct
SEQUENCE: 216
AAEQNPIYWA RYADWLFTTP LLLLALALLV DADEGTCG                           38

SEQ ID NO: 217          moltype = AA  length = 38
FEATURE                 Location/Qualifiers
source                  1..38
                        mol_type = protein
                        organism = synthetic construct
SEQUENCE: 217
AAEQNPIYWA RYADWLFTTP LLLLELALLV DADEGTCG                           38

SEQ ID NO: 218          moltype = AA  length = 38
FEATURE                 Location/Qualifiers
source                  1..38
                        mol_type = protein
                        organism = synthetic construct
SEQUENCE: 218
AAEQNPIYWA RYAEWLFTTP LLLLELALLV DADEGTCG                           38

SEQ ID NO: 219          moltype = AA  length = 39
FEATURE                 Location/Qualifiers
MOD_RES                 37
                        note = Lys(rhodamine)
MOD_RES                 38
                        note = Cys(phalloidin)
source                  1..39
                        mol_type = protein
                        organism = synthetic construct
SEQUENCE: 219
AAEQNPIYWA RYADWLFTTP LLLLELALLV DADEGTKCG                          39

SEQ ID NO: 220          moltype = AA  length = 37
FEATURE                 Location/Qualifiers
source                  1..37
                        mol_type = protein
                        organism = synthetic construct
SEQUENCE: 220
ACEQNPIYWA RYAKWLFTTP LLLLKLALLV DADEGTG                            37

SEQ ID NO: 221          moltype = AA  length = 37
FEATURE                 Location/Qualifiers
source                  1..37
                        mol_type = protein
                        organism = synthetic construct
SEQUENCE: 221
ACEQNPIYWA RYANWLFTTP LLLLNLALLV DADEGTG                            37

SEQ ID NO: 222          moltype = AA  length = 36
FEATURE                 Location/Qualifiers
source                  1..36
                        mol_type = protein
                        organism = synthetic construct
SEQUENCE: 222
AAEQNPIYWA RYADWLFTTA LLLLDLALLV DADEGT                             36

SEQ ID NO: 223          moltype = AA  length = 22
FEATURE                 Location/Qualifiers
source                  1..22
                        mol_type = protein
```

```
                               organism = synthetic construct
SEQUENCE: 223
AEQNPIYFAR YADLLFPTTL AW                                                 22

SEQ ID NO: 224          moltype = AA  length = 22
FEATURE                 Location/Qualifiers
source                  1..22
                        mol_type = protein
                        organism = synthetic construct
SEQUENCE: 224
AEQNPIYWAR YADLLFPTTL AF                                                 22

SEQ ID NO: 225          moltype = AA  length = 22
FEATURE                 Location/Qualifiers
source                  1..22
                        mol_type = protein
                        organism = synthetic construct
SEQUENCE: 225
AEQNPIYWAR YADLLFPTTL AW                                                 22

SEQ ID NO: 226          moltype = AA  length = 35
FEATURE                 Location/Qualifiers
source                  1..35
                        mol_type = protein
                        organism = synthetic construct
SEQUENCE: 226
ACEQNPIYWA RYADWLFTTP LLLLDLALLV DADET                                   35

SEQ ID NO: 227          moltype = AA  length = 36
FEATURE                 Location/Qualifiers
source                  1..36
                        mol_type = protein
                        organism = synthetic construct
SEQUENCE: 227
GGEQNPIYWA RYADWLFTTP LLLLDLALLV DADEGT                                  36

SEQ ID NO: 228          moltype = AA  length = 38
FEATURE                 Location/Qualifiers
source                  1..38
                        mol_type = protein
                        organism = synthetic construct
SEQUENCE: 228
AAEQNPIYWA RYADWLFTTP LLLLDLALLV DADEGTCG                                38

SEQ ID NO: 229          moltype = AA  length = 39
FEATURE                 Location/Qualifiers
source                  1..39
                        mol_type = protein
                        organism = synthetic construct
SEQUENCE: 229
AAEQNPIYWA RYADWLFTTP LLLLDLALLV DADEGTKCG                               39

SEQ ID NO: 230          moltype = AA  length = 36
FEATURE                 Location/Qualifiers
source                  1..36
                        mol_type = protein
                        organism = synthetic construct
SEQUENCE: 230
AKEQNPIYWA RYADWLFTTP LLLLDLALLV DADECT                                  36

SEQ ID NO: 231          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 231
cctcttacct cagttaca                                                      18

SEQ ID NO: 232          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
```

```
SEQUENCE: 232
cctcttacct cagttaca                                                 18

SEQ ID NO: 233          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 233
cctcttacct cagttaca                                                 18

SEQ ID NO: 234          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 234
cctcttacct cagttaca                                                 18

SEQ ID NO: 235          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 235
cctctgacct catttaca                                                 18

SEQ ID NO: 236          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 236
cctcttacct cagttaca                                                 18

SEQ ID NO: 237          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 237
cctctgacct catttaca                                                 18

SEQ ID NO: 238          moltype = DNA  length = 18
FEATURE                 Location/Qualifiers
source                  1..18
                        mol_type = other DNA
                        organism = synthetic construct
modified_base           1..18
                        mod_base = OTHER
                        note = N-(2-aminoethyl) glycine nucleosides
SEQUENCE: 238
cctcttacct cagttaca                                                 18

SEQ ID NO: 239          moltype = AA  length = 38
FEATURE                 Location/Qualifiers
source                  1..38
                        mol_type = protein
                        organism = unidentified
SEQUENCE: 239
AAEQNPIYWA RYADWLFTTP LLLLDLALLV DADEGTCG                            38

SEQ ID NO: 240          moltype = AA  length = 31
FEATURE                 Location/Qualifiers
```

```
source                          1..31
                                mol_type = protein
                                organism = synthetic construct
SEQUENCE: 240
AEDQNPYWAR YDWLFTTPLL LLDLALLVDC G                                   31

SEQ ID NO: 241                  moltype = AA  length = 32
FEATURE                         Location/Qualifiers
source                          1..32
                                mol_type = protein
                                organism = synthetic construct
SEQUENCE: 241
AEDQNPYWAR YADWLFTTPL LLLELALLVE CG                                  32

SEQ ID NO: 242                  moltype = AA  length = 36
FEATURE                         Location/Qualifiers
source                          1..36
                                mol_type = protein
                                organism = synthetic construct
SEQUENCE: 242
AEQNPIYWAR YADWLFTTPL LLLDLALLVD ADEGCT                              36

SEQ ID NO: 243                  moltype = AA  length = 35
FEATURE                         Location/Qualifiers
source                          1..35
                                mol_type = protein
                                organism = synthetic construct
SEQUENCE: 243
ACEQNPIYWA RYADWLFTTP LLLLDLALLV DADET                               35

SEQ ID NO: 244                  moltype = AA  length = 35
FEATURE                         Location/Qualifiers
source                          1..35
                                mol_type = protein
                                organism = synthetic construct
SEQUENCE: 244
AEQNPIYWAR YADWLFTTPL LLLDLALLVD ADEGT                               35

SEQ ID NO: 245                  moltype = AA  length = 31
FEATURE                         Location/Qualifiers
source                          1..31
                                mol_type = protein
                                organism = synthetic construct
SEQUENCE: 245
AEDQNPYWAR YADWLFTTPL LLLDLALLVD G                                   31

SEQ ID NO: 246                  moltype = AA  length = 31
FEATURE                         Location/Qualifiers
source                          1..31
                                mol_type = protein
                                organism = synthetic construct
SEQUENCE: 246
AEDQNDPYWA RYADWLFTTP LLLLDLALLV G                                   31

SEQ ID NO: 247                  moltype = AA  length = 34
FEATURE                         Location/Qualifiers
source                          1..34
                                mol_type = protein
                                organism = synthetic construct
SEQUENCE: 247
AEQNPIYWAR YADFLFTTPL LLLDLALLVD ADET                                34

SEQ ID NO: 248                  moltype = AA  length = 34
FEATURE                         Location/Qualifiers
source                          1..34
                                mol_type = protein
                                organism = synthetic construct
SEQUENCE: 248
AEQNPIYFAR YADWLFTTPL LLLDLALLVD ADET                                34

SEQ ID NO: 249                  moltype = AA  length = 34
FEATURE                         Location/Qualifiers
source                          1..34
                                mol_type = protein
                                organism = synthetic construct
SEQUENCE: 249
AEQNPIYFAR YADFLFTTPL LLLDLALLWD ADET                                34

SEQ ID NO: 250                  moltype = AA  length = 36
```

```
FEATURE                 Location/Qualifiers
source                  1..36
                        mol_type = protein
                        organism = synthetic construct
SEQUENCE: 250
AEQNPIYWAR YADWLFTTPL LLLDLALLVD ADEGCT                              36

SEQ ID NO: 251          moltype = AA  length = 34
FEATURE                 Location/Qualifiers
source                  1..34
                        mol_type = protein
                        organism = synthetic construct
SEQUENCE: 251
AEDQNPIYWA RYADWLFTTP LLLLDLALLV DCGT                                34

SEQ ID NO: 252          moltype = AA  length = 35
FEATURE                 Location/Qualifiers
source                  1..35
                        mol_type = protein
                        organism = synthetic construct
SEQUENCE: 252
AEDQNDPIYW ARYADWLFTT PLLLLELALL VECGT                               35

SEQ ID NO: 253          moltype = AA  length = 25
FEATURE                 Location/Qualifiers
source                  1..25
                        mol_type = protein
                        organism = synthetic construct
SEQUENCE: 253
ACEEQNPWAR YLEWLFPTET LLLEL                                          25

SEQ ID NO: 254          moltype = AA  length = 35
FEATURE                 Location/Qualifiers
source                  1..35
                        mol_type = protein
                        organism = synthetic construct
SEQUENCE: 254
AEQNPIYWAR YADWLFTTPL LLLDLALLVD ADEGT                               35

SEQ ID NO: 255          moltype = AA  length = 32
FEATURE                 Location/Qualifiers
source                  1..32
                        mol_type = protein
                        organism = synthetic construct
SEQUENCE: 255
AKEDQNPYWA RYADWLFTTP LLLLDLALLV DG                                  32

SEQ ID NO: 256          moltype = AA  length = 32
FEATURE                 Location/Qualifiers
source                  1..32
                        mol_type = protein
                        organism = synthetic construct
SEQUENCE: 256
AKEDQNDPYW ARYADWLFTT PLLLLDLALL VG                                  32

SEQ ID NO: 257          moltype = AA  length = 35
FEATURE                 Location/Qualifiers
source                  1..35
                        mol_type = protein
                        organism = synthetic construct
SEQUENCE: 257
AEQNPIYWAR YADWLFTTPL LLLDLALLVD ADEGC                               35

SEQ ID NO: 258          moltype = AA  length = 31
FEATURE                 Location/Qualifiers
source                  1..31
                        mol_type = protein
                        organism = synthetic construct
SEQUENCE: 258
AEDQNPYWAR YADWLFTTPL LLLDLALLVD C                                   31

SEQ ID NO: 259          moltype = AA  length = 31
FEATURE                 Location/Qualifiers
source                  1..31
                        mol_type = protein
                        organism = synthetic construct
SEQUENCE: 259
AEDQNPYWAR YADWLFTTPL LLLELALLVE C                                   31
```

-continued

```
SEQ ID NO: 260           moltype = AA  length = 36
FEATURE                  Location/Qualifiers
source                   1..36
                         mol_type = protein
                         organism = synthetic construct
SEQUENCE: 260
ACEQNPIYWA RYADWLFTTP LLLLDLALLV DADEGT                                   36

SEQ ID NO: 261           moltype = AA  length = 32
FEATURE                  Location/Qualifiers
source                   1..32
                         mol_type = protein
                         organism = synthetic construct
SEQUENCE: 261
ACEDQNPYWA RYADWLFTTP LLLLDLALLV DG                                       32

SEQ ID NO: 262           moltype = AA  length = 30
FEATURE                  Location/Qualifiers
source                   1..30
                         mol_type = protein
                         organism = synthetic construct
SEQUENCE: 262
ACEDQNPYWR AYADLFTPLT LLDLLALWDG                                          30

SEQ ID NO: 263           moltype = AA  length = 27
FEATURE                  Location/Qualifiers
source                   1..27
                         mol_type = protein
                         organism = synthetic construct
SEQUENCE: 263
ACDDQNPWRA YLDLLFPTDT LLLDLLW                                             27

SEQ ID NO: 264           moltype = AA  length = 27
FEATURE                  Location/Qualifiers
source                   1..27
                         mol_type = protein
                         organism = synthetic construct
SEQUENCE: 264
ACEEQNPWRA YLELLFPTET LLLELLW                                             27

SEQ ID NO: 265           moltype = AA  length = 25
FEATURE                  Location/Qualifiers
source                   1..25
                         mol_type = protein
                         organism = synthetic construct
SEQUENCE: 265
ACDDQNPWAR YLDWLFPTDT LLLDL                                               25

SEQ ID NO: 266           moltype = AA  length = 24
FEATURE                  Location/Qualifiers
source                   1..24
                         mol_type = protein
                         organism = synthetic construct
SEQUENCE: 266
CDNNNPWRAY LDLLFPTDTL LLDW                                                24

SEQ ID NO: 267           moltype = AA  length = 25
FEATURE                  Location/Qualifiers
source                   1..25
                         mol_type = protein
                         organism = synthetic construct
SEQUENCE: 267
ACEEQNPWAR YLEWLFPTET LLLEL                                               25

SEQ ID NO: 268           moltype = AA  length = 24
FEATURE                  Location/Qualifiers
source                   1..24
                         mol_type = protein
                         organism = synthetic construct
SEQUENCE: 268
CEEQQPWAQY LELLFPTETL LLEW                                                24

SEQ ID NO: 269           moltype = AA  length = 24
FEATURE                  Location/Qualifiers
source                   1..24
                         mol_type = protein
                         organism = synthetic construct
SEQUENCE: 269
CEEQQPWRAY LELLFPTETL LLEW                                                24
```

```
SEQ ID NO: 270          moltype = AA  length = 24
FEATURE                 Location/Qualifiers
source                  1..24
                        mol_type = protein
                        organism = synthetic construct
SEQUENCE: 270
ACEDQNPWAR YADWLFPTTL LLLD                                              24

SEQ ID NO: 271          moltype = AA  length = 24
FEATURE                 Location/Qualifiers
source                  1..24
                        mol_type = protein
                        organism = synthetic construct
SEQUENCE: 271
ACEEQNPWAR YAEWLFPTTL LLLE                                              24

SEQ ID NO: 272          moltype = AA  length = 22
FEATURE                 Location/Qualifiers
source                  1..22
                        mol_type = protein
                        organism = synthetic construct
SEQUENCE: 272
ACEDQNPWAR YADLLFPTTL AW                                                22

SEQ ID NO: 273          moltype = AA  length = 22
FEATURE                 Location/Qualifiers
source                  1..22
                        mol_type = protein
                        organism = synthetic construct
SEQUENCE: 273
ACEEQNPWAR YAELLFPTTL AW                                                22

SEQ ID NO: 274          moltype = AA  length = 34
FEATURE                 Location/Qualifiers
source                  1..34
                        mol_type = protein
                        organism = synthetic construct
SEQUENCE: 274
TEDADVLLAL DLLLLPTTFL WDAYRAWYPN QECA                                   34

SEQ ID NO: 275          moltype = AA  length = 37
FEATURE                 Location/Qualifiers
source                  1..37
                        mol_type = protein
                        organism = synthetic construct
SEQUENCE: 275
CDDDDDNPNY WARYANWLFT TPLLLLNGAL LVEAEET                                37

SEQ ID NO: 276          moltype = AA  length = 37
FEATURE                 Location/Qualifiers
source                  1..37
                        mol_type = protein
                        organism = synthetic construct
SEQUENCE: 276
CDDDDDNPNY WARYAPWLFT TPLLLLPGAL LVEAEET                                37

SEQ ID NO: 277          moltype = AA  length = 36
FEATURE                 Location/Qualifiers
source                  1..36
                        mol_type = protein
                        organism = synthetic construct
SEQUENCE: 277
AEQNPIYWAR YADWLFTTPL LLLDLALLVD ADEGCT                                 36

SEQ ID NO: 278          moltype = AA  length = 37
FEATURE                 Location/Qualifiers
source                  1..37
                        mol_type = protein
                        organism = synthetic construct
SEQUENCE: 278
AKEQNPIYWA RYADWLFTTP LLLLDLALLV DADEGTG                                37

SEQ ID NO: 279          moltype = AA  length = 36
FEATURE                 Location/Qualifiers
source                  1..36
                        mol_type = protein
                        organism = synthetic construct
SEQUENCE: 279
```

```
ACEQNPIYWA RYANWLFTTP LLLLNLALLV DADEGT                                      36

SEQ ID NO: 280         moltype = AA  length = 36
FEATURE                Location/Qualifiers
source                 1..36
                       mol_type = protein
                       organism = synthetic construct
SEQUENCE: 280
DDDEDNPIYW ARYADWLFTT PLLLLHGALL VDADET                                      36

SEQ ID NO: 281         moltype = AA  length = 36
FEATURE                Location/Qualifiers
source                 1..36
                       mol_type = protein
                       organism = synthetic construct
SEQUENCE: 281
DDDEDNPIYW ARYADWLFTT PLLLLHGALL VDADET                                      36

SEQ ID NO: 282         moltype = AA  length = 37
FEATURE                Location/Qualifiers
source                 1..37
                       mol_type = protein
                       organism = synthetic construct
SEQUENCE: 282
CDDDEDNPIY WARYAHWLFT TPLLLLHGAL LVDADET                                     37

SEQ ID NO: 283         moltype = AA  length = 37
FEATURE                Location/Qualifiers
source                 1..37
                       mol_type = protein
                       organism = synthetic construct
SEQUENCE: 283
DDDEDNPIYW ARYAHWLFTT PLLLLHGALL VDADEGT                                     37

SEQ ID NO: 284         moltype = AA  length = 37
FEATURE                Location/Qualifiers
source                 1..37
                       mol_type = protein
                       organism = synthetic construct
SEQUENCE: 284
DDDEDNPIYW ARYAHWLFTT PLLLLHGALL VNADEGT                                     37

SEQ ID NO: 285         moltype = AA  length = 37
FEATURE                Location/Qualifiers
source                 1..37
                       mol_type = protein
                       organism = synthetic construct
SEQUENCE: 285
DDDEDNPIYW ARYAHWLFTT PLLLLHGALL VNANEGT                                     37

SEQ ID NO: 286         moltype = AA  length = 32
FEATURE                Location/Qualifiers
source                 1..32
                       mol_type = protein
                       organism = synthetic construct
SEQUENCE: 286
AKEDQNDPYW ARYADWLFTT PLLLLDLALL VG                                          32

SEQ ID NO: 287         moltype = AA  length = 31
FEATURE                Location/Qualifiers
source                 1..31
                       mol_type = protein
                       organism = synthetic construct
SEQUENCE: 287
AEDQNPYWAR YADWLFTTPL LLLELALLVC G                                           31

SEQ ID NO: 288         moltype = AA  length = 28
FEATURE                Location/Qualifiers
source                 1..28
                       mol_type = protein
                       organism = synthetic construct
SEQUENCE: 288
AKDDQNPWRA YLDLLFPTDT LLLDLLWC                                               28

SEQ ID NO: 289         moltype = AA  length = 27
FEATURE                Location/Qualifiers
source                 1..27
                       mol_type = protein
                       organism = synthetic construct
```

```
SEQUENCE: 289
ACEEQNPWRA YLELLFPTET LLLELLW                                              27

SEQ ID NO: 290          moltype = AA  length = 25
FEATURE                 Location/Qualifiers
source                  1..25
                        mol_type = protein
                        organism = synthetic construct
SEQUENCE: 290
ACDDQNPWAR YLDWLFPTDT LLLDL                                                25

SEQ ID NO: 291          moltype = AA  length = 24
FEATURE                 Location/Qualifiers
source                  1..24
                        mol_type = protein
                        organism = synthetic construct
SEQUENCE: 291
CDNNNPWRAY LDLLFPTDTL LLDW                                                 24

SEQ ID NO: 292          moltype = AA  length = 24
FEATURE                 Location/Qualifiers
source                  1..24
                        mol_type = protein
                        organism = synthetic construct
SEQUENCE: 292
CEEQQPWAQY LELLFPTETL LLEW                                                 24

SEQ ID NO: 293          moltype = AA  length = 24
FEATURE                 Location/Qualifiers
source                  1..24
                        mol_type = protein
                        organism = synthetic construct
SEQUENCE: 293
CEEQQPWRAY LELLFPTETL LLEW                                                 24

SEQ ID NO: 294          moltype = AA  length = 37
FEATURE                 Location/Qualifiers
source                  1..37
                        mol_type = protein
                        organism = synthetic construct
SEQUENCE: 294
CDDDDDNPNY WARYANWLFT TPLLLLNGAL LVEAEET                                   37

SEQ ID NO: 295          moltype = AA  length = 36
FEATURE                 Location/Qualifiers
source                  1..36
                        mol_type = protein
                        organism = synthetic construct
SEQUENCE: 295
CDDDDDNPNY WARYAPWLFT TPLLLLPGAL LVEAEE                                    36

SEQ ID NO: 296          moltype = AA  length = 22
FEATURE                 Location/Qualifiers
source                  1..22
                        mol_type = protein
                        organism = synthetic construct
SEQUENCE: 296
AEQNPIYFAR YADLLFPTTL AW                                                   22

SEQ ID NO: 297          moltype = AA  length = 22
FEATURE                 Location/Qualifiers
source                  1..22
                        mol_type = protein
                        organism = synthetic construct
SEQUENCE: 297
AEQNPIYWAR YADLLFPTTL AF                                                   22

SEQ ID NO: 298          moltype = AA  length = 22
FEATURE                 Location/Qualifiers
source                  1..22
                        mol_type = protein
                        organism = synthetic construct
SEQUENCE: 298
AEQNPIYWAR YADLLFPTTL AW                                                   22

SEQ ID NO: 299          moltype = AA  length = 20
FEATURE                 Location/Qualifiers
source                  1..20
                        mol_type = protein
```

```
                           -continued organism = synthetic construct
SEQUENCE: 299
KEDQNPWARY ADLLFPTTLW                                                    20

SEQ ID NO: 300           moltype = AA  length = 24
FEATURE                  Location/Qualifiers
source                   1..24
                         mol_type = protein
                         organism = synthetic construct
SEQUENCE: 300
ACEEQNPQAE YAEWLFPTTL LLLE                                               24

SEQ ID NO: 301           moltype = AA  length = 25
FEATURE                  Location/Qualifiers
source                   1..25
                         mol_type = protein
                         organism = synthetic construct
SEQUENCE: 301
AAEEQNPWAR YLEWLFPTET LLLEL                                              25

SEQ ID NO: 302           moltype = AA  length = 25
FEATURE                  Location/Qualifiers
source                   1..25
                         mol_type = protein
                         organism = synthetic construct
SEQUENCE: 302
AKEEQNPWAR YLEWLFPTET LLLEL                                              25

SEQ ID NO: 303           moltype = AA  length = 38
FEATURE                  Location/Qualifiers
source                   1..38
                         mol_type = protein
                         organism = synthetic construct
SEQUENCE: 303
AAEQNPIYWA RYADWLFTTP LLLLDLALLV DADEGTGG                                 38

SEQ ID NO: 304           moltype = AA  length = 38
FEATURE                  Location/Qualifiers
VARIANT                  1
                         note = Ala or Asp
VARIANT                  2
                         note = Ala, Asp or Cys
VARIANT                  4
                         note = Gln or Asp
VARIANT                  11
                         note = Arg or Gln
VARIANT                  12
                         note = Tyr or Asp
VARIANT                  13
                         note = Ala, Asp or Tyr
VARIANT                  14
                         note = Asp, Asn, Glu, His, Lys, Ala or Trp
VARIANT                  15
                         note = Trp or Asp
VARIANT                  19
                         note = Thr or Asp
VARIANT                  20
                         note = Pro, Gly or Ala
VARIANT                  24
                         note = Leu or Asp
VARIANT                  25
                         note = Asp, Leu, Asn, Glu, His, Lys or Ala
VARIANT                  26
                         note = Leu, Asp or Gly
VARIANT                  31
                         note = Asp or Asn
VARIANT                  33
                         note = Asp or Asn
VARIANT                  34
                         note = Glu or Gln
VARIANT                  35
                         note = Gly or Cys
VARIANT                  37
                         note = Gly or Cys
source                   1..38
                         mol_type = protein
                         organism = synthetic construct
SEQUENCE: 304
XXEXNPIYWA XXXXXLFTXX LLLXXXALLV XAXXXTXG                                 38
```

```
SEQ ID NO: 305         moltype = AA  length = 42
FEATURE                Location/Qualifiers
VARIANT                1
                       note = May or may not be present
VARIANT                21
                       note = May or may not be present
VARIANT                29
                       note = May or may not be present
VARIANT                40
                       note = May or may not be present
source                 1..42
                       mol_type = protein
                       organism = synthetic construct
SEQUENCE: 305
DAAEQNPIYW ARYADWLFTT LPLLLLDLLA LLVDADEGTK GG                         42

SEQ ID NO: 306         moltype = AA  length = 38
FEATURE                Location/Qualifiers
source                 1..38
                       mol_type = protein
                       organism = synthetic construct
SEQUENCE: 306
GGEQNPIYWA RYADWLFTTP LLLLDLALLV DADEGTGG                              38

SEQ ID NO: 307         moltype = AA  length = 38
FEATURE                Location/Qualifiers
VARIANT                1
                       note = Gly, Asp or Ala
VARIANT                2
                       note = Gly, Asp or Cys
VARIANT                4
                       note = Gln or Asp
VARIANT                11
                       note = Arg or Gln
VARIANT                12
                       note = Tyr or Asp
VARIANT                13
                       note = Ala, Asp or Tyr
VARIANT                14
                       note = Asp, Asn, Glu, His, Lys, Ala or Trp
VARIANT                15
                       note = Trp or Asp
VARIANT                19
                       note = Thr or Asp
VARIANT                20
                       note = Pro, Gly or Ala
VARIANT                24
                       note = Leu or Asp
VARIANT                25
                       note = Asp, Leu, Asn, Glu, His, Lys or Ala
VARIANT                26
                       note = Leu, Asp or Gly
VARIANT                31
                       note = Asp or Asn
VARIANT                33
                       note = Asp or Asn
VARIANT                34
                       note = Glu or Gln
VARIANT                35
                       note = Gly or Cys
source                 1..38
                       mol_type = protein
                       organism = synthetic construct
SEQUENCE: 307
XXEXNPIYWA XXXXXLFTXX LLLXXXALLV XAXXXTGG                              38

SEQ ID NO: 308         moltype = AA  length = 44
FEATURE                Location/Qualifiers
VARIANT                1
                       note = May or may not be present
VARIANT                7
                       note = May or may not be present
VARIANT                22
                       note = May or may not be present
VARIANT                30
                       note = May or may not be present
VARIANT                40
                       note = May or may not be present
```

```
VARIANT                 42
                        note = Lys, Cys or absent
source                  1..44
                        mol_type = protein
                        organism = synthetic construct
SEQUENCE: 308
DGGEQNDPIY WARYADWLFT TLPLLLLDLL ALLVDADEGC TXGG               44

SEQ ID NO: 309          moltype = AA  length = 38
FEATURE                 Location/Qualifiers
source                  1..38
                        mol_type = protein
                        organism = synthetic construct
DISULFID                37
                        note = S-S-linker attqached to the nitrogen of
                         amino-phalloidin
SEQUENCE: 309
AAEQNPIYWA RYADWLFTTP LLLLDLALLV DADEGTCG                      38

SEQ ID NO: 310          moltype = AA  length = 31
FEATURE                 Location/Qualifiers
source                  1..31
                        mol_type = protein
                        organism = synthetic construct
DISULFID                30
                        note = S-S linker attached to 2-amino phalloidin
MOD_RES                 29
                        note = Lys(rhodamine)
MOD_RES                 1
                        note = acetylated
SEQUENCE: 310
AEDQNPYWAR YDWLFTTPLL LLDLALLVDC G                             31

SEQ ID NO: 311          moltype = AA  length = 34
FEATURE                 Location/Qualifiers
source                  1..34
                        mol_type = protein
                        organism = synthetic construct
SEQUENCE: 311
GLAGLAGLLG LEGLLGLPLG LLEGLWLGLE LEGN                          34
```